(12) United States Patent
Jain et al.

(10) Patent No.: US 11,456,080 B1
(45) Date of Patent: Sep. 27, 2022

(54) ADJUSTING DISEASE DATA COLLECTION TO PROVIDE HIGH-QUALITY HEALTH DATA TO MEET NEEDS OF DIFFERENT COMMUNITIES

(71) Applicant: Vignet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 16/985,566

(22) Filed: Aug. 5, 2020

(51) Int. Cl.
*G16H 50/80* (2018.01)
*G16H 50/70* (2018.01)
(Continued)

(52) U.S. Cl.
CPC ......... *G16H 50/80* (2018.01); *A61B 5/02055* (2013.01); *A61B 5/1112* (2013.01);
(Continued)

(58) Field of Classification Search
CPC ........ G16H 50/80; G16H 50/70; G16H 50/20; G16H 50/30; G16H 20/30; G16H 10/20;
(Continued)

(56) References Cited

U.S. PATENT DOCUMENTS

| 5,545,186 A | 8/1996 | Olson et al. |
|---|---|---|
| 6,039,688 A | 3/2000 | Douglas et al. |

(Continued)

FOREIGN PATENT DOCUMENTS

| EP | 2545468 | 1/2013 |
|---|---|---|
| IN | 202011013950 A | 5/2020 |

(Continued)

OTHER PUBLICATIONS

Adair II et al., "Chest CT findings of early and progressive phase COVID-19 infection from a US patient," Radiol. Case Reports, Apr. 20, 2020, 15(7)819-824.

(Continued)

*Primary Examiner* — Evangeline Barr
(74) *Attorney, Agent, or Firm* — Fish & Richardson P.C.

(57) ABSTRACT

Methods, systems, and apparatus, including computer programs encoded on computer-storage media, for adjustable data collection for individual and community disease management. In some implementations, user input data is provided by one or more individuals in a community to one or more user devices. Trigger data is accessed indicating one or more data collection triggers associated with monitoring of a disease. A particular data collection trigger indicated by the trigger data is detected by determining that the one or more criteria for the particular data collection trigger are satisfied. In response to detecting the data collection trigger: content is selected to prompt user input; a set of individuals associated with the community is selected to receive the selected content; and the user devices present the selected content that is configured to prompt for user input regarding of the type of data associated with the detected data collection trigger.

26 Claims, 27 Drawing Sheets

(51) Int. Cl.
*G16H 10/20* (2018.01)
*G16H 20/30* (2018.01)
*G16H 50/30* (2018.01)
*G16H 50/20* (2018.01)
*G16H 10/40* (2018.01)
*G16H 10/60* (2018.01)
*A61B 5/0205* (2006.01)
*A61B 5/16* (2006.01)
*A61B 5/11* (2006.01)
*G16H 40/67* (2018.01)
*A61B 5/021* (2006.01)
*A61B 5/024* (2006.01)
*G16H 20/40* (2018.01)
*G16H 20/60* (2018.01)
*A61B 5/1455* (2006.01)
*A61B 5/145* (2006.01)
*A61B 5/00* (2006.01)
*A61B 5/091* (2006.01)
*A61B 5/08* (2006.01)

(52) U.S. Cl.
CPC .......... *A61B 5/1116* (2013.01); *A61B 5/1118* (2013.01); *A61B 5/14532* (2013.01); *A61B 5/14551* (2013.01); *A61B 5/165* (2013.01); *A61B 5/4815* (2013.01); *A61B 5/4842* (2013.01); *A61B 5/7264* (2013.01); *A61B 5/7275* (2013.01); *A61B 5/748* (2013.01); *A61B 5/7465* (2013.01); *G16H 10/20* (2018.01); *G16H 10/40* (2018.01); *G16H 10/60* (2018.01); *G16H 20/30* (2018.01); *G16H 20/40* (2018.01); *G16H 20/60* (2018.01); *G16H 40/67* (2018.01); *G16H 50/20* (2018.01); *G16H 50/30* (2018.01); *G16H 50/70* (2018.01); *A61B 5/021* (2013.01); *A61B 5/024* (2013.01); *A61B 5/0816* (2013.01); *A61B 5/091* (2013.01)

(58) Field of Classification Search
CPC ... A61B 5/1118; A61B 5/7264; A61B 5/7275; A61B 5/0816
See application file for complete search history.

(56) References Cited

U.S. PATENT DOCUMENTS

| | | | |
|---|---|---|---|
| 6,260,022 B1 | 7/2001 | Brown |
| 6,269,339 B1 | 7/2001 | Silver |
| 7,076,534 B1 | 7/2006 | Cleron et al. |
| 7,170,993 B2 | 1/2007 | Anderson et al. |
| 7,213,009 B2 | 5/2007 | Pstotnik et al. |
| 7,330,717 B2 | 2/2008 | Gidron et al. |
| 7,447,643 B1 | 11/2008 | Olson et al. |
| 7,730,063 B2 | 6/2010 | Eder |
| 8,262,583 B1 | 9/2012 | Bryant |
| 8,583,453 B2 | 11/2013 | Plummer et al. |
| 8,589,175 B2 | 11/2013 | Glauser et al. |
| 8,684,922 B2 | 4/2014 | Tran |
| 8,706,521 B2 | 4/2014 | Ramarajan et al. |
| 8,707,392 B2 | 4/2014 | Birtwhistle et al. |
| 8,825,775 B2 | 9/2014 | Bohner et al. |
| 8,862,448 B2 | 10/2014 | Holmes et al. |
| 9,286,442 B2 | 3/2016 | Csoma et al. |
| 9,361,011 B1 | 6/2016 | Burns |
| 9,426,433 B1 | 8/2016 | Mazzarella |
| 9,461,972 B1 | 10/2016 | Mehta |
| 9,514,655 B1 | 12/2016 | Nusbaum et al. |
| 9,753,618 B1 | 9/2017 | Jain et al. |
| 9,844,725 B1 | 12/2017 | Durkin et al. |
| 9,848,061 B1 * | 12/2017 | Jain .......... G06F 8/71 |
| 9,858,063 B2 | 1/2018 | Jain et al. |
| 9,928,230 B1 | 3/2018 | Jain et al. |
| 9,983,775 B2 | 5/2018 | Jain et al. |
| 10,034,608 B1 | 7/2018 | Dintenfass |
| 10,069,934 B2 | 9/2018 | Jain et al. |
| 10,095,688 B1 | 10/2018 | Jain et al. |
| 10,198,779 B2 | 2/2019 | Pittman |
| 10,231,622 B2 | 3/2019 | Soyao et al. |
| 10,362,769 B1 | 7/2019 | Kartoun |
| 10,452,816 B2 | 10/2019 | Kidd et al. |
| 10,521,557 B2 | 12/2019 | Jain et al. |
| 10,546,339 B2 | 1/2020 | Jiao et al. |
| 10,565,894 B1 | 2/2020 | Jain et al. |
| 10,580,531 B2 | 3/2020 | Jiao et al. |
| 10,621,164 B1 | 4/2020 | Kain |
| 10,636,525 B2 | 4/2020 | Jiao et al. |
| 10,650,474 B2 | 5/2020 | Jiao et al. |
| 10,672,519 B2 | 6/2020 | Jiao et al. |
| 10,706,970 B1 | 7/2020 | Florissi |
| 10,756,957 B2 | 8/2020 | Jain et al. |
| 10,762,990 B1 | 9/2020 | Jain et al. |
| 10,902,955 B1 | 1/2021 | Federoff |
| 10,937,528 B2 * | 3/2021 | Mian .......... G16H 70/60 |
| 10,938,651 B2 | 3/2021 | Jain et al. |
| 10,998,101 B1 | 5/2021 | Tran |
| 11,056,242 B1 | 7/2021 | Jain et al. |
| 11,061,798 B1 | 7/2021 | Jain et al. |
| 11,082,487 B1 | 8/2021 | Jain et al. |
| 11,102,304 B1 | 8/2021 | Jain et al. |
| 2001/0019338 A1 | 9/2001 | Roth |
| 2002/0010596 A1 | 1/2002 | Matory |
| 2002/0022973 A1 | 2/2002 | Sun |
| 2003/0165954 A1 | 9/2003 | Katagiri et al. |
| 2003/0182429 A1 | 9/2003 | Jagels |
| 2004/0030424 A1 | 2/2004 | Corl |
| 2004/0203755 A1 | 10/2004 | Brunet et al. |
| 2005/0086587 A1 | 4/2005 | Balz |
| 2005/0186550 A1 | 8/2005 | Gillani |
| 2005/0246304 A1 | 11/2005 | Knight et al. |
| 2006/0041452 A1 | 2/2006 | Kukarni |
| 2006/0107219 A1 | 5/2006 | Ahya |
| 2006/0205564 A1 | 9/2006 | Peterson |
| 2006/0206861 A1 | 9/2006 | Shenfield |
| 2007/0021984 A1 | 1/2007 | Brown |
| 2007/0172844 A1 | 7/2007 | Lancaster et al. |
| 2007/0231828 A1 | 10/2007 | Beachy et al. |
| 2007/0259351 A1 | 11/2007 | Chinitz et al. |
| 2007/0276270 A1 | 11/2007 | Tran |
| 2007/0281285 A1 | 12/2007 | Jayaweera |
| 2008/0005679 A1 | 1/2008 | Rimas-Ribikauskas |
| 2008/0127040 A1 | 5/2008 | Barcellona |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0311968 A1 | 12/2008 | Hunter |
| 2009/0023555 A1 | 1/2009 | Raymond |
| 2009/0024944 A1 | 1/2009 | Louch |
| 2009/0031215 A1 | 1/2009 | Collier |
| 2009/0035733 A1 | 2/2009 | Meitar |
| 2009/0043689 A1 | 2/2009 | Yang |
| 2009/0076856 A1 | 3/2009 | Darby et al. |
| 2009/0125333 A1 | 5/2009 | Heywood |
| 2009/0163182 A1 | 6/2009 | Gatti |
| 2009/0170715 A1 | 7/2009 | Glinsky |
| 2009/0172002 A1 | 7/2009 | Bathiche |
| 2009/0276771 A1 | 11/2009 | Nickolov et al. |
| 2010/0041378 A1 | 2/2010 | Aceves |
| 2010/0082367 A1 | 4/2010 | Hains et al. |
| 2010/0179833 A1 | 7/2010 | Roizen et al. |
| 2010/0211941 A1 | 8/2010 | Roseborough |
| 2010/0250341 A1 | 9/2010 | Hauser |
| 2010/0262664 A1 | 10/2010 | Brown et al. |
| 2011/0015502 A1 | 1/2011 | Peyser |
| 2011/0093249 A1 | 4/2011 | Holmes et al. |
| 2011/0173308 A1 | 7/2011 | Gutekunst |
| 2011/0184748 A1 | 7/2011 | Fierro et al. |
| 2011/0200979 A1 | 8/2011 | Benson |
| 2011/0230360 A1 | 9/2011 | Stephan et al. |
| 2011/0273309 A1 | 11/2011 | Zhang et al. |

(56) References Cited

U.S. PATENT DOCUMENTS

| | | |
|---|---|---|
| 2012/0036220 A1 | 2/2012 | Dare et al. |
| 2012/0102050 A1 | 4/2012 | Button |
| 2012/0220835 A1 | 8/2012 | Chung |
| 2012/0266251 A1 | 10/2012 | Birtwhistle et al. |
| 2012/0272156 A1 | 10/2012 | Kerger |
| 2013/0024205 A1 | 1/2013 | Lyle et al. |
| 2013/0060922 A1 | 3/2013 | Koponen et al. |
| 2013/0110565 A1 | 5/2013 | Means |
| 2013/0166494 A1 | 6/2013 | Davis |
| 2013/0172774 A1 | 7/2013 | Crowder |
| 2013/0238686 A1 | 9/2013 | O'Donoghue |
| 2013/0318027 A1 | 11/2013 | Almogy |
| 2013/0329632 A1 | 12/2013 | Buyukkoc et al. |
| 2014/0019191 A1 | 1/2014 | Mulji |
| 2014/0058755 A1 | 2/2014 | Macoviak et al. |
| 2014/0088995 A1 | 3/2014 | Damani |
| 2014/0095417 A1* | 4/2014 | Herz .................... G16H 50/80 706/12 |
| 2014/0100883 A1 | 4/2014 | Hamilton |
| 2014/0156823 A1 | 6/2014 | Liu |
| 2014/0167917 A2 | 6/2014 | Wallace et al. |
| 2014/0181715 A1 | 6/2014 | Axelrod |
| 2014/0240122 A1 | 8/2014 | Roberts |
| 2014/0257058 A1 | 9/2014 | Clarysse et al. |
| 2014/0257852 A1 | 9/2014 | Walker et al. |
| 2014/0273913 A1 | 9/2014 | Michel |
| 2014/0278474 A1 | 9/2014 | McClure et al. |
| 2014/0297311 A1 | 10/2014 | Jackson |
| 2015/0019342 A1 | 1/2015 | Gupta |
| 2015/0025917 A1 | 1/2015 | Stempora |
| 2015/0025997 A1 | 1/2015 | Tilenius et al. |
| 2015/0056589 A1 | 2/2015 | Zhang et al. |
| 2015/0100330 A1* | 4/2015 | Shpits .................... G16H 50/80 705/2 |
| 2015/0135160 A1 | 5/2015 | Gauvin |
| 2015/0143470 A1 | 5/2015 | Stiekes et al. |
| 2015/0148061 A1 | 5/2015 | Koukoumidis |
| 2015/0199490 A1 | 7/2015 | Iancu et al. |
| 2015/0356701 A1 | 12/2015 | Gandy |
| 2016/0048652 A1 | 2/2016 | Spivey |
| 2016/0058287 A1 | 3/2016 | Dyell |
| 2016/0086505 A1 | 3/2016 | Hanlon |
| 2016/0132652 A1 | 5/2016 | Chapman Bates et al. |
| 2016/0140320 A1 | 5/2016 | Moturu et al. |
| 2016/0189317 A1 | 6/2016 | Papandrea |
| 2017/0000422 A1 | 1/2017 | Moturu et al. |
| 2017/0004260 A1 | 1/2017 | Moturu et al. |
| 2017/0011200 A1 | 1/2017 | Arshad et al. |
| 2017/0020444 A1 | 1/2017 | Lurie |
| 2017/0024531 A1 | 1/2017 | Malaviya |
| 2017/0039324 A1 | 2/2017 | Francois et al. |
| 2017/0116379 A1 | 4/2017 | Scott |
| 2017/0124276 A1 | 5/2017 | Tee |
| 2017/0132395 A1 | 5/2017 | Futch |
| 2017/0213007 A1 | 7/2017 | Moturu et al. |
| 2017/0235912 A1 | 8/2017 | Moturu et al. |
| 2017/0262604 A1 | 9/2017 | Francois |
| 2017/0262606 A1 | 9/2017 | Abdullah |
| 2017/0303187 A1 | 10/2017 | Crouthamel et al. |
| 2017/0308669 A1 | 10/2017 | Apte et al. |
| 2017/0323064 A1 | 11/2017 | Bates |
| 2017/0330297 A1 | 11/2017 | Cronin et al. |
| 2018/0001184 A1 | 1/2018 | Tran et al. |
| 2018/0025125 A1 | 1/2018 | Crane et al. |
| 2018/0046769 A1 | 2/2018 | O'Donnell |
| 2018/0052971 A1 | 2/2018 | Hanina |
| 2018/0068088 A1 | 3/2018 | Webb |
| 2018/0090231 A1 | 3/2018 | Liederman et al. |
| 2018/0096738 A1 | 4/2018 | Moturu et al. |
| 2018/0096740 A1 | 4/2018 | Moturu et al. |
| 2018/0181714 A1* | 6/2018 | Pillarisetty ............. G16H 50/30 |
| 2018/0197624 A1 | 7/2018 | Robaina et al. |
| 2018/0308569 A1 | 10/2018 | Luellen |
| 2018/0310890 A1 | 11/2018 | Li |
| 2018/0318643 A1 | 11/2018 | Klee et al. |
| 2018/0335939 A1 | 11/2018 | Karunamuni |
| 2018/0350455 A1 | 12/2018 | Rosen |
| 2018/0365028 A1 | 12/2018 | Hosabettu |
| 2019/0002982 A1 | 1/2019 | Wang |
| 2019/0019581 A1 | 1/2019 | Vaughan et al. |
| 2019/0043501 A1 | 2/2019 | Ramaci |
| 2019/0043610 A1 | 2/2019 | Vaughan |
| 2019/0043619 A1 | 2/2019 | Vaughan et al. |
| 2019/0074080 A1 | 3/2019 | Appelbaum et al. |
| 2019/0083031 A1 | 3/2019 | Hanina et al. |
| 2019/0102670 A1 | 4/2019 | Ceulemans |
| 2019/0122266 A1 | 4/2019 | Ramer et al. |
| 2019/0140892 A1 | 5/2019 | Jain et al. |
| 2019/0141914 A1 | 5/2019 | Nelson et al. |
| 2019/0147043 A1 | 5/2019 | Moskowitz |
| 2019/0148023 A1 | 5/2019 | Sadilek |
| 2019/0172588 A1 | 6/2019 | Tran et al. |
| 2019/0174289 A1 | 6/2019 | Martin |
| 2019/0180862 A1 | 6/2019 | Wisser et al. |
| 2019/0201123 A1 | 7/2019 | Shelton |
| 2019/0207814 A1 | 7/2019 | Jain et al. |
| 2019/0214116 A1 | 7/2019 | Eberting |
| 2019/0221306 A1 | 7/2019 | Kelkar |
| 2019/0243944 A1 | 8/2019 | Jain et al. |
| 2019/0272925 A1 | 9/2019 | Barrett |
| 2019/0286086 A1 | 9/2019 | Gardner et al. |
| 2019/0295725 A1 | 9/2019 | Morrow |
| 2019/0313934 A1 | 10/2019 | Lee et al. |
| 2019/0320310 A1 | 10/2019 | Horelik et al. |
| 2020/0005928 A1* | 1/2020 | Daniel .................... G16H 20/30 |
| 2020/0013493 A1 | 1/2020 | Moloney-Egnatios |
| 2020/0019995 A1 | 1/2020 | Krishnan et al. |
| 2020/0077942 A1 | 3/2020 | Youngblood |
| 2020/0082918 A1 | 3/2020 | Simhon |
| 2020/0112479 A1 | 4/2020 | Jain et al. |
| 2020/0119986 A1 | 4/2020 | Jain et al. |
| 2020/0135331 A1 | 4/2020 | Mohebbi |
| 2020/0227152 A1 | 7/2020 | Moturu et al. |
| 2020/0267110 A1 | 8/2020 | Nolan |
| 2020/0279464 A1 | 9/2020 | Llewelyn |
| 2020/0289534 A1 | 9/2020 | Peyman |
| 2020/0294680 A1 | 9/2020 | Gupta |
| 2020/0350079 A1 | 11/2020 | Thomas |
| 2020/0373018 A1 | 11/2020 | Segal |
| 2021/0006933 A1 | 1/2021 | Dean |
| 2021/0050116 A1 | 2/2021 | Sabeti et al. |
| 2021/0057091 A1 | 2/2021 | Gutekunst et al. |
| 2021/0144058 A1 | 5/2021 | Jain |

FOREIGN PATENT DOCUMENTS

| | | |
|---|---|---|
| WO | WO 2011/112556 | 9/2011 |
| WO | WO 2016/161416 | 10/2016 |
| WO | WO 2017/106770 | 6/2017 |

OTHER PUBLICATIONS

Blogs.BMj.com [online], "Patients' experiences of "longcovid" are missing from the NHS narrative," Jul. 10, 2020, retrieved on Aug. 26, 2020, retrieved from URL<https://blogs.bmj.com/bmj/2020/07/10/patients-experiences-of-longcovid-are-missing-from-the-nhs-narrative/>, 6 pages.

Burke et al., "Ecological Momentary Assessment in Behavioral Research: Addressing Technological and Human Participant Challenges," J. Med. Internet Research, Mar. 2017, 19(3):e77, 17 pages.

CBSNews.com [online], "NBA players can wear smart rings to detect COVID-19 symptoms when season returns," Jun. 19, 2020, retrieved on Aug. 26, 2020, retrieved from URL<https://www.cbsnews.com/amp/news/nba-players-oura-smart-rings-coronavirus-symptoms/#app>, 7 pages.

CDC.gov [online], "Contact Tracing," last updated Aug. 4, 2020, retrieved on Aug. 26, 2020, retrieved from URL<https://www.cdc.gov/coronavirus/2019-ncov/daily-life-coping/contact-tracing.html>, 6 pages.

CDC.gov [online], "Interim Clinical Guidance for Management of Patients with Confirmed Coronavirus Disease (COVID-19)," last

(56) References Cited

OTHER PUBLICATIONS updated Jun. 30, 2020, retrieved on Aug. 26, 2020, retrieved from URL<https://www.cdc.gov/coronavirus/2019-ncov/hcp/clinical-guidance-management-patients.html>, 10 pages.
CDC.gov [online], "Preliminary Criteria for the Evaluation of Digital Contact Tracing Tools for COVID-19," last updated May 17, 2020, retrieved on Aug. 26, 2020, retrieved from URL<https://www.cdc.gov/coronavirus/2019-ncov/downloads/php/prelim-eval-criteria-digital-contact-tracing.pdf>, 3 pages.
FierceWireless.com [online], "Verizon pinpoints location with centimeter-level accuracy for road safety, IoT," Aug. 13, 2020, retrieved on Aug. 26, 2020, retrieved from URL<https://www.fiercewireless.com/tech/verizon-pinpoints-location-centimeter-level-accuracy-for-road-safety-iot>, 5 pages.
Forbes.com [online], "Covid-19 Can Cause Heart Damage—Even if you are Asymptomatic," Aug. 17, 2020, retrieved on Aug. 18, 2020, retrieved from URL<https://www.forbes.com/sites/robertglatter/2020/08/17/covid-19-can-cause-heart-damageeven-if-you-are-asymptomatic/#2854d83c6cef>, 8 pages.
Forbes.com [online], "How Covid-19 Coronavirus May Cause Heart Damage, Here are Two New Studies," Jul. 29, 2020, retrieved on Aug. 26, 2020, retrieved from URL<https://www.forbes.com/sites/brucelee/2020/07/29/study-how-covid-19-coronavirus-may-affeet-your-heart/amp/>, 15 pages.
Fraser, "Long term respiratory complications of covid-19," The BMJ, Aug. 3, 2020, 370:m3001, 4 pages.
Grants.NIH.gov [online], "Department of Health and Human Services: Digital Healthcare Interventions to Address the Secondary Health Effects Related to Social, Behavioral, and Economic Impact of COVID-19 (R01—Clinical Trial Optional),"Jun. 26, 2020, retrieved on Aug. 26. 2020, retrieved from URL<https://grants.nih.gov/grants/guide/pa-files/PAR-20-243.html>, 22 pages.
Grants.NIH.gov [online], "OER Home Page," last updated Aug. 23, 2020, retrieved on Aug. 26, 2020, retrieved from URL<https://grants.nih.gov/grants/oer.htm>, 2 pages.
Greenhalgh et al., "Management of post-acute covid-19 in primary care," The BMJ, Aug. 11, 2020, 370:m3026, 8 pages.
IBM.com [online], "IBM Return-to-Workplace Advisor," available on or before Jun. 3, 2020, via Internet Archive: Wayback Machine URL<https://web.archive.org/web/20200603132649/https://www.ibm.com/products/return-to-workplace-advisor>, retrieved on Aug. 26, 2020, retrieved from URL<https://www.ibm.com/products/return-to-workplace-advisor>, 5 pages.
IBM.com [online], "IBM Watson Care Manager," available on or before Feb. 4, 2020, via Internet Archive: Wayback Machine URL<https://web.archive.org/web/20200204050606/https://www.ibm.com/products/watson-care-manager, retrieved on Aug. 26, 2020, retrieved from URL<https://www.ibm.com/products/watson-care-manager>, 10 pages.
Jones et al., "Two metres or one: what is the evidence for physical distancing in covid-19?," The BMJ, Aug. 25, 2020, 370:m3223, 6 pages.
KXAN.com [online], "CDC adds 3 new coronavirus symptoms to list," Jun. 25, 2020, retrieved on Aug. 26, 2020, retrieved from URL<https://www.kxan.com/news/cdc-adds-3-new-coronavirus-symptoms-to-list/>, 12 pages.
Mahase, "Covid-19: What do We know about "long covid"?," The BMJ, Jul. 14, 2020, 370:m2815, 2 pages.
Moskowitz et al., "Ecological momentary assessment: what it is and why it is a method of the future in clinical psychopharmacology," J. Psychiatry Neuroscience, Jan. 2006, 31(1):13-20.
Nature.com [online], "Coronavirus contact-tracing apps: can they slow the spread of COVID-19?," May 19, 2020, retrieved on Aug. 17, 2020, retrieved from URL<https://www.nature.com/articles/d41586-020-01514-2>, 9 pages.
Safer.me [online], "How To Guide: the contact tracing process for business," Apr. 2020, retrieved on Aug. 26, 2020, retrieved from URL<https://www.safer.me/en-NZ/how-the-contact-tracing-process-works/>, 9 pages.

Safeteams, "Safeteams: Proven Solutions to Protect Your Workforce and Maintain Operations," available no later than Jul. 13, 2020, 9 pages.
STATNews.com [online], "Watch: It's not just the lungs: The Covid-19 virus attacks like no other 'respiratory' infection," Jun. 26, 2020, retrieved on Aug. 26, 2020, retrieved from URL<https://www.statnews.com/2020/06/26/from-nose-to-toe-covid19-virus-attacks-like -no-other-respiratory-infection/>, 7 pages.
TheAtlantic.com [online], "Long-Haulers Are Redefining COVID-19." Aug. 19, 2020, retrieved on Aug. 20, 2020, retrieved from URL<https://www.theatlantic.com/health/archive/2020/08/long-haulers-covid-19-recognition-support-groups-symptoms/615382/>, 11 pages.
TheAtlantic.com [online], "This Is Not a Normal Mental-Health Disaster," Jul. 7, 2020, retrieved on Aug. 26, 2020, retrieved from URL<https://www.theatlantic.com/health/archive/2020/07/coronavirus-special-mental-health-disaster/613510/>, 9 pages.
TheWashingtonPost.com [online], "Cellphone apps designed to track covid-19 spread struggle worldwide amid privacy concerns," Aug. 18, 2020, retrieved on Aug. 25, 2020, retrieved from URL<https://www.washingtonpost.com/technology/2020/08/17/covid-tracking-apps-cellphones/>, 7 pages.
U.S. Department of Health and Human Services, "Digital Health Solutions for COVID-19: Solicitation No. 75N91020R00039," Jun. 26, 2020, 76 pages.
WVUMedicine.org [online], "WVU Rockefeller Neuroscience Institute announces capability to predict COVID-19 related symptoms up to three days in advance," May 28, 2020, retrieved on Aug. 26, 2020, retrieved from URL<https://wvumedicine.org/news/article/wvu-rockefeller-neuroscience-institute-announces-capability-to-predict-covid-19-related-symptoms-up-/>, 3 pages.
U.S. Notice fo Allowance in U.S. Appl. No. 16/985,440, dated Mar. 4, 2021, 12 pages.
U.S. Office Action in U.S. Appl. No. 16/927,952, dated Jan. 27, 2021, 37 pages.
U.S. Office Action in U.S. Appl. No. 17/000,114, dated Feb. 5, 2021, 16 pages.
Zhenxin et al., "Be Aware of the Hot Zone: A Warning System of Hazard Area Prediction to Intervene Novel Coronavirus COVID-19 Outbreak", Proceedings of the 43rd International ACM SIGIR Conference, Association for Computing Machinery, 2020, 2241-2250.
FDA.gov [online], "Digital Health Policies and Public Health Solutions for COVID-19," Mar. 26, 2020, retrieved on Sep. 21, 2020, retrieved from URL<https://www.fda.gov/medical-devices/coronavirus-covid-19-and-medical-devices-digital-health-policies-and-public-health-solutions-covid-19>, 3 pages.
Kveder et al., "Digital Medicines March on Chronic Disease", Nature Biotechnology, Mar. 2016, 34:1-8.
Pueng Vongs, Map: New live coronavirus tool compares growth of virus to SARS, H1N1 and Ebola, Feb. 13, 2020, The Mercury News, available at: https://www.mercurynews.com/2020/02/13/map-new-coronavirus-tool-compares-growth-of-virus-to-sars-h1n1-and-ebola/ (Year: 2020).
Similarities and Differences between Flu and COVID-19, Jul. 2, 2020, Centers for Disease Control and Prevention, available at: http://web.archive.org/web/20200703191044/https://www.cdc.gov/flu/symptoms/flu-vs-covid19.html (Year: 2020).
U.S. Office Action in U.S. Appl. No. 16/927,952, dated Sep. 24, 2020, 29 pages.
U.S. Office Action in U.S. Appl. No. 16/985,440, dated Nov. 24, 2020, 37 pages.
U.S. Office Action in U.S. Appl. No. 16/985,616, dated Sep. 25, 2020, 45 pages.
U.S. Office Action in U.S. Appl. No. 16/986,011, dated Nov. 24, 2020, 94 pages.
U.S. Final Office Action in U.S. Appl. No. 17/000,114, dated May 21, 2021, 16 pages.
U.S. Non Final Office Action in U.S. Appl. No. 17/372,020, dated Aug. 23, 2021, 27 pages.
U.S. Appl. No. 15/803,556, filed Nov. 3, 2017, Jain et al.
[No Author Listed] "Cancer Care Patient Navigation. A practical guide for community cancer centers," Association of Community

(56) References Cited

OTHER PUBLICATIONS

Cancer Centers, 2009, [retrieved on Jan. 2, 2018], retrieved from: URL <https://www.accc-cancer.org/resources/pdf/Patient-Navigation-Guide.pdf>, 40 pages.

[No Author Listed] "Digital therapeutics," Wikipedia, Nov. 20, 2017, [retrieved on Jan. 2, 2018], retrieved from: URL <https://en.wikipedia.org/wiki/Digital_therapeutics>, 4 pages.

[No Author Listed] "Methods for JIT AIs Just in Time Adaptive Intervention," 2016, Nov. 9, 2016, [retrieved on Nov. 9, 2016], from the internet <https://community.isr.umich.edu/public/Default.aspx?alias=community.isr.umich.edu/public/jitai&>.

Boulos et al., "How smartphones are changing the face of mobile and participatory healthcare: An overview, with example from eCAALYX", Biomedical Engineering Online, Dec. 2011, 10(10:24.

Braun et al., "Cancer Patient Navigator Tasks across the Cancer Care Continuum," J Health Care Poor Underserved, Feb. 1, 2012, 23(1):398-413.

Conner, "Experience sampling and ecological momentary assessment with mobile phones," 2015—http://www.otago.ac.nz/psychology/otago047475.pdf.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

Heron, "Ecological Momentary Intervention [EMI]: Incorporating mobile technology into a disordered eating treatment program for college women," Psychology—Dissertations, paper 157, 2011.

http://www.khanacademic.org, [online],"Khan Academy," May 12, 2017, retrieved on Jan. 2, 2018, retrieved from URL <Khanacademic.org>, 1 page.

Milward, "Ecological momentary assessment," Jul. 2015, [retrieved on May 12, 2017], from the internet <https://www.addiction-ssa.org/commentary/emerging-research-methods-series-ecological-momentary-assessment>, 3 pages.

Notice of Allowance in U.S. Appl. No. 17/000,114, dated Oct. 4, 2021, 13 pages.

Runyan et al., "Virtues, ecological momentary assessment/intervention and smartphone technology," Front Psychol, 2015;6:481.

Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.

Simon, "Patient Navigators Help Cancer Patients Manage Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.

Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.

U.S. Non Final Office Action in U.S. Appl. No. 16/881,084, dated Aug. 4, 2021, 19 pages.

The National Institutes of Health (NIH) U.S. Department of Health and Human Services (HHS) Digital Health Solutions for Covid-19, Issued on Jun. 26, 2020, 76 pages.

* cited by examiner

| Downloadable Module | Purpose | Applicable Users | Surveys provided | Data Tracked | |
|---|---|---|---|---|---|
| 1 | COVID-19 Detection and Risk Assessment | General Users | Energy level<br>Taste and Smell<br>... | Temperature<br>Heart Rate<br>Respiration Rate<br>Activity / Exercise<br>... | ... |
| 2 | COVID-19 Detection and Risk Assessment | High-risk Users (e.g., Age > 60 years) | Energy Level<br>Sleep Quality<br>Taste and Smell<br>Pain levels<br>... | Temperature<br>Heart Rate<br>Blood Pressure<br>Respiration Rate<br>Blood Oxygen Level (SpO2)<br>Activity / Exercise<br>... | ... |
| 3 | Treatment & Treatment Support | Users with current COVID-19 infections | Pain level<br>Breathing Difficulty<br>... | Respiration Rate<br>Blood Oxygen Level (SpO2) | ... |
| 4 | Recovery Support | Users with former COVID-19 Infections | Long-term effects<br>Social Activity<br>Cognitive Ability<br>... | Activity / Exercise<br>Heart Rate<br>Respiration Rate<br>... | ... |
| ... | | | | | |

FIG. 2

EXPOSURE RISK: HIGH
DETECTED CHANGE: Your sleeping habits have changed!

Your amount of deep sleep has increased indicating signs of exhaustion or fatigue.

And your time asleep has increased and with it, the number of apnea events throughout the night.

Based on your levels and current exposure risk, you should *avoid taking any nighttime sleeping aids*.

Do you have time now for a check-in?

[LATER]  [YES]

Question 1:
| Response | Weighting |
|---|---|
| A | 0 |
| B | +1 |
| C | +2 |
| D | +3 |

Question 2:
| Response | Weighting |
|---|---|
| A | 0 |
| B | +1 |
| C | +2 |
| D | +3 |

Question 3:
| Response | Weighting |
|---|---|
| A | 0 |
| B | +1 |
| C | +2 |
| D | +3 |

Based on your risk identified, a kit is being mailed to determine whether you have contracted a new strain of the virus.

FIG. 9B

 Location Type Risk Tags
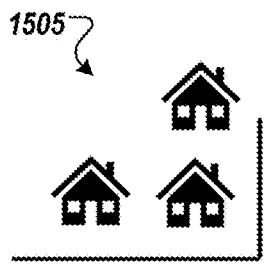
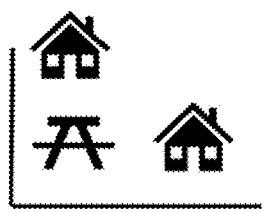
Tag No. 9164
Type: Doctor's Office
Disease Trans. Score: 7
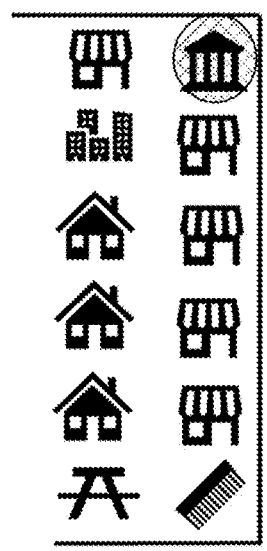
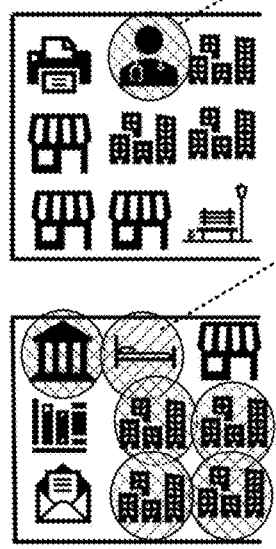
Tag No. 1143
Type: Hotel
Disease Trans. Score: 6
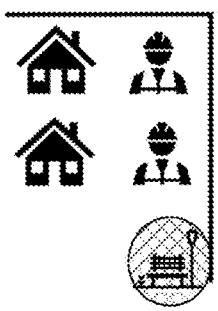
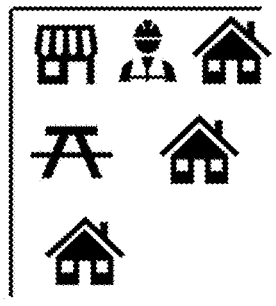
Notification:
Remember social distancing, you are in an area with a high-risk business type
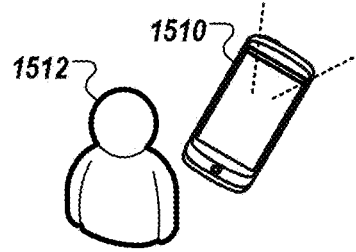
FIG. 15B

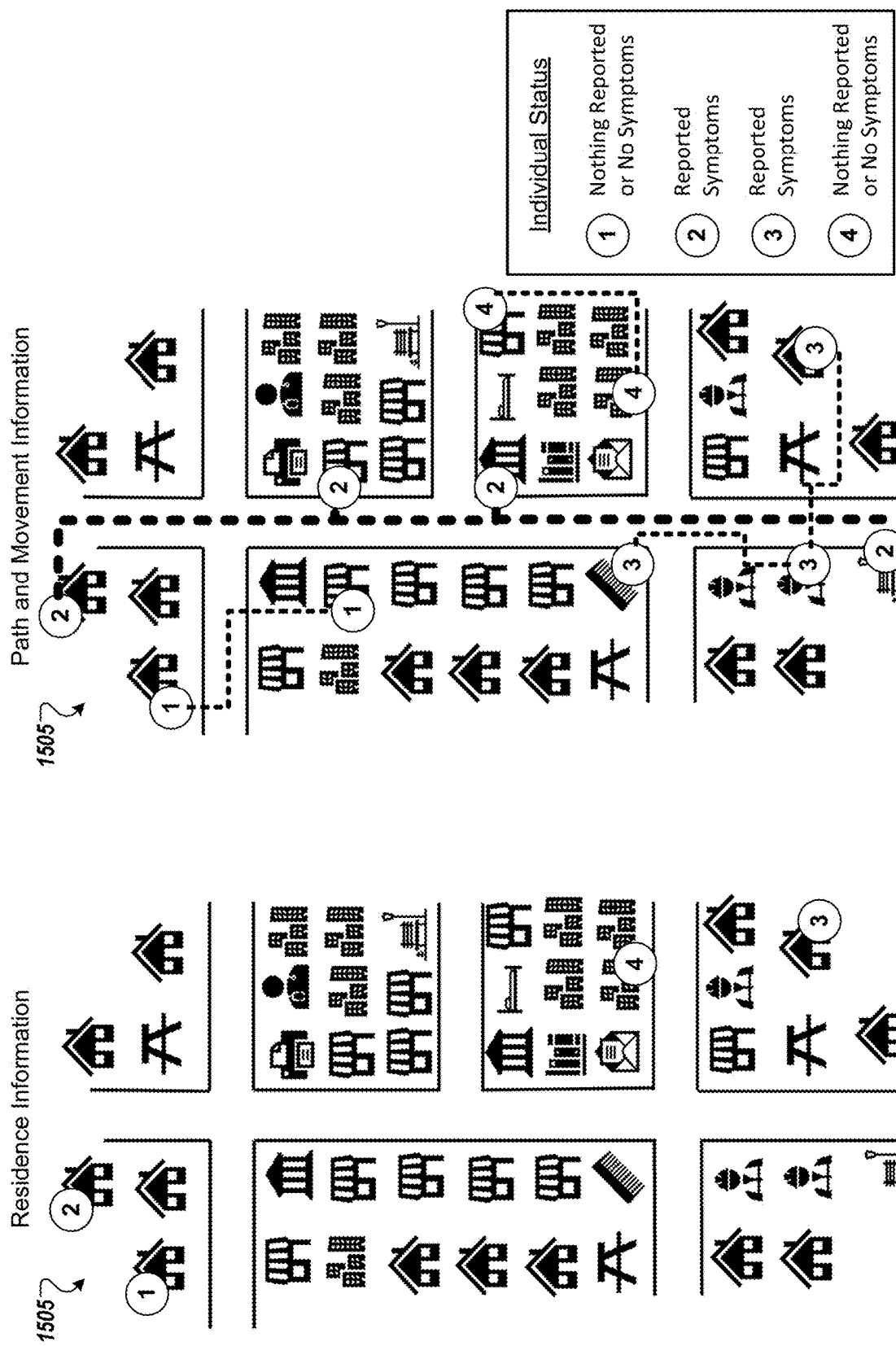

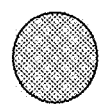 Population Volume Risk Tags
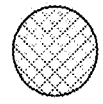 Location Type Risk Tags
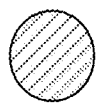 COVID-19 Exposure Tags
Risk Factor Combination
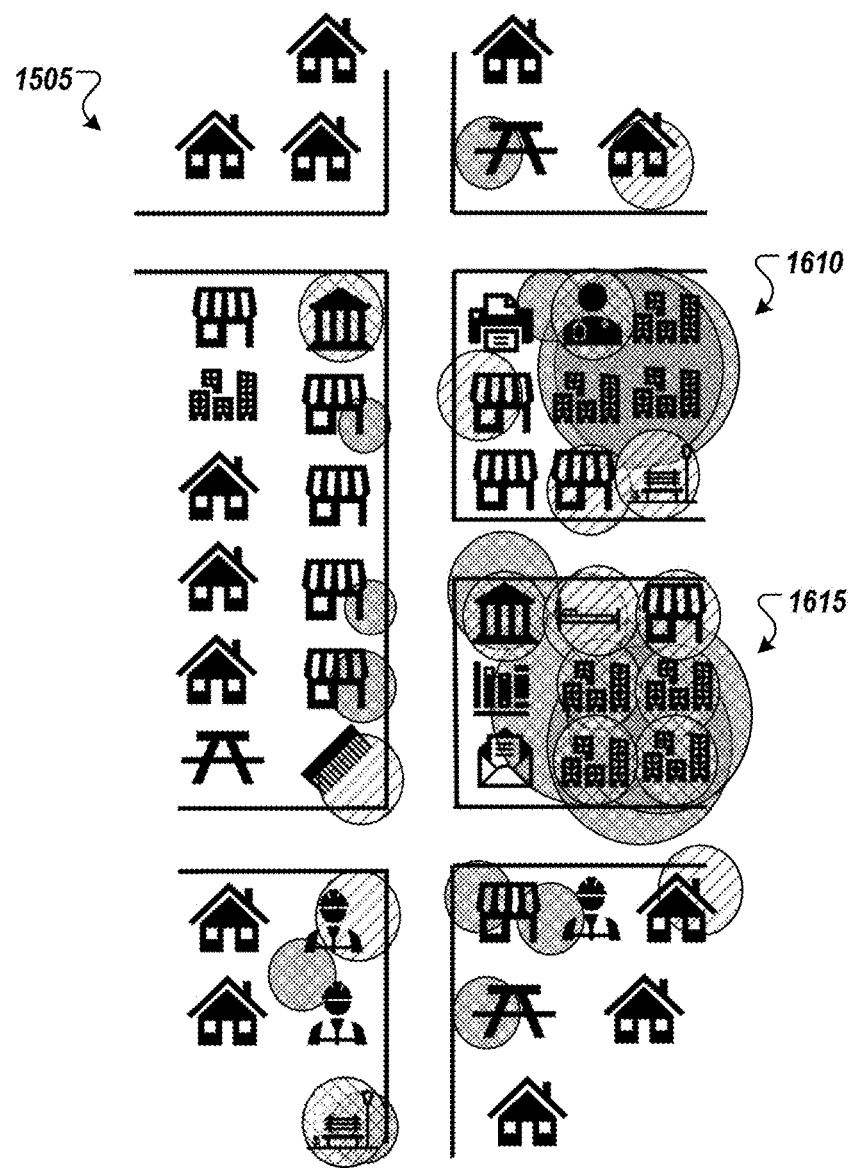
FIG. 16C

| 2100 | Data Collection Trigger Data | | | |
|---|---|---|---|---|
| Criteria | Type of Data to Collect or Measure | Collection Content or Tool | Data Collection Mode | Recipients |
| CDC data shows Community infection rate greater than a threshold | Disease Symtoms | Basic Disease Symtoms Survey | User input | All individuals in the community |
| User-reported positive disease test result for a user in the community | Social Activity | Question #243 | User input | Age > 60 years old |
| Health records indicate at least a threshold number of diagnoses of the disease | Travel | Travel Survey #11 | User input | Individuals for which location tracking data not available |
| Survey responses of at least a threshold number of people indicate disease | Breathing Capability Level | Guided Breathing Exercise | Sensing during system-prompted user activity | Age > 40 years old |
| New infection rate in the community is greater than a threshold | Physical Activity Level | Physical Activity Tracker Code Module | Passive Collection of Sensor Data | All individuals in the community |
| Average body temperatures increasing for a location | EMA regarding breathing difficulty | EMA #456 | User input | Individuals associated with the location |
| Body Temperature change with respect to personal baseline | Heart rate variability (HRV) changes during sleep | HRV detection module | Passive Collection of Sensor Data | Affected individuals and their families |
| ... | ... | ... | ... | ... |

FIG. 21

ADJUSTING DISEASE DATA COLLECTION TO PROVIDE HIGH-QUALITY HEALTH DATA TO MEET NEEDS OF DIFFERENT COMMUNITIES

GOVERNMENT LICENSE RIGHTS

This invention was made with government support under contract number 75N91020C00038 awarded by the National Institutes of Health. The government has certain rights in the invention.

BACKGROUND

Infectious diseases such as COVID-19 can be challenging to track and treat, especially on a large scale. Traditional techniques for detecting infection and delivering treatment may not provide a sufficiently rapid or personalized response to effectively detect and treat disease in some cases. In addition, the factors that affect the spread and impact of disease can be variable from location to location. As a result, different communities may have different risk profiles and need different strategies to prevent, contain, or otherwise manage the spread of disease.

SUMMARY

In some implementations, a system provides a technology platform to monitor, predict, and contain the spread of COVID-19 and other diseases. The system can evaluate the risks and needs of different communities to customize various disease-related measurements, predictions, and recommendations for the different communities. In some implementations, the communities can be different geographic regions, and fine-grained recommendations can be made for areas such as counties, cities, zip codes, or neighborhoods. Among the tools provided to communities, the system can predict areas that are likely to become disease hotspots, based on current behavior patterns of individuals in a community. Similarly, the system can predict disease measures (e.g., infections, hospitalizations, and so on) for future times based on a variety of factors, including real-time monitoring data. These and other predictions can be made using machine learning models that are generated using training data indicating monitoring data and outcomes over time for many different communities.

In some implementations, a medical treatment device provide one or more therapies for treating COVID-19 or COVID-19 symptoms. The medical treatment device provides features to perform data collection, including measurement of one or more physiological parameters of a user and location tracking. The medical treatment device can be configured to use location tracking data to determine whether and when to initiate treatment for COVID-19. For example, the medical treatment device can measure body temperature, heart rate, respiration rate, or other parameters, and based on the measured parameters determine that the user is likely to have contracted COVID-19. In addition, the medical treatment device can determined, based on location tracking data such as GPS data, that the medical treatment device has been in one or more regions that have elevated disease transmission potential for COVID-19, thus making infection with COVID-19 even more probable for the user. The identification of the one or regions can be based on, for example, location tracking data for other devices or based on information about movement patterns in a community. The one or more regions may be received from a server system or generated by the medical treatment device. Based on the physiological monitoring data and the detection of a location in the one or more regions of elevated disease transmission potential, the medical treatment device may automatically provide one or more therapies, e.g., by providing digital therapeutics interventions to promote behavior change or support specific functions (e.g., breathing, posture, exercise, etc.), dispensing a medication, etc.

The system can obtain monitoring data from individuals on an ongoing or continual basis using digital platforms, as well as obtain aggregated data regarding communities and the effects of a disease. The system can use these inputs to repeatedly generate updated predictions and also to update the predictive models. With incoming data streams showing real-time behaviors of individuals, the system can provide rapid and in some cases real-time responses to changing conditions in a communities and in surrounding communities. The system can use predictive modeling to forecast future disease-related measures and trends, identify factors contributing to those measures and trends, and recommend actions to more effectively improve a community's efforts to contain and eliminate a disease.

In addition, the predictions of the system can be used to personalize care for individuals. For example, the system's predictions of future disease measures and trends in a community can be used to personalize disease management actions taken for an individual in that community. If the system predicts that of disease prevalence or infection rates will increase in a community, for example, the system may change monitoring for detection of (e.g., infection prediction for) the disease for an individual, provide diagnostic testing for the disease for the individual, or to begin or modify treatment of the disease for the individual.

In addition, interventions and treatments can be provided across a community. For example, if a trip is planned for a family, a group of families, a business or other organization, etc., the system can detect a high risk of disease exposure and can take a disease management action in response. For example, based on the intended destination, the system can ship medical monitoring or treatment devices in advance, can schedule doctor appointments or laboratory tests, and vaccination can be scheduled or vaccination status checked, etc. The system can acquire information about disease prevalence in different areas, such as from government sources or public health agencies, to detect locations where outbreaks of COVID-19 are present. The same techniques can be used for other diseases, such as yellow fever, malaria, polio, measles, or any other infectious disease. As another example, if a field trip is planned for students, a vaccine for a disease can be distributed based on risk levels at a destination. As another example, a business may provide an employee program, so that if some employees are traveling, treatment or vaccines are provided for the office or business as a whole, to reduce susceptibility to a disease that travelers may acquire and then expose others to.

One of the significant advantages that the system can provide is to predictively localize hotspots of disease transmission risk with precision. Machine learning models can be trained using rich data about geography and behavior in different communities. The examples used for training can include data describing specific places, data characterizing occupancy and traffic over time, geographic relationships such as map data, and so on. The examples can also include individual and community-level disease outcomes (e.g., infections, hospitalizations, deaths, etc.) and monitoring data, such as location tracking data indicating locations that people visited and the times, durations, and activities of the visits. Contact tracing data, if available, can also be used to identify when and where different interactions leading to disease transmission occurred. With this data, machine learning techniques can train a model to incorporate relationships among travel patterns, location types, environmental factors, geographical factors, and other factors with disease transmission. For example, the model can learn to identify the relative risk of transmission posed by different types of locations when combined with different community characteristics and behavior or travel patterns. As a result, when the system assesses a community data set that has a location with this combination of factors, the model can indicate the high risk transmission risk for the location.

This approach can provide significant advantages over existing approaches. For example, conventional contact tracing is a useful tool that can track the chain of transmission of a disease among individuals who interact with each other or who are located at the same place at the same time. Conventional contact tracing for COVID-19 typically involves identifying individuals who have an positive diagnosis of COVID-19 (e.g., actual disease cases) and their contacts (e.g., anyone who was within 6 feet from a positive case for at least 15 minutes starting 48 hours before the person began to feel ill until they were isolated), and then working with diagnosed individuals and their contacts to prevent further spread of the virus.

However, conventional contact tracing has limitations. Adoption of conventional contact tracing technology is often limited and takes time to deploy. In addition, contract tracing to track close interaction of individual does not necessarily capture all of the routes of transmission of COVID-19 and other diseases (e.g., inhaled droplets, contaminated surfaces, aerosolized particles, etc.). For example, two people that visit the same location may not be detected through typical contact tracing, for example, for being outside a threshold distance (e.g., 10 feet), for visiting the location at slightly different times (e.g., a few minutes apart), etc. This type of visit could still result in disease transmission however, through a contaminated surface or other transmission mode. Another limitation of traditional contact tracing is the relatively high level of contact required before finding that two people are in contact (e.g., often proximity of roughly 10-20 feet or less). Another limitation is the technique is that individuals are usually required to be located in the same place at the same time to register contact, for example, being at the same place for overlapping time periods of some minimum duration. While these factors can be useful, they can also miss events that can nevertheless cause disease exposure, such as individuals passing through a region at times close to each other, but not actually entering close proximity to each other or being at the same location at the same time. For COVID-19, which is believed to be spread on surfaces and through the air, potentially through respiratory droplets or aerosolized particles, more versatile tools can better detect events and conditions that may spread COVID-19 but not be detected by traditional contact tracing that focuses on instances of people being at the same location at the same time.

The techniques discussed below enable a variety of features including geofencing, contact tracing, and proximity tracing. These features enable better communication with individuals, including those who have been officially diagnosed with COVID-19 to identify all individuals with whom they have had close contact ("close contacts") during the time period in which they may have been infectious. Communication can also be provided with those who are identified to be in close contact officially diagnosed individuals, e.g., a family member, a friend, a person living with them, or a random engagement. Communication can also be provided to those who are identified to visit the same area as another person within a set period of time, such as 16 hours, or any defined amount of time. Exposure scores can be adjusted or weighted based on the amount of time elapsed between the visits of different people. Communication can be provided for those who have experienced any high-risk related areas and their observations. Based on estimates of exposure, the system can refer individuals to appropriate testing services, treatment, and general guidance measures such as self-isolation steps. The system can also monitor individuals to maintain awareness of COVID-19 exposure rates and corresponding risk identifiers. The system can assist individuals with notifications, alerts, and community-related news of new, updated tags representing exposure events or significant exposure risks.

The system allows for the varying influence of different levels of proximity and timing to be reflected in an individual's risk level. In addition, the system can incorporate additional factors such as population volume or traffic levels, business types or activity types for different locations, and so on. This provides a more accurate indication of the exposure level or exposure risk of an individual, which allows the system to provide earlier and more appropriately customized disease management actions (e.g., disease prevention recommendations, testing, treatment, etc.).

In some implementations, location tags representing disease exposure events or risks can be based on symptom reports or infection likelihood predictions, in addition to or instead of disease testing results. For example, a location tag representing a visit of a person can be assigned a disease transmission score based on symptoms reported by a user, physiological measures tracked (e.g., with passively sensed data), detected changes in behavior, or other early signs of infections, before the individual obtains a positive diagnosis. A machine learning model can be used to determine an infection likelihood for the user, allowing a high-confidence indication whether a person is infected with COVID-19 before traditional testing occurs. By using these machine learning predictions or other data such as behavior data, physiological data, or symptom self-reporting data to assign scores to location tags, the system can better detect the spread of COVID-19 and recommend measures to slow the spread of the disease, even before testing is available or widespread.

Another advantage of the system is the ability to use machine learning to determine the types of events and contacts that result in disease transmission, and use that information to improve the scoring of location tags, ultimately resulting in a more accurate system over time. Many conventional contact tracing systems use predefined measures of contact, such as a specific proximity distance and amount of overlap in time, which may not be appropriate for the many varied types of interactions that occur and the varied locations people visit. The present system is more versatile, allowing individual tags (e.g., representing visits or events by individuals) to have different sizes and shapes of geofence areas and for the location tags to have transmission scores (e.g., indicating the intensity or risk of disease transmission) to be different and to vary over time (e.g., to diminish gradually following the exposure event). In addition, different thresholds and definitions of contact to be used to be customized, for example, for different communities, for different types of locations, and even for specific individual locations. For example, due to differences in ventilation and other environmental factors, the amount of time that a virus remains viable may be different for a grocery store compared to a department store or another location type. Similarly, the percentage of people at a location who have been vaccinated for a disease and/or who have recovered from the disease (e.g., and thus acquired immunity) limits the risk of disease transmission occurring. By analysis of the location tracking data and disease outcomes and related data, the system can learn the parameters that reflect the transmission environment of different activities, locations, and location types. This allows the system to adjust and customize scoring of exposure-tagged locations and the areas and tag timing for those locations (e.g., including patterns of exposure risk reduction to elapsed time or social distancing precautions), for better exposure estimates and risk measures overall.

In some implementations, a system provides a technology platform that can be used to assess risks of a disease for an individual and select treatment for an individual. The system can be personalized or tailored to the individuals and can be used as an ongoing risk assessment tool. The platform can include a downloadable data package (e.g., software module or set of configuration data) for managing the disease, which can be downloaded to and used by a user device such as a smartphone. The data package can instruct monitoring of a user, for example, to obtain physiological measurements, sensor data, survey responses, contextual information, and other types of data. This data can be provided to a server, and can be processed by the user device and/or the server. With the collected data, the system can estimate a user's level of exposure to the disease and a likelihood of infection of the user. The system can also select additional actions to improve detection of the disease, such as to change monitoring procedures (e.g., the types of data collected, the frequency of data collection, etc.) or to issue a physical testing kit to test for the disease. The system can also select and recommend treatment for the disease, such as through medication, behavioral changes, digital therapeutics, etc. In general, the system can predict a variety of items, such as a user's personal risk of contracting COVID-19, the severity of disease effects that may be experienced if the user were infected, a likelihood that the user is currently affected, and so on. The system can also take actions to prepare against new risks, for example, by encouraging a user to change behavior, to change or increase monitoring, or take other preventive or protective steps. As a result, the system can protect users from changing risks of disease by predicting or estimating those risks and recommending or carrying out actions to reduce them. These steps can prevent or at least reduce the incidence and severity of diseases, including viral outbreaks, for individuals.

The system can provide earlier and more accurate detection of disease using improved techniques for generating and updating personal baseline measures. The system can generate baseline measures for each of multiple aspects of a user's physiology and behavior. Many prior systems have not effectively used the predictive value of a user's behavior changes to detect and manage disease. In many cases, as discussed below, behavioral changes may be an early indicator of infection or a predictor of the severity or future symptoms of a disease. Nevertheless, behavioral changes can be subtle and the significance can vary for different individuals. Using repeated, ongoing data collection from mobile devices and other data sources, the system can maintain accurate baseline measures that take into account the contexts and activities of each individual, updating the baseline measures on an ongoing basis over time. In some cases, the baseline measures can include average values based on data collected over a time period. The baseline measures can also include more complex types of data, such as data indicating patterns and trends over time and classifications of those patterns and trends.

The system can also use data about each individual's community to enhance estimates or predictions of disease exposure, likelihood of infection, and other items. For example, the system can collect information about where a user resides, works, and generally spends time, as well as the types of locations the user visits and the specific visits and travel of the user. Information about infection rates and other disease measures for the communities where a user has been are used to better predict exposure and likelihood of infection. The system can use contract tracing data in this process, e.g., data tracking proximity of a user to specific other people over time. Nevertheless, in addition to or as an alternative to tracking contact with specific people, the system can use monitoring data indicating locations a user has been, amounts of time spent in the locations, occupancy or traffic at the locations, and other data to estimate exposure.

The system can progressively adapt the level of monitoring and types of interactions with a user according to the user's predicted exposure level or likelihood of infection. For example, as a user's exposure level increases, the system can automatically increase the frequency and extent of monitoring by user devices, e.g., smartphone, smartwatch or other wearable device, and so on. The system can vary the types of measurements made (e.g., types of sensor data collected) as well as the types of surveys, user prompts, or other user interactions that the system causes to be provided. The system can also vary the monitoring procedures used for a user to reach a desired level of confidence in the predictions.

The monitoring data and predictions of the system can be used to perform may different actions to manage a disease, such as to select a testing kit for the user to test for the disease, selecting a vaccine and administration regimen for the vaccine, and selecting treatment (e.g., selecting drugs and dosage, selecting medical devices and settings for them, selecting digital therapeutics, etc.). These actions and others recommended by the system can be selected based on monitoring data, clinical data (e.g., electronic health records (EHR) or electronic medical records (EMR)), community measures, and more.

One of the significant advantages provided by the present technology is the monitoring of user behavior and the user of that behavior data in disease detection and the selection of disease treatments. In many cases, subtle changes in behavior can occur during the very early stages of disease, well before a user recognizes a symptom or realizes that he or she may be affected by a disease. By detecting subtle changes in the types, frequency, and intensity of user behaviors, including changes in combinations of different behaviors at similar times and in sequences, the present technology can identify early signs and risk factors for infection that other systems cannot. These types of signs are also more accurately detected by comparison of observed data with personalized user baseline measures. Further, the present technology allows earlier indicators of changing behavior to be verified and enhanced through follow-up interactions such as surveys and other interactions that can help pinpoint the causes or factors influencing behavior. The combination of real-time behavior change detection with real-time physiological monitoring, with the two being correlated and tracked together allows for predictive modeling and detection of infection and other conditions much better than physiological monitoring alone.

In general, behavior can be tracked to allow detection of certain types of signs, symptoms, effects of disease and of disease treatment, including for items that are not readily detectable with physiological sensing alone. User behavior can be inferred from passively sensed data, such as location tracking, movement tracking, device pose and device usage, sounds detected with a microphone (e.g., detecting a user coughing), etc. The behavior data can include records of different activities and events, indications of discrete instances of behaviors, as well as patterns and trends. A baseline measure can be determined and stored, and also periodically updated, for a user for each of different types of activities. The baseline measures can indicate, for example, the type, frequency, duration, intensity, time of day, location, that the behavior takes place. Also, whether done alone or with others, who the activities are done with, how regular the activity is, etc. Among the many types of behaviors that can indicate signs of disease infection include changes in physical exercise, travel, social behavior, sleep, diet, and work behavior. Detected changes in behavior can also cause the system to initiate real-time interactions with a user to obtain relevant context and further information. For example, a user's device may detect that the user is spending a greater time or frequency in bathroom than usual, and so may send a survey asking if the user is experiencing GI distress, which is one of many potential COVID-19 symptoms.

The behavior data provides the system context to better interpret physiological data. For example, the behavior data can indicate whether a body temperature measurement represents a measurement during high, medium, or low activity, or during rest or sleep. This allows measurements made during different activities or contexts to be used and interpreted appropriately. This allows a greater range of data points than are typically used by prior systems. For example, the present system makes available new categories of measures and evaluations, which can allow detection of data patterns and disease signs and symptoms that would not be available if measurement were restricted to a single context, such as during sleep. For example, the system can evaluate changes in a user's work behavior, changes in a user's exercise, changes in a user's sleep, and more as indicators of potential disease. For example, a user may have a headache but not an elevated temperature, heart rate, or other physiological parameter that is tracked. Due to the headache, the user may change his behavior, such as going to bed early, skipping a workout, moving more slowly at work, or staying home from work. The system can infer from the behavior changes that the user is not feeling well, and can then initiate further monitoring and user interactions to better determine the cause of the changes.

Some prior systems use physiological measures and monitoring to predict infection, but are limited to observations made under a limited set of conditions, such as when the user is sleeping. The present technology is not so limited, and indeed can benefit from observations during diverse, varied types of actions. Along with sensor measurements obtained during different types of activities, the system captures context data that describes the users activities. This allows the system to categorize different physiological measurements according to the activities relating to those measurements. For example, rather than using only resting heart rate measures for infection prediction, the system can measure and use measures of heart rate while walking, while running, while standing, and even at different levels of intensity of those different activities. The system can also create a personalized user baseline measures for heart rate in the different types of activities. As a result, the system can detect heart rate changes with respect to baseline levels that may occur during certain activities, such as brisk walking, even though there may not be corresponding changes in heart rate during rest, such as during sleep.

In one general aspect, a method is performed by one or more computers, the method comprising: providing, by the one or more computers, a data package for managing a disease to a user device of a user, the selected data package being configured to cause the user device to acquire and report monitoring data to the one or more computers over a network; receiving, by the one or more computers, monitoring data provided by the user device as directed by the data package, the monitoring data comprising (i) sensor data generated using one or more sensors and (ii) user input comprising responses of the user to one or more surveys, wherein the monitoring data indicates one or more physiological measurements for the user and one or more behaviors of the user; generating, by the one or more computers, one or more scores for the user based on the monitoring data, the one or more scores comprising at least one of (i) an exposure score indicating a level of exposure of the user to the disease, (ii) a susceptibility score indicating a predicted measure of effects of the disease for the user if the user became infected with the disease, or (iii) a detection score indicating a likelihood that the user is currently infected with disease; based on the one or more scores, selecting, by the one or more computers, a disease management action from among a plurality of disease management actions, the selected disease management action comprising changing a disease detection or disease monitoring procedure for the user or changing a disease treatment for the user; and providing, by the one or more computers, data to the user device or another device to cause the selected disease management action to be recommended or carried out for the user.

In some implementations, the disease is COVID-19.

In some implementations, the monitoring data indicates that the user presents with one or more symptoms of COVID-19; the selected disease management action comprises delivering one or more digital therapeutics interventions that are selected, by the one or more computers, to incite a change in a behavior of the user to treat the one or more symptoms of COVID-19 indicated in the monitoring data, the one or more digital therapeutics interventions comprising adjusting at least one of a posture of the user, a manner of breathing of the user, or a level of physical exercise of the user; and providing the data to the user device or another device comprises providing data that causes the user device to deliver the one or more digital therapeutics interventions by initiating at least one interaction with the user configured to incite the change in the behavior of the user.

In some implementations, the method includes: determining, by the one or more computers and based on the received monitoring data, a diagnosis for the user indicating whether the user is infected with COVID-19; and providing, by the one or more computers, data indicating the diagnosis for presentation by the user device.

In some implementations, the one or more computers are one or more computers of a server system; the data package is provided to the user device over a communication network by the server system; and the monitoring data is received by the server system from the user device over the communication network. The selected disease management action comprises changing a disease detection or disease monitoring procedure for the user. Providing the data causing the causing the selected management action to be recommended or carried out for the user comprises providing data that changes a configuration of the user device or another device associated with the user to alter at least one of (i) a type of data collected or reported by the user device, or (ii) a frequency at which data is collected or reported by the user device.

In some implementations, providing the data causing the selected management action to be recommended or carried out for the user comprises: providing data that causes one or more digital therapeutic interventions designated for treatment of the disease to be provided to the user through the user device.

In some implementations, the provided data is configured to alter a type, intensity, or frequency of digital therapeutic interventions provided for the user.

In some implementations, the plurality of disease management actions comprises at least one of providing a vaccine for the disease, providing a testing kit for the disease, administering a drug to treat the disease, or delivering digital therapeutics to manage the disease.

In some implementations, the one or more scores are determined using one or more machine learning models.

In some implementations, the selected disease management action involves a vaccine for the disease, and the method includes selecting a vaccination option for the user from among a plurality of different vaccination options.

In some implementations, the selected disease management action involves a testing kit for the disease, and the method includes selecting a testing kit for the user from among a plurality of different testing kits.

In some implementations, the method includes determining a user baseline measure for one or more physiological attributes of the user and one or more behaviors of the user, wherein the one or more scores are based on the user baseline measures.

In another general aspect, a medical treatment device configured to treat COVID-19 for a user, the medical treatment device comprising: one or more sensors configured to measure a physiological parameter for a user, the physiological parameter comprising at least one of body temperature, blood pressure, heart rate, respiration rate, oxygen saturation, or blood glucose level; an input interface configured to receive user input; one or more output devices configured to provide one or more therapies to treat COVID-19 or symptoms of COVID-19; wherein the medical treatment device is configured to determine, based on location tracking data, that the medical treatment device was located in one or more regions of elevated potential for disease transmission, the one or more regions being determined through a process of: receiving monitoring data for a community, the monitoring data being generated using mobile devices of individuals in the community, the monitoring data comprising location tracking data that indicates locations visited by the individuals; accessing community data for the community that describes characteristics of the community and a geographic region associated with the community; accessing one or more predictive models that are configured to evaluate regions for potential for transmission of a disease based on behavior patterns of individuals in the community, the one or more predictive models being trained based on training data describing a plurality of different communities and behavior patterns and disease outcomes of individuals in the different communities over time; generating, using the one or more predictive models, an indication of one or more regions of elevated potential for disease transmission based on data, derived from the monitoring data for the community, that is indicative of behavior patterns of the individuals in the community; and providing output indicating the one or more regions identified using the one or more predictive models; wherein the medical treatment device is configured to provide the one or more therapies to the user based on (i) physiological measurements for the user using the one or more sensors and (ii) determining that the medical treatment device was located in the one or more regions of elevated potential for disease transmission.

In another general aspect, a method performed by one or more computers includes: receiving monitoring data for a community generated using mobile devices of individuals in the community, the monitoring data comprising location tracking data that indicates locations visited by the individuals; accessing community data for the community that describes characteristics of the community and a geographic region associated with the community; accessing one or more predictive models that are configured to evaluate regions for potential for transmission of a disease based on behavior patterns of individuals in the community, the one or more predictive models being trained based on training data describing a plurality of different communities and behavior patterns and disease outcomes of individuals in the different communities over time; generating, using the one or more predictive models, an indication of one or more regions of elevated potential for disease transmission based on data, derived from the monitoring data for the community, that is indicative of behavior patterns of the individuals in the community; and providing, to one or more devices over a communication network, output indicating the one or more regions identified using the one or more predictive models.

In some implementations, the disease is COVID-19.

In some implementations, the actions of the method are performed by software-as-a-medical-device (SAMD) on the one or more computers that is configured to diagnose and/or treat COVID-19. The method further comprises: determining an infection likelihood metric for a user that indicates a probability that the user has an active case of COVID-19, the infection likelihood metric being based at least in part on (i) a disease exposure score determined based on location tracking data indicating that the user entered the one or more regions and (ii) sensor data indicating one or more physiological measurements for the user; and providing the infection likelihood metric for the second user to a device associated with the user or a device associated with a healthcare provider for the user.

In some implementations, the method includes providing, to the second user, digital therapeutic interactions for a course of treatment for COVID-19 that includes exercises to assess and strengthen respiratory function of the second user, wherein the digital therapeutic interactions comprise one or more computer-directed therapies that require approval by the U.S. Food and Drug Administration for use to treat COVID-19.

In some implementations, the method includes determining, by the one or more computers, that a particular individual visited one of the regions indicated by the one or more predictive models to have an elevated potential for disease transmission. Based on the determination, the one or more computers select a disease management action for the particular individual, comprising at least one of: selecting, from among a plurality of COVID-19 testing kits, a testing kit for the particular individual; selecting, from among a plurality of COVID-19 vaccine options, a vaccine for the particular individual; or selecting, from among a plurality of digital therapeutics interventions, a digital therapeutics intervention determined to reduce or limit one or more symptoms of COVID-19; and recommending or carrying out the selected disease management action to the particular individual.

In some implementations, the method includes determining, by the one or more computers, that a particular individual visited one of the regions indicated by the one or more predictive models to have an elevated potential for disease transmission; generating, by the one or more computers, an infection likelihood score for the user indicating a likelihood that the user has contracted COVID-19, the infection likelihood score being based at least in part on output that a machine learning model provided based on processing data indicating physiological measures or behavioral measures for the particular individual; and based on the infection likelihood score, automatically recommending a medication or digital therapeutic intervention classified as treating one or more aspects of COVID-19 infection.

In some implementations, the method includes initiating, by the one or more computers, delivery of the recommended medication or digital therapeutic intervention classified as treating one or more aspects of COVID-19 infection.

In some implementations, the location tracking data for at least one of the mobile devices is based on at least one of GPS data from a GPS receiver or detected wireless signals from a Wi-Fi access point, wireless beacon, another mobile device, or a cellular base station.

In some implementations, the collected data further comprises (i) physiological data indicating one or more physiological measurements determined for the individuals using the mobile devices, and (ii) user input data indicating survey responses of the individuals provided using the mobile devices.

In some implementations, the one or more predictive models comprise one or more machine learning models that have been trained to provide disease transmission scores indicative of a disease transmission potential for locations, the one or more machine learning models being trained based on training data examples for different locations, each training data example indicating one or more location characteristic s for a location, one or more community disease measures for a community that includes the location, and one or more behavior measures for visitors to the location. Generating the indication of one or more regions of elevated potential for disease transmission comprises using the one or more machine learning models to determine a disease transmission score for each of multiple locations in the community, each of the disease transmission scores being based on one or more location characteristic s for the corresponding location, one or more community disease measures for the community of the corresponding location, and one or more behavior measures for visitors to the corresponding location.

In some implementations, generating the indication of one or more regions of elevated potential for disease transmission comprises: identifying locations in community that have a corresponding disease transmission score that satisfies a threshold; and generating data that designates the identified locations as regions of elevated potential for disease transmission.

In some implementations, the one or more machine learning models are trained based on data describing measures of disease transmission that occurred at the locations for different training data examples.

In some implementations, the one or more machine learning models are trained based on data indicating community characteristics of the communities in which the locations of the training data examples are located. Each of the disease transmission scores is an output generated by the one or more predictive models in response to receiving a set of input values for a location, the set of input values for a location indicating: one or more location characteristics for the location, one or more community characteristics for the community in which the location is located, one or more community disease measures for the community in which the location is located, and one or more behavior measures for visitors to the location.

In some implementations, the one or more machine learning models comprise one or more artificial neural networks.

In some implementations, generating the indication of one or more regions of elevated potential for disease transmission is based on the user input data indicating at least one of locations visited by the individuals or activities performed at the locations visited by the individuals.

In some implementations, generating the indication of one or more regions of elevated potential for disease transmission is based on measures of at least one of: traffic levels, determined based on the location tracking data, at different locations in the community; occupancy levels, determined based on the location tracking data, at different locations in the community; durations, determined based on the location tracking data, of visits to different locations in the community; or movement patterns, determined based on the location tracking data, of individuals during visits to locations in the community.

In some implementations, the method includes obtaining data indicating at least one of (i) disease prevention measures for the community or (ii) compliance with disease prevention measures at one or more locations in the community. Generating the indication of one or more regions of elevated potential for disease transmission is based on the disease prevention measures or the compliance with disease prevention measures.

In some implementations, the community comprises a group of individuals residing in a predetermined geographic area.

In some implementations, the predetermined geographic area is a county, city, or zip code.

In another general aspect, a medical treatment device is configured to treat COVID-19 for a user, the medical treatment device comprising: one or more sensors configured to measure a physiological parameter for a user, the physiological parameter comprising at least one of body temperature, blood pressure, heart rate, respiration rate, oxygen saturation, or blood glucose level; an input interface configured to receive user input; one or more output devices configured to provide one or more therapies to treat COVID-19 or symptoms of COVID-19; wherein the medical treatment device is configured to determine, based on location tracking data, that the medical treatment device was located in one or more regions of elevated potential for disease transmission, the one or more regions being determined through a process of: receiving location tracking data indicating locations of user devices over time, each of the user devices being associated with a corresponding user; generating location tags specifying visits of the user devices to different locations indicated by the location tracking data, each of the location tags having corresponding data indicating a location of a visit, a time of the visit, and a user device or user corresponding to the visit; assigning a geofence to each of the location tags that specifies a geofenced area corresponding to the location tag; assigning disease transmission scores to first location tags representing visits of a second user, the disease transmission scores being based on data indicating a disease status of the second user with respect to a disease; determining a disease exposure score for the user based on determining, using location tracking data for the user, that the user has entered at least one of the geofenced areas corresponding to the first location tags, the disease exposure score being based on an aggregation of disease transmission scores for different location tags for which the user is determined to have entered the corresponding geofenced area; and communicating a recommended disease management action to the user based on the determined disease exposure score for the user; wherein the medical treatment device is configured to provide the one or more therapies to the user based on (i) physiological measurements for the user using the one or more sensors and (ii) the exposure score for the user.

In another general aspect, a method performed by one or more computers includes: receiving, by the one or more computers, location tracking data indicating locations of user devices over time, each of the user devices being associated with a corresponding user; generating, by the one or more computers, location tags specifying visits of the user devices to different locations indicated by the location tracking data, each of the location tags having corresponding data indicating a location of a visit, a time of the visit, and a user device or user corresponding to the visit; assigning, by the one or more computers, a geofence to each of the location tags that specifies a geofenced area corresponding to the location tag; assigning, by the one or more computers, disease transmission scores to first location tags representing visits of a first user, the disease transmission scores being based on data indicating a disease status of the first user with respect to a disease; determining, by the one or more computers, a disease exposure score for a second user whose user device is determined, based on the location tracking data, to have entered at least one of the geofenced areas corresponding to the first location tags, the disease exposure score being based on an aggregation of disease transmission scores for different location tags for which the user device of the second user is determined to have entered the corresponding geofenced area; and communicating, by the one or more computers, a recommended disease management action to the second user based on the determined disease exposure score for the second user.

In some implementations, the disease is COVID-19.

In some implementations, the actions of the method are performed by software-as-a-medical-device (SAMD) on the one or more computers that is configured to diagnose and/or treat COVID-19. The method further comprises: determining an infection likelihood metric for the second user that indicates a probability that the second user has an active case of COVID-19, the infection likelihood metric being based at least in part on (i) the determined disease exposure score and (ii) sensor data indicating one or more physiological measurements for the second user; and providing the infection likelihood metric for the second user to a device associated with the second user or a device associated with a healthcare provider for the second user.

In some implementations, the method includes providing, to the second user, digital therapeutic interactions for a course of treatment for COVID-19 that includes exercises to assess and strengthen respiratory function of the second user, wherein the digital therapeutic interactions comprise one or more computer-directed therapies that require approval by the U.S. Food and Drug Administration for use to treat COVID-19.

In some implementations, the method includes, based on the disease exposure score for the second user, performing at least one of: adjusting, by the one or more computers, monitoring for COVID-19 for the second user; or initiating treatment for COVID-19 for the second user.

In some implementations, the method includes, based on the exposure score for the second user: selecting, by the one or more computers, one or more digital therapeutic interventions for the second user predicted to avoid or limit the severity of effects of the COVID-19; and providing, by the one or more computers, data over a communication network to cause the user device of the second user to provide the one or more digital therapeutic interventions to the second user.

In some implementations, the disease management action recommended to the second user comprises at least one of: limiting travel; limiting social contact; wearing a face mask; taking a medication; taking a test for the disease; or participating in a digital therapeutics program.

In some implementations, the method further comprises diagnosing, by the one or more computers, the second user with COVID-19 based at least in part on the disease exposure score.

In some implementations, the method includes collecting, for each of multiple users, (i) physiological data indicating one or more physiological measurements determined for the individuals using the user devices, and (ii) user input data indicating survey responses of the individuals provided using the user devices; and wherein at least one of the location tags or the disease transmission scores are determined based on the collected physiological data or the user input data.

In some implementations, the method includes informing a health agency of at least one of: data describing instances of individuals entering geofenced areas corresponding to location tags generated based on visits of users who are determined to have the disease or are predicted to have the disease; or aggregate statistics for interactions with geofenced areas corresponding to location tags generated based on visits of users who are determined to have the disease or are predicted to have the disease.

In some implementations, the location tracking data for at least some of the user devices is based on global positioning system (GPS) data generated using a GPS receiver.

In some implementations, at least one location tag for a visit to a location is generated in response to determining, based on the location tracking data, that a user device (i) remained at the location for at least a minimum amount of time or (ii) moved at the location in a manner that matches a predetermined movement profile.

In some implementations, for at least one of the location tags that represents a visit by a mobile device of a user to a location, the corresponding geofenced area has at least one of a size or shape based on a path of movement of the mobile device during the visit to the location or an area traversed by the mobile device during the visit to the location.

In some implementations, the disease status of the first user is determined based on a test result for the disease for the first user, a diagnosis for the first user with respect to the disease, or a health record for the first user.

In some implementations, the disease status of the first user is determined based on a predicted likelihood of infection with the disease for the first user, wherein the predicted likelihood is determined using one or more machine learning models and input to the one or more machine learning models that is derived from at least one of physiological monitoring data for the first user, behavioral monitoring data for the first user, or user inputs provided by the first user.

In some implementations, the location tracking data for at least one of the user devices is based on at least one of: GPS data from a GPS receiver; detected wireless signals from one or more Wi-Fi access points; detected wireless signals from one or more wireless beacon; detected wireless signals from one or more other user devices; and detected wireless signals from one or more cellular base stations.

In some implementations, a location tag is generated for a location in response to determining, based on the location tracking data, that a user device: remained at the location for at least a minimum amount of time; and/or moved at the location in a pattern characteristic of a particular activity.

In some implementations, the disease status of the first user is determined based on at least one of: a test result for the disease for the first user; an infection prediction score, determined using a machine learning model, that indicates a likelihood that the first user has the disease; a diagnosis for the first user with respect to the disease; a health record for the first user; one or more signs or symptoms of the disease reported by the first user; or one or more signs or symptoms of the disease detected by a sensor of a device associated with the first user.

In some implementations, the method of claim 1, wherein determining the disease transmission scores comprises: determining, for a particular location tag corresponding to a particular visit to a particular location by a particular user, a disease transmission score based on at least one of: a prediction of infection likelihood for the particular user; a duration of the particular visit at the particular location; an activity performed during the particular visit; a location type classification for the particular location; a level of movement that occurred during the visit; one or more characteristics of the particular location; user-reported data indicating one or more conditions at the particular location; and data indicating disease prevention measures instituted for a region that includes the particular location.

In some implementations, determining the disease transmission scores comprises: determining, for a particular location tag corresponding to a particular visit to a particular location by a particular user, a disease transmission score based on output of a machine learning model provided in response to receiving input data derived from data describing the particular visit and the particular location, wherein the machine learning model has been trained to provide an output indicative of a risk of transmission of the disease based on training data indicating visits of individuals to different locations and subsequent disease transmission outcomes for the individuals.

In some implementations, determining the disease exposure score for the second user comprises determining the disease exposure score for the first user based on output of a machine learning model provided in response to receiving input data derived from (i) data describing the visits of the second user and (ii) the disease transmission scores for the location tags for which the user device of the second user is determined to have entered the corresponding geofenced area. The machine learning model has been trained to provide an output indicative of a risk of contracting the disease based on training data indicating visits of individuals to different locations and subsequent disease transmission outcomes for the individuals.

In some implementations, aggregating the disease transmission scores comprises varying a level of influence of the disease transmission scores based on an amount of time elapsed between (i) a time of the visit represented by the corresponding location tag and (ii) a time of the visit to the geofenced area for the corresponding location tag by the second user.

In some implementations, the disease status of the first user indicates that the first user has or is likely to have contracted the disease. The method includes: determining that the user device of the second user has entered or is within a predetermined proximity of a particular geofenced area corresponding to one of the first location tags; and in response to determining that the user device of the second user has entered or is within a predetermined proximity of the particular geofenced area, providing a notification for presentation by the user device of the second user.

In some implementations, the exposure score for the second user is further based on population scores indicating of an occupancy or traffic level for different locations the user visited during a particular range of time.

In another general aspect, a medical treatment device configured to treat COVID-19 for a user, the medical treatment device comprising: one or more sensors configured to measure a physiological parameter for a user, the physiological parameter comprising at least one of body temperature, blood pressure, heart rate, respiration rate, oxygen saturation, or blood glucose level; an input interface configured to receive user input; one or more output devices configured to provide one or more therapies to treat COVID-19 or symptoms of COVID-19; wherein the medical treatment device is configured to gather response data from the user in response to a prompt for user input provided through the input interface, the prompt for user input being provided using content determined through operations comprising: collecting user input data provided by one or more individuals in a community to one or more user devices; accessing trigger data indicating one or more data collection triggers associated with monitoring of a disease, the data collection triggers respectively specifying one or more criteria and a type of data to be collected when the one or more criteria are satisfied; detecting a particular data collection trigger indicated by the trigger data by determining that the one or more criteria for the particular data collection trigger are satisfied; and in response to detecting the particular data collection trigger: selecting content configured to prompt user input of the type of data associated with the detected data collection trigger; selecting a set of individuals associated with the community to receive the selected content; and communicating with user devices associated with the individuals in the set to cause the user devices to present the selected content that is configured to prompt for user input regarding of the type of data associated with the detected data collection trigger; wherein the medical treatment device is configured to provide the one or more therapies to the user based on (i) physiological measurements for the user using the one or more sensors and (ii) the response data provided by the user.

In some implementations, the one or more therapies involve providing one or more interventions to change behavior of the user with respect to respiration, posture, exercise, sleep, or diet.

In another general aspect, a method performed by one or more computers includes: collecting, by the one or more computers, user input data provided by one or more individuals in a community to one or more user devices; accessing, by the one or more computers, trigger data indicating one or more data collection triggers associated with monitoring of a disease, the data collection triggers respectively specifying one or more criteria and a type of data to be collected when the one or more criteria are satisfied; detecting, by the one or more computers, a particular data collection trigger indicated by the trigger data by determining that the one or more criteria for the particular data collection trigger are satisfied; and in response to detecting the particular data collection trigger: selecting, by the one or more computers, content configured to prompt user input of the type of data associated with the detected data collection trigger; selecting, by the one or more computers, a set of individuals associated with the community to receive the selected content; and communicating, by the one or more computers, with user devices associated with the individuals in the set to cause the user devices to present the selected content that is configured to prompt for user input regarding of the type of data associated with the detected data collection trigger.

In some implementations, the disease is COVID-19.

In some implementations, the method comprises: receiving, by the one or more computers, response data indicating responses to the prompts; generating, for a particular individual in the selected set of individuals, an infection likelihood score indicating a likelihood that the individual has contracted COVID-19; and providing, to the particular individual or a healthcare provider for the particular individual, data indicating a diagnosis whether the user the user has contracted COVID-19 that is based on the infection likelihood score.

In some implementations, the method comprises: receiving, by the one or more computers, response data indicating responses to the prompts; using, by the one or more computers, the response data to assess suitability for one or more individuals of one or more digital therapeutics interventions classified as treating one or more aspects of COVID-19; and initiating, by the one or more computers, delivery of the one or more digital therapeutics interventions based on the suitability assessment.

In some implementations, the one or more criteria for the particular data collection trigger comprise an evaluation of an output of a trained machine learning model. Detecting the particular data collection trigger comprises: generating an output produced the trained machine learning model in response to receiving a set of input data derived from at least the collected user input data; comparing the output with a threshold; and determining that the output satisfies the threshold.

In some implementations, the trained machine learning model is an artificial neural network.

In some implementations, the user input data comprises responses to prompts to the individuals presented by the user devices. The user input data indicates at least one of: a location visited by an individual; a sign or symptom of a disease reported by an individual; a physiological attribute reported by an individual; or a result of a laboratory test or a test for a disease.

In some implementations, detecting the particular data collection trigger is further based on at least one of: a community disease measure for a community; an electronic health record or one of the individuals in the community; a physiological measurement for individuals in the community; or sensor data captured by the user device of one or more individuals in the community.

In some implementations, the data collection triggers are data collection triggers to trigger collection of data indicative of spreading of a disease, wherein at least one of the data collection triggers specifies criteria that includes detection of at least one of: a physiological attribute or physiological change for one or more individuals in the community; a sign or symptom of the disease for one or more individuals in the community; a behavioral change for one or more individuals in the community; a disease diagnosis for one or more individuals in the community; a positive disease test result for one or more individuals in the community; or a community disease measure for the community that satisfies a threshold.

In some implementations, at least one of the data collection triggers specifies a type of data to be collected that includes at least one of: a physiological measurement; an indication a sign or symptom of the disease for one or more individuals in the community; a behavioral change for one or more individuals in the community; a disease diagnosis for one or more individuals in the community; or a positive disease test result for one or more individuals in the community In some implementations, collecting user input data provided by one or more individuals in the community comprises collecting user input data regarding physiological attributes, behavior, and/or mental health through surveys that each include one or more prompts for user input regarding physiological attributes, behavior, and/or mental health.

In some implementations, the surveys comprise ecological momentary assessments (EMAs) configured to assess an individual's current experience, behavior, and/or mood at the time the EMA is provided and in the current environment and context of the individual.

In some implementations, collecting user input data provided by one or more individuals in the community comprises collecting user input data in response to a first survey provided to a first subset of members of the community. Selecting the set of individuals to receive the selected content comprises selecting a second subset of members of the community to receive a second survey, wherein the second subset is larger than the first subset, and wherein the second survey requests a different type of data than the first survey. Communicating with user devices to cause the user devices to present the selected content comprises sending content or instructions to the user devices to cause the user devices to present the second survey.

In some implementations, the trigger data specifies, for the particular data collection trigger, a particular content item to provide to prompt collection of the type of data associated with the detected data collection trigger. Selecting the content configured to prompt user input of the type of data associated with the detected data collection trigger comprises selecting the particular content item specified by the trigger data. The particular content item comprises a user interface element, text, a question, a survey, an EMA, a user interface, a media item, or an interactive element.

In some implementations, the one or more criteria for the data collection triggers represent indicators of at least one of presence of the disease, spread of the disease, or risk factors for the disease. The types of data respectively specified for the data collection triggers comprise types of data used by the one or more computers to assess spread of the disease in the community or impact of the disease in the community, the type of data comprising at least one of: physiological data, comprising at least one of heart rate, blood pressure, respiration rate, oxygen saturation, lung capacity, or blood glucose level; behavioral data, comprising a measure for at least one of travel, exercise, sleep, work, recreation, diet, or device usage; or mental health data, comprising an indicator for at least one of mood, responsiveness, anxiety level, or depression level.

In some implementations, selecting content configured to prompt user input of the type of data associated with the detected data collection trigger comprises selecting two or more different content items that are each configured to prompt user input of the same type of data associated with the detected data collection trigger. Causing the user devices to present the selected content comprises causing the user devices to each present one of the two or more different content items, wherein the specific content item caused to be presented is determined based on at least one of characteristics for a recipient, a user profile for the recipient, a prior interaction of the recipient, a medical history of the recipient, a disease status of the recipient with respect to the disease, a vaccination status of the recipient with respect to the disease, a sign or symptom of the disease indicated by the recipient, a physiological measure for the recipient, a behavior of the recipient, or a mental health attribute for the recipient.

In another general aspect, a medical treatment device is configured to treat COVID-19 for a user, the medical treatment device comprising: one or more sensors configured to measure a physiological parameter for a user, the physiological parameter comprising at least one of body temperature, blood pressure, heart rate, respiration rate, oxygen saturation, or blood glucose level; an input interface configured to receive user input; one or more output devices configured to provide one or more therapies to treat COVID-19 or symptoms of COVID-19 wherein the medical treatment device is configured to provide the one or more therapies to the user based on physiological measurements for the user using the one or more sensors; and wherein the medical treatment device is configured to assist the user to limit exposure to COVID-19 by presenting disease exposure prevention options that are determined by: receiving user data indicating a prospective action of the user of the medical treatment device; detecting a trigger based on evaluation of the received user data; providing content configured to cause a mobile device associated with the user to present a prompt for user input regarding the prospective action of the user; evaluating potential future exposure of the user to COVID-19 based on response data indicating a response to the prompt; selecting a disease exposure prevention option for the user that is predicted to reduce or avoid exposure of the user to COVID-19, wherein the disease exposure prevention option is selected or customized for the user based on at least one of the user data or the response data; and providing content configured to cause the medical treatment device associated with the user to present the disease exposure prevention option.

In another general aspect, a method performed by one or more computers includes: receiving, by the one or more computers, user data indicating a prospective action of a user of a mobile device; detecting, by the one or more computers, a trigger based on evaluation of the received user data; providing, by the one or more computers, content configured to cause the mobile device associated with the user to present a prompt for user input regarding the prospective action of the user; evaluating, by the one or more computers, potential future exposure of the user to a disease based on response data indicating a response to the prompt; selecting, by the one or more computers, a disease exposure prevention option for the user that is predicted to reduce or avoid exposure of the user to the disease, wherein the disease exposure prevention option is selected or customized for the user based on at least one of the user data or the response data; and providing, by the one or more computers, content configured to cause the mobile device associated with the user to present the disease exposure prevention option.

In some implementations, the disease is COVID-19.

In some implementations, the method includes, based on at least one of the received context data or the response data and physiological data for the user, generating, by the one or more computers, a score indicative of a likelihood that the user has been contracted COVID-19; and initiating, by the one or more computers, (i) delivery to the user of a testing kit for COVID-19 to the user or (ii) delivery to the user of one or more digital therapeutic interventions classified as treating one or more symptoms of COVID-19.

In some implementations, the received data comprises location tracking data for a mobile device associated with the individual.

In some implementations, the received data comprises a user input to a prompt provided by a mobile device associated with the individual.

In some implementations, the context data indicates a location or path of movement for the individual. The detected trigger is detected based on determining that the user has entered or is approaching a particular location visited, within a predetermined period of time, by a person classified as having COVID-19. The prompt requests information regarding an expectation of the individual regarding a current or upcoming visit to the particular location.

In some implementations, the prompt requests information regarding a destination, duration, or activity for the current or upcoming visit to the particular location by the user.

In some implementations, detecting the trigger based on evaluation of the received context data comprises determining that an output generated by a machine learning model based on the context data satisfies one or more criteria associated with the trigger.

In some implementations, the user data is context data indicating a current context of the user. The prospective action is related to the context of the user;

In some implementations, the user data comprises calendar data indicating an appointment for the user.

In some implementations, the user data comprises data indicating a behavior pattern or history of actions of the user.

In some implementations, detecting the trigger comprises determining that a likelihood of occurrence of the prospective action satisfies a threshold.

In some implementations, detecting the trigger comprises determining that a level of disease exposure risk for the prospective action satisfies a threshold.

In some implementations, detecting the trigger comprises determining that a context of the user has at least a predetermined minimum level of similarity with a prior context of the user or of one or more other users that preceded performance of the prospective action.

In some implementations, evaluating potential future exposure of the user to a disease based on response data indicating a response to the prompt comprises: determining (i) a disease transmission score for a location where the prospective action is predicted to occur or (ii) a disease susceptibility score for the user that indicate a likelihood or severity of disease symptoms if the user contracted the disease.

In some implementations, the response data indicates or confirms an intended activity of the user, wherein the disease prevention option comprises at least one of: wearing personal protective equipment, including at least one of a mask or gloves; maintaining a distance between the user and others; limiting a duration of the intended activity of the user; changing a location of the intended activity of the user; replacing the intended activity of the user with a lower-risk activity; or avoiding the intended activity.

In some implementations, selecting the disease prevention option comprises selecting the disease prevention option based on output of a machine learning model generated in response to receiving data indicating at least one of the intended activity, a location or location type for the intended activity, and collected data for the user.

In some implementations, selecting the disease prevention option that stored mapping data specifies as corresponding to the activity type of the intended activity, a location type for a location of the intended activity, a disease transmission level for the location and/or intended activity, a user disease susceptibility measure for the user, and/or user characteristics of the user. The mapping data associates different disease prevention options with different values of one or more of activity types, location types, disease transmission levels, user disease susceptibility measures, and/or user characteristics.

In some implementations, the prompt for user input regarding the prospective action of the user comprises a prompt to: confirm whether the user intends to perform the prospective action or another action; indicate a destination or mode of travel of the user; or describe conditions for the prospective action, including at least one of a location type for the prospective action, a location of the prospective action, characteristics of a location for the prospective action, a number of people at the location, an activity to be performed, or whether disease prevention measures are used.

Other embodiments of these and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIG. 2 is a table illustrating information about different data packages for managing a disease.

FIGS. 9A and 9B are user interfaces showing examples of user interfaces provided to a user.

FIGS. 15A-15C and 16A-16D show examples of associating disease risks with locations.

FIG. 21 is a table showing an example of trigger data.

Like reference numbers and designations in the various drawings indicate like elements.

DETAILED DESCRIPTION

Figure 1:
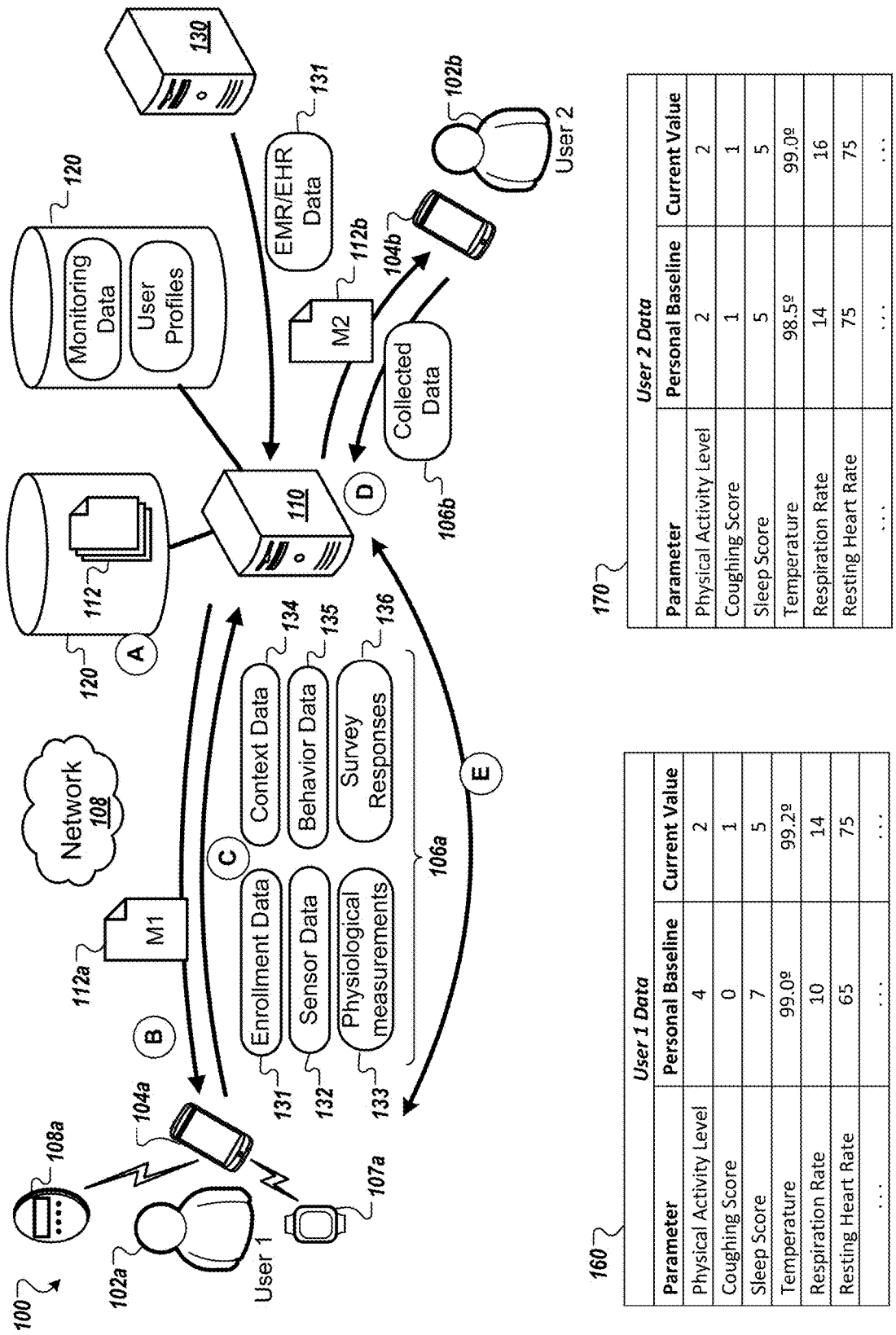
FIGS. 1, 3, and 5 are diagrams showing an example of a system for testing, tracking, and managing COVID-19 and other infectious diseases.

As discussed below, a system can collect and analyze data regarding physiological, behavioral, and cognitive patterns indicative of the onset of COVID-19 and risk of COVID-19 infection. The system obtains user-reported data (e.g., survey responses, reported symptoms, etc.) and sensor measurements (e.g., heart rate, movement, location, etc.) and compares these to baseline measurements for the user. From the variance of collected data and differences from the a user's baseline levels, the system makes predictions of a user's risk of contracting COVID-19, the user's likelihood of being currently infected with COVID-19, the current disease state, predicted disease progression, and so on. The system can use these predictions to, for example, provide disease prevention and treatment recommendations to individuals, provide decision support to clinicians, or determine the applicability of different testing kits for users. While various examples herein are focused on COVID-19, the same techniques can be used to detect, monitor, treat, and otherwise manage other diseases.

The system can generate and update measures of baseline characteristics of users, and then use the baseline measures to match users to appropriate treatments. Among other actions, the system can match individuals to digital health interventions that are selected or personalized for each individual. This can include selecting or adjusting the digital therapeutics interventions for individuals to provide the appropriate intensity of treatment, interaction, or support.

Digital therapeutics can be evidence-based therapeutic interventions driven by software programs (e.g., running at a client device, remote server system, or a combination of both) to prevent, manage, or treat a medical disorder or disease. The systems discussed herein can provide a real-time, interactive personalized medicine service that initiates communication and interaction with the user to deliver digital therapeutics. Among other effects, the digital therapeutics can involve interactions, initiated by the system or by the user, that change the user's behavior, for example, to reduce a symptom of COVID-19, to reduce a risk level for COVID-19, to speed recovery from or to improve function following COVID-19 infection, and so on. These user behaviors and outcomes that are affected are not merely behaviors interacting with devices, but often represent changes in real-world aspects of the user's life outside of human-device interaction. The digital therapeutics for a particular patient, and the timing for delivery, are dynamically selected and updated using one or more digital therapeutics programs that can address different aspects of a patient's care. Each program can have a separate set of content, rules, assessments, and interventions for providing a customized, adaptive experience for a patient. The system can operate in an "always-on" manner, frequently or continually assessing a data stream indicating the user's current status and context, and providing targeted interactions that are relevant to the user's current or estimated future needs.

Digital therapeutics interventions can include various interactions, such as interactions through a smartphone or other user device. As a few examples, the system can inform a user of a health risk (e.g., such as an exposure risk for COVID-19, a susceptibility of the user to COVID-19, a likelihood of infection or diagnosis of infection with COVID-19, etc.), provide media, generate an interactive form such as a survey, provide a test or assessment, send a notification message, provide recommendations, provide content from a social media platform, provide instructional activities or games, and so on. In some cases, the system can prompt a user to set, adjust, or view a goal, or challenge, remind, or inform the user about a goal. Similarly, the system may prompt a user to take an action, record a measurement from a device, provide content for a user to read or view, initiate a challenge for a user to change behavior (or to perform a specific action or task). The system may communicate with family of a user, friends of a user, or others regarding a user's goals or status, including with health service providers. In general, interactions may involve visual output, audio output, haptic output, typed or touchscreen input, voice input, gesture input, and other input/output modalities. The media provided as part of the interactions can include content such as text, videos, audio segments, images, interactive instructional materials, messages (e.g., indicating encouragement, reminders, etc.), games, and other content.

To make better predictions and provide more accurate diagnostic and treatment recommendations, the system can provide interventions that prompt users to complete an assessment at specific times during the day or in response to specific situations or contexts. Examples include ecological momentary assessments (EMA). The system can also support passive ascertainment of changes in clinical status, in behavior, or in other aspects. The system can be configured to behavioral support, such as self-management strategies, immediately following assessments or detection of triggering conditions. The approaches to data collection and treatment can be highly personalized. The system can tailor or personalize digital health interventions based on each individual's characteristics (e.g., race, gender, socio-economic status, etc.) for disease prevention, presentation, management, and outcomes and that ultimately contribute to a more individualized approach to health care.

The COVID-19 pandemic creates an urgent need to protect individuals from coronavirus exposure, for example, by developing effective prevention techniques, treatments, and vaccines. At the same time, it is critical to allow society to return to normal as quickly as possible. The currently available tools to contain the epidemic are limited, primarily social distancing and quarantine. There is a need for more precise deployment of containment efforts only where needed, so that larger segments of the population can return to less restricted living and reduce the risk of recurrence of devastating local outbreaks.

New digital health solutions can improve care, understanding of health outcomes, and risk factors related to the COVID-19 pandemic. Underserved populations can especially benefit, since they are often disproportionately affected by COVID-19 and often have limited access to healthcare services. This is also important in its potential to broaden the geographic understanding of factors related to exposure, spread, and containment.

The collection of large digital health datasets has potential privacy implications. Systems that collect health-related data need adequate privacy protections that enable personal health data to be used without unduly compromising civil liberties. Often, privacy concerns work against broad adoption of new technological data collection solutions. Ideally, a platform would address privacy concerns transparently, while also addressing the urgent need to interrupt the COVID-19 pandemic and facilitate society returning to normal.

Improvement in the treatment of COVID-19 requires a high-quality COVID-19 research data set that can allow academic, public health, and translational researchers to make discoveries that might otherwise not be possible from individual, isolated data sets. One area that these data sets can improve is in facilitating new research into digital health technologies. The data generated by digital health technologies has the potential to advance treatment and prevention of COVID-19 and other diseases. The same technologies can also improve public health responses and facilitate policies, organization, and other approaches that could improve future epidemic and pandemic planning.

Many research questions regarding COVID-19 still remain. As a result, the techniques discussed herein can be adaptive and customizable to tailor responses based on newly gathered data. An example, is the use of machine learning models and other technologies that can be continually updated based on new research results and population-level observations. For example, as new treatments are applied and longer-term data becomes available for existing treatments, machine learning elements can incorporate the data to better weight. This can allow new observations to feedback into the recommendations for disease prevention, monitoring, diagnosis, treatment, prognosis estimation, and long-term support. Many different technologies are likely to be helpful in generating comprehensive, effective responses to the pandemic. Indeed, some research questions may only be able to be answered by integrating and analyzing data generated by multiple different technologies and solutions.

The techniques discussed herein provide technological solutions, such as a smartphone application, commercial wearable technology, computational modeling algorithms, approaches to data analysis and/or aggregation, etc. which can address one or more the following objectives:
  tracing user contact with individuals diagnosed with or suspected of having contracted COVID-19;
  rapidly integrating commercial COVID-19 diagnostic test results, patient-reported symptoms, wearable sensor data, electronic health records, and/or other diverse data sources with central or decentralized databases;
  determining likelihood of user having undiagnosed COVID-19;

determining risk to a user of contracting COVID-19;
determining information that individuals, employers, government agencies, and others can use to evaluate risk of allowing individuals to return to normal work, travel, and public life activities;
determining information that healthcare providers can use to follow patients at home and intervene when or if physiological decompensation occurs;
matching individuals to clinical trials for COVID-19;
ascertaining patterns of movement that influence exposure, spread, and containment of COVID-19; and
providing strong privacy protections to allow integration, analysis, and federation of existing datasets for the purpose of COVID-19-related research.

The technology of the present application can be used to provide and evaluate digital health interventions (e.g., mobile health ("mhealth"), telemedicine and telehealth, health information technology (IT), and wearable devices) to address access, reach, delivery, effectiveness, scalability and sustainability of health assessments and interventions for secondary effects (e.g., behavioral health or self-management of chronic conditions) that are utilized during and following the pandemic, particularly in populations who experience health disparities and vulnerable populations. To achieve this goal, the system can provide digital health interventions that address health disparities or focus particularly on vulnerable populations. Digital health interventions can be based on existing social and behavioral science theories as well as best practice healthcare approaches. Interventions can take advantage of the unique functionality of mobile and wireless devices. The system can perform real-time data collection and feedback where appropriate.

The technology discussed herein can refine and test adaptive interventions and just-in-time interventions that can be 'pushed out' via mobile technology based on information regarding the individual's current state. For example, interventions can determine user state by prompting users to complete an assessment at specific times during the day or through passive ascertainment of changes in clinical status (e.g., ongoing passive monitoring by mobile devices, wearable devices, etc.). The system may immediately follow the determination of patient state by providing behavioral support, such as self-management strategies. The technology discussed herein can use electronic health record data in conjunction with digital health interventions to examine the clinical epidemiology, service utilization, an/or response to treatment, within or across large systems responsible for health service delivery, in order to inform timing and targets for intervening.

The techniques in the present application can also be used to support research to strengthen the healthcare response to Coronavirus Disease 2019 (COVID-19) caused by the Severe Acute Respiratory Syndrome Coronavirus 2 (SARS-CoV-2) and future public health emergencies, including pandemics. Similarly, techniques can support research to evaluate various digital health interventions with respect to COVID-19 or other diseases. For example, the techniques can be used to support studies designed to test if a proposed digital health intervention yields significant reductions in symptoms in individuals who exhibit clinically significant symptoms and/or functional impairment at baseline. As another example, the techniques can be used to conduct studies that use software, devices, and systems that are interoperable with existing infrastructure so that resulting data is interoperable with relevant health information systems where applicable. In some cases, studies can collect data via well-established assessments and measures and leverage common data elements. Studies can test generalizable principles or approaches to using technology to improve the accuracy and efficiency of assessment and the effectiveness and quality of intervention and service delivery. Studies may address known challenges with uptake and adherence or sustained use of technology-based approaches and attention to privacy and other safety or ethical considerations associated with the use of technology for research and clinical purposes.

The techniques of the present application can identify and/or implement strategies to increase the reach, access, engagement, efficiency, quality and sustainability of existing digital health interventions to accommodate individuals seeking screening, prevention, self-management, wellness behaviors and treatment both during and following the pandemic, particularly in health disparate and vulnerable populations where prior trials may not have focused on these populations of interest. In some cases, the techniques can be used to design or carry out clinical trials that incorporate strategies to address the digital divide (e.g., augmented digital interventions with non-digital components) as it relates to vulnerable populations, including low-income communities, older adults, as well as their caregivers, who cannot easily use or access many digital interventions. Studies can include a conceptual framework that clearly identifies the target mechanisms and the empirical evidence linking the mechanisms to the study outcomes, plans for assessing engagement of the target mechanisms, and analytic strategies that will examine target engagement and associations with clinical benefit. In the case of multicomponent interventions, strategies would address the target mechanisms corresponding to each intervention component, as appropriate in the effectiveness context.

One of the advantages of the technology disclosed herein is the ability to personalize risk measures, disease prevention, disease treatment, and other aspects of care. The technology can match individuals to digital health interventions of appropriate intensity. When used to support research, existing data (e.g., a database of prior collected data) can be used to rapidly identify and enroll participants in research studies. Collected data can be used to select and apply algorithms for assigning interventions to individuals. All of these strategies to increase treatment fidelity to Evidence Based Practices (EBPs).

In the area of medical research, prospective trials can test the effectiveness of algorithm-based intervention delivery, including stepped-care approaches. As discussed further below, not only can treatment actions be phased and adjusted for individuals, but prevention measures, testing techniques, and digital monitoring may also be dynamically adjusted, especially as the system predicts that a user's risk of contracting COVID-19, risk of experiencing severe effects from COVID-19, or likelihood of being infected with COVID-19 change. The techniques discussed herein can use artificial intelligence, machine learning, and natural language processing, whether through established methods or new methodology.

The techniques discussed herein can include integration and analysis of data from multiple sources, including multiple digital health platforms or systems. When available, common data elements can be leveraged to identify the long-term health impact and the cost effectiveness of providing digital health interventions at scale. In many cases, users of different types or with different attributes may have different compliance rates or usage rates for technology. Using the platform discussed herein, studies can test the differences in usage and effectiveness of technology solutions among different groups or populations. For example, the platform can be used in studies that investigate the influence of sex and gender on the use of digital health interventions for disease prevention, presentation, management, and personalized health care. Similarly, the platform can be used to facilitate studies that are designed to test whether digital interventions can mitigate racial/ethnic and gender disparities in access, service utilization, and health outcomes.

Technology platforms can sometimes improve access to medical care. For example, steps can be taken to promote adherence to and sustained use of digitally assisted interventions, including studies that use existing data to identify individual and intervention-level characteristics that are associated with discontinuation vs sustained use, including COVID-19 related stigma, and trials that test approaches to promoting sustained use and engagement. Some studies or data analysis can evaluate whether changes in service delivery (e.g., replacement or substitution of face-to-face services with digital health services) as a result of the pandemic will yield durable and sustainable system level changes in practice that improve or maintain quality care. The social isolation measures of the COVID-19 pandemic provides an opportunity to evaluate whether previously understudied or unknown services and care delivery pathways and ways to leverage these novel digital health pathways. Examples include ways to segment levels of care (e.g., crisis line support that could transfer to higher levels of telehealth psychiatric/addiction care for more complex cases when in person treatment is not feasible), bridge interventions, and therapy or treatment sessions. For therapies that involve skill acquisition, a platform can provide interactions to promote skill practice or skill acquisition between therapy sessions, and to facilitate the transition back to face-to-face care, when needed.

FIG. 1 is a diagram showing an example of a system 100 for testing, tracking, and managing COVID-19 and/or other infectious diseases. The system 100 includes a computer system 110, a communication network 108, data storage 120, a third-party server 130, and various user devices 104a-104b and other devices. The computer system 110 can be a server system, located remotely from the user device 104a-104b of users. The computer system 110 communicates with the other elements in the system to request data, collect data, initiate interactions with users, and adaptively adjust monitoring and interaction with users. The computer system 110 can also determine personalized predictions and disease management actions, such as selection of a testing kit, vaccine, medication, or digital therapeutic intervention.

The computer system 110 uses techniques of precision medicine and personalized medicine to tailor testing, detection, monitoring, diagnosis, treatment, and recovery assistance for COVID-19 and/or other infectious diseases for individuals. For example, the computer system 110 is configured to monitor information about each of a variety of users in order to make personalized assessments for each user based on information collected for that user. The computer system 110 can perform a variety of functions including generating estimates or predictions of a user's exposure to a pathogen, detecting and diagnosing infection in a user, and assisting in disease prevention, treatment, and recovery for a user.

In FIG. 1, there is a first user 102a, labelled "User 1," who uses a phone or other user device 104a. The user 102a also has a wearable device 107a, e.g., a smart watch, smart ring, or other instrumented device, and a medical monitoring device 108a. A second user 102b is shown, who has a user device 104b. In some implementations, the users 102a, 102b can be patients who may be receiving care from a physician or other medical care provider. In some implementations, the users 102a, 102b may be participants in a research study, such as a clinical trial. In some implementations, the users 102a, 102b are simply individuals who are not associated with a medical care provider or research study, but are interested in tracking their exposure to a disease or in finding out quickly if they contract the disease. In some implementations, the user device 104a is a medical treatment device that may be capable of providing digital therapeutics, dispensing a medication, dispensing or injecting a vaccine dose, etc. For example, features of the user device 104a or other user devices discussed herein may be incorporated into medical monitoring and treatment devices such as glucometers, insulin pumps, blood pressure cuffs, and so on.

In stage (A), the computer system 110 selects and provides a data package to one or more user devices. The data package can initiate interactions with users and collection of sensor data by the devices. Examples of sensors that can be used include accelerometers, light sensors, cameras, microphones, inertial measurement units (IMUs), GPS receivers, and compass sensors. Other devices can include other sensors, such as pulse or heart rate sensors, EKG sensors, and so on. The data package can be configured to cause a device that receives the data package to initiate monitoring and reporting of data to a server, such as the computer system 110, over the network 108. For example, a data package can cause a device to collection sensor data on a periodic basis or in response to the occurrence of certain conditions or triggers. The data package can also cause a user device that receives the data package to initiate interactions with a user, such as to present a survey or electronic form for receiving information from a user. Information about user interactions, e.g., user input provided in response to a survey, is then reported to a server, such as the computer system 110. In some implementations, a module 112 includes software or configuration data to direct data collection and reporting and interactions with the user. In addition, or as an alternative, the module 112 can include software or configuration data that cause a user device to receive and carry out data collection, reporting, and user interactions as directed by one or more servers, such as the computer system 110, which may specify different user device behavior and different user interactions at different times.

In FIG. 1, the computer system 110 stores multiple data packages, shown as modules 112. These modules can include executable software, configuration settings, instructions (e.g., to an application or operating system), media content, and/or other elements. A module 112 can include rules, models, logic, or other elements that enable local processing and analysis of collected data and condition initiation of actions based on the results of data analysis. In some implementations, the modules 112 are applications that can be installed on and run on a user device. In some implementations, the modules 112 enhance or change the functionality of an existing application. An application can download and install a module 112 to add functionality to or make available functionality of an application previously installed on a user device. This can customize or tailor the behavior of an application. In some implementations, the modules 112 include sets of configuration data in a format that an application can read and apply to carry out monitoring, data collection and reporting, user interactions, and so on that are specified by the module. The modules 112 can be modules as discussed in U.S. Pat. No. 9,858,063, issued on Jan. 2, 2018 and titled "Publishing Customized Application Modules," which is incorporated herein by reference. The modules 112 can be form data packages as discussed in U.S. Pat. No. 9,928,230, issued on Mar. 27, 2018 and titled "Variable and Dynamic Adjustments to Electronic Forms," which is incorporated herein by reference.

The computer system 110 stores a variety of modules 112 that are configured to assist in data collection and monitoring to manage a disease, e.g., to prevent a disease, detect a disease (e.g., determine exposure or infection), treat a disease, and/or support recovery from a disease. In some implementations, the modules 112, can be considered software as a medical device (SaMD), as it can be used to diagnose and treat a disease such as COVID-19. Indeed, in some implementations, the modules 112 (potentially in combination with another application and/or data and instructions from the computer system 110) can provide treatment directly to the user 102a through the user device 104a, through digital therapeutics interventions involving interactions with the user 102a that can, for example, incite behavior change in the user. Similarly, the software of the computer system 110 can be considered to be SaMD as it is designed to treat and/or diagnose disease, as well as to drive clinical management and inform clinical management. In some implementations, the interactions that the modules 112 cause can include digital therapeutics interventions, customize diagnosis and diagnostics, and recommendations for prevention, treatment, risk reduction for specific diseases. The selection of which module 112 to provide can be personalized for individual users. In addition, the types of interactions that the module 112 causes and the manner of collecting data or providing treatment to a user can also be customized for that user.

The modules 112 can be applications that are executed on the user device, for example, different mobile device applications. In some implementations, the modules 112 are packages that enhance or expand another application already installed on a user device. For example, a module 112 may include data causing a user device to perform various data collection and reporting functions. These can include providing surveys or other user interfaces for display, collecting responses, and providing them back to the computer system 110. As another example, a module 112 they include code, configuration data, or other elements that cause a user device to monitor certain types of sensor outputs, process the data, and report results to the computer system 110.

The modules 112 may specify various aspects of data collection and analysis. These can include types of sensors to monitor, frequency of monitoring, precision data collected, format of data collected, triggers for conditions that cause sensor data collection or alter sensor data collection, and so on. The module 112 can include rules that are executed by the user device to selectively perform monitoring actions, for example, to vary the types of data collected in manner of their collection using sensors and user prompts based on conditions or context detected or other factors.

The computer system 110 can provide the modules 112 to user devices to enable the user devices to collect and report data used by the computer system 110 and to interact with users. The modules 112 may be provided in response to a request from a device 104a, such as a request sent in response to a selection of the module 112 by the user 102a from a user interface of an application, from a selection of a link in a webpage, or other action. Because multiple modules 112 are available, the computer system 110 select an appropriate module from among the set of modules 112 available. For example, there may be multiple modules related to COVID-19, with different modules being tailored for different types of users, users with different demographic characteristics, different locations of residence, different professions, and so on. As another example, different modules 112 may be available for different aspects of managing COVID-19, with different modules 112 respectively tailored for treating active infections, assisting with recovery post infection, detecting and preventing infection, and so on.

Each module 112 can have associated data specifies the applicability of the module 112, e.g., metadata or a profile indicating sets of user characteristics that make that module 112 applicable or inapplicable to a user. The computer system 110 uses an initial set of information about a user, which may be provided by a user through a form, or may be provided by a clinician or from EHR/EMR, which may be stored in a user profile for the user based on prior interactions. The computer system 110 compares the characteristics of the user with user characteristics of the various modules 112 and selects one or more modules determined to be appropriate for the user. Additional information about the modules 112 and selection of modules is discussed with respect to FIG. 2.

In the example of FIG. 1, the computer system 110 users information about first user 102a obtained from medical records 131 to determine that a first module 112a is appropriate for the user 102a, based on the user's age, current health conditions, and other factors. For a second user 102b, the computer system 110 selects and provides a different module 112b based on the characteristics of the user 102b.

In stage (B), the user devices 104a-104b receive and process the received modules 112a, 112b. These modules initiate interactions with the users and also cause the user devices 104a, 104b to initiate collection of sensor data according to the parameters and code specified in the modules 112a, 112b. For example, the module 112a may cause the user device 104a to begin periodically measuring and recording location, physical activity or movement of the device 104a, and other parameters. The module until they may also cause the user device 104a to measure other parameters. The module until they may also cause the user device 104a to collect other data from other devices, such as wearable device 107A and a medical monitoring device 108a. Examples of medical monitoring devices include blood pressure cuffs, weight scales, glucometers, pulse oximeters, and so on. In some cases, the device 108a may be a medical treatment device. Examples of wearable devices include smart watches, smart rings, activity trackers (e.g., FITBIT devices), wristbands, necklaces, clothing, or other devices including sensors and data transmission capabilities. The user device 104a can connect with medical monitoring devices and wearable devices and other devices, e.g., entertainment systems, navigation systems, vehicles, home automation systems, smart appliances, and so on, to collect data as directed by a downloaded module 112.

In stage (C), the mobile devices 104a, 104b collect data and report data to the computer system, as directed by the previously received modules 112a, 112b. The data is sent over the network 108 and received by the computer system 110.

In the stage (D), the computer system 110 collects and processes the reported data. The computer system 110 can store each of the data items reported, and can use the data to generate personalized baseline measures for each user. Typically, a personalized baseline is determined for each of multiple measures, which can include behavioral measures, physiological measures, and more.

The personal baseline information can be based on information gathered over time. Such as the previous three days, the previous week, the previous two weeks and so on. In some cases, baseline measures are determined and stored for each of multiple different prior periods. The baseline can be specified in different ways. As an example, the baseline value for a parameter may be an average value over a period of time. Measures of variability over the period of time can be included (e.g., indicating range of values, standard deviation, etc.). As another example, the baseline can indicate patterns or trends. For example, a user's typical pattern of physical activity may show different levels of activity for different days of the week, and the baseline measures can indicate this pattern.

Personal baseline measures can be determined and stored for various different aspects of health and behavior. For example, in the FIG. 1, there are baseline parameters for physical activity level, a coughing score, a sleep score, body temperature, a respiration rate, and a resting heart rate, and potentially others. The types of parameters that are measured and for which baseline measures are determined and vary based on the Level of monitoring used for user. Different modules 112 can you collect different information, and so they allow different sets of baseline measures to be determined. As discussed further below, the level of monitoring used for a different user can vary based on many factors, such as a user's personal level of exposure to the disease, infection rates in the community where do user lives, or a user's personal susceptibility or risk for the disease (e.g., based on age, physical fitness, existing health conditions, and so on).

The example of FIG. 1 illustrates the importance of baseline data and contextual data in making accurate prediction and diagnosis of COVID-19 and other diseases. A user's personal baseline can have a significant impact on the way monitored values influence predictions and decisions of the system. In the example, User 1 and User 2 have different personal baseline measures, which results in different decisions by the system 110. FIG. 1 shows a table 160 with data for User 1, and a table 170 with data for User 2. Both users have a current physical activity level score of 2, representing activity over the previous day. For User 1, this represents a noticeable decrease compared to the baseline level, while this is consistent with the baseline for User 2. This is one example where the decrease in activity for User 2 may be an indicator of illness, where the same level of activity for user to does not indicate increased likelihood of illness for other users.

As another example, for the coughing score, both users have a level of one, indicating that some rare coughing was detected. For User 1, this is a change from the baseline behavior, and so it indicates an increased likelihood of illness, where the same score for user two does not because it is consistent with the user's baseline. Similarly, with the sleep score, the User 1 data shows a decrease in the quality and or quantity of sleep, which may be an indicator of disease. For the body temperature measurements, the current temperature of 99.2 for User 1 is elevated, but the difference is very slight given that users baseline temperature of 99.0. By contrast, User 2 has a lower temperature than User 1, but shows a larger increase compared to the User 2 baseline, and as a result, the computer system 110 may determine that this is a more significant indicator of possible disease than the temperature of User 1. For respiration rate, the user to respiration rate is higher at 16 breaths per minute then the User 1 respiration rate of 14 breaths per minute. However, the User 1's lower baseline shows that 14 breaths per minute is significantly higher than the User 1 baseline, and so this may be an indicator a disease for User 1, where it would not be for User 2. Finally the current resting heart rate values are the same for both users at 75 bpm, but this is an increase for User 1 where it is not for user two. As a result, the resting heart rate may be interpreted by the computer system 110 to increase the likelihood of disease for User 1, where it does not for User 2.

In general, the computer system 110 can generate and store personal baseline measures for a variety of different types of measures or parameters, including physiological measurements, behaviors, cognitive attributes, user performance levels, and mood and mental health. Physiological measurements include, e.g., heart rate, respiration rate, blood pressure, blood glucose level, oxygen saturation (e.g., SpO2), lung capacity or VO2 max, body temperature. A few examples of behavior that can be tracked, and for which a baseline can be provided include sleep, diet, exercise, travel, rest, and work. As noted above, the personal baseline measures can indicate scores or values for different parameters in each of the types or categories noted above. The baseline data can be provided in different ways, such as values or scores that are aggregated or synthesized over time (e.g., a score that is averaged or synthesized from multiple measurements or data collection events at different times. The baseline measures can include data specifying a range of values over time (e.g., the resting heart rate range over the last day, over the last 7 days, etc.) and/or statistical measures (e.g., standard deviation, variance, etc.). As another example, a time series of recent measurements for each of one or more parameters can be provided (e.g., the resting heart rate for each of the last seven days). In addition, or as an alternative, the personal baseline measures may describe or indicate patterns or trends that are identified or derived from collected data, e.g., a starting value along with an amount of change and direction of change, a curve or equation describing the patterns, a classification of the pattern selected from a group of different classifications (e.g., stable, fluctuating in a range, slight increase, moderate increase, large increase, slight decrease, etc.). Classification of different baseline conditions or patterns can be done using a trained machine learning model to determine the most likely classification, or by comparing characteristics of data patterns to references (e.g., thresholds, ranges, etc.) corresponding to different classifications. Personal baseline measures can also measure elements such as the frequency and timing of certain types of events or activities, measures of cognitive or physical performance during activities prompted or guided by the user device 104a, and so on.

In stage (E), the modules 112 facilitate interaction with users and collection of user reporting data. This can include generating prompts or surveys for the user, whether generated locally by a user device based on an application and or module 112, provided by the computer system 110 over the network 108, or generated through a combination of client and server actions. For example, the computer system 110 and/or the module 112 can cause an ecological momentary assessment (EMA), e.g., a survey or other interaction that assesses an individual's current experience, behavior, and mood as they occur in real time and in their natural environment.

In some implementations, the computer system 110 evaluates the quality of data received and may initiate adjustments to the monitoring process to improve the completeness or quality of data collected for a user. As another example, the computer system 110 can evaluate the incoming stream of data for each user, and compare it to evaluation standards. If the data is not of sufficient quality according to the standards, for example, if frequency of measurement, consistency of reporting, reliability of the data, and so on are not meeting the standards, the computer system 110 may communicate with his advice to change their collection and reporting settings to correct the problem.

As the computer system 110 receives additional information, the computer system 110 can also analyze the received data and determine whether another module 112 would be appropriate for the user, e.g., to supplement or replace a module already obtained.

FIG. 2 illustrates various examples of different modules 112 that can be provided to users. As illustrated, different modules 112 can be provided for different purposes (e.g., detection of infections, treatment of infections, support in recovery after the infection has subsided, etc.). There can also be different versions of the modules for different user populations, e.g., different modules 112 for groups of users having different risks of harm if they contract COVID-19.

The different modules 112 can provide different types of monitoring, suited to the expected needs and risks of different users. For example, the first module tracks a certain set of physiological data and behavioral data for a user, and also provides a set of surveys. The second module is intended for higher-risk users, such as those aged 60 year and older, and it includes more extensive monitoring and more surveys. The second module monitors the same types of data as the first module, but also adds several additional types of data to track. It also provides a more extensive set of surveys to provide.

The appropriate module 112 for a user can be selected in different ways. In some implementations, a physician or other medical care provider may recommend or prescribe a module 112 for a user. As another example, one or more of the modules 112 may be made available to users, and a user may select a particular module to download. For example, a web page or application may provide a user interface at the user device 104a that provides a list or gallery of available modules 112, and a user can interact with the user interface elements to select a module 112 to download and use.

The characteristics of a user and medical history of a user can be used to determine which module 112 to provide for a given user. For example, each module 112 can be associated with a profile or set of criteria specifying the conditions or set of user characteristics for which the module 112 is indicated for use. For example, among modules configured to detect, monitor, and/or treat COVID-19, the criteria for one module 112 may specify that it is applicable for users in a certain age range that do not have chronic conditions, the criteria for another module 112 may specify that it is applicable for users in a different age range that do not have chronic conditions, the criteria for another module 112 may specify that is applicable for users that have diabetes and are in a certain age range, and so on. Different modules 112 can be provided for different combinations of user attributes and health conditions, such as age, sex, height, weight, health conditions, physiological attributes, behavioral attributes, geographical region, and so on.

In some cases, in addition to or instead of having different modules 112 for different user types or user attributes, a module 112 (e.g., a general COVID-19 monitoring and treatment module) can be provided, and the monitoring and interactions that the module 112 directs can be personalized based on user attributes, health history, and other user data. Thus, if health history for a user indicates diabetes, high blood pressure, cancer, or other conditions that affect the need for monitoring and treatment, the device that receives the module 112 and/or the computer system 110 can use information about the user to personalize the actions performed based on the module 112. The module itself 112 can provide different profiles or sets of configuration data to address different combinations of user health factors or user attributes, and/or the computer system 110 can provide communications or otherwise cause interactions through the module 112 that are personalized for the user's characteristics, history, and medical condition. Further, any of the modules 112 discussed herein can be adaptive to change monitoring and treatment to suit the data collected and the user's behavior and changes in physiological attributes over time. This can be done taking into account the personal baseline measures, which are updated as new information is received. The adaptation in monitoring and treatment can also be responsive to changes in predictive measures for the user, such as user scores for disease exposure level, disease susceptibility, likelihood of infection, and so on as discussed below.

Modules 112 can be provided for different purposes. For example, some modules 112 may be used for clinical monitoring and treatment, while others may be for health research studies, others for community health monitoring, etc. In some cases, a different module 112 can be provided for different health research studies, with each research study module 112 directing data collection, monitoring, treatment, and reporting of data according to the study's study protocol, to provide collected data to the appropriate researchers. Of course, a single module 112 may combine functions to serve one or more of these different uses (e.g., clinical support, research, community monitoring, etc.).

The modules 112 can be configured to behave differently for users in different locations, or different versions of the modules 112 can be provided for different geographic regions. For example, privacy requirements are different in different countries, social distancing and other preventative measures vary from location to location, and social and cultural norms vary from location to location. The modules 112 can thus be configured to customize their actions for the location in which a user is located.

Figure 3:
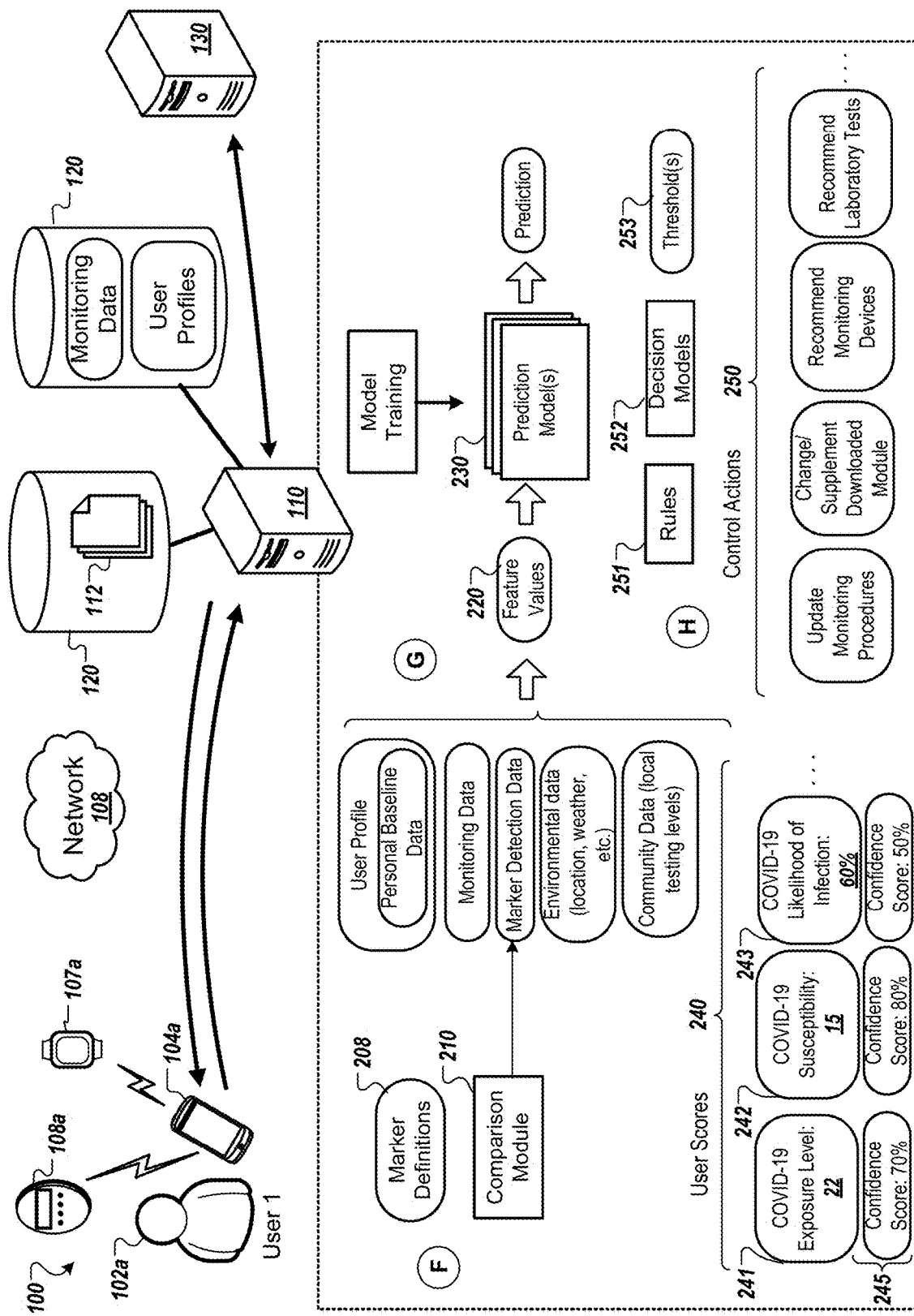

FIG. 3 shows additional operations of the computer system 110 and/or user device 104a to process data obtained through the monitoring discussed in FIG. 1. Various operations in FIG. 3 will be discussed with respect to the computer system 110, which can be a remote server system. Nevertheless, some or all of the operations can be done by the user device 104a. In general, FIG. 3 shows various stages (F) to (G) in which the system assesses incoming data for a user 102a and then uses predictive models 230 (e.g., trained machine learning models) to make predictions for a user regarding the user's exposure, susceptibility, and/or infection likelihood for COVID-19. With those predictions, the system selects personalized actions to improve monitoring or treatment for the user 102a, such as to adjust the type and intensity of monitoring according to the risks for the user, to change configuration data and monitoring procedures of the user device 102a, to recommend additional monitoring devices, to recommend laboratory tests, and so on. As discussed further below with respect to FIG. 5, the user scores 240 and other predictions can be used to select other disease management actions for a user, such as selecting and determining to provide a testing kit, a vaccine, digital therapeutics, pharmaceuticals, medical devices and medical device settings, and other therapies.

The predictive models 230 (and other predictive models discussed herein, including models 530a-530d and model 612 discussed below) can be machine learning models, for example, one or more neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used. The computer system 110 can analyze the examples data about many users in a database to determine relationships between data factors and COVID-19 disease outcomes and conditions, either through explicit analysis or through machine learning training, e.g., so that a model implicitly learns the predictive value of different data items on, for example, disease exposure, disease susceptibility, infection likelihood, etc. Training can incrementally or iteratively update the values of parameters in the models 230 to learn the impact of different factors on predicted outputs. In the case of neural networks, backpropagation can be used to alter neural network weights for neurons at various layers of a neural network model. Training can be done using stochastic gradient descent or other training algorithms.

In stage (F), the computer system 110 uses collected data about the user 102*a* to determine if any of various markers are present. The computer system 110 can store data that specifies marker definitions 208 that define different markers. The markers can represent different data elements that indicate or predict disease-related factors. A marker may be an indicator of a sign or symptom of a disease, but need not be. For example, some markers may represent factors that increase risk of contracting a disease or risk of increased severity of disease, even if presence of the marker on its own does not indicate any actual infection. The markers can be defined as one or more measurements or observations of physiological measures, behavioral measures, cognitive measures, mental health or mood measures, or a combination thereof. Markers can be based in part on long-term user attributes (e.g., age, sex, height, weight, chronic conditions, medical history, etc.) and/or recent or even real-time measures (e.g., monitoring data over the last hour, day, week, etc.). Disease effects and outcomes can be different for different people and different situations. As a result, a value (e.g., resting respiration rate over 70 breaths per minute) may serve as a marker for increased disease severity risk in one type of person (e.g., someone with high blood pressure) but not for another category of people (e.g., people without high blood pressure) The marker definition data 208 may include criteria associated with each marker to define when the marker is considered to be present. These criteria may include certain values for measures (e.g., a value above a threshold, a value in a predetermined range, a value with a certain type or level of change with respect to a corresponding personal baseline measure, etc.). In addition, or as an alternative, a marker may be defined as being present when a combination of measurements or conditions occur together in monitoring data, and/or when a pattern of monitoring data over time (e.g., when one or more measures changes in a certain way over a series of measurements).

The computer system 110 or another computer system can examine various data sources to identify data values, patterns, and combinations of them that are predictive of or indicative of, for example, infection, susceptibility, or exposure to a disease. For example, the markers may be defined to represent different data patterns that indicate the presence of one or more symptoms of COVID-19. As another example, markers may be defined to represent data patterns that indicate levels of exposure risk. For example, the types of locations a person visits, the amount of travel for different locations or use the visits, the length of time or user visits, and so on indicate risk factors for exposure to COVID-19. The computer system 110 can use statistical analysis and/or machine learning techniques to analyze collected monitoring data for various other users to define what factors (e.g., what types of data, values, combinations, and patterns) are correlated to different outcomes (e.g., disease infection, disease severity, specific disease symptoms, the need for specific interventions such as hospitalization or ventilator support, etc.). The factors that are most predictive of outcomes of interest are then recorded and saved as definitions for markers. In some implementations, the markers can then be used as machine learning features provided to trained models to make predictions for users.

A comparison module 210 compares monitoring data for the user 102*a* and user profile data (e.g., user attributes, medical history, etc.) for the user 102*a* to the criteria specified in the marker definitions 208. The comparison module 210 generates marker detection data 212 indicating which markers are determined to be present based on the most recent monitoring data and the user profile for the user 102*a*. The marker detection data 212 is used, along with the various other collected data, to make predictions and generate scores for the user 102*a*.

In stage (G), the computer system 110 generates user scores 240 for the user 102*a* for various aspects of disease management. These can include user scores 240 for the user's exposure level 241 to a disease, the user's susceptibility to the disease 242 if exposed, and a likelihood of infection 242 that the user is currently infected. The computer system 110 can use a variety of information to generate these scores, including the user profile, monitoring data, the marker detection data, environmental data, and community data.

The computer system 110 can derive feature values 220 from these different data sources and provide the feature values 220 to one or more predictive models 230, which have been trained based on data sets of many different individuals and their status with respect to the disease over time. The predictive models 230 maybe machine learning models, such as neural networks. In addition or as an alternative, the models 230 may be rule-based models, statistical models, or other types of models. The outputs of the predictive models 230 can be values that indicate predictions with respect to the disease, for example, exposure level 241, susceptibility 242, and likelihood of infection 243. A different model 230 can be used for each type of prediction.

The exposure level score 241 can be a measure of the likelihood, frequency, duration, and/or intensity at which the user 102*a* is predicted to have been exposed to COVID-19. In some cases, the exposure level score 241 is an exposure risk score indicating the user's level of risk of being exposed to the disease given the user's current behavior patterns, the disease prevalence and transmission patterns in the user's community, and other data. The model 230 that is trained to predict exposure level can be trained based on monitoring data for many users and the corresponding outcomes of contracting the disease, allowing the machine learning training process to train the model 230 to predict the combinations of markers, community measures, environmental measures, monitored physiological and behavioral measures, etc. that indicate disease exposure.

In calculating exposure level, the computer system 110 can use various types of location tracking information for the user 102*a*, to indicate recent travel and activities of the user 102a over one or more time periods (e.g., the previous day, the previous 3 days, the previous week, the previous two weeks, etc.). In some cases, data describing travel and tracked locations of the user 102a can be provided directly to a predictive model 230. For example, the feature values 220 may include indications of visits to specific places at specific times. In other cases, summary data or aggregate data characterizing the overall type, nature, or pattern of travel may be provided, such as a summary of the types of locations visited (e.g., grocery store, movie theater, outdoor park, etc.) and the number of visits and/or duration of time spent at the respective types of locations. In other words, the computer system 110 may optionally perform various pre-processing steps on the raw location tracking data to characterize the nature of the travel and activities of the user in order to determine feature values reflective of the user's actual travel and/or the user's typical travel habits (e.g., on a daily, weekly, or monthly basis).

Among the types of data that the computer system 110 can use to determine the feature values for the model(s) 230 used to predict exposure level include: locations visited, types or classifications of those locations, times of the visits, durations of the visits, modes of transportation (e.g., walking, public transportation, private vehicle, airplane, etc.), estimated or predicted occupancy of locations and transportation modes, and so on. Much of this information can be inferred by correlating GPS location data from the user device 104a with map data (e.g., to determine the location and location type corresponding to time spent at a certain GPS-specified region), and by determining which transportation mode has a motion profile matches the motion detected (e.g., a trip segment having movement along roads with an average speed of 30 mph could be classified as driving in a private vehicle). Other data, such as occupancy estimates, can be determined from EMAs or in-the-moment surveys using the user device 104a (e.g., asking, "roughly how many people are in the store today?") or through historical averages for transportation modes and for locations or location types. The computer system 110 can also access the community-level disease data for the user's community and for any other geographic regions that the user visited, to determine disease prevalence rates for those regions (e.g., COVID-19 infection rates, COVID-19 transmission rates, data quantifying COVID-19 positive tests and negative tests and changes in them over time, COVID-19 infection trends, etc.). This community level data, combined with map data describing regions and the user's travel data enable the computer system 110 to determine the amount of time the user spent in different areas, how frequently the user visited, what the activities of the user were, and what the local disease prevalence is in those visited areas.

For example, the computer system 110 may determine, from the location tracking data and map data sources and community data, that over the last week (1) the user 102a spent 2 hours at a particular grocery store (e.g., most likely shopping around other customers), in a region that has a high prevalence of COVID-19 and increasing numbers of positive tests over the last week, and (2) the user 102a spent 4 hours in a particular outdoor park in a region having low prevalence of COVID-19 and a steady or decreasing number of positive tests over the last week. The computer system 110 then provides this information to the machine learning model 230 at the level of detail that the model 230 has been generated and trained to accept information, which may be at an aggregate or summary level (e.g., among other feature values, a feature value of "2" for a feature representing the number of hours spent in a high disease prevalence area, and a feature value of "4" representing the number of hours spent in a low disease prevalence area). On the other hand, the model 230 may be generated and trained to process more detailed information, such as features indicating the types of locations (e.g., grocery store, public outdoor park, etc.), the specific locations visited (e.g., the specific grocery store and specific part visited), the times and durations of individual visits, the modes and routes of transportation, more specific community disease measures for the locations visited, and so on. From this and other information about the user, a trained model 230 can predict the exposure level 241 or risk level that the user 102a has or will contract COVID-19. Machine learning models such as neural networks are well-suited to this type of prediction, and with example training data based on the location tracking data and community disease measures for many different individuals (as well as disease outcomes for those individuals, e.g., when and whether they tested positive or developed COVID-19 symptoms), the models 230 can be trained to learn the factors and relationships that increase exposure to and risk of contracting COVID-19.

Contact tracing data can optionally be used in this exposure prediction process, e.g., with contract tracing results used to provide feature values to the models 230 (e.g., indicating how many people determined to have COVID-19 the user 102a actually came near, when, and for how long), or to weight or adjust the exposure level score 241 of a model 230 (e.g., to boost the exposure level when contact tracing shows contact with one or more infected people, with the boost amount scaled by the number of instances and duration of contact).

The disease susceptibility score 242 can indicate a predicted level of vulnerability of the user 102a to COVID-19 if the user were to contract the disease. For example, separate from the user's exposure level, the susceptibility may be an estimate or predicted measure of how vulnerable the user would be would be to the disease (e.g., the degree that the user may be affected, such as the expected severity of the disease) if the user were to be exposed to the disease and/or if the user were to become infected. This could reflect factors such as the likelihood that the user would contract the disease if exposed, the likelihood of experiencing different symptoms of the disease if the user became infected, the likely severity of those symptoms, the risks of death or long-term impairment due to the disease, etc. In the example, the susceptibility score 242 is shown as a numerical value. The susceptibility score 242 could be, for example, indicative of a risk category (e.g., high, medium, or low risk of a certain level of harm occurring). For example, one or more models 230 may provide values indicating the relatively likelihood that different risk categories are applicable for a user (e.g., 0.1 for low risk, 0.6 for medium risk, 0.3 for high risk, showing that the medium risk category is most appropriate). The susceptibility measure could be a prediction of a likelihood that a user, if infected, would have a symptomatic case rather than an asymptomatic case. The susceptibility prediction may be made in general (e.g., a level of severity for disease effects as a whole), or with respect to specific outcomes or harms of the disease (e.g., a prediction of risk of stroke, a prediction of risk of hospitalization needed, a risk of sepsis, a risk of death, etc.). For example, a general susceptibility score 242 may be provided to indicate the risk level for the user 102a experiencing a severe case of COVID-19, according to a predetermined set of criteria. Additional measures or scores may indicate risk levels or likelihoods for each of multiple different symptoms or outcomes.

The model 230 used to predict the susceptibility score 242 can be trained using, for example, monitoring data and health record data for individuals that contracted COVID-19. Data characterizing the symptoms, outcomes, and recovery profiles of those individuals can be assessed to assign a score (e.g., on a scale of risk or disease severity) as a label for that data set. During training, the each example input (e.g., providing data about user attributes, user behaviors, and other user parameters for a user) can be provided as input to a model 230, and the assigned risk score labels (e.g., reflecting symptoms and outcomes experienced) can be used as the target outputs that the model is trained to predict.

The infection likelihood score 243 indicates a likelihood that a user is currently infected with COVID-19. The model 230 to predict infection likelihood can use information about changes in behavior, as well as physiological monitoring data and user-reported information, to detect likely infections before traditional symptoms are detected. For example, changes in user physical activity, cognitive measures, and mood relative to the user's personal baseline measures can be used to identify infection at very early stages. Changes in behavior (e.g., changes in diet, activity levels, movement patterns, sleep patterns, etc.) may not individually be conclusive indicators of infection, but subtle changes taken together can demonstrate combinations or progressions of observations that are consistent with infection. By placing behavior changes and physiology changes in context of short-term (e.g., hours, days or weeks) and long-term personal baseline measures (e.g., weeks, months, or years), the model has information to be able to more accurately assess risks. In addition, detection of changes with respect to baseline levels provides the computer system 110 an opportunity to confirm or obtain further context about those changes. For example, when a user's behavior changes are detected through passive sensing and comparison to baseline measures, the computer system 110 can act in response to initiate EMAs or other surveys or interactions to ask the user 102a about those changes, e.g., the cause of the changes, whether the user noticed the changes, whether there are related changes, etc. This additional data can confirm the significance of changes or allow extraneous or non-disease-related changes to be filtered out or discounted.

To predict infection likelihood, collected data for the user 102a from various sources (e.g., health records, user input such as EMA responses, sensor data, treatment data, user demographic data, and so on) can be used. The collected data used can be data for a current time period (e.g., the current day, week, etc.) as well as collected data for prior time periods and/or long-term historical data. These data items may be input to a model 230 or analysis process in any of various ways, e.g., as measurement values (e.g., a body temperature measurement of 99.0°), as classifications of measurements or data patterns (e.g., activity level is high, medium, or low), as binary feature values (e.g., whether an event or condition was detected or not), as indications of whether markers were detected in the user's data (e.g., according to the marker definitions 208), as a count of how many times an event or behavior occurred, as an aggregate measure (e.g., an average, maximum, minimum, etc.) based on multiple observations, as values indicating whether and to what extent collected data varies from personalized baseline measures (and/or values providing the personalized user baseline measures), and so on. Detected markers for signs or symptoms of a disease can be indicated and used as input also, for example, as a result of pre-processing the collected data set for a user and comparing collected data patterns with criteria of marker definitions to see which markers are reflected in the collected data. Baseline measures for a user, demographic attributes of the user, and other types of data can also be provided as input to the infection likelihood determination.

There are many potential symptoms of COVID-19, and additional symptoms are being identified over time. Examples include coughing, shortness of breath or difficulty breathing, fatigue, muscle or body aches, headache, new loss of taste or smell, sore throat, congestion or runny nose, nausea or vomiting, diarrhea, skin rash, blood clots, stroke, cognitive impairment or confusion, and so on. The predictive models 230 may use instances of detecting these symptoms, or data patterns from which these symptoms may be inferred, in making predictions, but it is not limited to these. Indeed, the infection prediction model 230 can use physiological measures and changes, behavioral measures and changes, and other data to detect infection with high confidence, even if symptoms are not specifically identified and called out. Further, when symptoms are used, contextual data, baseline data, and data characterizing the symptoms (e.g., not just that a headache occurred, but the timing, duration, and severity of the headache) to distinguish between symptoms that are likely caused by COVID-19 and those that are not.

The models 230 used to predict infection can take into account the exposure estimates for the user. For example, a score or other output of an exposure estimation model may be used as an input to the infection prediction model. In addition, or as alternative, the activities of a user and locations a user has been, as well as the infection rates in the user's community, can be used to determine the likelihood of infection. For example, an elevated body temperature may generally be a sign of potential COVID-19 infection. But if the user's community has a very low prevalence of COVID-19 (e.g., according to community measures for infection rate, disease prevalence, etc.) and/or the user's activities indicate very low contact with others (e.g., based on location tracking of the user's phone and smartwatch, from user-reported survey answers, and/or contact tracing data), the likelihood of infection may be indicated to be lower than it would otherwise be for someone with more travel or someone in an area with higher prevalence of the disease. Thus, at least in some implementations, the computer system 110 can weight the detected signs and symptoms of a disease (or simply the data patterns indicative of infection risk) according to the community data related to the disease.

In some implementations, the predictive models 230 for predicting infection likelihood and/or other items may receive indicators of community characteristics and community exposure levels, and the training of the models 230 may automatically account for the variation in the predicted item due to factors such as user locations, user activities, user exposure level, community characteristics, community exposure levels, etc. In other words, the predictive models 230 can be trained to receive and process input feature values indicative of any of these factors, and potentially any or all of the data items collected for the user 102a. Through the model training process, the models 230 learn the relative importance and predictive value of different types of input, as well as how different combinations of input values increase or decrease likelihoods, so that the trained models 230 generate predictions using the relationships implicitly learned through machine learning training from a training data set showing many examples of other users (e.g., training data sets describing different users, their disease outcomes, their monitoring data, their communities' disease measures, and so on).

Along with each prediction, the computer system 110 may provide a corresponding confidence score 245 indicating how confident the system 110 is the assigned score. The confidence scores may be based on various factors, such as variability in the model or data patterns used in training the model. The confidence score there also based on the tape, quantity, and quality of data available for the user. In some implementations, computer system 110 can determine when additional data is needed to increase the level of confidence in the scores, and can automatically take actions to acquire they needed data. For example, the computer system 110 may identify gaps in the monitoring data obtained for a user, and take action to request the missing information from the user, request a change in monitoring and reporting actions of the user device 104a to provide the missing data, and so on.

The user scores 240 can be predicted measures for the user at the current time. For example, the infection likelihood score 243 can be a score indicating the predicted likelihood that the user is currently infected. Nevertheless, other scores can be generated using similar techniques to predict measures for different time periods. For example, a model 230 can be trained to predict whether a user has previously been infected. Similarly, a model 230 can be trained to predict whether a user will become infected over a certain time in the future (e.g., the next day, the next week, the next month, etc.), given the current physiological attributes of the user 102a, the observed behavior patterns of the user 102a, and community disease measures (e.g., disease prevalence, infection rate, infection rate trends, etc.). This kind of time offset for predictions can be built into a model 230 by training the model with training examples that themselves have a built in time offset. For example, examples can be used that include (i) data of users and their communities up for respective time periods, and (ii) training targets or ground truth labels that indicate outcomes not at the end of the time periods, but at some time in the future (e.g., the next day, the next week, the next month, etc., depending on the time frame for which prediction is desired).

In some implementations, the user scores 240 are communicated to the user 102a, for example, provided through a notification, a user interface of an application running on the user device 104a, etc. The user scored 240 may also be used to select messages to the user even if the scores themselves are not provided. For example, if the user's susceptibility score is above a threshold, this may be communicated to the user 104a along with recommendations or instructions for preventative measures. As another example, when the infection likelihood score 243 exceeds a predetermined level, the user 104a can be provided a notification that the user is likely infected and should monitor certain potential symptoms, avoid contact with others, etc. The user scores 240 and collected monitoring data can be provided to the user's doctor, stored in the user's medical records, and, if the user is a participant in a research study, provided to researchers involved in the study.

In stage (H), the computer system select from among various control actions to perform to improve monitoring and prediction for the user 102a. For example, the computer system 110 can store rules, decision models, and thresholds used to select from among a set of actions 250, such as updating monitoring procedures, changing and supplementing downloaded modules 112, recommending monitoring devices, recommending laboratory tests, etc. As an example, the system can change or adapt the data collection or disease monitoring actions performed for the user 102a according to the predictions made for the user. Other disease management actions that can be based on the user scores 240 are shown and discussed with respect to FIG. 5.

The computer system 110 can store and use rules 251, decision models 252, thresholds 253, or other techniques to determine how to adjust the monitoring and data collection actions for the user 102a. This allows for multiple levels of testing and monitoring, where the level of monitoring changes over time according to the conditions detected and the predictions made. As more monitoring data is collected and the predictions for a user change, the system can make progressive changes in monitoring, including through sensor data collection, providing surveys and direct user interactions with digital devices, requesting laboratory tests or COVID-19 tests (e.g., nasal sway test, antibody tests, etc.).

Figure 4:
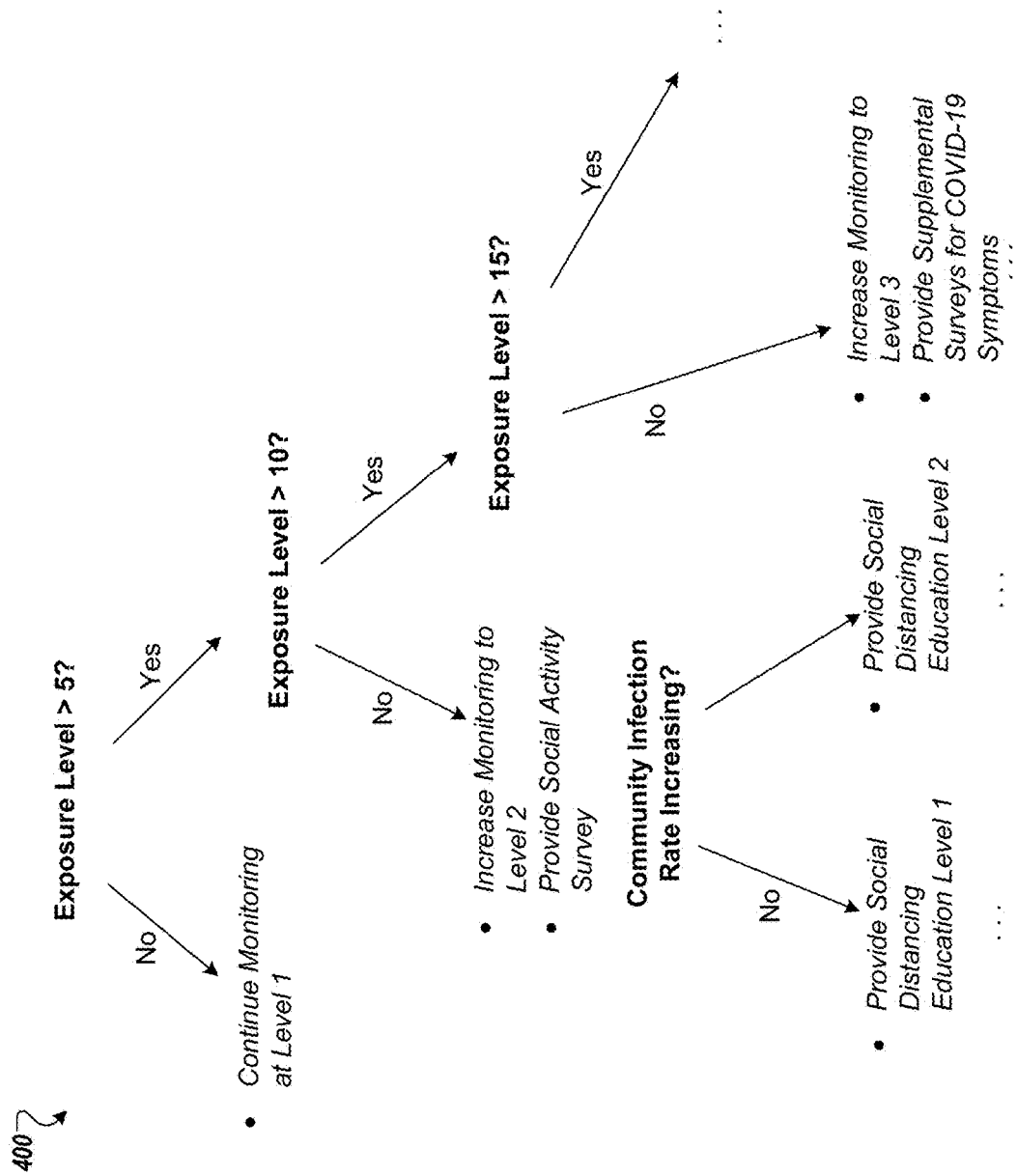
FIG. 4 is a diagram showing examples of a decision process performed by the system to manage a disease and customize interactions for individuals.

FIG. 4 shows an example decision tree that the computer system 110 can use to vary the level of monitoring according to the conditions detected and risk levels predicted. Although depicted as a decision tree here, this is simply to illustrate the changes in actions for different conditions more clearly. The data used to drive the selection and adjustment of monitoring actions (or treatment actions as discussed below) can be stored in any appropriate data structure or format. For example, the data can be provided as a decision tree, a table, a set of rules, a machine learning model configured to classify or predict which actions are appropriate given input about a user and the user's community, and so on.

In general, the computer system 110 can adjust the intensity and type of monitoring to provide more intensive and heightened monitoring as factors such as exposure level, likelihood of infection, susceptibility to disease, and so on. Other decision trees or selection processes can be used for those factors, or a combined decision process can take into account all of the various predictions and monitored factors. The computer system 110 can thus automatically tailor the burden on the user and the intensity of monitoring to increase or decrease the level of monitoring and interaction with the user, as the situation or predicted risk levels for the user change. As FIG. 4 shows, there are different levels of monitoring for signs and symptoms of COVID-19 (e.g., Level 1, Level 2, etc.), each of which may involve measuring different physiological parameters, different behavioral parameters, different mental health or cognitive parameters, and so on. Similarly, different monitoring levels may involve different frequency, intensity, or precision of data collection.

As an example, if a user's exposure score 241 indicates that the exposure level is less than five, monitoring continues at a minimum of Level 1. As monitoring data comes in (e.g., through sensor data for the user and self-reported data for the user), and community statistical reports for COVID-19 are updated, the user's exposure level can be re-evaluated. If the exposure level is determined to be greater than 10 but not greater than 15, then the system causes the user device 104a to perform monitoring at Level 2, which may include activating a different set of sensors (e.g., using more sensors), recording data more frequently, and so on. The system also causes the user device 104a to provide a social activity survey to better understand the user's exposure risk. The data from this enhanced monitoring and from the survey provides new information, which causes the system to again re-evaluate the exposure level for the user. Based on the result, the system may dial back monitoring to Level 1 if the exposure level decreases below 5, may maintain the monitoring level at Level 2 if the exposure level remains between 5 and 10, or increase the monitoring level if the exposure level is predicted to be greater than 10.

Figure 5:
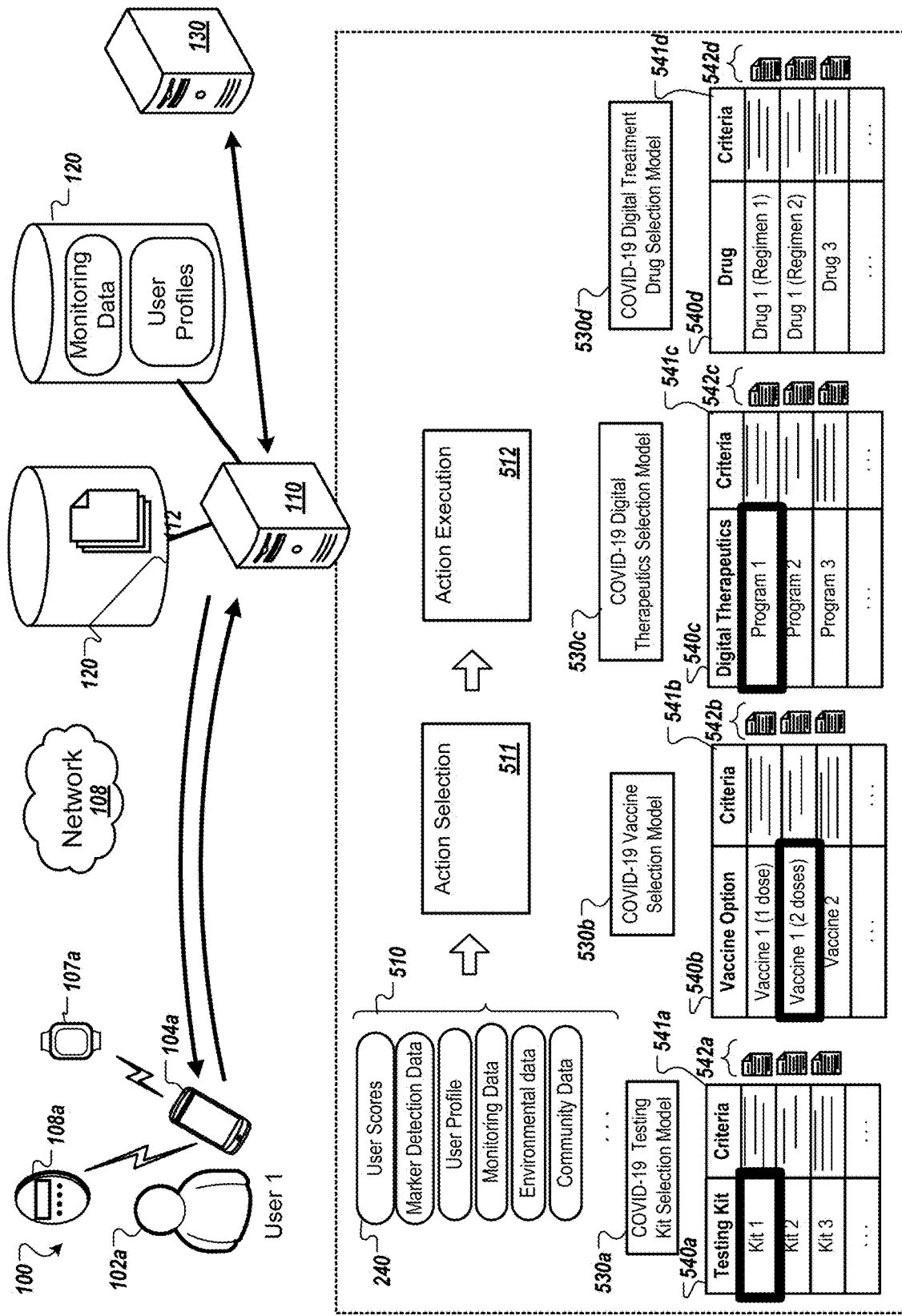

FIG. 5 shows how the system 100 can use collected data and generated user scores 240 to select and execute various actions. For example, the system 100 (e.g., through operations of the user device 104a and/or the computer system 110) can select a testing kit from among various different testing kit options. As another example, the system 100 can select a vaccine and vaccine administration procedure from among various options. As another example, the system 100 can select a digital therapeutics program for the user 102a from among multiple different digital therapeutics programs. As an example, the system 100 can select medications and other treatment actions from among multiple different options. The system 100 can provide recommendations for the selected disease management options to the user 102a and/or to a physician or other medical professional. In some implementations the system 100 carries out the treatment action directly by ordering a test kit, changing monitoring or other interaction options through the user device 104a, etc. In the example of FIG. 5, based on the user scores 240 and other collected information 510, and using the techniques discussed below, the computer system 110 selects to provide the user 102a with (i) the COVID-19 testing kit labeled "Kit 1," (ii) a vaccine option including two doses of "Vaccine 1," and (iii) digital therapeutics using a digital therapeutics program "Program 1." The user's infection likelihood score does not indicate a high-confidence diagnosis of COVID-19 yet or the need for drugs to be prescribed, so the system does not select any of the drug options or other therapies to be provided to the user 102a. Of course, if the testing kit results indicate that the user 102a has contracted COVID-19, or as other information is obtained about the user 102a, then the computer system 110 can re-evaluate and may recommend a drug option at that time, as well as re-evaluate whether a vaccine is appropriate and whether the digital therapeutics option should be changed.

The computer system 110 can use the user scores 240 described in FIG. 3, as well as other information about the user 102a and the user's community, to select disease management actions. The computer system 110 can include different models 530a-530d used to select different disease management actions. In some implementations, selection of disease management actions for a user can be made based on only a few factors, such as user scores. For example, the decision whether a user should receive a disease testing kit or a vaccine may be based on the user scores 240 for exposure, susceptibility, and/or infection likelihood. In some implementations, more information about a user can be incorporated for more complex decisions, such as which of multiple testing kits to use, which of multiple vaccine options to provide, which of multiple digital therapeutics to provide, which medications or other therapies to provide and the parameters for them (e.g., frequency, dosage or intensity, etc.), and so on. This can include using a user profile that shows user history and long-term attributes (e.g., age, sex, height, weight, race or ethnicity, chronic conditions, medical history, user residence address and contact information, etc.), monitoring data (e.g., recent or current physiological data, behavioral data, etc., and patterns and changes in them), and so on.

The various collected data 510 for a user 102a can be processed and used in action selection 511, and then carried out in an action execution 512 process. As discussed further below, the computer system 110 can store various information to aid in selection of appropriate disease management actions, such as selection models 530a-530d, data tables 540a-540d, sets of selection criteria 541a-541d for different actions, as well as profiles 542a-542d for different options. Once the computer system 110 determines that a disease management action is appropriate or needed for the user 102a, the action execution module 512 can cause that action to be carried out, sometimes directly by the computer system 110, other times through communication with the user device 104a or third-party systems, or by making recommendations to the user 102a, medical care providers, or others. For example, once a testing kit is selected for the user 102a, the computer system 110 can order the kit and have it delivered to the user 102a. As another example, once a vaccine option is selected for the user 102a, the computer system 110 can schedule an appointment for the user 102a to receive the vaccine (e.g., initiate interactions through the user device 104a for the user 102a to select and confirm an appointment location and time). As another example, the computer system 110 can cause selected digital therapeutics to be delivered through the user device 104a, whether through instructing specific interactions, providing software or configuration data for the user device 104a to determine appropriate interactions, enrolling the user 102a in a program of digital therapeutics, etc. Finally, if pharmaceuticals or other treatments are needed, the computer system 110 can provide digital interactions through the user device 104a to educate the user and instruct proper usage, order the needed drugs and doses for delivery to the user 102a, order needed monitoring device or medical treatment devices, schedule prescription pickup at pharmacies or schedule appointments with doctors, etc.

Examples of selecting disease management actions will now be discussed. For example, a testing kit selection model 530a can be used to determine whether a testing kit should be provided for the user 102a, and if so, which one is most appropriate. The selection model 530a can be, for example, a set of rules, a decision tree, a lookup table, a trained machine learning model, etc. In some cases, the determination whether to send a testing kit may simply be based on the user scores 240, for example, whether one or more of the user scores 240 satisfies a corresponding threshold. More complex decision-making models can be used, for example, taking into account measures of disease prevalence and spread in the user's community, using patterns and trends in monitoring data for the user, and so on, potentially using any of the totality of information about the user.

The associated table 540a identifies different COVID-19 testing kit options. These may represent, for example, different types of testing kits (e.g. nasal swab testing kits, throat swab testing kits, finger prick blood test kits, etc.), kits from different manufacturers, kits with different numbers of tests included, and so on. For each testing kit option, there is a set of criteria 541a that can describe user attributes or other factors that make a kit indicated or contraindicated for use. For example, some kits may be appropriate for (or have different accuracy of testing for) different stages of COVID-19, or may be appropriate for different age ranges of individuals, or may be appropriate for different combinations of physiological or behavioral attributes of users. In addition, or as an alternative, profiles 542a for the kits can be stored and updated, and the profiles 542a may indicate characteristics of the kits and their results. For example, the profiles 542a may indicate false positive rates, false negative rates, availability of the kits in different geographic regions, indications, contraindications, measures of the difficulty or burden for using the test, the time or delay involved in obtaining results, effectiveness of the test for different populations, and other characteristics.

The selection model 530a may use the criteria 541a and/or the kit profiles 542a to determine which kit option is best for the user 102a, given the monitoring data for the user and other data available for the user 102a. For example, the computer system 110 can compare user data with the data in the profiles or criteria to determine which option best matches the user's collected data and user profile. As another example, if a machine learning model is trained for testing kit selection, the computer system 110 can provide input feature values derived from the user data (e.g., values indicating user age, sex, location, physiological attributes, or other data relevant to kit selection) to the model and receive outputs indicative of the likelihoods that different testing kit options are appropriate for the user. In some cases, multiple kits having different effectiveness profiles may be selected, to provide additional accuracy or verification of results. Once a kit option is selected for the user 102a, the computer system 110 causes the selected kit to be ordered and shipped to the user 102a.

In a similar manner to selection of the testing kits, the computer system 110 can also select vaccines, digital therapeutics (e.g., programs or combinations of therapeutic interventions, or specific interventions), pharmaceuticals for treatment, devices for monitoring the user 102a, devices for treatment, settings for devices for treatment, and so on, even for other decisions (e.g., such as when the user should rest, when the user needs to visit a hospital or a doctor, when the patient may need ventilator support, etc.). For each, a corresponding set of options can be determined, each with criteria or profiles being determined to specify the conditions when the various options are indicated. In addition, or as an alternative, the system can train machine learning models to score the appropriateness of the various options, without explicitly specifying the criteria or conditions in which different options are appropriate.

For example, a vaccine selection model 530b can be used to determine whether a vaccine should be provided for the user 102a, and if so, which one is most appropriate. The selection model 530b can be, for example, a set of rules, a decision tree, a lookup table, a trained machine learning model, etc. In some cases, the determination whether to provide a vaccine for the user 102a may simply be based on the user scores 240, for example, whether one or more of the scores 240 satisfies a corresponding threshold. In particular, high susceptibility scores and/or exposure scores may indicate increased need for a vaccine, as would high levels of COVID-19 prevalence indicted by the community data. More complex decision-making models can be used, for example, taking into account measures of disease prevalence and spread in the user's community, using patterns and trends in monitoring data for the user, and so on, potentially using any of the totality of information about the user.

The associated table 540b identifies different COVID-19 vaccine options. These may represent, for example, different types of vaccines (e.g., live-attenuated vaccines, inactivated virus vaccines, subunit vaccines, recombinant vaccines, polysaccharide vaccines, conjugate vaccines, etc.), different modes of administration (e.g., hypodermic needle vs oral ingestion), vaccines from different manufacturers, vaccine administrations with different parameters (e.g., different dosages, different numbers of doses, different spacing between doses, etc.) and so on. For each vaccine option, there is a set of criteria 541b that can describe user attributes or other factors that make a vaccine option indicated or contraindicated for use. For example, some vaccines may be appropriate for (or have different levels of effectiveness for) individuals in different age ranges, individuals with different chronic conditions, for individuals with different combinations of physiological or behavioral attributes, etc. In addition, or as an alternative, profiles 542b for the vaccine options can be stored and updated, and the profiles 542b may indicate characteristics of the vaccines and their results. For example, the profiles 542b may indicate effectiveness statistics (e.g., including effectiveness of the vaccine option for different populations), duration of protection provided, availability of the vaccines in different geographic regions, indications or contraindications, potential side effects, and other characteristics.

The vaccine selection model 530b may use the vaccine option criteria 541b and/or the vaccine option profiles 542b to determine which vaccine option is best for the user 102a, given the monitoring data for the user 102a and other data available for the user 102a. For example, the computer system 110 can compare user data with the data in the profiles 542b or criteria 541b to determine which vaccine option best matches the user's collected data and user profile. As another example, if a machine learning model is trained for vaccine option selection, the computer system 110 can provide input feature values derived from the user data (e.g., values indicating user age, sex, location, physiological attributes, or other data relevant to vaccine selection) to the model 530b and receive outputs indicative of the likelihoods that different vaccine options are appropriate for the user 102a. Once a vaccine option is selected for the user 102a, the computer system 110 may cause the selected vaccine to be ordered and shipped for administration, as well as notify the user 102a and his or her doctor.

As another example, a digital therapeutics model 530c can be used to determine whether digital therapeutics should be provided for the user 102a, and if so, which interventions or programs are most appropriate. The selection model 530c can be, for example, a set of rules, a decision tree, a lookup table, a trained machine learning model, etc. In some cases, the determination whether to provide digital therapeutics for the user 102a may simply be based on the user scores 240, for example, whether one or more of the scores 240 satisfies a corresponding threshold. More complex decision-making models can be used, for example, taking into account measures of disease prevalence and spread in the user's community, using patterns and trends in monitoring data for the user, and so on, potentially using any of the totality of the collected information 510 for the user.

The associated table 540c identifies different COVID-19 digital therapeutics options. These may represent, for example, different categories of interventions (e.g., posture therapy, breathing therapy, mental health therapy, exercise therapy, sleep therapy, nutrition therapy, and so on), specific interventions (e.g., different discrete items of media, questions, forms, etc.), different programs (e.g., care plans or ongoing campaigns of therapy), different modes of communication (e.g., visual, audible, text, video, etc.), digital therapeutics of different levels of dosage or intensity, and so on. For each digital therapeutics option, there is a set of criteria 541c that can describe user attributes or other factors that make a digital therapeutics option indicated or contraindicated for use. For example, some digital therapeutics may be appropriate for (or have different levels of effectiveness for) individuals in different age ranges, individuals with different chronic conditions, for individuals with different combinations of physiological or behavioral attributes, etc. In addition, or as an alternative, profiles 542c for the digital therapeutics options can be stored and updated, and the profiles 542c may indicate characteristics of the digital therapeutics and their results, both positive and negative (e.g., side effects). For example, the profiles 542c may indicate effectiveness statistics (e.g., including effectiveness for different populations), duration of effect or benefit provided, availability of the digital therapeutics in different geographic regions, indications or contraindications, potential side effects, and other characteristics.

The digital therapeutics selection model 530c may use the digital therapeutics option criteria 541c and/or the digital therapeutics option profiles 542c to determine which option(s) are best for the user 102a, given the monitoring data for the user 102a and other data available for the user 102a. For example, the computer system 110 can compare user data with the data in the profiles 542c or criteria 541c to determine which digital therapeutics option best matches the user's collected data and user profile. As another example, if a machine learning model is trained for digital therapeutics option selection, the computer system 110 can provide input feature values derived from the user data (e.g., values indicating user age, sex, location, physiological attributes, behavior patterns, baseline measures, or other data relevant to digital therapeutics selection) to the model 530c and receive outputs indicative of the likelihoods that different digital therapeutics options are appropriate for the user 102a. The computer system 110 can also re-calculate the selection periodically or in response to additional collected data for the user 104a, and can add, remove, or modify which digital therapeutics are provided in response. Once a digital therapeutics option is selected for the user 102a, the computer system 110 may cause the selected digital therapeutics to be provided, for example, by providing software, instructions, program modules, configuration data, and so on to the user device 104a to cause appropriate interventions to be provided.

As another example, a drug selection model 530d can be used to determine whether pharmaceuticals should be provided for the user 102a, and if so, which drugs, drug administration regimens, and drug combinations are most appropriate. In addition to or instead of selection of drug options, the computer system 100 can characterize and select from among other treatment and therapy options, such as ventilator support options, antibody therapy options, and so on, using the same techniques. The selection model 530d can be, for example, a set of rules, a decision tree, a lookup table, a trained machine learning model, etc. In some cases, the determination whether to provide drugs for the user 102a may be based at least in part on the user scores 240, for example, whether one or more of the scores 240 (e.g., the infection likelihood score 243) satisfies a corresponding threshold. More complex decision-making models can be used, for example, taking into account medical history data, patterns and trends in physiological and behavioral monitoring data for the user, and so on, potentially using any of the totality of the collected information 510 for the user.

The associated table 540d identifies different COVID-19 drug options. These may represent, for example, different categories or classes of drugs, specific drugs, different regimens or administrations of drugs (e.g., combinations of different parameters for dosage, frequency, administration with or without food, etc.), drugs known to have different side effects or effectiveness profiles, and so on. For each drug option, there is a set of criteria 541d that can describe user attributes or other factors that make a drug option indicated or contraindicated for use. For example, some drug options may be appropriate for (or have different levels of effectiveness for) individuals in different age ranges, individuals with different chronic conditions, for individuals with different combinations of physiological or behavioral attributes, etc. In addition, or as an alternative, profiles 542d for the drug options can be stored and updated, and the profiles 542d may indicate characteristics of the drugs and their results, both positive (e.g., in reducing symptoms and speeding up recovery) and negative (e.g., side effects). For example, the profiles 542d may indicate effectiveness statistics (e.g., including effectiveness for different populations), duration of effect or benefit provided, availability in different geographic regions, indications or contraindications, potential side effects, and other characteristics.

The drug option selection model 530d may use the drug option criteria 541d and/or the drug option profiles 542d to determine which option(s) are best for the user 102a, given the monitoring data for the user 102a and other data available for the user 102a. For example, the computer system 110 can compare user data with the data in the profiles 542d or criteria 541d to determine which drug option best matches the user's collected data and user profile. As another example, if a machine learning model is trained for drug option selection, the computer system 110 can provide input feature values derived from the user data (e.g., values indicating user age, sex, location, physiological attributes, behavior patterns, baseline measures, or other data relevant to drug selection) to the model 530d and receive outputs indicative of the likelihoods that different drug options are appropriate for the user 102a. The computer system 110 can also re-calculate the selection periodically or in response to additional collected data for the user 104a, and in response can add, remove, or modify which drug(s) are provided. With drug selection and any other disease management action, the system 110 can inform a physician of the system's determinations and recommendations, and may require approval of a physician before implementing the selected option. Once a drug option is selected for the user 102a (and approval of a physician is obtained if needed), the computer system 110 may cause the selected drug to be provided, for example, by communicating a prescription to a pharmacy system, entering the recommendation or prescription into medical records, communicating the recommendation and usage instructions to the user 102a, ordering doses of the medication to be delivered to the user 102a, etc.

Figure 6:
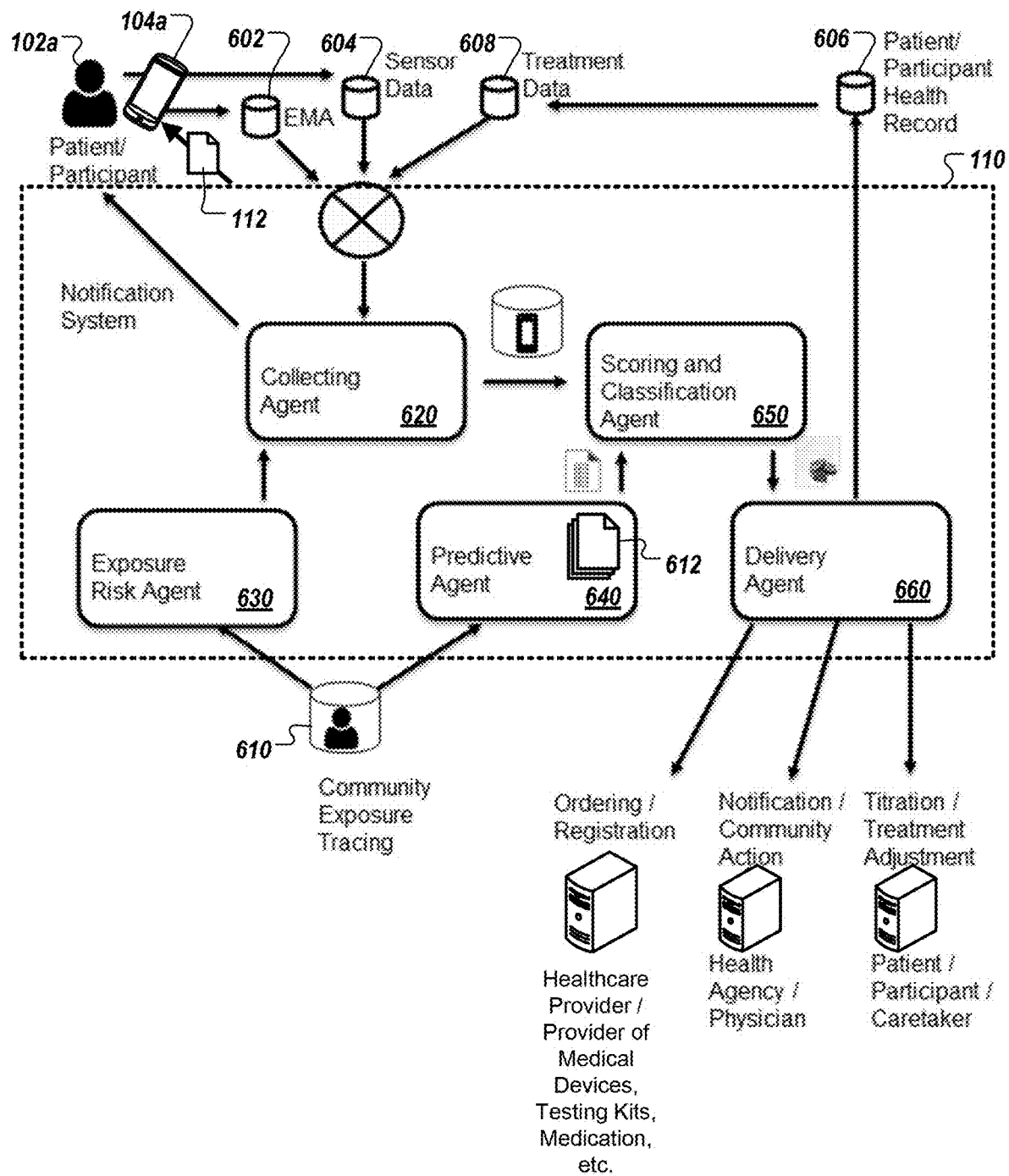
FIG. 6 is another diagram illustrating the system.

FIG. 6 illustrates additional aspects of the system 100. Although the example shows actions for a single user 102a, the computer system 110 can be used to concurrently monitor and treat one or more diseases for many different users in different geographical areas.

As discussed above, the computer system 110 can select and provide a data package module 112 to the user device 104a, which specifies how the user device 104a and potentially other devices interact with the user and collect information (e.g., sensor data, survey responses, etc.). The module 112 can be received by a client device from a server in order to treat a patient or participant, or more generally to manage a disease (e.g., monitor exposure, detect infection, monitor disease effects, minimize symptoms, improve recovery, and so on). The module 112 can be downloadable, such as an mobile device application or an add-on module or configuration data that supplements or augments an application and alters how the application operates. The module 112 can run on user devices, such as a phone, tablet computer, smart watch, web browser, etc.

The module 112 can be configured to acquire information that would indicate the presence or absence signs and symptoms of a disease. The module 112 can be used to detect events and conditions (e.g., behaviors, physiological attributes, patterns, and so on) that are indicative of exposure to a disease or infection with a disease, so that exposure levels and infection by a person can be determined. For example, the module 112 can include rules or code to cause detection of specific signs and symptoms of a specific disease, such as COVID-19. The module 112 may additionally be configured to monitor progress of a disease and treatment. In other words, a module 112 may be a treatment package that is used during treatment, after a user has been diagnosed to have the disease, to monitor the effects of treatment and monitor effects of the disease, so that the computer system 110 and/or the module 112 can suggest and in some cases implement changes to treatment.

The computer system 110 can create a profile or user account for the user to store collected information, for example, once the user 102a signs up or enrolls to participate in disease management. Once the module 112 is downloaded, a client application is adjusted based on the module 112 to monitor the user 102a using measures that are locally monitored through various techniques, such as (i) user input data 602 indicating responses to ecological momentary assessments (EMAs) or other surveys or prompts provided by the system 100, (ii) device usage data indicating how the user device 104a or other devices are used, and (iii) sensor data 604 from the device 104a or other devices (e.g., a wearable device 107a, a medical monitoring device 108a, etc.). The computer system 110 also obtains additional information for the user 102a, such as EMR/EHR data 606, including potentially treatment data 608 that indicates how a user is being treated for the disease being monitored. The EMR/EHR data 606 can be used for various purposes, including to determine baseline measures for a user and to determine existing conditions and comorbidities, which the computer system 110 can use to make predictions and estimates (e.g., to estimate the susceptibility or risk that a disease poses for the user 102a) and to adjust decisions for the user (e.g., about which testing kit, vaccine, module 112, medication, digital therapeutics, monitoring procedures, or other intervention is recommended or provided by the computer system 110).

The computer system 110 can also acquire community data 610 that describes the community in which the user 102a resides, works, or otherwise spends time. The community data 610 can include data indicating population levels, demographic information, types of locations present in the region, mapping data, and so on. The community data can also include measures that aid and assist in determining exposure risks, infection or exposure hotspots, and general disease outbreak related conditions. For example, the community data can include infection rates for COVID-19 for different regions of the community, trends of COVID-19 infection rates in the community, treatment outcomes in the community (e.g., death rates, hospitalization rates, etc. due to COVID-19), and so on. The same type of information can be obtained for nearby regions or other regions having similar population characteristics.

The community data 610, as well as the other data collected (e.g., data 602, 604, 606, 608, and so on), be updated and refreshed periodically on an ongoing basis. As new collected data for the user 102a is received, the computer system 110 may re-evaluate the predictions for the user (e.g., exposure level, susceptibility to the disease, likelihood of infection, etc.) and also re-evaluate the actions that the computer system 110 recommends or carries out for the user 102a.

In some implementations, the module 112 that is downloaded to the user device 104a includes rules, logic, models or other elements to interpret and act on monitored data. The monitored information is received and measured using data that characterizes signs and symptoms of a disease, and the data to specify indicators of a disease may be included in the module 112 or may be downloaded later through updates to the module 112 or as other supplemental information provided over the communication network. The module 112 can include data specifying or defining markers to look for in order to detect a disease such as COVID-19. The set of markers can be dynamically updated through communication of the user device 104a with the computer system 110. The computer system 110 may maintain, update, and distribute definitions of markers known to be indicative of signs or symptoms of a disease. As new scientific research and medical research becomes available, and more data about different types of patients is obtained, the computer system 110 can fine-tune the set of markers, adding new markers for data combinations that indicate signs of the disease, modifying existing marker definitions to be more accurate in predicting signs or symptoms of a disease, and removing marker definitions that are not sufficiently effective. The user device 104a, using an application that uses the data in the module 112, can receive and process the marker definitions, as well as assess incoming data streams and detect and record when the criteria for detecting a marker is satisfied.

For example, certain measurements or detected items (e.g., body temperature above a threshold, coughing frequency above a threshold, etc.), whether reported by the user 102a or detected through passive sensing, may be designated as predetermined markers or indicators that, while not conclusively showing that a person is infected with COVID-19, nevertheless indicate increased probability of infection. Markers or indicators may be more complex, involving evaluation with respect to personalized references, involving combinations of measurement types or data types, having conditional applicability, and other features. For example, a marker may be based on the user's personal baseline, e.g., with criteria for a marker being present as a change of at least a certain magnitude or degree from a corresponding personal baseline measure for the user 102a or from a previous measurement for the user 102a. Criteria for a marker may be involve multiple different measurements or data items that must each meet a corresponding requirement (e.g., value in a predetermined range, an amount or direction of change relative to a reference value, etc.) at or near the same time (e.g., within a threshold amount of time of each other). As an example, a marker could have criteria that requires three measures, body temperature, blood pressure, and resting heart rate, to each be measured as having a value in a respective reference range at least once during a 4-hour period. Similarly a marker might require two out of three different conditions to be met in order for the marker to be considered present. Similarly, a marker may have conditional properties. A marker may have criteria that involve a certain data measure (e.g., a behavioral or physiological measurement) occurring in a predetermined context or set of contexts. For example, a marker may be defined as elevated resting heart rate (e.g., relative to an absolute reference level or a person's personal baseline level), but only if measured at certain times of day or during certain activities. A data item may be considered to occur in a certain context (e.g., during a certain activity, time, location, condition, etc.) when the measurement or condition represented by the data item occurs within a predetermined level of proximity in time and/or location of the context.

The module 112 may include risk assessment components, such as predictive models, which can be refined through machine learning. For example, the computer system 110 can generate and train machine learning models 612 based on the data collected about many users, which can indicate changing behavioral and physiological measures of patients, behavior patterns and corresponding exposure and infection, vaccination responses, side-effects of drug delivery, and more. Models 612 can be provided to the user device 114a as part of the module 112, as updates to the module 112, or through other means. In addition, or as an alternative, the models 612 may reside on a server, such as the computer system 110, and be used there to evaluate data that is received. The models 612 can provide outputs that are based on a diverse set of data sources. The outputs of the models can serve as inputs for scoring the likelihood of disease outcomes and risks.

The computer system 110 can include features to detect and identify needed steps to improve detection and prediction. For example, the computer system 110 can identify the absence of data for certain factors and initiate actions to collect the needed data. If the computer system 110 determines that there is a low confidence score for a prediction for the user 102a, the computer system can take actions to improve the confidence level. As an example, the computer system 110 can identify a measurement that is relevant to the current prediction and for which data is inadequate (e.g., missing, outdated, outside a standard or expected range, etc.). The computer system 110 can then cause data collection procedures to be changed to acquire or confirm the measurement needed. If the data needed is exercise data, for example, the computer system 110 may send a message to the user device 104a causing the user device 104a to present an EMA or survey asking the user to input the exercise data needed. In addition, or as an alternative, the computer system 110 can instruct the user device 104a to turn on exercise monitoring, to report stored exercise data, to collect and report exercise data from an activity tracker device, and so on. In some cases, the computer system take action to obtain data or confirm data received through administered tests, conditional effects of treatment changes related to medication delivery, suppression mechanisms, and behavioral or environmental adjustments.

Based on the outputs of the machine learning models 612, the computer system 110 can determine an action to change a disease detection procedure for the user 102a or change a disease treatment for the user 102a. For example, changing the disease detection procedure can include changing one or more of: the types of data monitored; the types of situations or conditions in which data is acquired (e.g., adding or removing triggers for collecting sensor data or triggering presentation of an EMA); the types of devices used for monitoring; the frequency of data collection; the precision or format of data collection; adding a laboratory test (e.g., blood test, urine test, etc.); adding a test for a specific disease (e.g., a test to detect COVID-19, whether to detect antibodies or current infection); and so on. This can include selecting a detection component, such as a treatment kit to be sent to the user 102a. Changes in disease treatment can be varied and are highly personalized for the user. Changing a treatment can include may different types of actions, and a few examples include providing a vaccine, providing a medication, providing digital therapeutics interventions, changing settings of a medical treatment device (e.g., ventilator) or a medical monitoring device, and so on. Once selected, changes to monitoring or treatment can be recommended to the user 102a, the user's healthcare provider, and/or a caretaker for the user 102a, and in some cases can be carried out by the computer system 110.

The models 612 can be neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used.

In the example of FIG. 6, the computer system 110 includes a collecting agent 620, an exposure risk agent 630, a predictive agent 640, a scoring and classification agent 650, and a delivery agent 660.

The collecting agent 620 obtains and processes data about the user 102a, e.g., EMA data 602, sensor data 604, and treatment data 604, as well as data potentially from any other systems containing patient health records. The collecting agent 620 can format and store the data in a database 622, where historical data about the user 102a is maintained as well. The database 622 can include various other types of information about the user 102a, such as race, gender, age, and other user attributes. The database 622 can make the collected data, as well as data derived from it, such as personal baseline measures for the user 102a, available to any or all of the other components of the computer system 110.

The exposure risk agent 630 accesses and uses geographic information systems (GIS) at multiple levels, e.g., neighborhood, community, city, county, state, regional, and country levels. The exposure risk agent 630 combines this data with collected user data through contact tracing, exposure identification measures, and treatment response indicators to determine hotspots, potential outbreaks and re-emergences of risks associated directly with a disease, indirectly due to the related suppression mechanism or the treatment of a virus. This information is delivered to the collecting agent 620 in order to synchronize relevant events. For example, the collecting agent 620 can align or associate actions of the user 102a and input of the user 102a, as well as context data indicating the times, locations, and activities of the actions and inputs, with the disease corresponding disease prevalence measures. If a user visits a restaurant, for example, the collecting agent can detect the visit from GPS location data, log the amount of time the visit lasted, and associate the visit with an occupancy level at the restaurant (e.g., a value which may be typical, average, recent, or expected value if the actual value is not available) and the disease infection rate in the area of the restaurant, so that the exposure risk to the user 102a of that particular visit to that particular restaurant at that particular day and time can be estimated.

The predictive agent 640 uses predictive models 612 to estimate the exposure of the user 102a and the likelihood of infection by the user 102a. The predictive models 612 can be trained based on training data of many different users and situations, and the models 612 can be repeatedly or continually updated as addition information comes in. The predictive agent 640 predicts an exposure level based on, for example, the community exposure data (e.g., infection rates and trends for areas the user 102a has been over a period of time, such as the last few days, the last 1-2 weeks, etc.) and the tracked data about the user (e.g., locations the user 102a has been, frequency of travel, amount of time spent outside the home, types of locations visited, contact tracing data, and so on). This can provide a measure of exposure, such as a predicted likelihood that the user 102a has been exposed to a disease, a frequency or intensity with which the user 102a has been exposed, a likelihood that the user will be exposed in the future (e.g., over a particular time period in the future, such as the next day, week, month, or year) estimated based on the user's recent and long-term behavior patterns as well as community exposure measures, a general exposure score or exposure level classification based on various exposure factors, and so on.

The predictive agent 640 can also predict whether the user 102a is currently infected or, in some cases, whether the user 102a has previously been infected. To do this, the predictive agent 640 can use the collected data from various sources (e.g., health records 606, user input such as EMA data 602, sensor data 604, treatment data 608, user demographic data, and so on), using collected data collected for a current time period (e.g., the current day, week, etc.) as well as collected data for prior time periods and/or long-term historical data. These data items may be input to a model or analysis process in any of various ways, e.g., as measurement values (e.g., a body temperature measurement of 99.0°), as classifications of measurements or data patterns (e.g., activity level is high, medium, or low), as binary feature values (e.g., whether an event or condition was detected or not), as a count of how many times an event or behavior occurred, as an aggregate measure (e.g., an average, maximum, minimum, etc.) based on multiple observations, and so on. Detected markers for signs or symptoms of a disease can be indicated and used as input also, for example, as a result of pre-processing the collected data set for a user and comparing collected data patterns with criteria of marker definitions to see which markers are reflected in the collected data. Baseline measures for a user, demographic attributes of the user, and other types of data can also be provided as input to the infection likelihood determination.

The models 612 used to predict infection can take into account the exposure estimates for the user. For example, a score or other output of an exposure estimation model may be used as an input to the infection prediction model. In addition, or as alternative, the activities of a user and locations a user has been, as well as the infection rates in the user's community, can be used to determine the likelihood of infection. For example, an elevated body temperature may generally be a sign of potential COVID-19 infection. But if the user's community has a very low prevalence of COVID-19 and/or the user's activities indicate very low contact with others (e.g., based on location tracking of the user's phone and smartwatch, from user-reported survey answers, and/or contact tracing data), the predictive agent 640 may interpret the likelihood of infection to be lower than it would otherwise be for someone with more travel or someone in an area with higher prevalence of the disease. Thus, at least in some implementations, the computer system 110 can weight the detected signs and symptoms of a disease according to the community data related to the disease. In some implementations, the predictive models 612 for predicting infection likelihood and/or other items may receive indicators of community characteristics and community exposure levels, and the training of the models 612 may automatically account for the variation in the predicted item due to factors such as user locations, user activities, user exposure level, community characteristics, community exposure levels, etc. In other words, the predictive models 612 can be trained to receive and process input feature values indicative of any of these factors, and potentially any or all of the data items collected for the user. Through the model training process, the model 612 learns the relative importance and predictive value of each type of input, as well as how different combinations of input values increase or decrease likelihoods, so that the trained models 612 automatically generate a prediction using the relationships implicitly learned through machine learning training from a training data set showing many examples of other users.

The predictive agent 640 may be used to predict other items as well. For example, the predictive agent 640 can include a model 612 trained to predict, based on information about the user 102a, a susceptibility of the user 102a to COVID-19 if the user were to contract the disease. For example, separate from the user's exposure level, the susceptibility may be an estimate or predicted measure of how vulnerable the user would be would be to the disease (e.g., the degree that the user may be affected) if the user were to be exposed to the disease and/or if the user were to become infected. The susceptibility measure could be, for example, indicative of a risk category (e.g., high, medium, or low risk of a certain level of harm occurring). The susceptibility measure could be a prediction of a likelihood that a user, if infected, would have a symptomatic case rather than an asymptomatic case. The susceptibility prediction may be made in general (e.g., a level of severity for disease effects as a whole), or with respect to specific outcomes or harms of the disease (e.g., a prediction of risk of stroke, a prediction of risk of hospitalization needed, a risk of sepsis, a risk of death, etc.). As with other predictions of the predictive agent 640, all of these predictions of a user's susceptibility to the disease can be based on relationships implicitly learned or trained into a model 612, such as a neural network, based on training data describing data of other users, e.g., data collected for users of different types and characteristics who experienced the disease and the disease outcomes they experienced. The models 612 can also be repeatedly or continually updated with further training and refinement as additional training data examples are obtained. To determine a user's susceptibility to the disease, the appropriate model 612 may use (e.g., receive inputs indicating) various types of data about a user, such as a user's demographic characteristics (e.g., age, sex, etc.), the user's physiological data (e.g., blood pressure, height, weight, respiration rate, resting heart rate, etc.), the user's behavioral data (e.g., current and historical records for exercise, sleep, nutrition, the user's medical records (e.g., data indicating comorbidities and chronic conditions, such as diabetes, heart disease, lung disease, COPD, cancer, etc.), and so on.

As another example, the predictive agent 640 may generate estimates of a user contracting COVID-19 based on the user's behavior patterns and community exposure levels. For example, the collected data about a user, including the locations visited, activities performed, and so on, can indicate behavior patterns and behavior trends of the user. The predictive agent 640 can thus use the collected data, including any determined patterns or trends, to predict a likelihood that the user would become infected over a future time period, such as the next day, week, month, year, etc. if the current patterns or trends continue. Similarly, the prediction can take into account the patterns and trends of infection in the user's community, and use those in making the prediction. For example, a model 612 can be trained to make this type of prediction based on training data examples that indicate tracked behaviors of different individuals, along with their community exposure measures and outcomes of whether the individuals contracted COVID-19 and when.

The scoring and classification agent 650 takes the collected input elements (e.g., records and measures of what has occurred, such as physiological readings, user actions and behavior patterns, etc.) and combines them with the predictive input elements and determining overall risks associated, and what recommendations can be shared with the delivery agent. The output of the predictive agent 640 may be provided to the scoring and classification agent 650 to be factored into the processing of the scoring and classification agent 650. Based on the predictions of the predictive agent 640 and potentially other data, the scoring and classification agent 650 can generate scores and classifications to be indicated to the user 102*a*, a physician, a caregiver, community health teams, and so on. For example, based on the predicted likelihood of infection the agent 650 may determine a diagnosis of whether the user 102*a* currently is infected with COVID-19 or not. This may be involve assigning a score or classification for the user 102*a* based on where the predicted likelihood of infection falls with respect to various ranges of predictions, e.g., unlikely to be infected (0%-20%), low likelihood of infection (20-30%), moderate likelihood of infection (30%-50%), high likelihood of infection (50%-80%), diagnosis of actual infection (e.g., 80%-100%). Similarly, exposure levels, infection likelihood, and other items may be scored or classified for any appropriate scale or set of classes.

The delivery agent 660 uses outputs of the scoring and classification agent 650 to select, notify about, and carry out actions with respect to COVID-19. The delivery agent 660 can act on the scores and classifications indicated by the scoring and classification agent 650 to decide to change monitoring, notify the user 102*a* or an associated person (e.g., physician, caregiver, etc.), provide or change treatment, and so on. As options for managing the disease, the delivery agent 660 can consider actions such as the ordering of or registration of a user for laboratory tests (e.g., blood test, urine test, etc.), sending the user a disease testing kit to detect the disease, providing a vaccine for the disease, providing or using a certain type of device (e.g., for providing treatment or for improving monitoring), changes in the configuration or software of the user device 104*a*, changes in data collection procedures of the user device 104*a* (e.g., types of data monitored, frequency of collection and reporting, etc.), and adding or changing medications for the user. The actions that the delivery agent 660 selects can be identified and communicated to the user 104*a* through an appropriate communication medium, e.g., email, phone call, short message service (SMS) text message, or paper mail delivery. The delivery agent 660 can also connect to centralized registries to report actions taken for the user 102, to allow continued identification of community hotspots, outbreaks, and risks related to the disease and its treatment.

In some implementations, the delivery agent 660 can provide recommendations to titrate, adjust, or replace elements of treatment or other management of the disease. Titration can involve repeatedly (e.g., in some cases continually or continuously) measuring and adjusting the a drug dosage, digital therapeutic intervention, or other aspect of treatment. The delivery agent 660, having information about recent collected data for the user 102*a*, as well as the health records 606 and treatment data 608 for the user 102*a*, can recommend varying medication, sleep aids, over-the-counter solutions, intensity or type of digital interventions (e.g., interactions for behavioral modification or behavioral support) related to treatment for the disease. The recommendations for changes in treatment can be communicated to the user 102*a* (e.g., through the device 104*a*) and/or to device of a physician, a caretaker, a family member, or other person associated with the user 102*a*. In some cases, the recommended actions, along with the predictions, scores, and classifications of the other agents 640, 650 for the user 104*a*, can be provided as a form of decision support to a physician, to indicate a recommended risk level, diagnosis, prognosis, and treatment for the user 102*a*, which can inform the decision making of the physician in caring for the user 102*a*. The delivery agent records decisions for the user 102*a* into the health records 606 for the user 102 within the system 110, and can allow access to external systems.

In some implementations, the delivery agent 660 does more than simply select, store, and notify of personalized actions selected to manage the disease for the user 102*a*. For example, the delivery agent 660 can implement disease management actions by causing actions selected for the user 102*a* to be carried out. This may be done automatically, for example, when the delivery agent 660 has at least a minimum level of confidence that an action is appropriate for the user 102*a*, and/or when rules or conditions for carrying out the action are satisfied. In some implementations, carrying out the actions may be predicated on confirmation or approval from another source, such as an approval or acceptance by the user 102*a* through the user device 104*a*, approval of a physician for the user 102*a*, approval of an insurance company for the user 102*a*, etc. To obtain this approval, the delivery agent 660 can provide data prompting a device to present a user interface requesting confirmation of an action to be performed.

The actions performed by the delivery agent 660 can include causing an item to be delivered to the user 102*a*, for example, a disease testing kit, a medical monitoring device, a laboratory test sample collection kit, an at-home laboratory testing kit, a medication, etc. The delivery agent 660 may carry this out by communicating with an fulfillment system to initiate ordering and/or shipment of the items that it selects. The actions performed by the delivery agent 660 can include changing settings of the user device 104*a*, the wearable device 107*a*, the medical monitoring device 108*a*, or other devices.

Although the remote computer system 110 cannot actually administer a vaccine to a user, the delivery agent 660 may nevertheless facilitate administration of the vaccine by, for example, informing the user 104*a* of the selected vaccine and locations to obtain it, scheduling an appointment for the user to receive the vaccine, prescribing the vaccine or indicating the vaccine recommendation in medical records of the use 102*a*, initiating communication to prompt the user's physician to prescribe the vaccine for the user 102*a*, causing an appropriate type and dose of vaccine to be ordered and shipped, and so on. Similar actions can be performed for medications and other types of treatment.

The disease management actions that the delivery agent 660 selects among and carries out can include providing digital therapeutics to manage COVID-19. This can include providing interactions to prevent, detect, monitor, treat, or support recovery from the disease. The delivery agent 660 can initiate delivery of new digital therapeutics through the user device 104*a* and/or other devices, such as devices wirelessly connected to the user device 104*a*. The delivery agent 660 may cause new digital therapeutics programs or treatment plans to be started. In some implementations, the delivery agent 660 may adjust digital therapeutics programs or treatment plans that are already being used. For example, the delivery agent 660 may adjust the type, frequency, intensity, or type of digital therapeutics, or adjust conditions in which they are provided, e.g., contexts in which they are administered, triggers for administration, and so on. The digital therapeutics may instruct a user to take actions, refrain from actions, or change behaviors in order to reduce or avoid symptoms of the disease or to speed recovery from the disease. As an example, if a COVID-19 patient is having light or moderate difficulty breathing, digital therapeutics can be provided to recommend that the user change the pose of their body, for example, to lie on his stomach rather than on his back. Similarly, digital therapeutics may instruct changes to a level of physical activity or specific exercises (e.g., recommending more rest or recommending a gradual increase in physical activity, depending on the stage of the disease and the user's capabilities).

The computer system 110 can cause digital therapeutics to be delivered in various ways. The computer system 110 can send modules 112 or updates to modules 122, where the modules 112 configure a user device 104a (e.g., through an application resident on and able to be executed by the user device 104a) to locally detect conditions and triggers and provide interactions (e.g., notifications, surveys, games, media, user interfaces, education, etc.) that the user device 104a selects as appropriate for the detected situation of the user 102a. As another example, the computer system 110 can assess the collected data for the user 102a and initiate specific interactions. For example, the computer system 110 can select specific interactions and the timing of those interactions based on the collected data, and then send messages to the user device 104a causing the user device 104a to initiate the interactions with the user 102a.

The computer system 110 can be used to monitor the effectiveness of treatment of the user 102a and adjust treatment accordingly. For example, if provided digital therapeutics do not result in the expected or desired improvements in physiological attributes or user behaviors, the computer system 110 can select and provide different digital therapeutics interventions. As another example, if medications provided do not yield the desired effects, or if the collected data indicates that there are problematic side effects, the computer system 110 can recommend changes to the medication regimen, such as changing the dose, type of medication, frequency or timing of administration, and so on. In making treatment decisions and recommendations, the computer system 110 can use data indicating medical research results and best practices, for example, to provide actions based on clinically validated and evidence-based treatment steps that can be captured in rules, look-up tables, databases, or other data structures.

In addition, or as an alternative, the computer system 110 can derive treatment recommendations from a database of example cases of the disease. That data may describe instances of people who have had the disease, the attributes and monitored data for those people, their symptoms and indicators of disease, treatments provided, and the response of the people to the treatments. From analysis of these examples, the computer system 110 can derive rules and relationships that indicate, for example, the likelihood that certain treatment elements improve different symptoms, and with what magnitude and speed of improvement is typical. The analysis can take into account that different individuals have different characteristics and situations and so may respond differently. Thus, the result may be a set of rules or other data that indicate, for different disease symptoms, user characteristics, and user behaviors, the corresponding treatment actions that are predicted to have the greatest benefit to the user (e.g., most likely to improve symptoms or speed recovery, providing the greatest benefits, providing the lowest risks or side effects, or some combination of these or other criteria). The training data can be used to train machine learning models to predict the treatment actions to recommend and carry out, where the machine learning models can receive input of a user's demographic data or other characteristics, the user's physiological data, and the user's behavioral data, and then provide output indicating treatment options that the model predicts are most appropriate for that combination of input user data.

Figure 7:
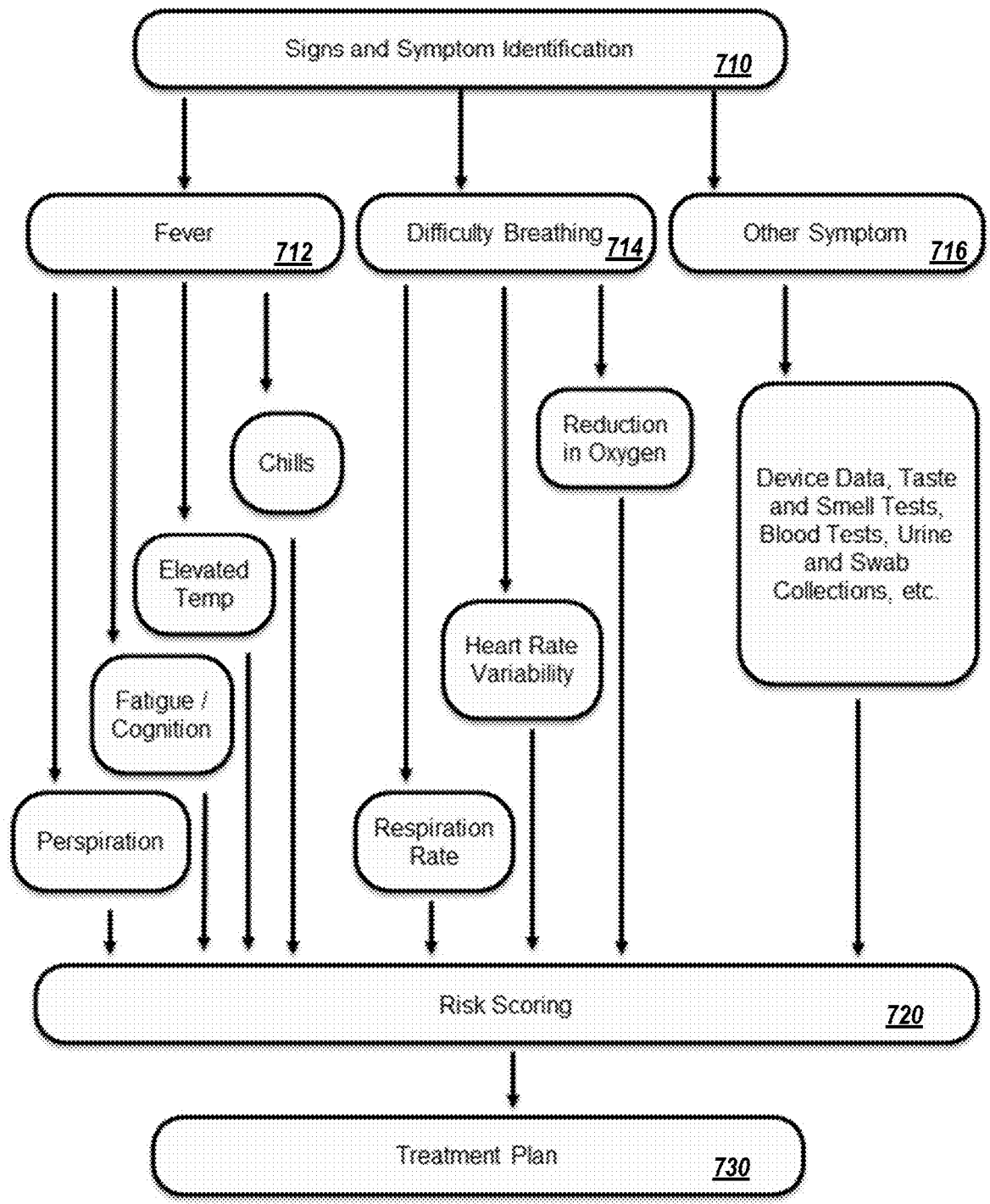
FIG. 7 is a diagram showing processing of data regarding collected data.

FIG. 7 shows an example process 700 for tracking signs and symptoms of disease and generating a treatment plan for a patient. This general process 700 can be used for detecting and providing insight for various different situations, including scenarios such as: (1) detecting signs and symptoms of viral infection worsening or Improving; (2) detecting signs of vaccines being effective or ineffective; and (3) detecting signs of morbidities and co-morbidities.

As discussed above, a user is provide with a digital treatment package, such as one of the modules 112 discussed above. The user has several signs and symptoms that require monitoring for associated risks due to an illness worsening or improving. Further, there are additional risks or changes to treatment possibly required based on morbidities, co-morbidities, and other related illnesses and the treatment of these.

The example of FIG. 7 shows that a portion of a treatment plan involves identifying signs and symptoms of a disease 710, which can be used to detect infection and/or to monitor the progression of a disease. A treatment package or module 112, and/or processing of the computer system 110, can be designed for monitoring with respect to a specific disease or set of diseases, and so can be configured to detect and characterize (e.g., determine the frequency, severity, etc.) a specific set of conditions determined to be signs or symptoms of one or more diseases. In the example, this includes fever 712 and difficulty breathing 714 as signs of COVID-19 infection. Other symptoms 716 can also be monitored, for example, to detect general behavior changes and physiological changes that may indicate other symptoms.

For each of various types of signs or symptoms, there may be multiple elements, e.g., measurements, types of data, or tracked behaviors, that indicate or confirm that a the sign or symptom is present. For example, to detect a fever, the system can detect an elevated temperature, but may also detect signs like chills, perspiration, fatigue or changes in cognition that may be related and may be used to confirm or verify the presence of a fever. Similarly, difficulty breathing may be detected with respiration rate, heart rate variability, and/or reduction in oxygen, with these measured parameters being compared with baseline values, thresholds, or other reference values to identify difficulty breathing. Other symptoms may be detected using device data (e.g., sensor data, device usage data, etc.) and results from various tests, such as taste and smell tests, blood tests, urine tests, swab collections, and so on. The data sets that can be used include active sensing data, passive sensing data, user inputs (such as user responses to surveys and EMAs, EHR/EMR data, clinical data set, and insurance claims data.

For a disease like COVID-19, the signs and symptoms can be very different for different individuals. Some include loss of taste and smell, coughing, difficulty breathing, fatigue, fever, gastrointestinal distress, confusion or disorientation, skin rash in toes or extremities, blood clots, stroke, and more. The system performs risk scoring 720 that takes into account the prevalence of different symptoms for different individuals, to better predict the likelihood of infection. For example, fever is a sign of COVID-19 infection, but can also be a sign of other illnesses or conditions. The combination of different signs and symptoms, as well as the data collected that may represent markers or indicators for the disease, can all be used together to determine an overall likelihood of infection.

The system then generates a treatment plan 730 based on the estimated level of risk and likelihood of infection of the person. This can include selecting and initiating a testing or treatment action based on the distributed monitoring techniques discussed above.

For instance, an individual with respiratory illnesses, such as chronic obstructive pulmonary disorder (COPD), may have reduced pathways for breathing and increased risk in delivering oxygen to vital organs. When combined with an illness like COVID-19, which creates additional risks to breathing, it becomes increasingly important to measure the health of the body under varying situations. These can include measuring the user's capabilities, actions, and physiological attributes when exerting energy while standing, sitting, walking, running, talking, and managing cognition during events like driving. Similarly, it is helpful to measure how well the user recovers energy or resumes normal breathing while resting, relaxing, sleeping, or meditating. Unlike some systems that are limited in the situations or activities in which monitoring data can be effectively used, the system described herein can gather and use information about each of these different actions or contexts, and this diversity is a significant advantage in obtaining accurate results. By monitoring changes in physiological and behavioral measures during different activities that place different types or levels of stress on the user, as those activities take place naturally from day to day and without prompting by the system, the system can better characterize and detect a user's risk, early signs of a disease, and the effects of a disease and treatment. In many cases, this variety of monitored situations and the ability to detect changes with respect to personal baselines for the different activities can lead to earlier and more accurate diagnoses and better treatment selection decisions.

In the case of a person with COPD, due to increased risk when person is exposed to or contracts COVID-19, the system can select to recommend or require a pulse oximeter as a trusted source for monitoring, in order to provide more accurate data than, for example, self-reported indicators of breathing difficulty. This step may be made before infection is determined, e.g., to better detect potential future infection, or after infection is predicted to have occurred or has been confirmed through laboratory tests, or even after the infection is cleared as a person is dealing with lingering effects of the disease.

As another example, the risk of loss of life while sleeping may be significant for some users that have reduced lung function or conditions such as sleep apnea, when they are unable to manage their ability to breath due to the inability to consciously control the increased demand for air flow. Given this risk, the system can provide recommendations and behavioral support to manage the risk. For example, the system can provide recommendations to eliminate all sleep aids in many cases. The negative effect of the elimination of sleep aids may inadvertently increase the risk for apnea events if the patient also suffers from a chronic co-morbidity of chronic insomnia. In many cases, patients that have apnea events tend to suffer most during periods of light sleep. Where a sleep aid may help ensure periods of deep sleep, the likelihood for dying during sleep may be more likely during periods of light sleep which along with REM sleep is more common for insomniacs.

In some cases, in co-morbidity situation, a ventilator may be the only course of action combined with the original COVID-19 treatment package and any pre-existing co-morbidity treatment packages.

Figure 8:
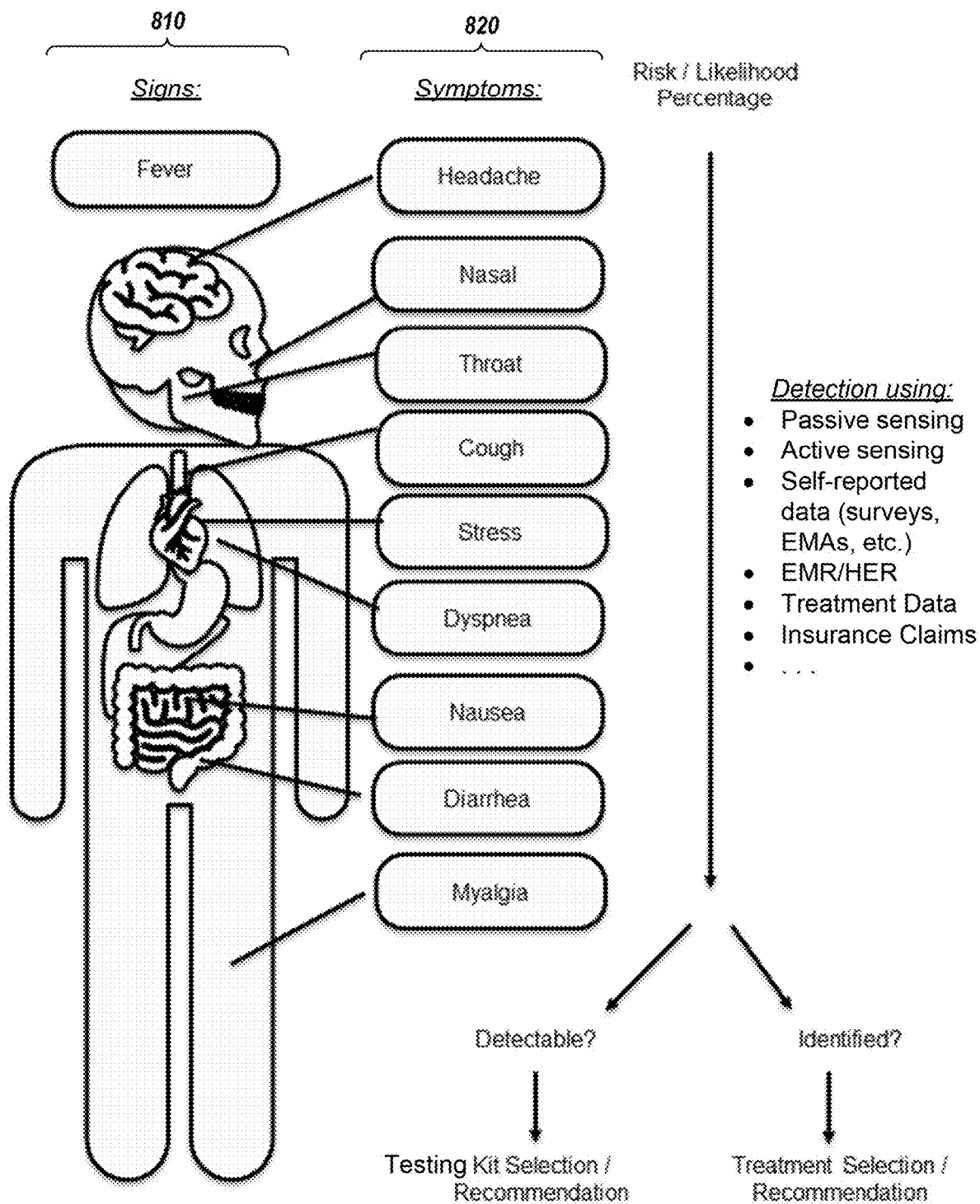
FIG. 8 is a diagram showing signs and symptoms of disease and their use in disease detection, selecting testing kits, and adjusting treatment.

FIG. 8 shows additional examples of signs and symptoms of a disease such as COVID-19 and how they can be used. Signs 810 can include physiological measures such as the presence of a fever, increased resting respiration rate, and so on. Symptoms 820 can include physiological effects such as headache, nasal symptoms, throat ache or dryness, coughing, stress, dyspnea, nausea, diarrhea, myalgia, loss of taste or smell, and so on. Although not listed, behavioral signs or symptoms can also be determined, such as confusion, reduced energy or activity, reduced social engagement, change in types of activities, changes in sleep patterns, and so on. Many of these signs and symptoms may occur individually for different reasons, and so the system evaluates the combinations of detected items and their timing related to each other to evaluate likelihood of infection. Similarly, the system considers the severity or intensity of the signs and symptoms, for example, through qualitative indicators from a user, measures of frequency that events such as coughing are detected, the degree to which measurements or behaviors are changed and so on. Signs and symptoms can be detected using a variety of information, such as passive sensing, active sensing, self-reported data, EMR/EHR data, treatment data, insurance claims data, and so on.

In general, when using a downloaded treatment package or module 112 a user can perform a series of events based on content delivered to the user and data collected for the user. The client device 104a, based on the downloaded treatment package and/or communications from a server such as the computer system 110, provides advice and interactions to the user 102a based on collected results. Treatment packages can provide various services discussed below. Examples include interactions to perform treatment check-ins, processing to determine containment and exposure risks, and measurement of side effects of treatment. These can be performed using self-reported data, for example, responses to medication reminder messages, questions whether the user has any trouble breathing, questions about whether the user has experienced loss of taste and smell, etc. The system can also use device data, e.g. sensor data indicating behaviors and physiological measures for monitoring for real-time stress indications. The system can also use health records data, e.g., to generate an initial baseline using prior measurements. This could be used, for example, when considering whether blood pressure measurements are higher or lower than the baseline either in in general to detect infection, or after a treatment action (such as receiving a vaccine or a medication), etc. The system can also use disease exposure data for both the individual and the community, e.g., community infection level information, contact tracing, data indicating disease hotspots, and so on.

Other functions of the downloaded treatment package or module 112 and/or computer system 110 include adjustments to monitoring and disease detection, including potentially ordering laboratory test materials or disease testing kits. The module 112 and/or computer system 110 can determine when additional devices, such as a pulse oximeter, thermometer, sleep sensor, etc., is needed, whether to detect infection with greater certainty or to monitor treatment. Similarly, the system can determine disease test kit needs, such as to initiate delivery of at-home testing kits. The system can also determine laboratory testing needs and can schedule laboratory tests (e.g., specimen collection, blood testing, urine testing, etc.)

Other functions of the downloaded treatment package or module 112 and/or computer system 110 include providing changes to treatment and providing advice for changes in user behaviors. These include activities to detect impairment of cognition and to improve cognition. Some can include rest and relaxation activities, e.g., puzzles, games, non-digital recommendations, reading material, etc. These can be used to both help calm a user and improve mood, as well as provide an activity in which to monitor the user's responses and performance. The system can provide sleeping guidance, including contraindications to sleep medications and sleep aids. The system can instruct the user to, for example, take breaks, to stand up from time to time, to move rather than stay sedentary, and so on. The system can provide periodic check-in interactions to assess mood, pain level, or generally ask how the user feels. The system can monitor calorie consumption needs and provide eating reminders, as well as recommend changes to improve nutrition to provide meal options and ideas. The system can provide exercise recommendations, e.g., programs for stretching, aerobic exercises, step activities, strength training, etc. The system can also provide hydration reminders and recommendations.

Other functions of the downloaded treatment package or module 112 and/or computer system 110 include changing medication, such as adjustments to the type, quantity, frequency, or combination of mediation taken. The system can also make titration changes, periodically check for contraindications, determine the need for medication refills, and so on.

Other functions of the downloaded treatment package or module 112 and/or computer system 110 include providing social modifiers to managing the negative impacts of disease suppression mechanisms like social isolation. The system can recommend or initiate communication with someone, e.g., through a phone call or video conference call. The system can monitor speech patterns to identify speech pattern differences, which may be a sign of cognitive impairment, extreme fatigue, or other potential disease symptoms.

In some implementations the system uses collaborative assessments to determine impacts and change in a user. For example, the system may initiate communication with a device associated with a friend or family member of the user 102a, and ask if the friend or family member has noticed changes in the user 102a, and if so, the type and extent of changes. This can provide confirmation for signs or symptoms of disease that may be indicated in other collected data or may reveal additional signs or symptoms.

Additionally, the system can use using passive sensing to determine risk and recovery. For example, within the realm of social isolation a patient or participant in a treatment package is determined to manage suppression mechanism like social isolation. The patient or participant is at risk for mental health related depression symptoms based on prior episodes but has been managing using a specific drug. While socially isolated, the increased symptom clustering insight detects higher than normal situations related to depression. Ultimately causing an increased titration or dosage of medication to the patient. This detection through symptom clusters utilizes multiple sensors within these clusters. One symptom cluster is a physical activity decrease, which the system can detect through accelerometer data, step counting data, motion detection, and so on. Another is changes in food intake, such as changes in caloric intake indicated through self-reported responses to EMAs or other user interfaces, food diaries, etc. Another cluster is reduction in social activity, which can be detected through records of phone call duration and number of calls, records of social application usage, and so on. Another example is sleep-related changes, such as duration and quality of sleep, which can be detected through phone and application usage (e.g., detecting when a phone or app is used and when it is not used), light sensor data, and so on. Another example, is mood changes, which can be determined based on self-reported data, physical activity sensor data, heart rate and heart rate variability data, which can indicate stress and other symptoms, and so on.

FIGS. 9A-9B show examples of user interfaces that may be provided through a disease management data package, e.g., one of the modules 112, at a client device. The client device 104a can include a client-side delivery component, configured to provide interactions with the user 102a to cause data gathering to detect or monitor COVID-19, as well as to monitor the administration and effects of treatment of the disease and even to provide digital therapeutics to treat the disease (e.g., reduce symptoms, improve mental state and physiological function, etc.).

FIG. 9A shows an example user interface 900, presented on the user device 104a, which indicates results of processing collected data for the user 102a. The system has determined that the user has a high exposure risk to COVID-19 and indicates this to the user. The system also has determined a significant change with respect to the user's personal baseline for sleep. In this example, the user's amount of deep sleep and total sleep has increased significantly, which is potentially a sign of exhaustion or fatigue. As a result, the system recommends that the user should not take any nighttime sleeping aids, as these would pose an undue risk to the user 102a in the current situation. The user interface 900 also includes controls for a user to begin further interactions to acquire information about other topics.

FIG. 9B shows another example user interface 950 that shows different questions and corresponding answers from the user 102a, along with score weightings for the user's answers that together result in a significant level of risk of contracting COVID-19, and so the system determines to send the user 102a a testing kit to test for the disease. For example, the score weights for each answer can be added and compared to a threshold, and when score satisfies the threshold, the system determines to send a testing kit for the disease.

Figure 10:
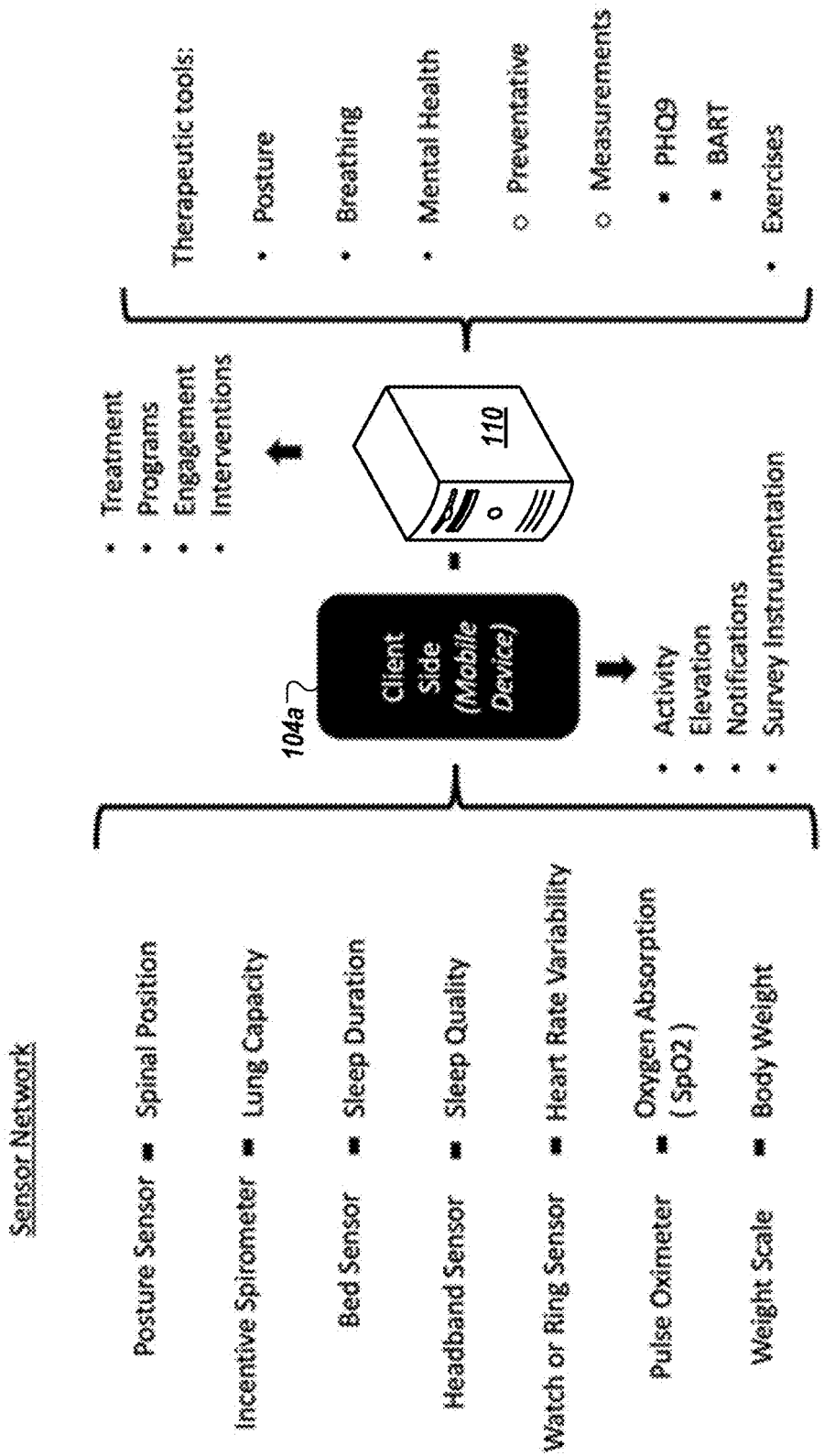
FIG. 10 shows examples of sensor data collected and digital interventions that can be provided using the system.

FIG. 10 provides examples of digital therapeutic delivery as a suite of exemplary tools or components. These tools can be used to provide treatment for COVID-19 or other diseases. The example shows a sensor network, e.g., a set of different devices and sensors that can communicate with the user device 104a to provide information about the user 102a. The information from these sensors can be used by the user device 104a and the computer system 110 to provide identified treatments, programs, engagements, and interventions. Activities and physiological attributes of the user 102a are detected using various sensors, which provide sensor data through the user device 104a or another personal network. The computer system 110 communicates with the user device 104a, or alternatively other devices, to receive sensor data and to distribute therapeutic tools capable of managing preventative, predictive, treatment and post-treatment needs of the user 102a. A few examples of tools and digital therapeutics that can be provided include interventions to provide posture training and support, breathing training and support, mood and mental health assessment and support, and exercise training and support.

A variety of personalized digital interventions can be provided for users. The user device 104a and the computer system 110 can communicate to perform in-the-moment monitoring to promote active engagement with the user. The user device 104a, by its own local processing or in response to instructions from the computer system 110 over a network, can provide instructions or cues on screen to describe what the user should do. For example, the user device 104a can instruct the user to assume certain poses or perform certain physical exercises, and monitor physiological measures while the user takes the instructed actions. The actions can also be timed or otherwise monitored. From the captured information, the system can update the user's baseline measures, classify the user's performance, and select an appropriate type and intensity of digital therapeutics to deliver in the future. The techniques can be used throughout the entire disease management cycle, for detection of or prediction of infection, treatment of the disease, and supporting long-term recovery from the disease (e.g., monitoring and improving function after the infection has cleared).

The selection and delivery of which interventions to provided, and the timing of when to provide them can determined based on the personal baseline measures for the users, current monitoring data for the users, and trained machine learning models. For example, as discussed below, posture training and support can be provided as a therapeutic tool to address COVID-19 symptoms or to speed recovery. Machine learning analysis can be performed using monitoring data showing postures over time of different patients who have contracted COVID-19 and corresponding breathing ability and recovery over time. The data can provide monitored data and results for individuals of different attributes, backgrounds, and situations. The data can show monitored results after interventions as well as results from postures that patients choose on their own without prompting. Similar information such as breathing patterns, exercise patterns, and so on can be monitored and assessed using machine learning techniques.

As an example, the computer system 110 and the user device 104a can provide digital therapeutics to monitor and improve the body posture of the user 102a. Many recovering individuals spend time laying down, whether in a hospital or at home, and this can lead to additional medical problems and well as overall physical fitness deconditioning. By measuring posture regularly throughout the day, both the amount of time sitting and standing and lying down can be collected and compared against reference values (e.g., thresholds, ranges, etc.) that specify desirable levels for treatment of disease and providing effective post-treatment recovery. For example, treatment of COVID-19 may involve changing posture such as: a user varying posture with at least a minimum frequency; a user spending a majority of time or at least a minimum amount of time in certain desirable postures; minimizing time in or avoiding undesirable postures; spending desired amounts of time or portions of the data in specific desired postures; and so on.

Posture can be measured in a variety of ways. In some cases, the sensors of a phone or smart watch that sense direction and movement (e.g., accelerometers, IMUS, etc.) can be used to estimate posture or changes in posture. Posture can also be measured using an instrumented patch or a garment, for example, wearable sensors like UPRIGHT GO and LUMO LIFT can effectively detect a position of the wearer, and can provide the detected position of the individual to a smartphone, e.g., using a wireless communication link such as BLUETOOTH.

The computer system 110 and/or user device 104a can provide various interactions to deliver posture training and feedback to the user. These include educational materials, media, reminders, alerts (e.g., triggered when an undesirable posture is detected or when an appropriate posture is received), assessments, surveys, games, and so on. These interventions can be triggered in a variety of ways. For example, posture training and support may be prescribed by a doctor for the user 102a. As another example, the computer system 110 and/or 104a may determine to provide posture training and support to the user 102a automatically upon detecting one or more conditions, such as determining that resting respiration rate has increased above a threshold, the likelihood of infection exceeds a threshold level, and/or the user's posture as tracked using the user device 104a or another device fails to meet certain standards (e.g., the user spends too much time in an undesirable posture or does not spend enough time in desirable postures). Thus, the delivery of posture training and support, as with other digital therapeutics, can be personalized and tailored to the specific current needs and symptoms of the user 102a. The posture training and support may be provided in response to detected respiratory symptoms, as a way to alleviate symptoms after onset. In addition, or as an alternative, the support may be provided in advance of symptoms, for example, to an individual with a high risk of exposure, as a preventative measure to improve habits and lessen the potential impact of COVID-19 on an individual, thus potentially helping to minimize or avoid at least some COVID-19 symptoms.

The system enables posture training and support as a therapeutic, as part of an approach that provides varying stages of predictive, preventative, and treatment support. The behavioral support for improving posture can have a number of beneficial physiological effects, such as increased respiratory and diaphragm function, opening the throat and windpipe, reducing pressure on kidneys and other organs, and increasing circulation. By contrast, bad posture can restrict the throat and airway and can compress the lungs and other organs, which can worsen COVID-19 respiratory symptoms.

As another example, the computer system 110 and the user device 104a can provide digital therapeutics to monitor and improve breathing of the user 102a. For example, digital therapeutics can include education, instruction, games, and other interactions to train the user 102a to breathe more effectively. Monitoring data that describes the user's breathing can be collected and analyzed to determine scores for the user's breathing outcomes. The system can also use active exercises, in some cases monitored or assisted using digital technology, to help educate, inform, and assess the user 102a's breathing performance.

As an example, the system can provide instructions and media to prompt a user to perform, and guide a user through, a diaphragmatic breathing exercise. This exercise can occur when an individual is on their back with their legs and head elevated. The individual breathes through the nose, expanding their chest and abdomen while positioning their hands on or above the chest and abdomen to monitor the ascent. The user then exhales through their mouth while monitoring with their hands the descent. This process is usually timed and continues to repeat, sometimes for a minute or longer. The mobile device 104a or another device can optionally be placed on the user's chest or abdomen and can monitor the ascending movement and descending movement as the user breathes in and out. The device can collect sensor data on an approximate change in elevation of the ascension and descension accordingly. This data can be used for compliance qualifiers (e.g., to verify that the user successfully completed the exercise as requested) and to measure objective outcomes in improvements (e.g., to determine whether the user is breathing more easily and more deeply). For example, for an individual that had difficulty at first, the sensor data can be used to determine if the user is later able to breath deeper breaths and hold breath for longer times.

Another example exercise that the system can instruct the user to perform is an incentive spirometer exercise. This exercise can be done while an individual is sitting with good posture. After breathing out completely, the individual places an incentive spirometer to their mouth and breaths in to their maximum inhalation capacity. The individual then breaths out slowly and repeats, sometimes for a minute or longer, while taking breaks occasionally. The spirometer is a device that the individual can breathe into to help strengthen the overall force and air exhalation of the individual's lungs. The device itself can be connected to a phone or other smart device to monitor volume and exchange of air between the participant and the device. Coupled with a phone or other digital device, this exercise can further be gamified through digital counting and goal setting. These and other breathing exercises can be provided by the system at regular times as part of a care plan developed for a patient. As with other digital therapeutics, the intensity of support, e.g., the frequency and duration of the exercises, can be personalized and adapted for the user and the symptoms that are detected, whether through self-reported data or through passive sensing.

As another example, the user device 104a and/or the computer system 110 may cause digital therapeutics to be provided to assess and improve mood or mental health of the user 102a. Various interventions available in the system related to an individual's changing mood or behavior can be characterized as either mental health risk prevention or mental health risk detection.

For example, for therapeutic mental health risk prevention, various interventions can be provided to produce positive outcomes. One is prompting a user to engage in regular communication with others. This can include reminders to individuals to talk to people and engage in conversation. Communication can stimulate the mind and provides renewed processing of information. The level of communication of the user 102a can be measured through tracking of phone calls, application usage, and social media presence on the user device 104a. The measures can be compared to the user's baseline measures for communication through those channels. The system can also measure and provide recommendations or behavior change interactions for each of the following areas:

Healthy Diet—the system can initiate interactions to check-in on meal plans and calorie consumption tracking among micro and macro nutrients consistent with challenging regular healthy eating behaviors. This can be cross-compared with mood and sleep related measurements as contextual baseline and further changes to the baseline.
  Sleep—processing of consistent sleep and duration of guidance based on the age of the individual, utilizing sensors in the bed, ring sensors (e.g., worn on the user's finger), and other wearable devices or sensors capable of physiological, behavioral or environmental related context to sleep duration and sleep quality.
  Exercise—regular exercise plans and time of the day as context to other situations like sleep. The system can perform automatic detection of exercise in a wearable device such as a watch, ring or a mobile device.
  Caffeine Intake—specific consumption as it relates to energy levels throughout the day and into the night, prohibiting good sleep through contextual cues.
  Alcohol—dehydration and sleep cycle disturbances can be identified as context to sleep phase alterations and arousal events and other abrupt shifts in brain wave activity. Disturbances can be measured using EEG data and heart rate variability HRV.
  Blue Light Exposure—measuring reduction in screen time from devices like television, laptops, and mobile devices before bedtime.
  Meditation—measuring EEG and HRV changes during meditation related events prior to bedtime to assist with restfulness.
  Consistent daily events—keeping on track with sleep time, meals, exercise and other routine behaviors can support healthy chemical levels in the mind and support recovery and overall mental loading.

As therapeutic mental health risk detection, mental health can be measured by various surveys and battery tools, gamification tools, and responses through physiological monitoring. In general, the system can measure and record COVID-19 signs and symptoms. The system can be configured to ask a user daily questions, such as "did you go outside," "how are you feeling," "is a certain factor better or worse than yesterday?" Across a community of users, the system can determine a statistically-relevant set of users that cuts across different contexts/situations. For example, the system can identify that exposure to blue light is a trigger for sleep disruption and mental health issues that may be particularly significant for individuals already dealing with other COVID-19 symptoms. Some of the tools for mental health assessment include the PHQ9 assessment for depression severity, which can be useful in monitoring the severity of depression in response to a treatment. Where while providing a new pharmaceutical or other treatment, an individual's risk of depression could worsen and thus lead to other risks related to their well-being. The computer system 110 may quantify those risks and inform clinical staff and/or provide supporting interventions to the individual. The system can store a baseline measure for the person with respect to depression, as well as data indicating the medications user is already taking. This can enable the system to determine combinations of medications to avoid, either based on prior research or by assessing the outcomes for users after being prescribed the drug.

As another example, the system can provide a Balloon Analogue Risk Task (BART) as a conceptual frame for the individual's balancing of reward versus loss. Risk can be associated with an individual's willingness to put themselves in a position of risk for a benefit or gain of some kind. Such risk could be further exposure to COVID-19 when treatment appears to show positive gain. As an example, a person contracting COVID-19 may be less of a risk taker, at their initial diagnosis when symptoms limit options. As the person starts to improve, however, they may increase their tolerance for risky behavior, including behaviors that may potentially infect others. If risk tolerance is determined to be increasing, the system can provide warnings, alert the user to their risky behaviors, and so on. If the computer system 110 detects trends or patterns of risk changes in certain classifications of individuals or certain situations (e.g., approaching locations with at risk populations), the system can warn the individuals, remind them that treatment is not complete yet, remind them to wear a mask, etc. The computer system can also define markers for the factors that relate to changing risk tolerance to enable the computer system 110 to track and predict it.

As another example, the system can be used to instruct and monitor exercises in order to treat COVID-19 and to monitor disease progress or recovery. A user can be instructed to wear or hold a device during certain exercises. A sensor patch, sensor ring (e.g., worn on a finger), a smart watch, or other device may be used for monitoring. The sensed data can detect changes in physiological parameters, such as heart rate or breathing rate, as the user changes position changes (e.g., from seated to a standing position) or performs exercise. Among other items measured, the system can collect data indicating the time of the activity, duration, physiological measures for quality of breathing, heart function, etc. Responsive to those monitored parameters, the system can provide interventions, such as providing warnings, instructing the user to slow down, ending an exercise session, and so on. The system can also set and monitor user goals, and try to push the user through goals from week to week through a treatment and recovery plan.

Various pulmonary rehabilitation exercises exist for individuals who are recovering from COVID-19. In addition to the breathing exercises noted earlier, some other exercise therapeutics that the user device 104a and computer system 110 can provide include:

Sit-to-Stand Squats—Sit in a chair, extend your arms forward as a counter-balance, and rise to a standing position. Relax, then place arms out again, and sit down while maintaining posture. Repeat.

Standing Marching—Stand, pull a knee in the air, balance and then set it down. Repeat.

Seated Arm Reaches—Sit in a chair, cross arm in front and then up and across the body slightly arching the back with finger pointed up. Repeat.

Standing Heel Raises—Stand, come up on tippy toes, then back down to heals. Repeat.

Sidestepping—Stand legs together, take a lateral step to one side. Repeat.

Wall Pushups—Stand arms extended forward with palms flat against the wall, lower into the wall and then push back away from the wall. Repeat.

Walking—increasing the number of minutes each week during recovery.

Risk measures are collected before and after and, in some cases, throughout the given exercise. For example, throughout exercise, SpO2 should never go below 88%. The user device 104a, as directed by an application or downloaded module 112, can monitor the SpO2 value compare it to the threshold, and initiate interventions if the threshold is crossed (or if the user is in a range near the threshold). A healthy range is above 95%, depending on the individual. Reduction in oxygen or SpO2 can result in passing out and damage to one's self, creating further risk of breakage and recovery risks in individuals with higher frailty concerns. Sustained low oxygen can lead to further organ and systematic shutdown of the body.

The system can educate and advise individuals about the recovery progress and goals, e.g., for the day or for the week, and are encouraged while systematically monitored for risk. The measurements that the system makes during the various exercises and interventions can also be used by the system as a diagnostic tool. For example, during the poses and exercises notes above, decreases in oxygen or SPO2 (or changes other parameters, e.g., respiration rate, blood pressure, heart rate, user report of light-headedness or shortness of breath, etc.) of certain magnitude may be indicative of or predictive of clinically-relevant parameters. These parameters may include the overall severity of COVID-19 effects, the onset of specific additional symptoms or disease effects, the current stage or progression of COVID-19, risk levels for the type or severity of future disease symptoms, length of time of recovery or future impairment in function, and so on. Using data analysis or machine learning techniques to assess monitoring data of different users, the computer system 110 can identify which monitored physiological parameter changes or ranges during certain activities are predictive of which current or future outcomes. Then, the computer system 110 can detect when the monitored data during an intervention meets the identified combination of factors that triggers the need for an intervention.

Machine learning can be used to determine which user actions are effective to treat a disease such as COVID-19, and which actions are most effective for different users and situations. For example, the computer system 110 can perform analysis to determine the types and ranges of postures that lead to reduction in symptoms and early recovery, as well as types and ranges of postures that may worsen or have no effect on symptoms of the disease. This information can be used to identify what constitutes good posture for a COVID-19 patient, or which postures and posture changes are most helpful for specific symptoms. This analysis process can include determining, based on the examples of longitudinal data of many individuals, different postures and posture parameters are most helpful for patients of different attributes (e.g., different body types, different ages, different underlying health conditions), for different disease states (e.g., early onset of COVID-19 vs. later, different levels of severity of the disease, etc.), and so on. This can enable the system to provide a personalized, contextual treatment recommendation customized for each individual, based on factors such as the patient's age, sex, comorbidities or chronic conditions, physiology (e.g., height, weight, etc.), and so on. The results of analysis may be provided as thresholds or ranges used to select and provide treatment. As another example, the relationships may be implicitly learned through training of a model, such as a neural network, to output data scoring different postures and posture parameters, or different posture interventions, based on an input data set indicating characteristics and symptoms of a user. In the same manner, in addition to or instead of analysis and modeling for posture-related parameters, the system can use analysis and machine learning to determine which factors provide greatest improvement for respiration training, exercise, mental health, and other treatment areas.

Figure 11:
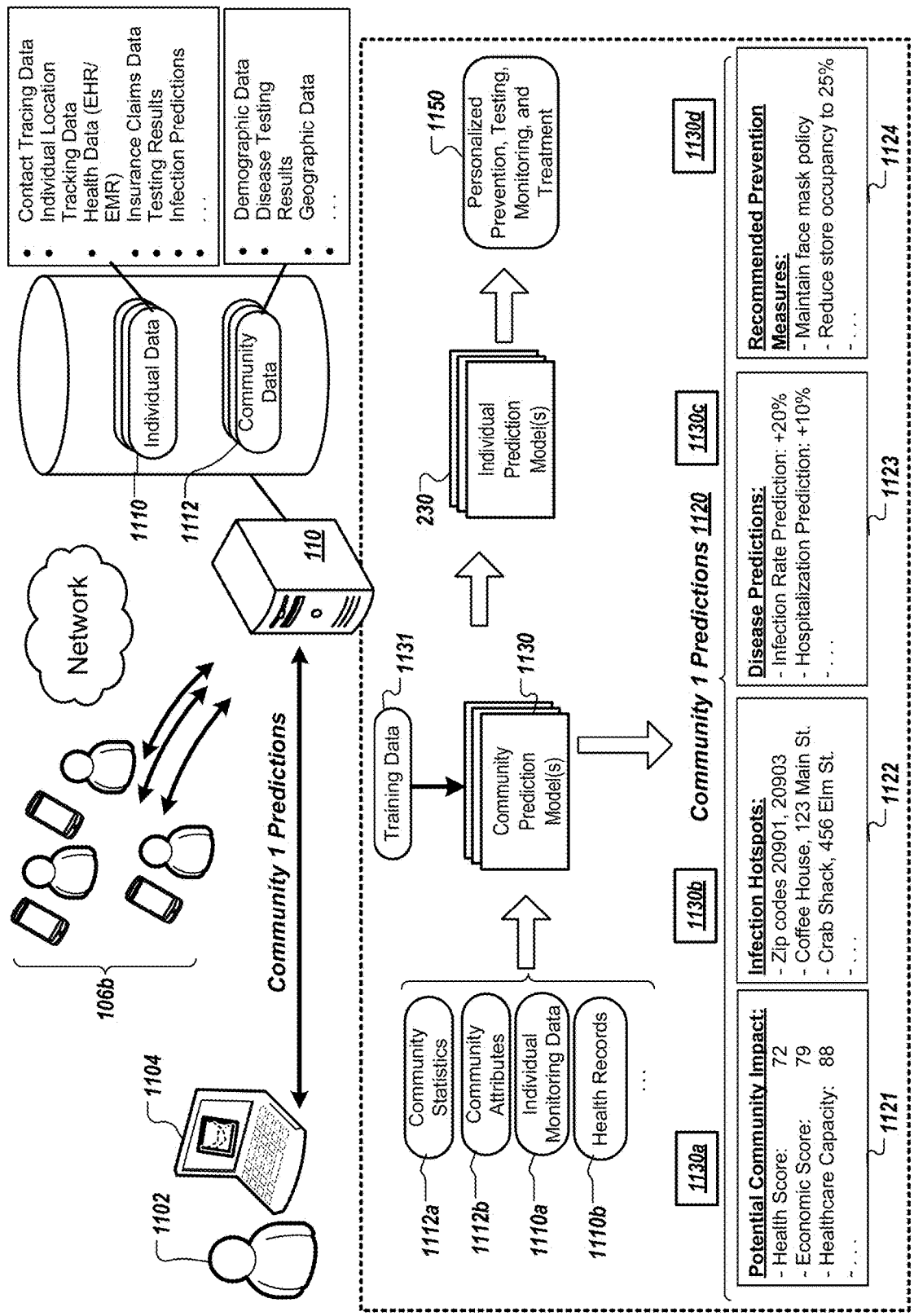
FIG. 11 shows an example of the system being used to make predictions for a community.

FIG. 11 shows how the computer system 110 can be used to track and predict risk factors for COVID-19 for communities. Using community-level data as well as individual-level monitoring data, the computer system 110 can provide customized disease tracking and disease predictions for many different communities.

As used herein, a community refers a group of people. The group of people in a community can be defined in different ways, e.g., based on one or more of geography, shared characteristics of individuals, membership in a group, interests, etc. For example, a community can be defined as a group of people associated with a particular geographical area, such as a state or province, a county, a city, a zip code, a neighborhood, etc. The community may be the group of people that reside in the area, the group of people that work in the area, a group of people that work or reside or otherwise visit the area, etc. The computer system 110 can store data that defines and describes different communities. The stored data can associate a unique community identifier for each community and data describing the criteria for membership in the community, e.g., geographical boundaries of the community and other features of the community. A community may be defined independent of a geographic area, for example, such as a family, a group of people that work for the same business, a group of people that work in the same office or building, the members of a certain organization, individuals in a certain profession, a set of people that have visited a geographical area within a certain time (not necessarily permanently residing in that area), etc.

In some implementations, a community can be a cohort of individuals enrolled as participants in a research study, which may involve ongoing monitoring or data collection as part of the study protocol. In various examples below, a community refers to the individuals that reside in a particular geographical area. Different communities can refer to different geographic areas and the people who reside in them, for example, different neighborhoods, different zip codes, etc.

The predictions and recommendations for a community can be provided to devices of users associated with a community. This can include researchers studying the disease, doctors treating patients in the community, government leaders in the community, business owners for businesses having locations in the community, and so on. The predictions may be provided to individual members of the community.

As discussed above, the computer system 110 can track the behaviors, physiological attributes, and medical records of many different individuals. This is represented in FIG. 11 with individual data 1110 that has been collected. The computer system 110 can store or access individual data 1110 for many different individuals, not only those in the specific community of interest. For example, while information about the those who reside in a community has a high impact on the community, the health and behavior of outside visitors the community has an impact, as does the health and behavior of those in outside areas where community members visit.

The system 110 can use machine learning techniques to learn from the outcomes experienced in many different communities of diverse types. Predictive models 1130 use the information learned through a generation or training process to give better predictions for individual communities. This process can be repeated to continue updating and refining the models 1130 as new data becomes available. In particular the process of model generation or training can include using many examples from different communities to represent how different factors (e.g., community characteristics, individual behaviors, physiological data, etc.) affect different disease outcomes, e.g., for transmission for COVID-19, for impact on community disease measures for COVID-19, and so on.

The predictive models 1130 can be machine learning models, for example, one or more neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used. The computer system 110 can analyze the training data about many individuals and communities to determine relationships between data factors and COVID-19 disease outcomes and other effects on individuals, locations, and communities, either through explicit analysis or through machine learning training, e.g., so that a model implicitly learns the predictive value of different data items on, for example, disease exposure, disease susceptibility, infection likelihood, etc. Training can incrementally or iteratively update the values of parameters in the models 1130 to learn the impact of different factors on predicted outputs. In the case of neural networks, backpropagation can be used to alter neural network weights for neurons at various layers of a neural network model. Training can be done using stochastic gradient descent or other training algorithms.

The computer system 110 acquires and stores community data 1112 for each of various communities. The community data 1112 can be collected for many different communities on an ongoing basis, to update the predictive models and to be able to provide accurate, up-to-date inputs to the models for making predictions. The community data can include information such as demographic data for the community, mapping data for the community, traffic data indicating movement patterns and traffic flows, economic data indicating the types of businesses or industries present in the community, and more. The community data 1112 also indicates disease measures for the community, such as results of COVID-19 testing, COVID-19 predictions for the community, transmission rate metrics, and more. The community data can indicate periodic (e.g., daily) counts of individuals in the community who have (i) been diagnosed with COVID-19, (ii) been hospitalized for COVID-19, (iii) died of COVID-19, or who have been affected in other ways. In addition, the community data 1112 can indicate the policies and rules that a community has put in place, including those effective currently, those in effect in the past (e.g., and the times they were used), and those planned or scheduled for the future. These disease prevention measures can include, for example, social distancing recommendations, mandatory business closures, restricted occupancy guidelines, mask usage instructions, and so on. As discussed below, this information about the nature of many different communities (e.g., their population attributes, geography, and other characteristics), as well as disease measures over time provides the computer system 110 with many instances of training data that can be used to train machine learning models to predict disease risks and outcomes for other communities, as well as the disease prevention measures that may be most effective for different communities.

As part of training the models 1130, the computer system can generate and use training data designed for the particular model or type of prediction. From the set of collected data about different communities, the system 110 can extract may different examples including (i) feature data indicating the situation in a community at one point in time, and (ii) corresponding outcomes that the model is designed to measure, such as a score representing a measurement or calculated statistic for the community. During training, the feature data represents an input to the model, and the corresponding outcome data represents the training targets used to guide the training of the model.

For example, a model can be trained to predict the next day's number of new COVID-19 infections for communities. For training this model, time series data indicating the actual numbers of new infections day by day can be used, along with other collected data. The feature data for an individual training example can represent the state of a community at a point in time, such as information indicating current and prior community disease measures for the community, community characteristics, user behavior patterns in the community, and so on, all reflecting the state of a particular community on a particular day. Different examples can reflect data for different communities and different days. The feature data or that state of the community can be labeled with the corresponding outcome, which in this example is the actual, recorded number of infections for the subsequent day, e.g., the day following the particular day that the feature data describes. A neural network model can be trained through backpropagation or other techniques, feature data as an input to the model and using the corresponding outcome as a training target for the model. As a result, the model can be trained to receive input describing the state of a community on a particular day (e.g., day N) and output a prediction of the number of new infections for the next day (e.g., day N+1). This technique involves an offset (e.g., one day) between the time the input feature data represents and the time the training target or model output represents, and different offsets can be used to predict conditions at different points in the future. Further, no time offset is needed. For example, the input and output may both represent the same time period. A model to predict the disease transmission risk of a location can use current information about the location (e.g., location characteristics, location type, etc.) and other current or recent data (e.g., user behavior patterns, community disease measures, disease prevention measures in place, etc.) to predict a score indicating the current disease transmission risk of the location.

The computer system 110 can include one or more community impact prediction models 1130a that predict the impact of COVID-19 on a community. This can generate a prediction of current effects of the disease on the community, which may be very helpful when data gathering is limited or results are delayed. The impact scores 1121 can additionally or alternatively indicate predicted impact at a future time, such as the next day, the next week, the next month, the next year, and so on, or even an overall permanent or cumulative impact expected.

The community impact predictions can be made for each of multiple different dimensions, such as predicted impact to health of members of the community, the economy of the community, the health care capacity of the community (e.g., hospital utilization and stress on health care providers), and more. To predict the impact scores 1121, the computer system 110 can use a prediction model 1130a that has been trained, based on, the training data of many different communities, to predict a score based on input data indicating features such as community disease measures, community attributes, and current or recent behavior patterns for members of the community. Measures of behavior can take various forms. For example, the computer system 110 can aggregate tracked information about individuals and provide statistics about frequency of travel, types of activities performed, distance of travel, duration of activities, and so on. As another example, the computer system 110 may use the individual behavior data to classify certain behavior patterns into classes, and the class assignments can be used as inputs to a prediction model 1130a. For example, a community's level of use of public transportation may be classified on a numerical scale, or indistinct classes such as high, medium, or low, or statistics about public transportation usage (e.g., number of daily trips for bus, metro subway, etc.) can be provided.

Beyond predicting exposure to COVID-19 and risks or impacts expected, the computer system 110 can also identify hotspots of risk or exposure in a community. These hotspots can be areas where increased or high transmission of COVID-19 has occurred or where it is predicted to occur in the future. For example, the computer system 110 can use records of travel and activities of individuals within a community to identify areas associated with COVID-19 exposure. This can be areas where individuals known to be infected with COVID-19 have been, locations where users having high likelihoods of infection have been (e.g., based on infection likelihood prediction measures rather than diagnostic results for earlier detection and better prevention of transmission), and so on. The information about diagnosed patients and those expected or predicted to have COVID-19 can be used along with behavior data indicating the typical and recent patterns of traffic, travel, activity, and other behavior of people in a community. These parameters, along with other community measures, such as COVID-19 infection rates and other disease measures, can serve as input to a prediction model 1130b. The hotspot prediction model 1130b can be one that has been trained based on examples of disease transmission in this community and preferably many other communities.

The computer system 110 can also make predictions about future disease measures for a community. These predictions can be based on behavior patterns of individual users that are tracked by the system. For example, rather than simply extrapolate from previous infection rates, the computer system 110 can use a community disease prediction model 1130c that takes into account community-specific factors such as distribution of different types of locations, traffic patterns within the community, actual visits of individuals in the community to specific locations, and so on. As discussed above, the training of the model 1130c can involve training data sets that include (i) feature data representing information about the state of a community at one time (including current and prior disease measures at that time) and (ii) a label or training target indicating a desired community disease measure created at a future time. The times of the different examples may be different, but for across all of the examples, the time offset (e.g., difference in the time the feature data represents and the time the label or training target represents) can be consistent. Through the training process, the model learns to predict future disease measures, specifically, measures expected at the a time having the time offset. If the time offset used in training is a week, then the model will be trained to predict the disease measures that will be present a week after the time represented by input to the model 1130c. Examples of community disease measures that can be predicted include values quantifying cases of a disease, hospitalizations for the disease, deaths from the disease, rates or percentages of positive and negative tests for the disease, RO metric (e.g., measure of how many people an infected person infects), etc.

The computer system 110 can also recommend disease prevention measures for a community. For example, given the characteristics of the community and the tracked behavior patterns of members of the community, the computer system 110 can generate a set of input data for a prevention measure prediction model 1130d. The prediction model 1130d can be one that has been trained based on data indicating community characteristics, community disease measures, and the prevention measures, if any, that the respective communities have enacted. The training data can include time series data or other indications of disease prevalence over time, as well as the disease prevention measures used and compliance rates over time.

Through the process of training, the prediction model 1130d learns which disease prevention measures are correlated to changes in disease transmission and other disease measures, as well as the timing of those changes. For example, instructing individuals to wear face masks may reduce disease transmission, but may do so at different rates or different magnitudes of effect for different types of communities (e.g., communities with different combinations of characteristics, or four communities at different stages of an outbreak (e.g., for certain transmission rates, or certain ranges of exposure to the population as a whole, and so on. as preparation for training the prevention measure prediction model 1130d. The computer system 110 can process the available training data and extracted specific examples of instances where prevention measures were initiated, changed, or removed and the corresponding changes in disease measures over one or more times (e.g., the next day, each of the next seven days, the next month, and so on. The model 1130d can be trained using a cost function or objective function that rewards certain types of changes in disease measures (e.g., decreases in transmission rate, decreases in new infection rate, and so on) and penalizes others (e.g., increases in transmission rate, increases in new infection rate, and so on). In addition, or as an alternative, a label or training target can reflect an assessment of how well a given disease prevention measure performed. For example, based on examining collected data and patterns occurring over time, an effectiveness score of 7 can be assigned to reflect how well masks benefited a community at one time. For a data set representing a different community or different situation an effectiveness score of 5 may be assigned, showing that less benefit was achieved. The model 1130d can learn, through training with this type of effectiveness score targets, to predict effectiveness scores along the scale used to create the labels, thus learning how to assign effectiveness scores based on input data when the actual results are not yet known.

The output of the model 1130d can be a value for each of a set of recommend prediction measures prevention measures, (e.g., a score of five for maintaining or implementing mandatory face mask usage, a score of three for closing certain types of locations in the community, and so on). The set of outputs from the model 1130d can indicate the relative predicted effect or absolute effect of enacting the different prevention measures the model 1130d is designed to assess.

The prediction scores for the community can be provided as input to the individual prediction models 230 discussed above. For example, the community impact prediction scores 1121, infection hotspots 1122, and disease prediction scores 1123 can affect the exposure score and infection likelihood score for an individual. For example, high or increasing disease prediction scores 1123 for an individual's community can increase the user's exposure score and likelihood of infection score. As another example, if a user is determined to have visited an area identified as a hotspot of exposure, the information may be used to increase the exposure score for the user. Similarly, a community impact score indicating that hospitals are near capacity may prompt the system to choose more aggressive testing and treatment approaches, for example, to send testing kits earlier or for lower exposure scores to give the community earlier or more comprehensive view of an outbreak.

The individual prediction scores that are based on the community predictions can then be used to personalize testing and treatment. For example, based on the community-level predictions and their effects on individual predictions, the system can initiate disease management actions including sending disease testing kits, selecting or recommending a vaccine, recommending or initiating digital therapeutics, recommending or providing pharmaceuticals or other treatments, and so on.

Figure 12:
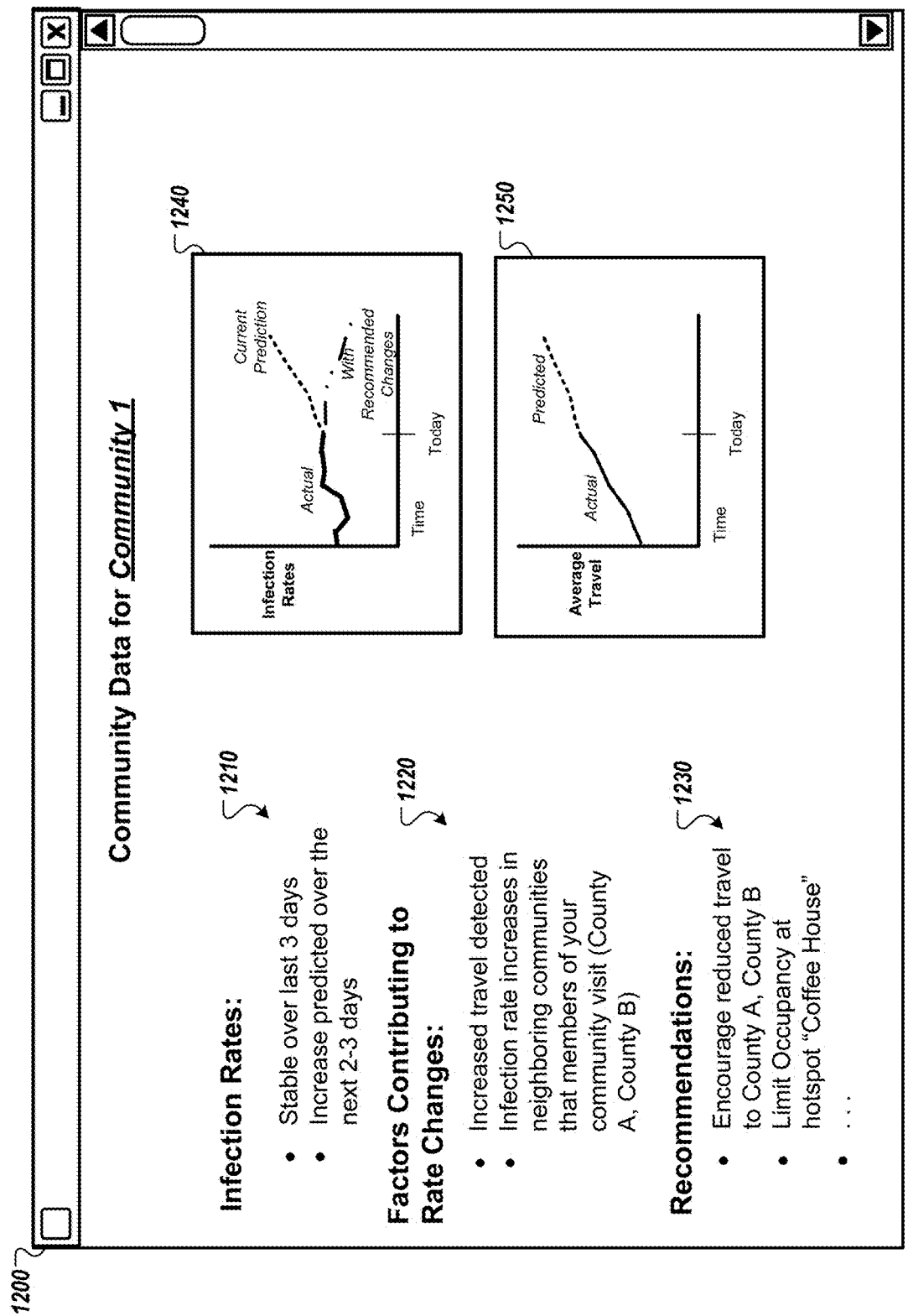
FIG. 12 shows an example of a user interface showing predictions for a community.

FIG. 12 shows an example user interface 1200 showing data determined based on the predictions 1120 for a community. The user interface 1200 can be provided to business or government leaders for the community, to researchers, to members of the community, or others.

The user interface 1200 shows infection rate data 1210 which include data indicating tracked measures of actual infection rates (e.g., stable over the last three days), as well as a prediction of future infection rates (e.g., increase predicted over the next 2-3 days). This information is also reflected in a chart 1240 or other visualization which can show the pattern of change infection rate that is predicted.

The user interface 1200 shows an indication 1220 of factors contributing to the expected infection rate changes. These include the fact that increased travel has been detected in the community and that the infection rate has increased in neighboring communities that members of this community visit. These factors can be determined through analysis of the training data 1131 of FIG. 11, which shows examples of different communities, including their members' behavior and characteristics and resulting disease spreading outcomes. Factors that are correlated to increased disease spread (e.g., increased frequency of travel and infection rate increases in traveled-to locations in this example) can be indicated to users. The user interface 1200 indicates a chart 1250 or other visualization that shows actual and predicted levels of travel for the community, illustrating the factors leading to a prediction of increased risk.

The user interface 1200 includes recommendations 1230 that show recommendations to reduce the spread of COVID-19. These recommendations are customized for the specific community, based on the community's characteristics, the recent disease measures for the community, the geography of the community (e.g., the number, types, and proximities of different businesses and other destinations), tracked behavior of members in the community, and so on. For example, the recommendations 1230 can indicate prevention measures indicated by the scores 1124 of FIG. 11. In this example, the recommendations include encouraging a reduction in travel to two nearby counties with high infection levels and also to limit occupancy at a popular restaurant identified as a disease exposure hotspot. Other types of recommendations, including community-wide recommendations can be determined and provided, customized for the predicted effectiveness of the disease prevention measures given the characteristics of the community, the current community disease measures, the types of locations in the community, the current and historic user behavior patterns in the community, and so on. For example, the recommendations may indicate a level of distancing between individuals, whether masks should be required and for what locations or activities, whether a general stay-at-home instruction should be given, etc.

Figure 13A:
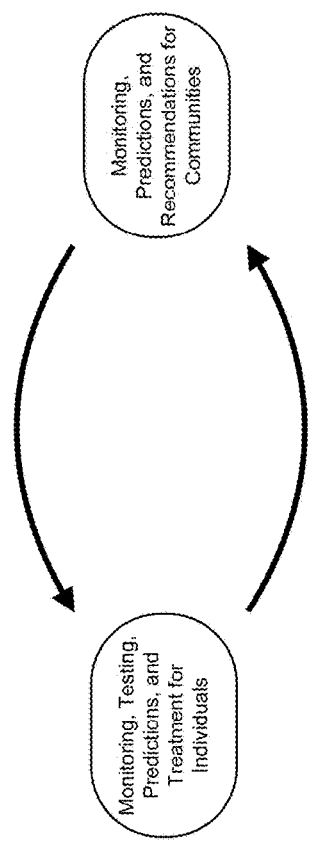
FIG. 13A shows an example of interactions between community-level data collection and predictions and individual-level data collection and prediction.

FIG. 13A is an illustration of the feedback that can occur between community-level data and predictions and individual-level data and predictions. Each can influence the other. Monitoring results from individuals can be used to make predictions about the community. For example, aggregated information about individuals can show the patterns and trends for the community as a whole. Similarly, the exposure risks and predictions about the community, in turn, can influence the level of disease testing and digital monitoring needed for individuals in the community. Community data provides a way to interpret the data factors for individual behavior. The level of travel and social activity of a user can be weighted by the community disease measures, for example. When disease prevalence and infection rates are high or increasing, the system can respond with more aggressive testing and monitoring. Similarly, the system can provide digital therapeutics and even vaccines and medications, based on collected data meeting corresponding criteria or thresholds, to address infections early. For example, certain medications or vitamin supplements can be recommended or even prescribed or shipped to a user based on community exposure levels, as can medical devices, software applications, and more. Thus, all of the community-level factors ultimately affect the diagnosis and treatment for individuals.

In further detail, community-level measures can influence individual risk levels. As discussed above, the predictions of level of exposure that an individual has experienced can be determined based on measures of disease prevalence and transmission in the user's community. For example, the current infection rate measures and/or predicted infection rate measures can influence the prediction of how likely a user has been exposed or is likely to be exposed. This in turn leads to different measures for the user's infection likelihood.

For example, two users with similar behavior patterns may have different exposure levels or risk levels based on differences in their communities. For example, a first user may be in a community where infection rates are determined to be increasing or are predicted to increase. On the other hand, a second user may be in a community where infection rates are stable or decreasing, or are predicted to decrease. As a result, because the communities of the two users present different levels of exposure risk and likelihood of infection even with similar behaviors of the users.

The data collection and predictions for a community and for individuals can interact in different ways. Observations about an individual can be used to select and provide disease management (e.g., treatment, monitoring, and exposure prevention) for the individual, as well as other individuals that the user has come into contact with. In addition, data for a community can lead to disease management for the community as a whole. For example, when community disease measures reach certain reference levels, the system 110 can provide testing kits, surveys, digital therapeutics, mask and distancing policies, and other disease management elements can be provided throughout the community. Data for a community can also be used to select and provide disease management for specific individuals in the community. For example, the system 110 may respond to increasing community disease measures by recommending or providing vaccines or heightened monitoring for users whose measures of susceptibility or disease exposure satisfy certain threshold. Data for an individual can also be used to select and provide disease management for the community as a whole. For example, the positive test of one individual in a community may prompt monitoring, testing, and treatment for some or all others in the community, even if the others were not determined to or likely to have had contact with the individual.

The collected data for one or more individuals can prompt disease management actions for the broader community that the individual is a member of. For example, if a user is diagnosed with COVID-19 (e.g., tests positive or has significant signs or symptoms of the disease), then monitoring and/or treatment for the disease may be initiated broadly throughout the community. In some implementations, the computer system 110 determines and implements treatment for a disease, such as COVID-19, across a community. Consider a case where a students in a class are going on a trip and will be in proximity on a bus, plane, or other setting. The susceptibility of one or more of the students to a disease can lead to a recommendation for vaccination of all of the students in the class. Similarly, if one student show symptoms of the disease or tests positive (e.g., after a trip together or after regular classroom interaction), then treatment may be applied broadly to the entire group, since all were likely exposed together (e.g., due to close proximity, visiting the same locations at the same times, etc.). Thus, in some situations, if one member of a community shows signs and symptoms of disease, treatment can be provided for the entire community, because it is probable that all are infected. A community in this situation can be a class of students, a sports team, a business, a family, or other group of people that is in proximity to each other.

The computer system 110 may select and provide any of a number of treatments for COVID-19 across a community as a whole when an appropriate condition is detected (e.g., one or more community members test positive, have signs or symptoms, have an infection likelihood above a threshold, etc.). Digital therapeutics are a good option, such as interventions to encourage physical exercise, breathing training, posture training, and so on. These interventions can be a low-risk form of treatment that are likely to benefit and not harm users that do not have the disease. These interventions can strengthen a person's diaphragm and chest muscles and help establish habits of deeper breathing (e.g., increase breath volume), which can limit at least some respiratory symptoms of COVID-19. These therapeutics can be especially helpful when in the face masks are used, which when worn may cause some individuals to breathe more shallowly and take fewer deep breaths. As a result, people may not be exercising their muscles to the degree needed to prepare for or overcome COVID-19 infections. Specific digital therapeutics can be evaluated and qualified for treating COVID-19 and its symptoms, and in some cases may receive or require approval from regulatory agencies such as the U.S. Food and Drug Association (FDA).

In some implementations, the computer system 110 may select and recommend a preventive measure, such as a vaccine, across an entire community or a portion of a community, based on planned events or external aspects. For example, even if community disease measures are low in a first community, COVID-19 cases in nearby communities may lead the computer system 110 to recommend vaccinations in the first community. Similarly, if one or more people in a community (e.g., school class, business, sports team, etc.) are planning travel to or activities in an area with high exposure risk, a vaccination, medical device, or treatment may be provided to all of the members of the community. Thus predictive prevention steps and monitoring can be based on planned actions and the exposure that might occur.

Figure 13B:
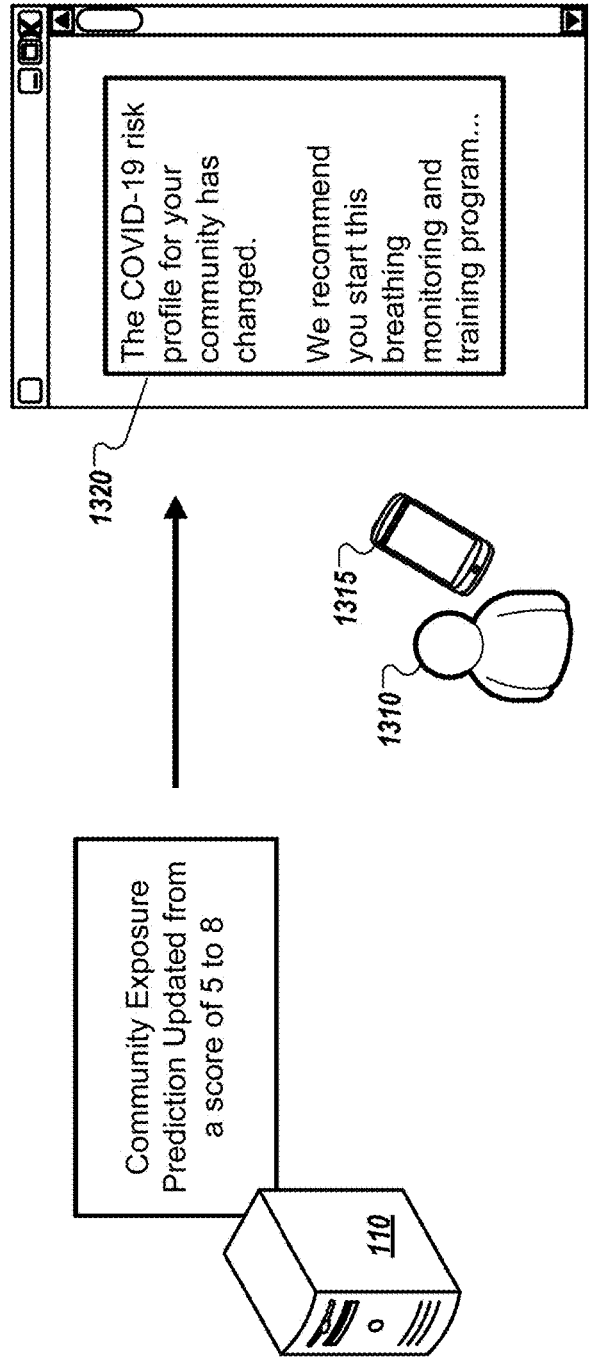
FIG. 13B shows an example of providing notifications to individuals based on community measures and predictions.

FIG. 13B shows an example in which the community exposure prediction score for a community has increased and the system provides an alert to a user 1310 through a device 1315. In this example, the level of exposure in the community has increased, and the system instructs the user 1310, with a notification 1320, to start a digital therapeutics program for breathing monitoring and training. This program can have a multiple goals, such as to detect breathing difficulties at an earlier stage, to strengthen the user's breathing, and to start good habits in the event that the user does contract COVID-19. The computer system 110 and the device 1315, including an application on the device 1315, can cooperate to initiate interventions using the digital therapeutics program, perform monitoring, and take other actions based on the community exposure level.

Figure 14:
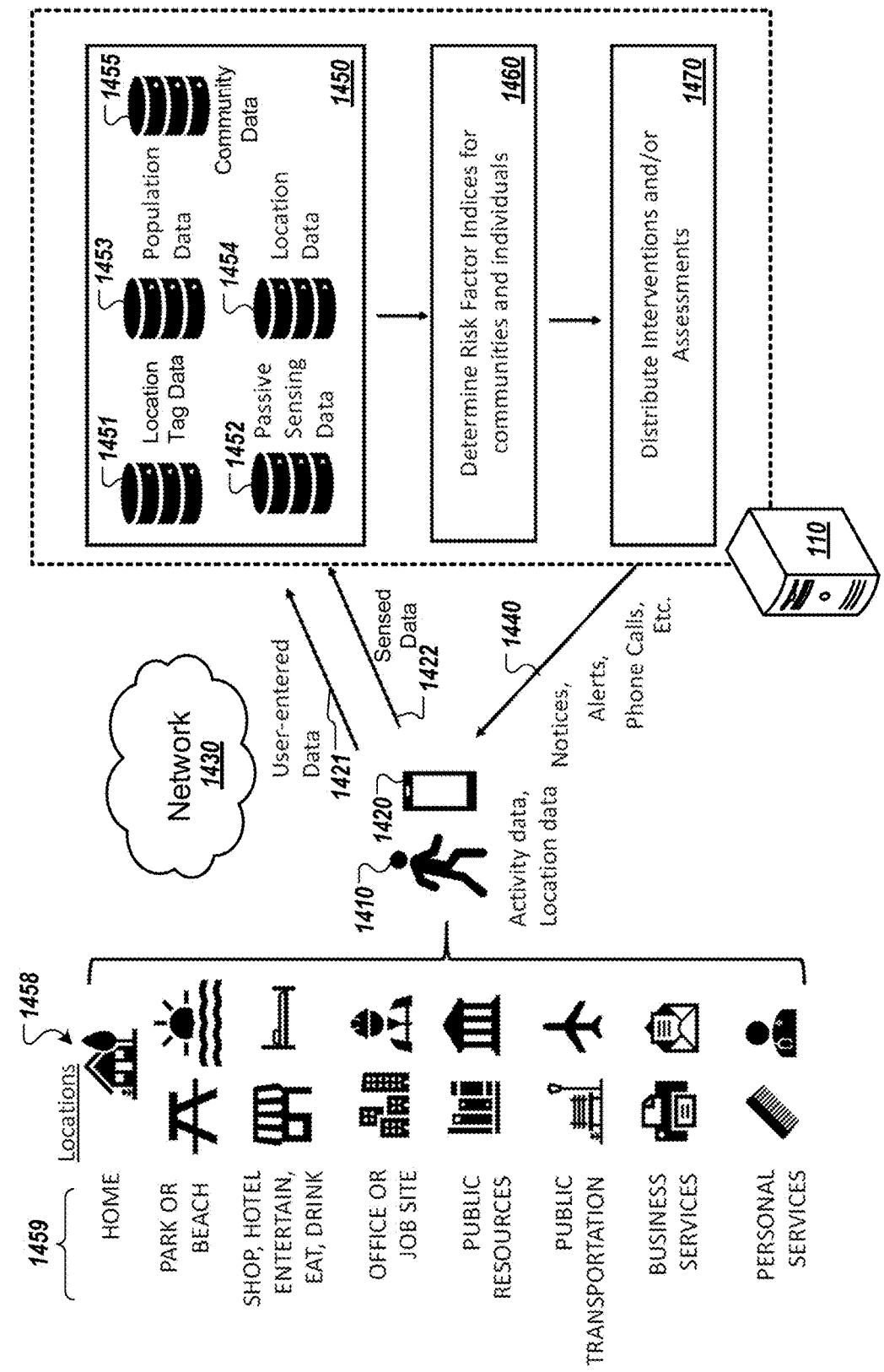
FIG. 14 shows an example of the system being used to use location tracking and geofencing to determine disease exposure risks for individuals and communities.

FIG. 14 shows an example of a system that can use geofencing or other location tracking techniques to monitor and characterize COVID-19 exposure risk. The system can use passive sensing by a mobile phone application to determine COVID-19 exposure risks. The system can alert an individual when behaviors result in significant risks, e.g., when an aggregate level of exposure is reached or when a specific action or condition associate with exposure risk occurs.

In the example, a user 1410 has a user device 1420, such as smartphone or other mobile device. A software application is installed on the device 1420 to enable various interactions with the user 1410, including providing prompts to the user 1410, receiving responses (e.g., inputs and interactions) from the user 1410, providing recommendations, collecting sensor data about the user 1410, and so on. The application sends user entered data 1411 to the computer system 110 over a communication network 1430, which can be a public or private network and can include the Internet. The application also sends sensed data 1422 to the computer system 110. The sensed data can include sensor data or measurement results generated using one or more sensors of the device 1420 or of another device. For example, the mobile device 1420 may communicate another device over a wireless connection (e.g., Bluetooth, Wi-Fi, near field communication (NFC)) to request and receive sensed data 1422, and in some cases can even initiate measurements with the other device. Examples of other devices that can communicate with the device 1420 and provide sensor data or measurement results include a smartwatch or other wearable device, a medical monitoring or treatment device (e.g., a pulse oximeter, a digital thermometer, a glucometer, a weight scale, etc.).

Data can be collected from the mobile device 1420 in a repeated or ongoing manner, e.g., periodically at an interval, on-demand as requested by the computer system 110, in response to a condition being met, etc. In some implementations, data is streamed in substantially real time, such as in response to detecting changes in conditions of a certain type or magnitude, thus providing the computer system 110 a data feed indicating the user's current context, location, activity, and other information so the computer system 110 can detect and respond to the current situation the user 1410 is in. Further, the reported data can be recorded and processed by the computer system 110 to determine the pattern of behavior over time, such as the progression from location to location at different times and the corresponding environmental conditions, user inputs, context data, etc. for those times. While only one user 1410 and corresponding device 1420 are illustrated in FIG. 14, the computer system 110 can receive data from and interact with devices of many different users, including different users in a single community and users in many different communities.

The behavior of the application can also be adjusted through communication from the computer system 110. The computer system 110 can send configuration data, content, rules, or other data that changes a configuration of the application. The computer system 110 can also provide messages that instruct or otherwise cause the application to initiate interactions with a user. For example, the computer system 110 can send transmissions 1440 that cause the mobile device 1420 to present notices or notifications, alerts, recommendations, digital therapeutics interactions, surveys, ecological momentary assessments (EMAs), ecological momentary interventions (EMIs), games, and so on. The computer system 110 can instruct the application on the device 1420 to present specific content (or initiate specific interactions) at specific times or in response to detection of specific circumstances. Examples of interactions that may be provided for users are discussed further below, including interactions to recommend disease prevention actions, to alert the user 1410 to COVID-19 cases or exposure events nearby, to warn the user 1410 of risk levels or risky events (e.g., such as entering an area where COVID-19 exposure has occurred), and so on.

The computer system 110 determines which interactions to initiate and the timing of interactions by evaluating the collected data for the user 1410, including user-entered data 1421, sensed data 1422, health records for the user 1410 (e.g., EHR/EMR), user scores 240 (e.g., predictions for disease exposure level, disease susceptibility, likelihood of infection, and so on). In addition, the computer system 110 can use collected data for other users in the same community as the user 1410, as well as data for the community of the user 1410 generally (e.g., disease measures for the community, demographics for the community, map data for the community, etc.) to select and initiate interactions.

The computer system 110 collects, stores, and uses various types of data 1450. The data 1450 includes location tag data 1451, passive sensing data 1452, population data 1453, location data 1454, and community data 1455. Other data can be stored including user interaction data (e.g., responses to prompts, data entered into forms, application and device usage statistics, etc.), health record data, and so on. The location tag data 1451 indicates location-based records of events and conditions that affect disease exposure. A location tag refers to a record, entry, or data element that corresponds to a specific location, and so a location tag is a record that "tags" or provides information (e.g., an event, condition, status, etc.) for a certain location or region. A location tag can be applicable only for a certain period of time, e.g., a window of time or can apply to a discrete event. There are various types of location tags, and these will be discussed further below.

The passive sensing data 1452 represents data collected through passive sensing techniques, such as without requiring user action to initiate the data capture and often without any output or indication to the user signaling that measurement or data capture has occurred. An example is the automatic capture of sensor data from sensors of a device, e.g., a measurement or output from a GPS sensor, a compass, accelerometer, a inertial measurement unit (IMU), a light sensor, a heart rate sensor, a camera, and so on. The sensors used for data capture can be part of the device that runs the application for data collection and user interaction, e.g., a user's smartphone, or on another device, such as a smartwatch or other wearable device, a medical device, a dedicated sensor, etc. Passive sensing be performed by the application initiating sensor data capture automatically, for example, on an ongoing basis (e.g., periodically at a determined interval) or in response to the application or the computer system 110 detecting a condition (e.g., in response to a change in behavior, location, etc.). Many different types of data can be captured using passive sensing, including location data, environmental data, physiological data, behavior data (e.g., regarding sleep, exercise, physical activity, movement, movement profiles for different tasks or activities, etc.), The passive sensing data 1452 includes the recorded data streams from the various users. The sensor data for each user can be associated with metadata indicating the context in which the data capture occurred (e.g., a timestamp, a location, etc.), as well as a user identifier for the associated user and a community identifier for the user's community.

The population data 1453 can indicate the population level at different locations. This can include measures of population, population density, occupancy, traffic, etc. Population can be determined at a fine-grained level, e.g., for specific regions or portions of a community, such as for different neighborhoods, city blocks, subdivisions, buildings or even for specific addresses.

The location data 1454 can indicate characteristics of different locations in one or more communities. For example, the location data 1454 can include map data indicating where different locations are in relation to each other. The location data 1454 can also indicate location types and other location characteristics, e.g., whether a location is indoors or outdoors, building characteristics (e.g., square footage, year built, type of ventilation system, etc.), occupancy levels (e.g., current, average, maximum, etc.), and so on. A community may include may include locations 1458 of many different location types 1459 or categories. Not only do the locations of different types have differing physical characteristics, the locations of different types are often used for different purposes, and so the patterns of activities and behaviors of individuals at different types of locations vary (and even among locations of the same type), which results in differing disease transmission and exposure risks. The location type (e.g., a category or classification for the characteristics and/or use of the location) of visited locations is one of several factors that the computer system 110 can use to determine the disease exposure risk that individuals face given to their individual activities and travel.

The community data 1455 can include information about various different communities. For example, the community data 1455 can indicate, for each community, a corresponding community identifier, a geographic boundary for the community, demographic data for the community, a classification for the community (e.g., urban, suburban, rural, etc.), and so on. The community data 1455 can also include community disease measures obtained from public health agencies (e.g., CDC, HHS, local governments, etc.) or as aggregations of data collected by the computer system 110 for individuals. Community disease measures can include values quantifying cases of a disease, hospitalizations for the disease, deaths from the disease, rates or percentages of positive and negative tests for the disease, etc. Measures for confirmed and/or probable cases can be collected, and data for different time periods can be stored to show the progression of different measures over time.

With respect to the location tag data 1451, there are different types of location tags for different factors that affect disease exposure risk. For example, one type of tags may indicate population levels (e.g., population density, traffic, occupancy, etc.). Another type of location tags may indicate location types and corresponding different levels of disease exposure risk due to the location types. Another type of location tags may indicate exposure risk due to visits to locations by specific individuals, such as when an infected person may leave infectious particles behind. All of these types, population-based location tags, location-type-based location tags, and visit-based location tags can be used together to quantify past disease exposure, detect and warn of current disease exposure risks, and initiate interactions to limit or avoid future exposure.

Location tags of any or all types can also be associated with metadata that further describes the level or type of risk represented by the location tag. One example is a geofence or geographic boundary indicating the area of influence represented by the tag. Another example, is a disease transmission score that indicates the degree to which entry into the corresponding geofence or area for the location tag increases exposure potential. Similarly, information indicating a vaccination rate for the location (or for the broader community that the location falls within) can be associated with a location tag and may be used to adjust the disease transmission risk. For example, exposure risks based on population and location type decrease as the level of vaccination of people at a location increases, and the calculations of the computer system 110 can take this into account. For example, the disease transmission score for a population-based location tag or location-type-based location tag can be weighted or scaled according to the level of vaccination among people at the location (e.g., either at specific times or generally over a time period). As another example, statistical analysis or machine learning can be used to learn the relative change in transmission risk for different vaccination levels (e.g., the impact of 50% vaccination vs. 60% vs. 70% etc.), to provide evidence-based generation of disease transmission scores reflecting disease transmission risk.

Another example of information that can be associated with the location tags is data describing disease prevention measures that are applicable for the location (e.g., whether masks are mandatory, whether occupancy is restricted, whether distancing of individuals is required, and so on). These measures, and the compliance or adherence of individuals with them, affect the risk of disease transmission significantly. Community data can indicate the disease prevention measures that apply to a location. In addition or as an alternative, the computer system 110 may cause user devices to present questions that ask users about disease prevention measures that are in effect. The computer system 110 may cause user devices to present questions that ask about their own disease management actions (e.g., "Are you wearing a mask now?") and those of others (e.g., "What percentage of people at this location are wearing masks?," "Were there disease prevention requirements for this business?"). The computer system 110 can be configured to ask about any of various preventive measures These types of question can be particularly important to find out about the actions of the person whose visit causes the tag to be created, for assigning disease transmission scores for visit-based location tags. A user can be asked about his or her mask usage at a location during the visit (e.g., through an EMA while at the location) or later (e.g., a day after the visit, in response to determining from a positive disease test result that the user was infected at the time). In some implementations, a machine learning model is trained to provide output of disease transmission scores for a location, based on input data such as one or more of community disease measures, location characteristics, population levels, behavior patterns for the location, disease prevention measures in place, compliance levels with disease prevention measures, etc.

The computer system 110 and user devices can use the location tags to inform users of disease exposure risks. For example, the computer system 110 or the user device 1420 can obtain location monitoring data indicating a location or direction of travel of the user device 1420. When the user is detected to be near a tagged location (e.g., approaching the tagged location, within a predetermined distance of the tagged location, at the tagged location, etc.), the device 1420 provides a notification to alert the user to the current or upcoming risk. The notification can inform the user of the risk presented, e.g., "Approaching a populated area which increases COVID-19 risks," "warning, a person with COVID-19 was here less than 12 hours ago," "movie theaters present a high risk of COVID-19 transmission," and so on. The notification can additionally or alternatively recommend measures to reduce the risk of disease transmission, e.g., "wear a face mask to reduce COVID-19 exposure," "move your visit to after 4 pm when the store is not as busy," "given diagnosed cases of COVID-19 here, it is recommended that you return home," or "Store X has confirmed COVID-19 exposure, try Store Y instead."

In addition to warning users of current and/or prospective disease exposure risks, the computer system 110 can use the location tags to estimate the overall exposure that has occurred for an individual. The computer system 110 can track the locations of users and determine which tagged areas each user enters during a time period (e.g., during a day). The levels of exposure or risk for each event are then aggregated to determine an overall exposure level for the user. Specific instances of high exposure risk can also be identified and indicated to individuals as well as potentially to community health agencies and governments. For example, these high-risk events may be determinations that the visit of a user to a location overlapped in time with, or occurred within a threshold period of time after, a person diagnosed with COVID-19 visited the same location, whether the diagnosis occurred before or after the visit. Other factors can be taken into account, such as whether the paths of movement of the users within the location crossed (e.g., if the two people passed through the same portion of a store), whether disease prevention measures such as masks were used, the duration of the visits, the activities performed (e.g., shopping, exercising at a gym, etc.), the characteristics of the location (e.g., building size, layout, occupancy at the time, etc.), etc.

The analysis of location tracking data and visit-based location tag data can generate result data similar to that of contact tracing, e.g., by providing indications of instances where specific individuals overlap in time and location with other users, but does not require device-to-device communication for users' devices and does not require trained workers to investigate interactions. The present system can also capture high-risk events where there is no overlap in time of visits (e.g., a second user may arrive 15 minutes after an infected first user has left, but the second user may nevertheless be exposed based on residual infectious particles). In addition, the present system can quantify the level of exposure or exposure risk that occurred, based on data that describes the durations of the visits by two users, behaviors and activities during the visits, the period of overlap or amount of time between the visits, characteristics of the location, disease prevention measures in place at the location and compliance with those measures, and so on.

As location information is determined about users, the computer system 110 generates indicates location tags representing visits of users to locations. When a user's device is located in an area for at least a minimum amount of time (e.g., 5 minutes), a visit-based location tag can be automatically generated to represent the visit. Each location tag can have a corresponding record that associates a unique location tag identifier with descriptive data about the visit, such as the location of the visit (e.g., an address, GPS coordinates, etc.), a classification or category for the location (e.g., a business type), beginning time and end times of the visit (e.g., arrival and departure times) and/or the duration of the visit, a path traveled or area covered during the visit, an activity or movement pattern that occurred during the visit, a task performed during the visit, conditions present during the visit (e.g., current occupancy or traffic level during the visit, an indication which disease prevention measures were in effect, a level of compliance with those measures, etc., which may be determined through surveys presented to the user or other users at the location), and so on. Other information can be associated with or linked to the location tag, such as a vaccination rate of people at the location, characteristics of or a reference to a profile of the user whose visit caused the location tag to be generated, etc.

The location tags can be provided for visits by any individual who has the application on an appropriate device, regardless of whether the individual is a member of the community. It can nevertheless be helpful to associate location tags with an identifier for the community of the individual whose visit caused the location tag to be created. The computer system 110 can use this to track the manner in which communities interact and the level of impact that members of different communities have on the disease exposure risk of other communities. For example, the computer system 110 can use the visit-based tags and associated community identifiers to identify other communities that led to disease exposure for an individual or community, as well as the breakdown or percentage of disease exposure that resulted from people from different communities.

As discussed further below, in some implementations, a geofence can be associated with each location tag. The geofence can represent the geographic area in which the visiting user may have spread infectious particles if the visiting user was infected. The geofence may represent a standard area for the location, such as the entire store for a visited store, or a more customized area, such as only a particular region of the store that the visiting user passed through, as determined by GPS data, wireless beacon detection data, etc.

Each visit-based location tag can be associated with a disease transmission score also. The disease transmission score can indicate the extent or magnitude of disease transmission potential that the specific visit by a specific user provides for other users that may concurrently or subsequently enter the geofence area for the location tag. The disease transmission score can be based on various factors, such as a health status of the visiting user, e.g., a COVID-19 diagnostic test result, a diagnosis from a doctor, an infection likelihood score generated by the computer system 110, signs or symptoms of COVID-19 detected by the computer system 110, etc. As the health status is updated for the visiting user whose visit the location tag represents, the transmission score can be updated also. For example, if a user has not been diagnosed with COVID-19 at the time of a visit, but then receives a positive test result the next day, the disease transmission scores for location tags for all visits by that user for a prior time period (e.g., the previous 3 days or 5 days) are updated to reflect the likelihood that the user was most likely infected at the time those visits occurred. The disease transmission score can also be based on other factors that affect the potential that the visit had for disease transmission, such as disease prevention measures of the visiting user (e.g., whether a face mask was worn), the duration of the visit, the path traveled during the visit, the activities performed during the visit, the characteristics of the location, and so on.

Location sensing can be performed using sensors for proximity detection to other areas, locations, buildings, and devices. Global positioning system (GPS) receivers in phones and other mobile devices can be used to determine device locations with precision. As another example, locations can be determined based on mobile phones or devices detecting radio-frequency emitting energy sources such as Bluetooth advertising agents (e.g., location beacons or other mobile devices), Wi-Fi access points, cellular base stations (e.g., cell towers), etc. The strength of signals received and the identity of the transmitters can be used to characterize a location, e.g., to triangulate a position based on relative signal strength between different transmitters. Nearby mobile devices can show relative activity of nearby individuals and population densities present at different places at different times.

The system can receive location tracking data from the devices of many different individuals. Location tracking data, such as GPS data and detected signals from other transmitters provide a stationary fixed point at which to associate users and events. Exposure risks due to visits can be mapped to or associated to these locations using location tags. When a user is determined to have a COVID-19 infection or a high likelihood of infection, the locations visited by that user can be give an location tag to indicate the presence or high likelihood of COVID-19 exposure at that location. Each location tag can also be assigned a geofenced indicating a geographic region estimated to be affected by the exposure event. The geofence can define an area, e.g., a geofenced area, that can be set based on the path of movement of the user visiting the area, for example, whether the user was tracked at only a portion of a store or moving throughout the store. Each location tag can be assigned a timestamp indicating the time the exposure event occurred. The location tag can be considered to be a risk to visitors to the geofence area for some amount of time after the initial exposure event (e.g., visit by a user). The system can diminish the effect or risk represented by the exposure event for different times, for example, by removing the location tag after a predetermined amount of time has elapsed.

Each location tag can be assigned a transmission score, indicating an intensity or severity of exposure estimated to have occurred. This transmission score can be based on a number of factors, such as the location type, the duration of the visit, the activity of the user that visited, environmental conditions, the likelihood of the user having an active COVID-19 infection, etc. The scores can be assigned using machine learning techniques in some implementations, with one or more models that have been trained based on examples of different exposure events and the corresponding disease transmission outcomes. In addition, the transmission score may be diminished or discounted based on the amount of time that has passed from the initial exposure event and a subsequent visit by a different user to the corresponding geofence area. For example, the transmission score may be gradually or incrementally decreased or weighted lower for increasing amounts of time since the exposure event. Thus, a first transmission score may be used to assess the risk of a user that enters the geofence area an hour after the exposure event, a lower transmission score may be used to assess the risk of a user that enters the geofence area two hours after the exposure event, and so on. The transmission score can be weighted or adjusted according to a pattern of equation for aging of location tags, and this pattern can also be determined through machine learning.

As noted above, the computer system 110 can vary the effective disease transmission score or level of influence of a visit-based location tag on the exposure calculation of another user based on the amount of time that has elapsed since the visit that caused the location tag to be created. One way to do this is to assign a base disease transmission score based on the characteristics of the visit (e.g., exposure event) that the location tag represents. Then, when calculating the exposure score for a user based on entering the tagged area, a weight or scaling factor is applied to the tag's disease transmission score to discount or reduce the effect to show lessened risk based on the passage of time. The weight or scaling factor can be based on, for example, the amount of time between the potentially infected user's departure and the subsequent arrival at the location of the user whose exposure score is being calculated.

The aging of tags, e.g., weighting or scaling the scores based on the passage of time, can be dependent on the environment at the visited location. As COVID-19 may be is airborne, additional interventions to quantify and reduce the risk of airborne transmission are delivered with this system. Accordingly, environments with air conditioning, air filtering, or an open-air environment with increased airflow may present lower risk and the disease transmission scores for these locations can be lower than for similar visits to areas with poorer ventilation. Treated air may reduce the aging or time that an exposure risk is present to individuals. A message could be delivered as "This area was recently tagged, perhaps tomorrow would be better for a visit?" or "Remember to wear your mask, and if possible, delay your arrival by 1 to 2 hours."

The system can support social observation of an individual or a community by determining the intersection of geolocation data, data indicating proximity to others, and/or usage behaviors of mobile devices.

In some implementations, the computer system 110 classifies geolocation information to determine and store information about the type of location a user visits, in addition to or instead of the exact location. For instance, knowing that the user is at a pub or a church can be an important cue that could describe social relevance but also an exposure risk potential based on the location type. Likewise, a library or a user's home might show low social interaction and thus low risk. Beyond location type, the computer system 110 may use indications of actual behavior, such as responses to a question such as "how many people did you talk to at the store today?" and sensor data or device-to-device communication data indicating how many other user devices a user was in close proximity with and for how long.

In some implementations, radio-frequency (RF) sampling can help with positional guidance inside of a home when considering Wi-Fi, Bluetooth, and cellular signals. This can give a relative guidance to social exposure indications like being in a public area when GPS isn't shared, and the increase Wi-Fi hotspots or nearby mobile phones and wearables increase or decrease in availability. Signal strength, sometimes called a received signal strength indicator (RSSI), is a key metric collected that describes the relative strength between one device and another device. This can give approximate location information when considering nearby sources, type of radio, and other contexts known about the structure and the population densities ratings for the given location. Building structures, human bodies, and other articles can limit signal strength based on the position of one radio to another. In a free or open air environment, these signals can produce more predictable results. This can further describe a level of accuracy when considering location tag creation while entering or exiting a location and the context of that location. In other words. when an individual's location data is used to tag a location for COVID-19 exposure, that location's quality of data and characteristics describing the location can affect the score for the location tag.

In some implementations, behavioral data from individuals, such as phone activity, can further help in determining if the user is nearby other phones, which can be used as a measure of risk of exposure. For example, phones may transmit wireless messages, such as Bluetooth advertisement messages or beacon messages, which can be received by other phones and used to detect which other devices are nearby and the times the devices were near each other. The computer system 110 can measure changes in phone usage behaviors of users as part of comparative analysis to other digital markers. For example, increased application or screen time usage can be an indicator of decreased exposure risk in some instances.

Various classifiers can be enabled for day-to-day tracking of behavior of individuals, as well as to track behavior patterns and trends for the community more generally. When an individual reports COVID-19 symptoms or a community describes outbreaks, information from the individual or community can be used to create location tags within the server infrastructure to inform other individuals and the community of increased risks in locations or establishments.

To promote and protect privacy, the system can support restrictions on sharing certain privacy-protected "safe harbor" data elements, such as identifiers for individuals or their devices, that are collected during the geofencing and contact tracing process. Once data classifiers are generated, information related to "safe harbor" element are marked for exclusion when transmitting data between individuals to the system for use by the community. Examples of "safe harbor" data elements include individuals' names. Names can be replaced by unique identifier for the purpose of identifying areas of repeated visits of an individual, as well as determining the frequency and timing of visits in association with other individuals who are also identified by their own unique identifiers. The unique identifiers are assigned to the respective individuals but do not reveal the individuals' true names to others in the system. As another example, phone numbers and IP addresses of individuals can similarly be protected. Additional uniquely generated identifiers are generated for tracking repeated access, duration of access, calls made, and other elements as behavioral usage information that deliver context to the individual's unique personal identifier.

Location tags, along with population data, location data, and passive sensing data, are periodically updated for individuals connected to the system and for the community of individuals as a whole. These ongoing data feeds allow the computer system 110, potentially in coordination with another server, to deliver notices, alerts, and phone calls to individuals as methods of intervention, both to a specific individual that may be facing a disease exposure risk and to other individuals in the community.

For example, using the data 1450 shown in FIG. 14, the computer system 110 can determine risk factor indices for communities and individuals (step 1460). For communities, the risk factor indices can be community predictions 1120 as discussed for FIG. 11 or statistical measures based on aggregations of information for individuals in the community (e.g., a count of positive test results, a count of individuals having infection likelihoods above a threshold, etc.). For individuals, the risk factor indices can be user scores 240 as discussed with respect to FIG. 3, exposure scores based on travel to locations with location tags representing exposure potential, statistical measures based on individual data, etc.

The computer system 110 then distributes interventions and/or assessments to individuals based on the risk factor indices (step 1470). For example, if the disease exposure score for a first user exceeds a threshold, an alert or recommendation can be provided to the first user. For example, the user can be warned of the high exposure level, asked about signs or symptoms of COVID-19, and be instructed to remain home for a period of time. In addition, interactions can be provided to other users, such as those that visited a location that the first user visited recently (e.g., in the last 12 hours, or the last day, etc.), or more generally to members of the community as a whole. These interactions may be different, for example, to ask for different types of input to better characterize the risk and pattern of disease spread through the community, as well as to inform and give recommendations regarding individual exposure risks. Similarly, interventions to individuals can be provided in response to community disease risk scores, such as actual community disease measures (e.g., retrospective or current measures based on testing results), predicted community disease measures (e.g., current or prospective expected measures or trends), etc. These interventions can be provided selectively, for example, as community risk levels rise, members of the community having higher susceptibility to COVID-19 can be identified (e.g., based on susceptibility scores 242, user information such age and underlying health conditions, etc.) and warned first or with stricter prevention measures recommended.

Figure 15A:
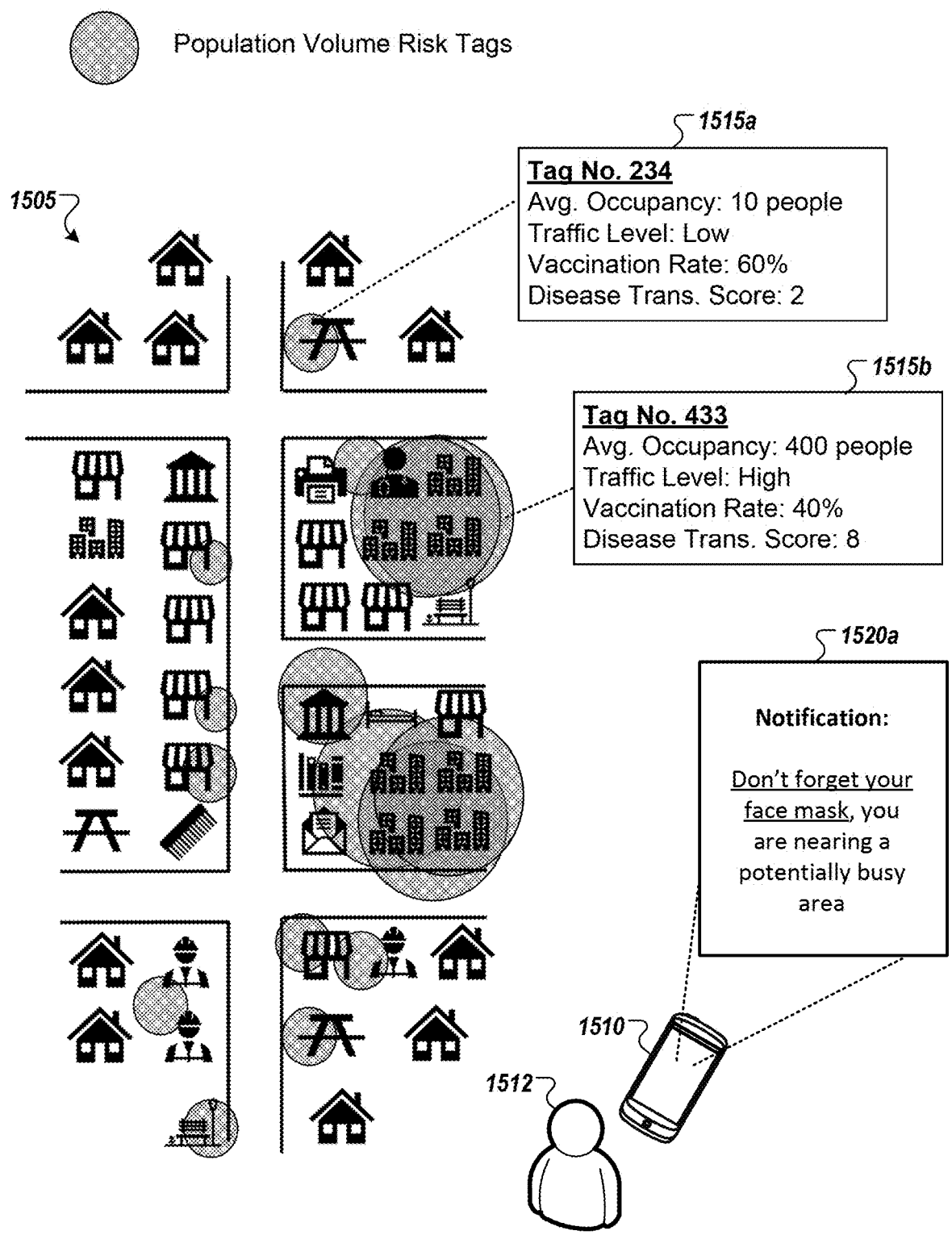
Figure 15C:
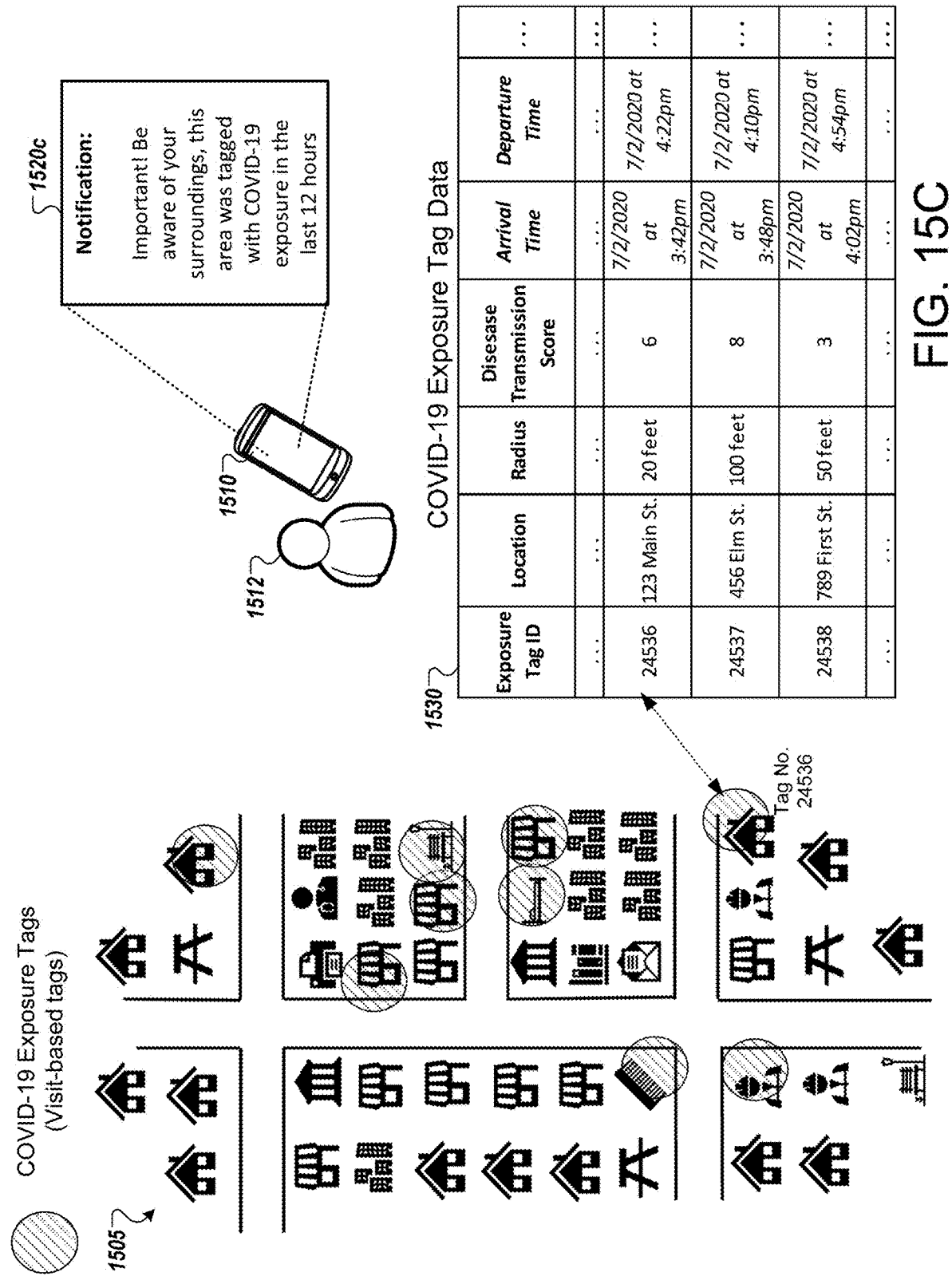

FIGS. 15A-15C show examples of risk identification strategies to assessing risk through population volume, location types (e.g., business types), and COVID-19 exposure events. These types of risks and others can be represented as location tags, e.g., records or data entries associated with locations, that indicate risk factors for disease transmission or spread that are applicable to particular areas. In many cases, these tags can done on a fine-grained scale, such as by address, by building, by portions of buildings (e.g., specific rooms or portions of buildings), by custom areas defined with a radius or a custom boundary, etc. Although the areas for which tags are applicable are illustrated as circles, they may instead have other shapes, e.g., polygons, irregular shapes, the shape of a building or other property, etc. In FIGS. 15A-15C and 16A-16D, examples are provided for a particular community, for which a basic map 1505 is shown to represent the locations in the community.

The location tags can be used for various purposes. One is that entry into the corresponding area (e.g., geofence) for a location tag can prompt a notification to the user that enters the area. The figures show various examples of notifications that can be shown, for example, to warn a user of potential exposure risk, to inform of exposure that has occurred, to recommend preventative measures, etc. The notifications for different figures can be provided independently or can combined with those of other figures. Notifications can be provided by an application on a user device 1510, e.g., smartphone, of a user 1512 in response to the application or the server system 110 determining that the user device 1510 entered the geofence of a location tag (e.g., based on user-reported location data, responses to surveys, based on GPS data, cellular tower identifiers, detection of wireless beacon messages such as Bluetooth advertisement messages, etc.). Along with determinations of and notifications of previous, current, prospective, and cumulative exposure levels or exposure risk, individuals can be provided recommendations and other interventions determined based on those exposure levels, such as recommendations for disease prevention measures, vaccines, behavior changes, disease treatment, and so on.

Another use of the location tags is to track and report instances or actual or probable exposure to COVID-19, whether detected contemporaneously or after the fact. This can provide contact tracing data that does not require communication between user devices, does not require human contact tracers to question individuals about their contacts, and can capture exposure that occurs when two people visit the same location but are not present at the same time. This type of exposure information may be provided to individuals as well as to public health agencies and governments.

Another use of the location tags is to determine the overall exposure level or risk level at which an individual has been exposed over a period of time. For example, the aggregate level of exposure due to different tagged areas a user has entered can be determined and used to provide personalized recommendations and treatment for a user.

Another use of the location tags is to identify the areas of high disease transmission risk, for example, disease transmission hotspots. These can be determined by aggregating the tag data for a location, e.g., the number of tags, types of tags, and/or disease transmission scores for the tags applicable to a location. The areas with single-tag or aggregate disease transmission scores exceeding a threshold, or a set of those that have the highest scores in a community, can be identified as high-risk areas for disease transmission. As another example, the actual exposure resulting at a location (as opposed to potential for exposure) can be determined by aggregating disease exposure scores for visits of users to locations, to quantify the level of exposure that occurred. These disease exposure scores can also be used to identify hotspot locations In FIG. 15A, various areas are tagged based on population levels. The population can refer to the typical occupancy and/or traffic to those areas. Locations with high populations and/or high traffic (e.g., high turnover in the set of individuals present) can be determined to present higher risk of disease transmission. The population data can come from information reported by businesses, by individuals that visit the locations (e.g., who can be asked through the application on their devices how many people are present at different times), census data and other public records, and so on.

The figure shows examples of various tags, where the size of the tag (e.g., the radius of the circle in this case) represents the area that the tag applies to, the population level, the disease transmission score, or a combination of these or other factors. The area can represent the area enclosed within a geofence for the tag. Associated data 1515*a*, 1515*b* for two example tags is shown. Each location tag can be associated with information such as average occupancy at the location, a traffic level at the location, a vaccination rate for individuals at the location (and/or an immunity rate to include people who have acquired immunity through contracting and recovering from COVID-19), and an overall disease transmission risk score due to the population level and population movement patterns at the location.

The figure also shows an example of a notification 1520*a* that can be provided on the device 1510 in response to entry of the device 1510 to the geofenced are of one of the tags having a disease transmission score (or other characteristics, such as typical number of people present) meeting a threshold or other criteria. In this case, upon entering the area of a tag such as tag number 433, the user is reminded to wear a face mask because the user is nearing a potentially busy area.

In FIG. 15B, location types are determined for different locations, and locations of a type that has high risk for COVID-19 transmission are associated with exposure tags. Certain businesses or other locations are arranged in or are used in ways that lead to greater COVID-19 transmission risk. The location types for location-type-based tags can be determined based on map data, online databases, business directories and public records, reported data from users or business owners, etc. The example shows associated data 1516*a*, 1516*b* for two of these tags, such as the type of location (e.g., doctor's office, hotel, etc.) and a corresponding disease transmission score. Upon entry of the geofence area of one of these tags, or more generally in response to proximity to one of the tagged locations, a notification 1520*b* can be provided, such as the one shown that encourages social distancing due to the presence of a high-risk business type.

In FIG. 15C, incidents of COVID-19 exposure or potential exposure are tagged with location tags. These can represent visits by people who have been determined to have active COVID-19 infections through diagnostic testing. In addition, or as an alternative, these may represent visits by people who, although not yet receiving a positive test result, have other factors (e.g., physiological data patterns, machine learning prediction scores, etc.) indicative of high infection. In some implementations, visit-based tags are only generated and used to contribute to the disease exposure of others when a person has tested positive for COVID-19, has been diagnosed with COVID-19, and/or has at least a minimum likelihood or confidence score of being infected. Nevertheless, location tracking data can be saved for several days for all users, and if a positive test result is later received for a user, location tags can then be created based on the visits made during the previous days, to represent the exposure the user caused even before being tested.

The size, shape, location, and other properties of the geofenced area for a visit-based location tag can be based on the properties of the visit by the user, such as the duration of the visit, the path or area traversed by the user during the visit, and so on. Each location tag can be associated with information about the visit, the location, and/or the user whose presence the tag represents. Table 1530 shows records for several visit-based location tags, with each row representing data about a location tag for a different visit. Information such as a tag identifier, location corresponding to the tag (e.g., GPS coordinates, street address, etc.), radius or other size of area affected, a disease transmission score, an arrival time that starts exposure, a departure time when the user causing exposure leaves, and so on. Other information can be associated with a tag, such as a type of activity the user performed, a path of movement during the visit, whether the user wore a mask or took other preventative action, etc. A single location may have multiple different visit-based tags, representing visits at different times and/or by different individuals. An example notification 1520*c* warns a user that the area the user has entered a location (or is near the location, e.g., within a threshold level of proximity) has been tagged with COVID-19 exposure.

FIG. 16A shows locations where different individuals or groups reside. In the example, there are four individuals or groups, represented as (1) through (4). Individuals can be clustered into groups for data sharing purposes, such as a family or a home, or for association purposes, such as a treatment group. This allows the ability to identify and process correlated data within a larger set of individuals, similar to the analysis for a sub-study within a larger research study. Relationships with other individuals can be exposed in a way that can help describe disproportionate risk and elevated notifications and precautionary measures to deliver to individuals. This can be especially useful when individuals have the potential to cross paths with some individuals at a high frequency and others at a low frequency. The computer system 110 can track and identify the frequency with which different individuals and groups interact, and use this information in determining exposure risks as well provide this information to the individuals or groups or public health agencies.

FIG. 16B shows an example of tracked paths travelled by the users through the community over a period of time, such as a day. The paths shown can represent paths determined through passive location tracking, active questions to users about their activities, or other techniques. The paths that users travel, and the activities that their paths and destinations represent, can be used by the computer system 110 to determine the exposure risks (e.g., general potential for exposure) and exposure levels (e.g., amount or frequency of actual and/or probable exposure to the disease). The paths of individuals and other location tracking data is also used to determine the overall behavior patterns of users in the community generally, which can be used to compare to the behaviors of users in other communities and determine predictions of disease spread, hotspot locations, and other data as discussed with respect to FIG. 11.

For each individual, e.g., (1) through (4), the health status and exposure is tracked. For example, for users (1) and (4), no symptoms or signs of COVID-19 are reported for the current day. For users (2) and (3), some symptoms of COVID-19 are reported.

FIG. 16C shows the overlay or combination of risk factors for population levels, location type, and COVID-19 exposure. This represents how the risk factors and tag types are all used together to determine individual and community risk and exposure levels. The figure shows the population-based tags of FIG. 15A, the location-type tags of FIG. 15B, and the visit-based tags of FIG. 15C overlaid together on the map 1505. Note that the first two types, based on population volume and location type, are indicators of general risk for exposure, while the visit-based location tags can represent actual or probable exposure at an area. The number of these tags clustered together, as well as the individual and aggregated disease transmission scores for the tags, can show where hotspots for disease transmission are. Two example hotspots are shown as regions 1610 and 1615.

Figure 16D:
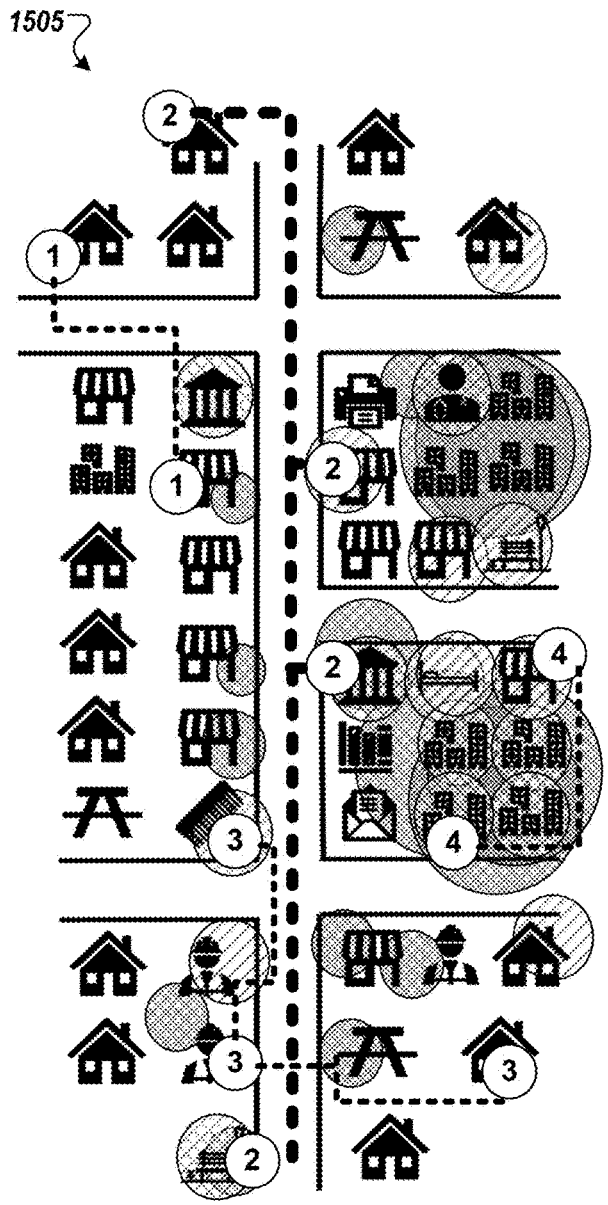

FIG. 16D shows the combination of all of the risk tagging information as well as the paths of travel shown in FIG. 16B. The computer system 110 uses all of this information to assess the personalized exposure levels or risk levels for the different individuals of groups, as well as to determine personalize notifications for the users. For example, taking the paths of travel of the individuals (1) through (4), the computer system 110 can determine which geofences corresponding to location tags that each individual entered. The computer system 110 then examines the data for the corresponding tag, and the information about the user and the nature of the visit to that area, to determine whether the entry to the location represents an event that justifies a notification or other intervention (e.g., sending a testing kit, scheduling a vaccine appointment, adjusting monitoring done using passive sensing and/or active engagement, etc.). In some implementations, certain criteria about the nature of the entry to a geofence may be used to filter out low-risk visits. For example, the computer system 110 may require a minimum duration of time in the geofenced area, a minimum level of activity or movement in the geofenced area, a motion profile that differs from certain excluded motion patterns (e.g., simply driving through or walking through an area), etc.

The analysis of and notification about events that present exposure risk can be done in real-time, e.g., in response to entry to or proximity to one of the geofenced areas and while the user is still in the geofenced area. The analysis and notification can also be done retrospectively, e.g., at the end of the day, to assess the overall exposure and risk for that day. Examples of notifications 1620a-1620d are provided, where the notifications inform the different individuals (1) to (4) of their respective COVID-19 exposure risks for the day. Exposure scores, information about specific locations or instances of exposure, recommendations about prevention of future exposure, community-level disease information and predictions, and other information may be provided with these or other notifications.

As discussed above and also further below with respect to FIG. 20, the contribution of exposure risk or exposure received from different tags can be combined to generate an overall disease exposure score for a visit and/or for a period of time (e.g., which may include multiple visits to different locations). The computer system 110 can retrieve the disease transmission scores for location tags that a user entered during a certain period of time, or other information characterizing the type of exposure and/or level (e.g., severity, intensity, duration, etc.) of exposure at the different locations visited. The computer system 110 can then aggregate the different risk contributions for multiple tags, e.g., using a summation, a weighted summation, processing by a machine learning model, an equation of function, etc. The aggregated information can be used to determine an overall exposure score for a visit or a time period, which can then trigger different notifications or interventions, such as recommended disease management actions (e.g., for prevention, monitoring, diagnosis, treatment, etc.).

The location tagging and disease exposure scoring of the computer system 110 can be used to identify and quantify the disease transmission potential of different locations, e.g., disease transmission hotspots. FIG. 11 showed an example of using a predictive model 1130c to predict which locations are or are likely to become hotspots of increased disease transmission potential. The computer system 110 can additionally or alternatively use the aggregation of information about location tags for a location to determine the current level of disease transmission risk at the location. Comparing the aggregated measures for different locations allows the computer system 110 to identify hotspots having the highest transmission potential. The aggregated measures themselves can be individually compared to threshold or reference to determine whether they represent a risk level that warrants labeling as a hotspot and initiating warnings or other notices.

In addition, the examples of aggregated disease transmission scores for locations, (along with other information about user behaviors, location characteristics, etc.), can be used as training data to train the predictive model 1130c. For example, the system 110 determines time series data indicating the location-tag-based aggregate disease transmission scores for a location for different times, e.g., each day over a period of time. The disease transmission scores can be used as a label or training target for the set of information that describes the location, community, user behaviors, and so on at the time corresponding to the disease transmission score. Using many instances of scores for different locations having varying characteristics, the model 1130b can be trained to predict transmission scores for locations based on community and location characteristics, allowing transmission scores to be determined even when location tagging data is not available for a location. Similarly, the training may incorporate a time offset between the time of the input data and the time of the training target, allowing the model to predict the disease transmission score at a time in the future. In addition, the examples showing instances of different or changing risk levels, and the corresponding changes in situation that caused them (e.g., adding a certain disease prevention measure, removing a disease prevention measure, changes in user behavior, etc.) can incorporate into a model relationships between different conditions or actions and the effects on disease transmission risk.

In some implementations, the computer system 110 uses information about different types of disease status in generating location tags and corresponding information such as transmission scores. In particular, the system 110 can assign and use more classifications of disease status than simply whether an individual is infected (e.g., has an active case of COVID-19) or not. The more fine-grained classifications can be used by the system 110 to generate more accurate, personalized measures of disease transmission risk, infection likelihood, and so on.

As an example, COVID-19 status classifications can include whether a person is: currently infected (e.g., active case of the disease); previously infected (e.g., has recovered from a prior case of the disease); vaccinated against the disease; not vaccinated and not infected; and unknown. Within these classifications, there may also be sub-classifications. For example, active cases of COVID-19 may be further classified according to the stage of the disease, such as early stage (e.g., 0-4 days from infection), progressive stage (e.g., 5-9 days from infection), peak stage (e.g., 10-14 days from infection), or late or recovery stage (e.g., 15 days or later). Classifications may be made based on one or more of likely number of days since infection, physiological measures, disease symptoms present, the severity of symptoms, or other factors.

The ability of an infected person to spread infectious particles can vary significantly over the progression of COVID-19, often being rather high at the earliest stage, even before symptoms appear. The computer system 110 can take these differences into account when assigning disease transmission scores corresponding to location tags. For example, the disease transmission score for a visit by a person determined to have an early stage case of the disease can be higher than the disease transmission score for a visit by a person determined to have a later stage of the disease when less transmission potential is expected. In addition, a person determined to have an early stage infection compared to a late stage infection may have location tags set to indicate transmission potential for different periods of time, e.g., transmission potential for the previous 4 days for an early stage case, or for the prior 10 days for an intermediate stage case. As another example, the amount of viral shedding may correspond to the type and severity of symptoms, and so the disease transmission score can be based on the symptoms, or symptom classification, of the user. In addition, the difference in disease transmission potential may vary for reasons other than biological effects. For example, people with early stage infections may be more active and less careful than those with later stage cases, who are more aware of their risks and whose activities are restrained due to disease symptoms.

The computer system 110 can estimate the differences in potential for disease transmission for different stages or symptom profiles using the data collected for many cases of infection and subsequent spread. For example, contact tracing data and data generated from location tagging and geofencing can provide examples of how likely people having different disease stages are to spread the disease to others. With techniques such as statistical analysis or machine learning, the computer system 110 can determine the differences in disease transmission for different disease case characteristics (e.g., symptoms present, time since infection, type of treatments being administered, patient attributes, etc.). For example, the computer system 110 can examine the rate at which different location tags representing visits by different types of disease cases result in new infections, and then adjust the disease transmission scores for later-generated location tags with the relationships learned. As another example, the computer system 110 can use clustering algorithms, such as K-means clustering, to group data sets by similarities, and then use the clusters as indications of combinations of factors (e.g., disease stage, symptoms, patient characteristics, etc.) that represent different levels of transmission risk. In addition or as alternative, the computer system 110 can receive and use third-party research or measures that specify different levels of disease transmission potential for different In addition, vaccinated individuals may be further classified by the type of vaccine used, number of vaccine courses received, whether vaccination is complete or partial (e.g., whether courses are still remaining), an amount of time since vaccination (e.g., less than 1 month, 1-6 months, 6 months to a year, greater than a year, etc.). Vaccination status and prior infection status can have a large impact on a person's ability to become infected and to infect others. Thus vaccination status can be used to generate predictions such as a user's susceptibility to the disease and the user's current likelihood of infection. These factors are also used to calculate the potential of a user to infect others, e.g., as specified by the disease transmission score for a visit-based location tag. The protective effect of vaccination or a prior case of the disease may decline over time, however, and so the amount of time elapsed since infection or recovery can be a factor in determining the susceptibility of an individual, the current infection likelihood, and the disease transmission score for a visit to a location.

In some implementations, the computer system 110 can store and use information indicating whether individuals have been vaccinated for a disease, such as COVID-19. Vaccination status can be obtained from, for example, electronic medical records, insurance claims data, or from asking individuals in a survey or other interaction through the application on the user device. Location tracking data can then show where people are at different times, allowing the system 110 to determine, for different locations and at different times, the percentage of people who are vaccinated. Not all people present at a location are likely to be participating in the data collection and tracking program, and not all people will have a suitable device, or have it powered on, etc. Nevertheless, the tracking data that is available can be used as a sampling of the population present at a location, and the percentage among those tracked can still be a valuable estimate for the percentage at the location generally. Vaccination statistics for a community as a whole may also be obtained, such as from public health agencies.

The vaccination rate at different communities and for different locations within a community can be used to customize the disease exposure levels calculated. For example, a population-based location tag for a location where 80% of people present are vaccinated will present a much lower risk than a population-based location tag for a location with a similar population density but only a 30% vaccination rate. Accordingly, the vaccination rate at a location that a user visits can be used to weight or scale (e.g., to decrease) the contribution of population-based location tags to a user's disease exposure score. In some implementations, location tags can be associated with data vaccination rate data for the location, e.g., a vaccination rate measured for a certain day, week, or other time associated with a tag. In other implementations, a dynamic, time-varying vaccination rate is determined, e.g., based on the variation in the sets of people coming and going to result in different vaccination rates at different times within a single day. For example, for calculating the exposure risk contribution of a specific visit at a specific time, the computer system 110 can use the vaccination rate for the location at the time of the visit or for a time window including the visit (e.g., a 2-hour window in which the user visited the location).

Figure 17:
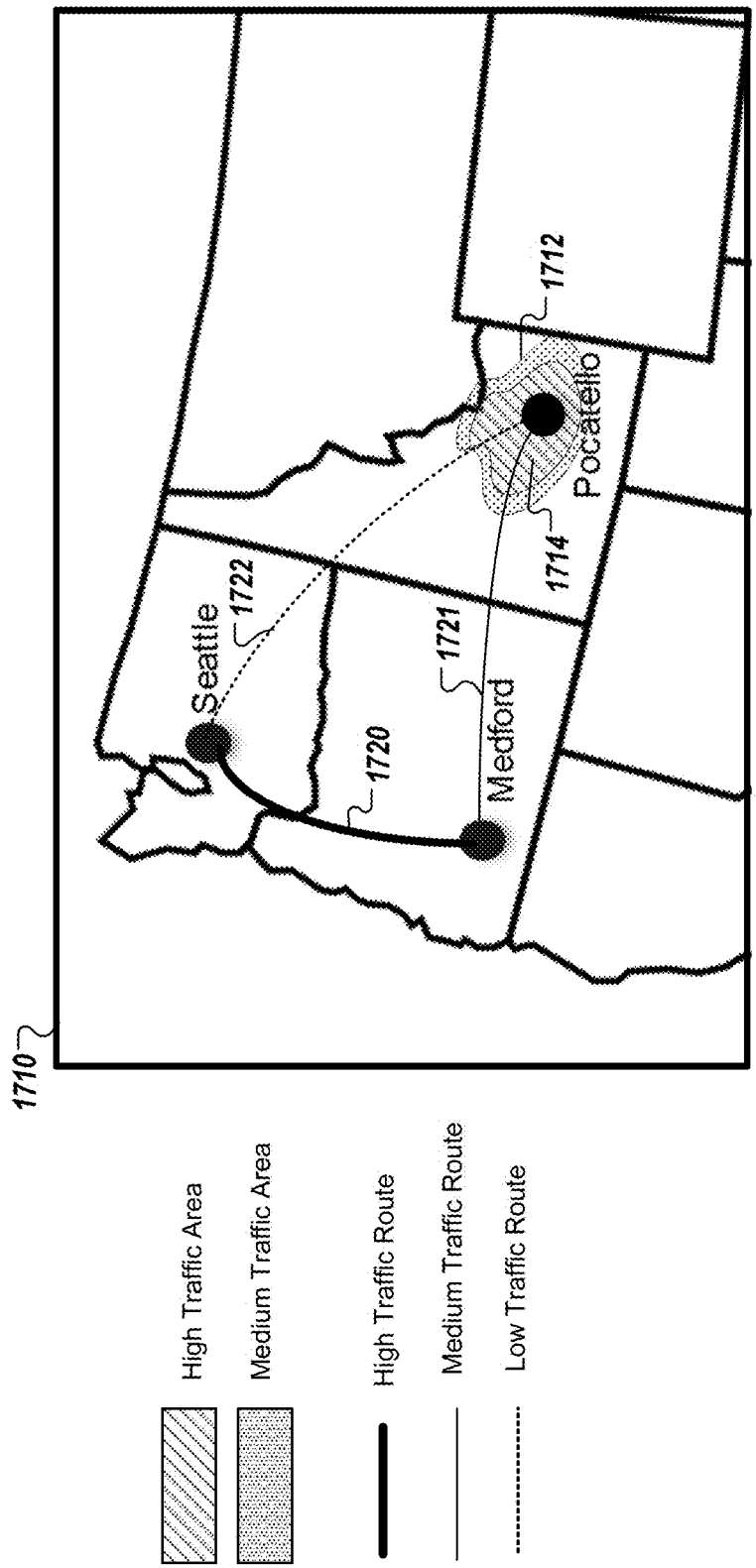
FIGS. 17 and 18 are examples of maps showing travel monitoring and location tracking data used by the system.

FIG. 17 shows an example of traffic data that the computer system 110 can use for analyzing traffic patterns for communities. In addition to assessing travel within communities, the computer system 110 can analyze travel of individuals between communities and how it impacts the spread of disease and the effectiveness of different disease prevention measures. The example focuses on travel patterns relating to the city of Pocatello, Id. The figure shows a map 1710 with different areas 1712, 1714 showing different levels of traffic in the area around the city. The map 1710 also shows different travel paths 1720, 1721, 1722 between different cities. These areas 1712, 1714 and paths 1720, 1721, 1722 represent an aggregation of tracked location data (e.g., tracked through sensor data capture, such as GPS, and/or through user-reported data) over a period of time such as a day, a week, a month, etc. The different levels of traffic for different areas and different paths represents different levels of connection or disease transmission risk among different areas.

The computer system 110 can use the travel information to calculate or predict how disease measures in one region or community will affect the disease measures in another community. For example, the disease measure predictions for Pocatello can be adjusted based on the disease measures for Medford and Seattle based on observed travel patterns from these locations to Pocatello. Nevertheless the level of influence that disease measures of Medford and Seattle have different levels of influence on disease measures for Pocatello, due to the different amount of travel to and from these cities with Pocatello. In other words, travel between Medford and Pocatello is more frequent or more regular than between Seattle and Pocatello, so Medford's disease measures impact those of Pocatello more than do the disease measures of Seattle.

Figure 18:
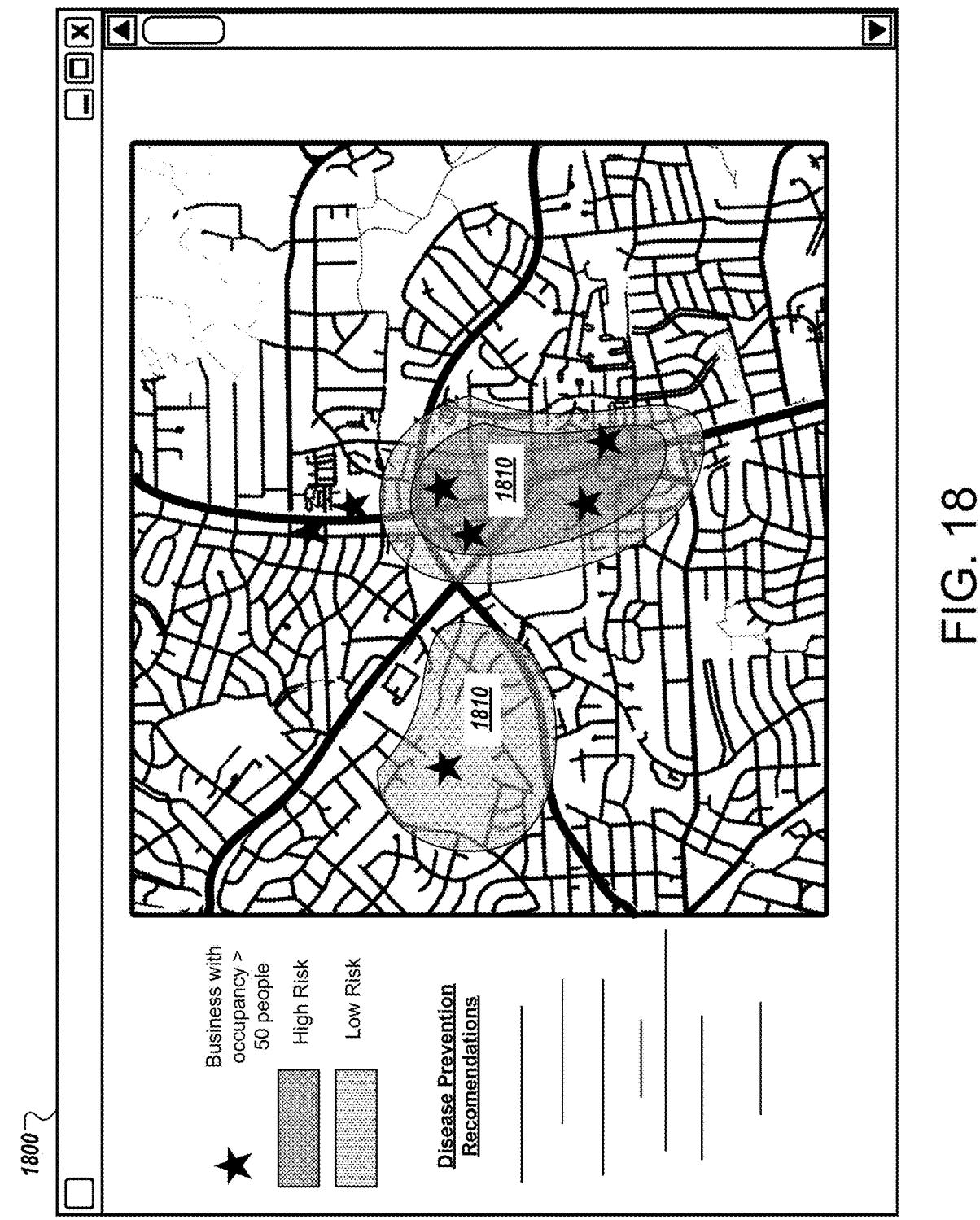

FIG. 18 shows an example of a user interface 1800 showing sample data of a map that can be provided to a user, such as a member of a community, a business owner, a government worker, a member of a public health agency, etc. As shown, hotspots of disease transmission 1810 or disease prevalence can be indicated, along with different affected businesses or other locations, as well as disease prevention recommendations.

In addition to the tools discussed above, the computer system 110 provides support through a suite of individual and community management tools. These can be provided to contact tracing staff, communities and businesses, health care providers, public health agencies, governments, and other individuals and organizations. These tools can be used to manage communication with individuals and data access and sharing.

The computer system 110 can provide a population data management tool, such as user interfaces (e.g., in an application, web application, web page, etc.) or application programming interfaces (APIs) that support adding or retrieving population data for communities and locations. Various techniques can be used to request, track, and update population data, including prompts to users and responses, passive tracking, census information, and so on.

The computer system 110 can provide COVID-19 community exposure data management. This can include providing user interfaces and APIs that enable adding and retrieving information related to COVID-19 for communities, such as information about disease exposure or transmission events, disease cases (e.g., confirmed, probable, active, resolved, etc.), treatments applied or ongoing, hospitalizations, and deaths.

The computer system 110 can provide location classification and business context data management. The computer system 110 can provide user interfaces and APIs for managing building information and traffic-related information. This can include entering and retrieving information about locations, such as a number of individuals allowed (e.g., maximum occupancy), typical occupancy, business size, operating hours, environment, air conditioning, outdoor seating capacity, and type of business.

The computer system 110 can provide adjustment of tag data (e.g., to implement the aging or progressive decrease in impact of visit-based location tags over time) and path tracking data management. The computer system 110 can provide user interfaces and APIs for receiving and providing information about factors that affect the progression by which the influence of location tags decreases over time. Examples of these conditions include conditions at the location of a location tag, conditions at surrounding areas, whether the location an open area or an enclosed space, a level of airflow or ventilation, environmental information such as humidity and moisture levels, sanitization procedures at the location, and so on. Due to variation in the characteristics and conditions at different locations, the decrease in impact of an exposure event can vary for different locations. For example, location tags for different locations may respectively persist for 48 hours, 16 hours, 1 hour, or other lengths of time, depending on the environment at the location and characteristics of buildings at the location. The location tag no longer contributes to the exposure risk of a person visiting the location after the end of the persistence period. The disease risk presented over the persistence period of a tag may also diminish according to a pattern, e.g., a linear decrease, an exponential decrease, etc.

The computer system 110 can provide notification messages and alert management. The computer system 110 can enable support for generating and sending various types of messages through the application on users' devices or through other communication channels. The types of messages can include predictive messages (e.g., indicating predictions for an individual or the individual's community), risk notifications (e.g., alerting users to contact with a person that has contracted COVID-19 or an area where an infected person is or has been), messages regarding anticipated future risks, messages educating or instructing users of disease prevention measures (e.g., face masks, social distancing, etc.), warning users of current or future exposure risks, informing users of changes in risk levels (e.g., for the individual and/or for the individual's community). In many cases, the system 110 is configured to automatically alert or educate users about the risks occurring from associated interactions with specific individuals, with other individuals or groups of potentially unidentified individuals, and in the community generally.

The computer system 110 can provide case management tools. The computer system 110 can provide user interfaces and APIs for managing appointment scheduling for individuals and health care systems. The system 110 can facilitate management of healthcare staff schedules, automatically assign specific cases to staff members to promote efficient staff management, provide additional information about individuals when available from data from previous interviews, and provide elements to escalate a case to emergency services in situations where interviewees require immediate assistance. Additionally, the system can provide a logical model for communicating with participants, where the state of an interview or evaluation process can be saved, so that interactions can be seamlessly restarted if a contact (e.g., someone identified as having or likely to have had contact with a person with a case of COVID-19) is later identified to present with a case of COVID-19, or if a case is reopened for repeated infection.

The computer system 110 can provide consent management tools. Individuals may be required to provide consent in order to participate in a research study, community health initiative, information gathering program, disease monitoring or treatment program, etc. The computer system 110 can provide user interfaces and APIs for individuals to provide consent through a digital interface (e.g., via email, application, website, or SMS text message) or via phone engagements.

The computer system 110 can provide configurable identity protection. As workers collect sensitive personal identifying information (PII), the system 100 reduces unnecessary exposure of staff to PII by restricting the number of situations where PII of contacts are exposed to interviewers.

The computer system 110 can provide contact deduplication. As contacts are reported by multiple COVID-19 positive interviewees, the system ensures that contacts who are already assessed are not scheduled for unnecessary repeated assessments.

The computer system 110 can provide contact tracing script management. As public health staff begin contact tracing by notifying exposed individuals of their potential exposure as quickly and sensitively as possible, the system 110 improves the quality and efficiency of these engagements.

The computer system 110 can calculate dates for disease onset and quarantine periods of time. This can assist contact tracing staff and interviewees so they do not need to calculate onset dates or recommendations for quarantine periods. The calculation of disease onset dates can be based on the symptoms reported by users, physiological and behavioral data collected through passive sensing, incidents of interaction with other individuals and locations presenting exposure risks. For example, the location tracking history for a user and geofence entry information can indicate one or more likely times when a person came into contact with the SARS-COV-2 virus. In addition, the timing and pattern of symptoms the user reports (e.g., breathing difficulty, headache, etc.), or which are reflected in physiological monitoring data (e.g., temperature, heart rate, heart rate variability (HRV), etc.), can be indicative of the stage of disease at the times the symptoms and physiological measurements were reported. Using reference data (e.g., patterns, guidelines, models, etc.) that aligns symptom progressions and physiological changes to disease states, the system can align the individual's pattern of symptom progression with that of the reference data to estimate a time of infection. When contact tracing data or potential exposure event data is available, the comparison with reference data can be used to select which of different exposure events most likely led to the infection. The reference data can be learned from training data for disease progression for many different people, e.g., through statistical analysis, machine learning, etc.

The computer system 110 can provide scripts (e.g., a series of prompts, guided dialogues, questions, etc.) to assist in recalling any potential close contacts during time periods where they have been infectious, which can assist recall and improve the quality of interaction. The computer system 110 can customize scripts that limit unnecessary questions to contacts, using adaptive logic to ask comprehensive questions only when higher order questions identify the need. For example, the default script can include an initial set of basic questions each targeted to a different subject area, and when a user provides a response indicating a risk or uncertainty, the system can expand the set of questions to ask more detailed questions in the corresponding area. Similarly, when available data indicates that data is already collected is sufficient to rule out a risk or meets a collection need, further questions can be skipped. Scripts can be shared with other agencies, teams, and processes to improve standardization for data collection and ensure expedient convergence on common data elements as yet unpublished within the hub/spoke model. Forms are designed to increase the speed of data entry to limit the inconvenience to interviewees and improve interviewer efficiency. Scripts can take into account the regional guidance of local participant contexts to ensure consistency with each jurisdiction. The computer system 110 can facilitate collection of preferred contact information across multiple modes of communication including phone, email, SMS, and mobile application push notification, where possible. The computer system 110 can provide direct support for installation of contact tracing mobile applications and for distribution of digital health wearables for participants who consent to this data collection. The computer system 110 can provide proximity reporting tools that allow for interviewees to report information such as a dates, times, physical locations, and characteristics of exposures.

The computer system 110 can provide tools for privacy management. Disease cases, contacts tracked by the geofencing and contract tracing system, and any other data collected or generated can be associated with (e.g., linked to or annotated with) information about how data is collected, how long it is stored, and how it is to be used. Additionally, if requested, the computer system 110 can provide secure login capability to participants, to enable individuals to update their information at a later date (e.g., after initial enrollment and consent). Similarly the system can provide interfaces or functionality allowing participants to delete their personally identifying information and request no further contact. Additionally, the computer system 110 can be assessed by a publicly-accessible auditing process to ensure that participants can be provided evidence of trustworthiness, security, and privacy. In some implementations, access to collected data is limited to research staff (e.g., study staff working with data for a cohort of individuals in a research study) and public health authorities in key jurisdictions, and can be restricted by role or be available on a need-to-know basis only.

The computer system 110 can provide tools for contact assistance. The computer system 110 can provide tailored educational materials to engage with both COVID-19-positive interviewees and individuals who may have been in contact with them. The materials can be directly provided via in-application notifications, device notifications, text messages, email, or paper mailed directly to participants directly. Additionally, these materials can be made available on a public website, can be used by interviewers in direct conversations as necessary, and can be provided in mobile applications for participants with eligible devices. The materials are updated in real-time as new data emerges, so that contact tracing personnel do not need to be continuously educated. This multi-modal approach enables staff to expediently transmit information efficiently (e.g., in less than 30 seconds, in a single button press, to transmit information to a de-identified person). For example, the computer system 110 can provide different types of messages or interactive forms, which a user can select among so that the message or interaction can be provided to a specific individual or a group of individuals, potentially to a whole community. The messages can include content to: inform individuals of their risk; instruct individuals to separate themselves from others who are not exposed; monitor themselves for COVID-19; inform individuals about transmission risks to others even when non-symptomatic; provide valuable, tailored, self-quarantine support that encourages individuals in contact with an infected person to stay home, monitor their physical health, maintain social distance, and provides guidance on the safest way to procure necessary supplies; provide treatment articles, equipment, or medication; provide support materials for mental health issues encountered during a quarantine period due to contact with infected person or generally.

In addition to or instead of providing content for users to manually select and send to others, the computer system 110 can include mapping data that associates different conditions with corresponding messages or interactions to send to users whose situations meets the conditions. The computer system 110 can evaluate collected data for individuals on an ongoing basis, detect when one of the conditions is present, and automatically send to a user a message of the type that the mapping data indicates as corresponding to the condition. For example, the mapping data may indicate that a message informing a user of exposure risk and an instruction to self-quarantine for 14 days should be provided when a user is exposed to COVID-19. When an exposure event is detected, such as using location tracking and geofence data to identify that a person visited a location at the same time or shortly after an infected person, the corresponding message can be automatically selected and set to the user's device for presentation. The conditions for sending messages or interactions can be based on one or more of the various types of data collected and generated by the computer system 110, including predictions for individuals, predictions for the community of an individual, physiological data, behavior data, sensor data, user interaction data or user input data, medical records, and so on.

Figure 19:
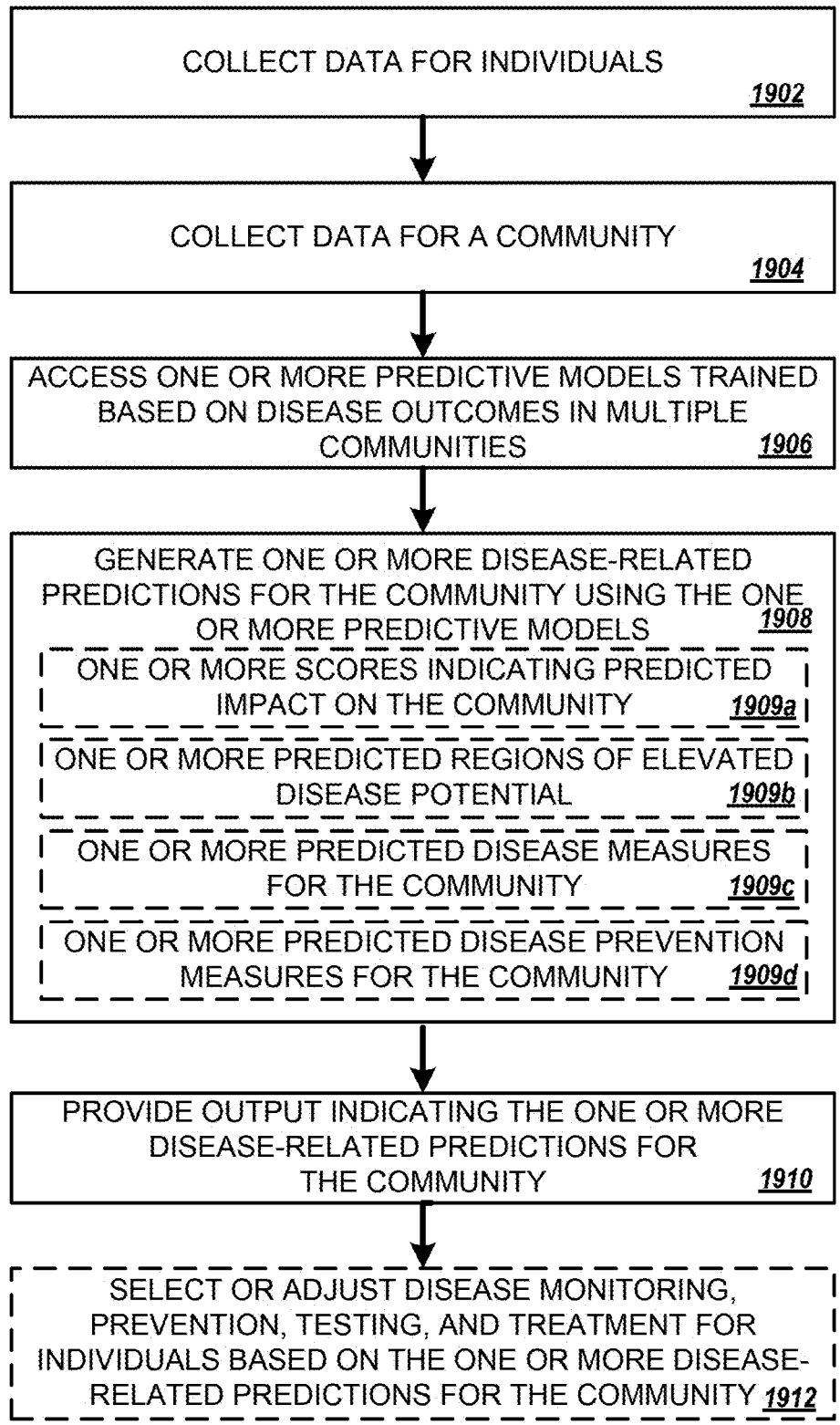
FIG. 19 is a flow diagram showing an example of a process for generating disease-related predictions for a community.

FIG. 19 is a flow diagram showing an example of a process 1900 of generating disease-related predictions for a community. The process 1900 can be performed by one or more computers, such as the computer system 110. In general, the operations of the process 1900 can be performed by one or more servers, one or more client devices, or a combination of them. In addition to the operations illustrated, the process 1900 can optionally include other operations discussed with respect to FIG. 11. In the example, the disease mentioned can be COVID-19, or it can be another infectious disease.

The process 1900 can be used to leverage the rich data set that the system 110 collects about individuals in a community to provide various types of information for the community. As discussed above, the predictions and recommendations about the community can be used to provide better disease monitoring, diagnosis, testing, and treatment for individuals in the community.

As discussed above, the system 110 can collect information about individuals such as physiological data, behavior data, medical records (e.g., EHR/EMR), sensor data from mobile devices and medical devices, and more. The system 110 can also obtain information about individual communities, such as demographic data, map data showing the locations and location types in the community, and disease measures in the community. With the community data and the individual data for members of the community, the system 110 can make predictions and recommendations that are tailored for the characteristics of the community. For example, the data about individuals can be used to better characterize and predict the current and future disease measures for the community, the risks and impacts of the disease on the community, the current and future "hotspots" of disease transmission, and preventative measures most likely to be effective for a particular community, e.g., taking into account the actual behavior patterns of members of the community, the geography of the community, and other community-specific factors. By tracking behavior of members of the community, and by detecting responses or behavior changes of members of the community over time (e.g., as social distancing policies change, as public health interests increase and decrease, etc.), the system 110 can provide accurate and useful predictions and recommendations that are customized for actual conditions in a community.

As one example of the types of predictions that can be provided, the process 1900 can be used to identify or predict regions of high disease transmission potential. The training of the machine learning models allows the system 110 to make predictions about current and/or future hotspots of disease transmission, e.g., regions where high or increased levels of disease transmission are likely to occur. Importantly, the predictions can be determined based on behavior data for individuals (e.g., location tracking data, self-reported location data, activity data, etc.), which can show the actual, current behavior patterns of people with respect to the locations being evaluated. This can often allow very timely, up-to-date predictions, for example, with same-day results or even real-time updates as monitoring data is received. The predictions can be based on information about specific locations (e.g., the business type, occupancy measurements or patterns, type of building or physical conditions, etc.). The predictions can also take into account other factors such as community disease measures, disease prevention measures in place, and more.

Unlike many systems, the hotspot identification can be based on more than simply tracking where past transmissions occurred. While contract tracing data and data indicating actual disease transmission events is helpful and can be used, that data is often a lagging indicator, often not available until days after transmission occurs and the transmission risk of the location is elevated. It also depends on rapid, widespread accurate disease testing and significant investment in contact tracing, both of which are not always available. Similarly, location type is a significant factor but on its own does not account for the differences of each location and actual use of the locations, and so may not be an accurate measure of disease transmission risk. For example, two locations may both be classified as grocery stores, but may have vastly different disease transmission potential due to factors such as different levels of traffic, different physical layouts resulting in different in-store proximity, different proximity to population centers, and so on.

The present techniques allow for more accurate predictions customized for the characteristics of a community, for disease transmission hotspots and other predicted items. For example, the use of actual behavior patterns for individuals in a community and the characteristics of individual locations allows higher accuracy. As another example, the predictions can take into account the disease preventions measures (e.g., masks, social distancing, occupancy reductions, etc.) that are in place and the compliance level for those measures (e.g., the percentage of people actually wearing face masks when recommended or required). The present system can use additional or different factors as inputs to identify and characterize hotspots, often well before traditional retrospective-focused techniques indicate a potential risk. As a result, the present system provides an improved technique to identify (i) regions are currently regions of increased disease transmission potential for a particular disease, such as COVID-19, as well as (ii) regions that are predicted or expected to become regions of increased disease transmission in the future. The models can be used to generate scores that quantify or classify the levels and types of risks presented by different regions.

In many cases, the system 110 also allows predictions of hotspots without requiring contact tracing between individuals. Optionally, contact tracing data can be used as an input to the process when available. Also, contact tracing data, if available, can be used to train machine learning models. Nevertheless, even without contact tracing data, and for communities where contact tracing is not robust or reliable, the machine learning models and other techniques can use the learned relationships between behavior patterns and other data (e.g., location characteristics, community disease levels, community demographics, geography, etc.) to predict how a disease may spread in the community and the extent or risk of spread at specific locations.

The process 1900 includes collecting data for individuals in a community (step 1902). Various users in a community can have a software application installed on their mobile devices, e.g., cellular phones, which facilitates sensing of data on an ongoing basis as well as interactions with the user. The application can request information from a user, through interactive forms, surveys, ecological momentary assessments (EMAs), etc., and provide the responses to the computer system 110. The application can also facilitate monitoring of user behavior, such as through capture of sensor data. The data collection can obtain any of various types of information about a user, such as behavior data (e.g., data indicating location, movement, activity or task being performed, etc.), physiological data, mood and mental health data, and more. Data collected for a user can be associated with a user identifier for the user, so that the computer system 110 can organize and group the data received for each individual.

Collected data for individuals monitoring using sensors of a device of a user, such as sensors of a phone, smartwatch or other wearable device, medical device, or other device. This can include collecting data using wirelessly connected devices, such as a pulse oximeter, digital thermometer, weight scale, or other device that provides sensor measurements to a user's mobile device. This monitoring can include tracking the locations of individuals, using a GPS receiver or received signals from cellular base stations, Wi-Fi access points, Bluetooth beacons, other mobile devices, etc.

Collected data for individuals can also include user interaction data, such as responses to questions and other prompts provided by an application at the user's mobile device. For example, surveys and EMAs can ask users about the user's health and current situation, and responses are collected and reported to the computer system 110 over a network. The computer system 110 may send instructions or content causing mobile device applications to prompt users, such as to ask certain questions or request certain types of data from users. The information request of users can include, among other items, information describing a user's current location, conditions or context at the current location, a current activity of the user, the user's plans for subsequent actions, the user's health status, physiological measurements for the user, and so on.

Collected data for individuals can also be acquired from other sources, such as electronic health records (EHR/EMR), a device of a physician or health care provider for a user, devices of friends or family of a user (e.g., who can be prompted regarding the user), etc.

The process 1900 includes collecting data for a community (step 1904). The computer system 110 can be designed to collect data for, and provide predictions and recommendations for, many different communities. For clarity, the process 1900 emphasizes actions for one community, but the process 1900 may be repeated for any of many communities that the computer system 110 is configured to monitor and assist.

As discussed above, a community can represent a group of people. For example, a community can be defined as a group of people associated with a predetermined geographical area, such as a state or province, a county, a city, a zip code, a neighborhood, etc. The community may be the group of people that reside in the area, the group of people that work in the area, a group of people that work or reside or otherwise visit the area, etc. The computer system 110 can store data that defines and describes different communities. The stored data can associate a unique community identifier for each community and data describing the criteria for membership in the community, e.g., geographical boundaries of the community and other features of the community. A community may be defined independent of a geographic area, for example, such as the members of a certain organization, individuals in a certain profession, a set of people that have visited a geographical area within a certain time (not necessarily permanently residing in that area), etc. In various examples below, a community refers to the individuals in the community can be those that reside in the corresponding geographical area. Different communities can refer to different geographic areas and the people who reside in them, for example, different cities, counties, neighborhoods, zip codes/postal codes, etc.

Examples of the community data that can be collected for the community include map data or geographical data, community characteristics, community policies, and community disease measures. Any or all of these types of community data can be determined for a community to make a prediction for the community, as well as for other communities so the community data can be used as training data for predictive models. This information can be requested and received from public databases, map data services, and other sources. The map data or geographical data can include data indicating the locations in the community, their location types (e.g., business types, such as grocery store, shopping mall, library, etc.), the distances and spatial relationships of locations, roads, and other geographical aspects of the community. The community characteristics can describe properties of a community for different dimensions or aspects, such as population size, population density, demographic characteristics (e.g., population measures by age, sex, race, ethnicity, economic status, income, education level, etc.), urbanicity (e.g., a degree to which the community is urban), classifications for the community (e.g., urban, suburban, or rural), prominent industries in the community, percentage of residential vs. commercial space, and so on. The community characteristics can include characteristics of population structure for the community, such as population size, geographic distribution of the population, and composition of the population. The community characteristics can also describe measured of demographic processes for a community, such as measures of fertility, mortality, and migration. The community policies can indicate rules or regulations of the community, including disease preventions measures that may be recommended or required (e.g., social distancing of a certain distance between individuals, stay-at-home isolation, wearing of face masks, etc.). Community disease measures can include, for example, indicators for a quantity of cases of a disease, hospitalizations for the disease, deaths from the disease, rates or percentages of positive and negative tests for the disease, etc. Measures for confirmed and/or probable cases can be collected.

The community disease measures can be provided in various forms, such as cumulative values over time, values for individual time periods (such as a most recent day or week), time series indicating different values for different times, etc. The community disease measures can data provided by public health agencies at the national and/or local levels, e.g., data from the Center for Disease Control (CDC), U.S. Department of Health and Human Services (HHS), state-level public health departments, etc. Community disease measures can also be provided from hospitals, clinics, physicians and other sources. In some cases, the computer system 110 may compile some community disease measures from the collected data from individuals, such as self-reported data and health record data that may indicate when users began showing symptoms of the disease and when and if positive disease test results were obtained.

In general, the data collection steps 1902 and 1904 are performed repeatedly, e.g., continually in an ongoing manner. For example, new information can received, and in some cases requested, hourly, daily, or at another appropriate frequency. In some implementations, the monitoring data and user interaction data for many different individuals can be provided as a data feed or data stream collecting reports in substantially real time as the data is collected.

The process 1906 includes accessing one or more predictive models trained based on disease outcomes in multiple communities (step 1906). For example, the a predictive model can be trained based on training data that describes (i) a plurality of different communities (e.g., includes community data for the communities as discussed above) and (ii) behavior patterns and disease outcomes of individuals in the different communities over time. The model can thus be one that has been trained, based on the relationships indicted by the training data examples, to indicate how characteristics of a community and behavior patterns of members of the community affect the disease outcomes (e.g., geographical spread or distribution of disease cases, number of disease cases, rate of change of disease cases, severity of symptoms, number of hospitalizations, number of deaths, community disease measures, etc.) for a disease. The data describing the community can be any of the aspects of community data discussed above (e.g., community characteristics, community policies, community disease measures, etc.).

The data that describes behavior patterns can indicate behaviors of individuals separately or show an aggregate measure of how individuals in the community act. The behavior data can describe, for example: characteristics of travel within or outside of the community (e.g., as determined from location tracking data, self-reported location information, etc.), including modes of transportation used, common destinations or types of destinations, and so on; activities performed by members of the community (e.g., jogging, shopping, attending movies, working, etc.); sleep behaviors; diet, such as what users are eating, how much, and when; exercise levels and types of exercise; medical treatments and appointments (e.g., what treatment steps are taken for the disease or other disease, whether they are visiting the doctor and how often, etc.); and so on. For all of these types of behavior, the data can indicate characteristics such as the frequency, duration, timing, level of consistency or regularity, etc. of the different behaviors. When training a predictive model, the computer system 110 may take records of behavior of many individuals, and determine from those records the patterns or behavioral characteristics that are most common or most representative of the community, then use the patterns as features provided to the model. Similarly the input to the model may be features representing aggregate measures for different behavioral aspects, e.g., an average number of hours of sleep per night for members in the community, an average level of exercise (e.g., step count, miles walked, etc.), an average number of public areas visited daily or an amount of time spent in public areas daily, etc. More complex distributions showing the variation in behavior measures among members of a community and over time may additionally or alternatively be used.

The training data for the model can indicate disease outcomes for individuals and their corresponding disease outcomes of the individuals (e.g., whether the individual became infected, what symptoms were reported, the duration of disease symptoms, whether the individual was hospitalized, needed ventilator support, or died, etc.) In particular, the models can be trained with data about the disease outcomes of individuals and/or communities over time, in other words, the patterns, changes, and progressions of community disease measures over time. Similarly, the training data can indicate behavior patterns of individuals over time, allowing the model to learn how different types of changes in behavior of people in different types of communities affects the changes in disease outcomes.

As discussed with respect to FIG. 11, the computer system 110 can store various community prediction models 1130 (e.g., models 1130a-1130d) that are trained to make various predictions 1120 current and future items for a community. These can be machine learning models that have been trained based on examples of a diverse set of communities and behavior patterns and the corresponding infection rates for the disease or another disease.

As an example, the computer system 110 can capture data describing various communities, the behaviors patterns for individuals in those communities, and community disease measures showing the spread of COVID-19 in those communities over time. With these examples, the computer system 110 can train a machine learning model, such as a neural network, to predict any of various results of interest. This can include predicting the disease outcomes for a community (e.g., rate and extent of the disease spreading) either at the present time or at a future time (e.g., a predetermined time such as a day, a week, or a month in the future. Another prediction that the models can be trained to provide is an expected impact of the disease, e.g., a speed, magnitude, or extent of change to economic indicators, hospital utilization and other infrastructure indicators, and other outcomes in the community.

The training data can include explicit or implicit data that indicates, for each of the training examples, the type of measure the model is being trained to predict. For example, if a model is trained to predict future disease measures a week later, the training examples can include a dataset showing a "snapshot" of the state of communities at certain times, each with the corresponding disease measures a week later. In other cases, the model may learn from implicit outcomes, such as training data providing example data sets that show examples of communities, changes in disease prevention measures, and resulting disease outcomes. While these do not explicitly specify which disease prevention measure was best for each community at each time, the training process can nevertheless teach a model to prefer or score higher disease prevention measures that produced better community disease measures in different situations. With a cost function or objective function structured to do this, a model can be trained to receive community data and (i) output a prediction of the community disease measures that would produce the best results, and/or (ii) score the expected effectiveness or results of different community disease measures, given the patterns reflected in the training data.

As another example, the computer system 110 can use the collected data to train a model to evaluate the infection transmission risks presented by different locations and behavior patterns. The computer system 110 can use the tracked and/or self-reported behaviors individuals (e.g., indicating items such as locations and activities of individuals) and their subsequent disease status (e.g., symptoms, infection likelihood scores, disease testing results, etc.) as examples. The data sets used in training can indicate the nature of a user's visits to different locations, such as activity performed, duration of visits, conditions at the time (e.g., level of traffic or occupancy at a location, whether face masks were worn, prevalence of the disease in the community at the time of the visit, etc.) and other behavior information. The many examples showing user interactions at different locations and subsequent outcomes (e.g., whether users contracted the disease or not) can be used to estimate the levels of disease transmission risk for different locations.

As an example, the system 110 can determine a correlation between visits to different locations and subsequent contraction of the disease by individuals that visited the location. The system 110 can further determine the correlation between contracting the disease and the different properties of a location, a community, and user behavior. For example, the model may learn and incorporate into its training that smaller convenience stores with high traffic and longer-than-average visit durations may have elevated disease transmission potential. As another example, the training may incorporate that, based on the example, sporting goods stores have high transmission potential when one movement profile or in-store behavior profile is detected, but have low transmission potential when a different set of behaviors is typical. Thus, a model can be trained to predict the disease transmission risk or disease transmission potential for a location given the location's characteristics and the characteristics of the surrounding community and the behaviors and characteristics of members of the community.

Note that in addition to or as an alternative to training based on patterns of individual behavior and individual disease measures, the aggregate behavior patterns of individuals across a community can be used. For example, the numbers of people at different stores or locations and the correlation with changes in disease measures can indicate which locations have greatest potential for transmission. A public park may show an great increase in the number of people visiting in a day or number of people present at a time, but there may be no corresponding increase in disease transmission over time, which can teach the model that the park is not a high risk for disease transmission. On the other hand, if examples show that grocery stores reducing their hours or occupancy are followed by resulting community disease measures that indicate reduced rates of disease spread, this can show (accounting for other variables and conditions in the community) that the grocery stores are likely areas of disease transmission and that the changes in use of the location were an effective disease transmission measure.

The process 1900 includes generating one or more disease-related predictions for the community using the one or more predictive models (step 1908). For any of the predictions, one or more predictive models trained to predict that type of output can be used. The model can be provided a set of input data, such as a feature vector including feature values for each of various types of data that the model was trained to process during training. The input data can include values indicative of characteristics of the community and of individuals in the community. Data regarding individuals provided as input to the models can be provided in an aggregated form to represent typical or general patterns of behavior or user attributes, through aggregations such as averages, minimum and maximum values, etc.

The input values for the predictive models can be tailored to the level of prediction needed. For example, to evaluate the disease transmission potential of a particular location (e.g., a specific store in a community), data indicating the characteristics of the store and behavior patterns at that particular location can be provided, in addition to or instead of community-level features. A model trained for the purpose would receive the same types of data in training to be able to process this type of data. As another example, a model may receive community-level characteristics and behavior patterns to evaluate the effectiveness of different disease prevention measures for the community generally. Nevertheless, a different model may be trained and configured to receive location-specific characteristics and behavior patterns for individual locations (e.g., often along with community-level characteristics and behavior patterns), in order to provide scores indicating the effectiveness or suitability of different disease prevention measures for each location individually.

The predictions can be of any of various types. For example, a model can be used to generate one or more scores 1909a indicating a predicted impact of the disease on a community. As another example, a model may be used to provide output indicating one or more regions 1909b predicted to have elevated disease potential. For example, a neural network or other model can be trained to receive information about a location, and output a disease transmission score indicating a level of risk that that location poses for transmitting the disease. The input can indicate current or typical attributes for the community and for behavior patterns of users at the location, allowing the prediction to be tailored for the specific conditions at the specific location at a specific time—including the way user are monitored to be behaving with respect to the location. The output for the model can be a disease transmission score for a location, where the score quantifies a risk level for or predicted level of disease transmission at the location, given the characteristics of the location, the characteristics and disease prevalence in the community, and the behaviors of individuals in the community and/or at the location. The computer system 110 can then evaluate the disease transmission scores for different locations by comparing them with a predetermined threshold. Disease transmission scores having values that exceed a threshold (e.g., indicating disease transmission risk above a certain level) can be identified as disease transmission hotspots. As another example, a model may be used to provide one or more predicted disease measures 1909c for the community. As another example, a model may be used to provide output indicating one or more disease prevention measures 1909d for the community. For example, this may be provided as effectiveness scores that indicate, for each of one or more different disease prevention measures, how effective the disease prevention measure is expected to be given the training examples observed during training. In other words, the effectiveness score can indicate how well a disease prevention measure is expected to reduce disease transmission, given the training data showing effects of that disease prevention measure being used in other communities or locations having similar characteristics, user behavior patterns, and other attributes similar to the current community or location for which a prediction is being made.

The process 1900 includes providing output indicating the one or more disease-related predictions for the community (step 1910). For example, the predictions can be provided to individuals that live in the community, to warn them of disease transmission hotspots, to indicate which disease preventions measures are most likely to be effective in their community or in the locations they visit, or to inform them of the potential impact of the disease or the predicted future disease metrics and trends predicted. This can be provided through the software application used to collect data for individuals, or through other channels (e.g., email, text messages, etc.). As another example, the predictions can be provided to businesses, governments, health agencies, hospitals, and other organizations. For example, predictions regarding disease impact and predicted disease measures can help with planning, by indicating the urgency of further disease prevention measures or show progress in controlling the disease. Similarly, the predicted effectiveness of different disease prevention measures can aid in making policy decisions, such as determining which disease prevention measures to encourage or require, the extent that businesses should open or operate, etc. The predictions can also be provided to hospitals and doctors to help them prepare for potential imminent increases in demand for resources, such as needs for increased disease testing, hospital beds, etc.

The process 1900 includes adjusting disease management for individuals based on the disease-related predictions for the community (step 1912). This can include selecting or adjusting monitoring, detection, prevention, testing, and/or treatment for the disease for an individual. For example, a prediction of a future a community disease measure may indicate an increase in disease prevalence or a location where a user works may be predicted to be (or be likely to become) a disease transmission hotspot. In response, the computer system 110 can adjust the personal predictions for an individual in the community, and can take steps to more aggressively encourage avoidance of disease exposure, and/or to increase the level of monitoring, testing, and treatment for the disease for the individual. This can include selecting and recommending a mediation or vaccine for the user, and/or to initiate or change the intensity of digital therapeutics interventions classified as treating or limiting symptoms of the disease. For example, if a user is diabetic and is determined to be in a community with an increasing prevalence and transmission rate for COVID-19, the computer system 110 can communicate with the user's mobile device to instruct caution and disease exposure avoidance, and may also initiate or intensify interventions to improve respiratory fitness and monitoring to help the user better prepare for or overcome COVID-19 symptoms.

Figure 20:
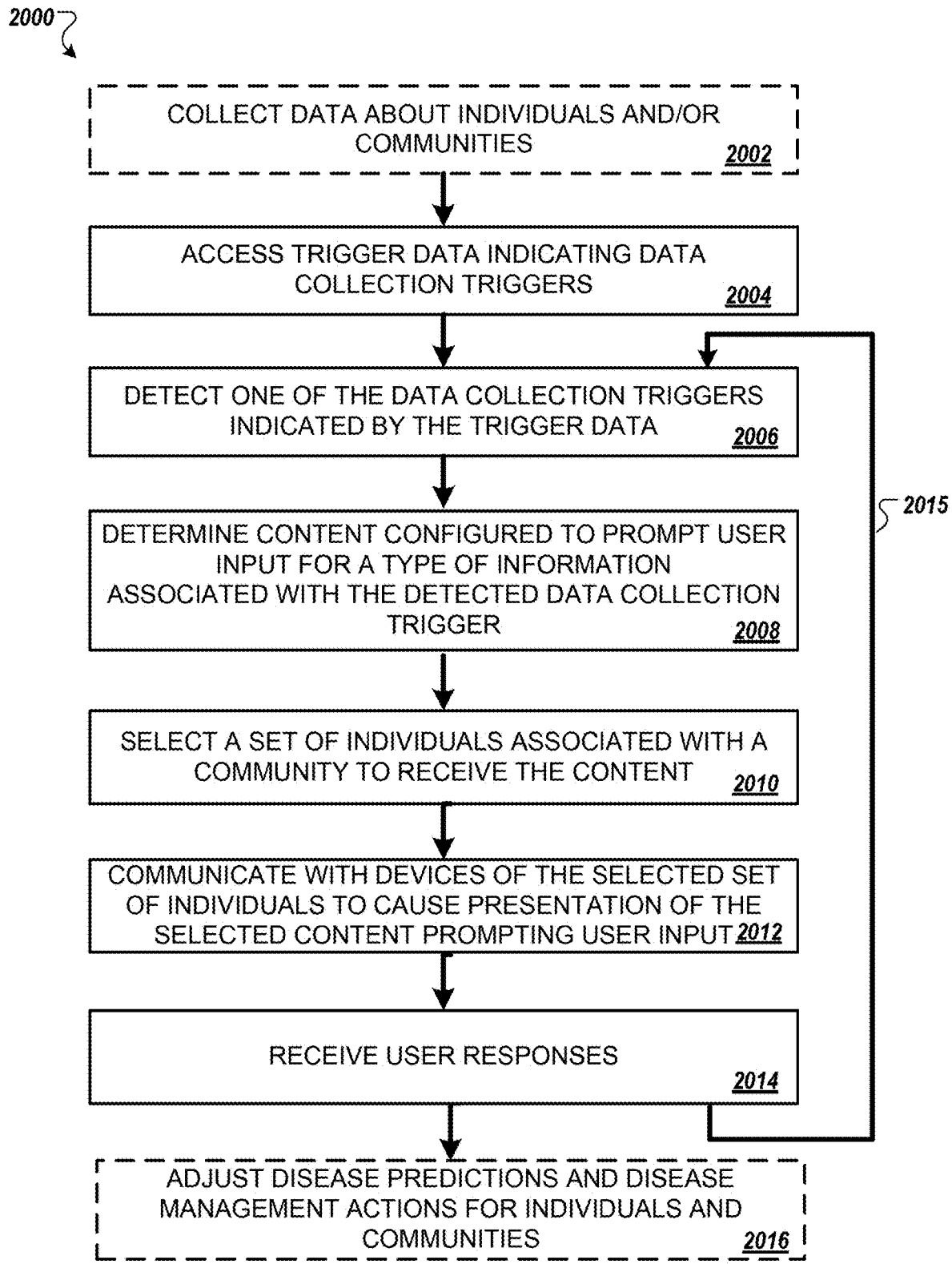
FIG. 20 is a flow diagram showing an example of a process for of collecting data and utilizing the data to improve disease management for individuals and communities.

FIG. 20 is a flow diagram showing an example of a process 2000 of collecting data and utilizing the data to improve disease management for individuals and communities. The process 2000 can be performed by one or more computers, such as the computer system 110. In general, the operations of the process 2000 can be performed by one or more servers, one or more client devices, or a combination of them. In addition to the operations illustrated, the process 2000 can optionally include other operations discussed with respect to FIG. 11. In the example, the disease mentioned can be COVID-19, or it can be another infectious disease.

The process 2000 can be used in an ongoing, iterative way to respond to changing conditions in a community and tailor the data collection in the community. This allows the computer system 110 to customize the level of interaction and disease monitoring performed for individuals in a community (e.g., through capture of sensor data and though capture of user responses to surveys and other prompts). The computer system 110 can collect data about individuals and/or communities. When certain characteristics of the collected data are detected (e.g., certain values, patterns, trends, etc.), this triggers changes in the data collection process used. The changes can include, for example, expanding data collection to a larger set of individuals or communities, changing the types of data collected or manner of collecting data, initiating specific, focused questions or interactions determined to be relevant to detected conditions in a community, and so on. This allows the computer system 110 to adapt data collection procedures quickly to changes in a community, such as changes in disease prevalence or disease transmission patterns or to changes in user behavior patterns.

As an example, the computer system 110 may initially cause certain monitoring actions to be performed for a first group of users. For example, EMAs or survey may ask questions such as "Is the store you are in busy today?," or "Has anyone you know been diagnosed with COVID-19?," or "have you had a headache in the last 24 hours?" These questions or other interactions can be designed to gauge certain disease measures or risk factors for an individual or the individual's community. The computer system 110 then evaluates responses with respect to a set of criteria and, if the criteria is met, the computer system 110 expands or otherwise adapts the data collection process. For example, if one or more users in the first group indicate exposure or high risk of COVID-19 infection, the computer system 110 may naturally respond with follow-up questions to find out more from those users. In addition, or as an alternative, the computer system 110 may adjust data collection for other users in response, such as by initiating questions to users in a second group, who may be unrelated and have had not any contact with the users in the first group. For example, the computer system 110 can initiate more widespread surveys throughout a community, where the content is selected or adjusted based on the conditions or criteria that the responses for the first set of users met.

As a result, from the results of data collection for one or more users in a community, the computer system 110 can adapt the data collection for other users in the community. Various types of data can trigger the adaptation or can have their collection processes adapted, such as behavior data (e.g., location tracking data, activity data, movement data, food intake, social activity monitoring, etc.), physiological data (e.g., blood pressure, heart rate, glucose levels, oxygen saturation such as SpO2, breathing rate, lung capacity or VO2 max, body temperature, etc.), mood and mental health data, health records (e.g., EMR/EHR), and so on. This data can be manually entered data (not only data from device-driven collection), data from medical records or historical records, and so on. Data collection for a user can involve third-party devices, which may or may not be networked or communicatively connected with the user's device, e.g., smart phone, medical treatment device, etc.

The process 2000 optionally includes collecting data about individuals and/or communities (step 2002). This data collection can be done as described with respect to FIG. 19 (see steps 1092, 1094), FIG. 11, and others discussed above. Nevertheless, this step is optional, as the computer system 110 may access or evaluate data from a repository that has been previously collected or compiled (e.g., by another system).

As noted above, data collection can include collecting user input data provided by one or more individuals in a community to their respective user devices, e.g., mobile devices. These inputs can be prompted by interactions initiated by software applications on the user devices or through communications from the computer system 110 over a network. The computer system 110 can instruct a software application running on user devices to provide certain questions or prompts to users, where the questions or prompts may be standardized (e.g., common or the same for multiple members of a community) or customized for individual users according to their respective contexts and needs. Of course data collection can occur through other techniques, such as passive collection of sensor data, obtaining data from third-party computer systems (e.g., to collect health records), and so on.

The process 2000 includes accessing trigger data indicating data collection triggers (step 2004). The trigger data can specify triggers designed or designated for monitoring of a specific disease, such as COVID-19. Each data collection trigger can specify one or more criteria used to determine whether the trigger is present or not. The criteria can be any of various types, such as a value of a measurement satisfying a threshold or being in a range, a particular response or combination of responses being received, a pattern or trend being present in collected data for one or more individuals, the presence of a biomarker or digital marker for health status, a change in behavior over time, etc. The criteria may be based on physiological measures, behavioral measures, user-reported symptoms, collected sensor data, health records, and/or other types of data or combinations of multiple types of data. Depending on the trigger, the corresponding criteria may be based on collected data for a single individual in a community, based on collected data for multiple individuals in the community, or for community-level statistics or data.

Each data collection trigger can specify a type of data to be collected when the corresponding one or more criteria are satisfied. In some implementations, the data collection trigger is focused on data collection for a community, and not particular for the user whose collected data may have caused the data collection trigger to occur. As a result, the type of data associated may be focused on assessing the conditions and characteristics present in the community generally, not necessarily the situation of any specific user. In other words, the data collection trigger can indicate a risk factor or situation of one user, and the type of data to be collected can be used to assess the overall conditions of the community or to prepare to more quickly detect new disease-related conditions that are now more likely to develop in the community.

Examples of trigger data are shown in FIG. 21, which shows a table 2100 in which different rows represent different data collection triggers. Column 2010 indicates criteria for the different triggers. Each indicates a condition, and the computer system 110 evaluates the collected data to determine if any of the conditions are present. Column 2020 shows types of data to be measured when the corresponding criteria are met. In the example, these are general categories, but in implementations may be more specific. For example, for the first trigger, if the community infection rate is greater than a threshold, the trigger data indicates that information about disease symptoms should be collected. Optionally, more specific data such as data about specific symptoms (e.g., headache, gastrointestinal discomfort, coughing, etc.) and/or physiological data could be specified. The criteria can be based on conditions measured for a community as a whole, a sub-group within the community, or for individuals in the community.

The conditions can be based on physiological measures, behavior, indicators of mental health, disease status (e.g., community disease measures or individual disease status), and so on. In some cases, the criteria for a data collection trigger can be based at least in part on physiological measurements. For example, digital thermometers may be used at locations in a community or may be distributed to a random group within the community. Body temperature changes can signal a need for increased monitoring, such as asking about further symptoms (e.g., breathing difficulty). Physiological data for individuals can also trigger data collection for other information from the individuals as well as others, such as their family members or household, others at their place of employment, groups at high risk for COVID-19 exposure or disease severity, etc.

Other columns in the table 2100 show other optional types of data that can be used to collect information. Column 2030 indicates content or a tool to be used in collecting the data, such as a specific question, survey, sensor, device, etc. Column 2040 indicates a data collection mode to be used to collect the data, such as through user input, sensing during a user activity (e.g., an exercise, game, or other activity) prompted by the system, or through collection of sensor data. Column 2050 indicates a set of individuals for whom the detected trigger causes data collection to be performed.

Other techniques for specifying trigger data can be used, for example, a decision tree can specify different actions (e.g., data collection actions) for the community based on different data or factors determined to be present. The technique shown in FIG. 4 for determining actions for individuals can be applied for communities and groups of individuals within communities, to specify different data collection actions to perform.

Referring again to FIG. 20, the process 2000 includes detecting one of the data collection triggers indicated by the trigger data (step 2006). The computer system 110 can detect that a particular data collection trigger occurs by determining that the one or more criteria for the particular data collection trigger are satisfied. For example, the computer system compares characteristics of collected data with predetermined criteria for the data collection triggers and determines when the criteria for a trigger is satisfied. The detection can be done in substantially real time, such as in response to receiving collected data. Additionally or alternatively, the analysis to detect triggers can be done periodically, e.g., hourly, daily, etc.

The process 2000 includes determining content configured to prompt user input for a type of information associated with the detected data collection trigger (step 2008). This can involve selecting a specific question, user form, survey, or other interactive content to obtain a user input providing the needed data. While this example emphasizes user input as the mode of data collection, the computer system 110 may additionally or alternatively determine to initiate data collection through other techniques, such as through initiating or adjusting collection of sensor data, through requesting or retrieving medical records, and so on.

The trigger data may associate a specific existing content (e.g., an EMA, a form, a question, a survey, etc.) with the trigger, and the same content may be provided to each recipient. As another example, the computer system 110 may use the indication of the type of data to be collected (e.g., resting heart rate) to generate or customize tailor different interactions for different recipients. For example, one user whose device can measure resting heart rate (or is wirelessly connected to a device that can) can be instructed to measure and report this data. Another user whose device does not have heart rate monitoring capability can be provided a question asking the user to enter the user's resting heart rate. As another example, for generating content to prompt for information about breathing symptoms one option is to provide every member of the community the same question, e.g., "Have you experienced any trouble breathing today?" Another option is to generate different questions to acquire the needed information, customized for the information known about users, with different users respectively receiving questions such as "You had trouble breathing yesterday. Was it any better today?," "Your respiration rate has increased. Are you having trouble breathing?," and so on.

The process 2000 includes selecting a set of individuals associated with a community, so that the individuals in the set can receive the content that prompts user input (step 2010). The computer system 110 can store, for each community, data indicating a set of individuals associated with the community. This can be, for example, a set of people in the community who have enrolled or registered to participate in a community health program, a research study, or other initiative. These individuals in the community can each have a user device with the software application that enables data collection and reporting. In response to detecting the data collection trigger, the computer system 110 selects a group of the individuals associated with the community. The set of individuals may be all members of the community or a subset having fewer than all of the members of the community. For example, the trigger data may specify certain selection criteria that are used to determine the subset of people for which the additional data will be collected. As another example, the computer system 110 may determine the set of individuals based on the characteristics or needs of the community. For example, the computer system 110 can identify risk factors for disease spread or gaps in information about the community, and can select a set of individuals who can provide information to assess the risk factors or fill the gaps in information about the community.

The process 2000 includes communicating with devices of the selected set of individuals to cause presentation of the selected content that prompts user input (step 2012). For example, the computer system 110 can send a message or configuration data to the user device of each individual in the selected set of individuals. The message can instruct the user devices to perform the needed data collection, e.g., to cause each user device to present the content (e.g., a survey) that prompts user input of the needed type. The computer system 110 can store data indicating the user devices or user accounts for different users and use this to target content delivery to the right individuals. The content can be pushed to user devices, such as through a notification that appears and alerts the user. In other cases, the content can be provided through an application interface or web page that a user sees when the user opens the application or web page.

The process 2000 includes receiving user responses to the prompts for user input (step 2014). The computer system 110 receives and stores the user responses. These responses can be, for example, interactions with buttons, sliders, checkboxes, and other interactive user interface elements. Other responses can be entered text, numbers, or other data provided. When data collection actions involve changes to the collection and reporting of sensor data, the computer system 110 can further receive collected data generated through those functions.

After receiving the user responses, the computer system 110 can evaluate the received responses to determine whether any additional data collection triggers are detected. This is represented in FIG. 20 by the arrow 2015 showing that user responses can lead to detection of additional data collection triggers, which can then further customize the disease monitoring processes performed for a community.

The process 2000 optionally includes adjusting disease predictions and disease management actions for individuals and communities (step 2016). This can include selecting or adjusting monitoring, detection, prevention, testing, and/or treatment for the disease for an individual, as discussed above. The information can also be used to perform an iteration of the process 1900 of FIG. 19, to generate updated predictions for a community based on the collected data. As discussed for FIGS. 1-5, 11-13B, and other areas above, the data collected for individuals and communities can prompt a variety of interventions, including changes to data collection techniques, selecting and providing disease testing kits, selecting and recommending disease prevention measures, selecting and providing medical treatment or monitoring devices, selecting and providing vaccines, selecting or and providing treatment, and so on.

In some implementations, the process 2000 can be used to initiate disease management actions other than data collection. In the same manner that the table 2100 shows data collection triggers and corresponding data collection actions, the computer system 110 can store and use triggers for corresponding actions for other purposes, such as disease management actions, providing treatment, providing vaccines, providing testing kits and so on.

Figure 22:
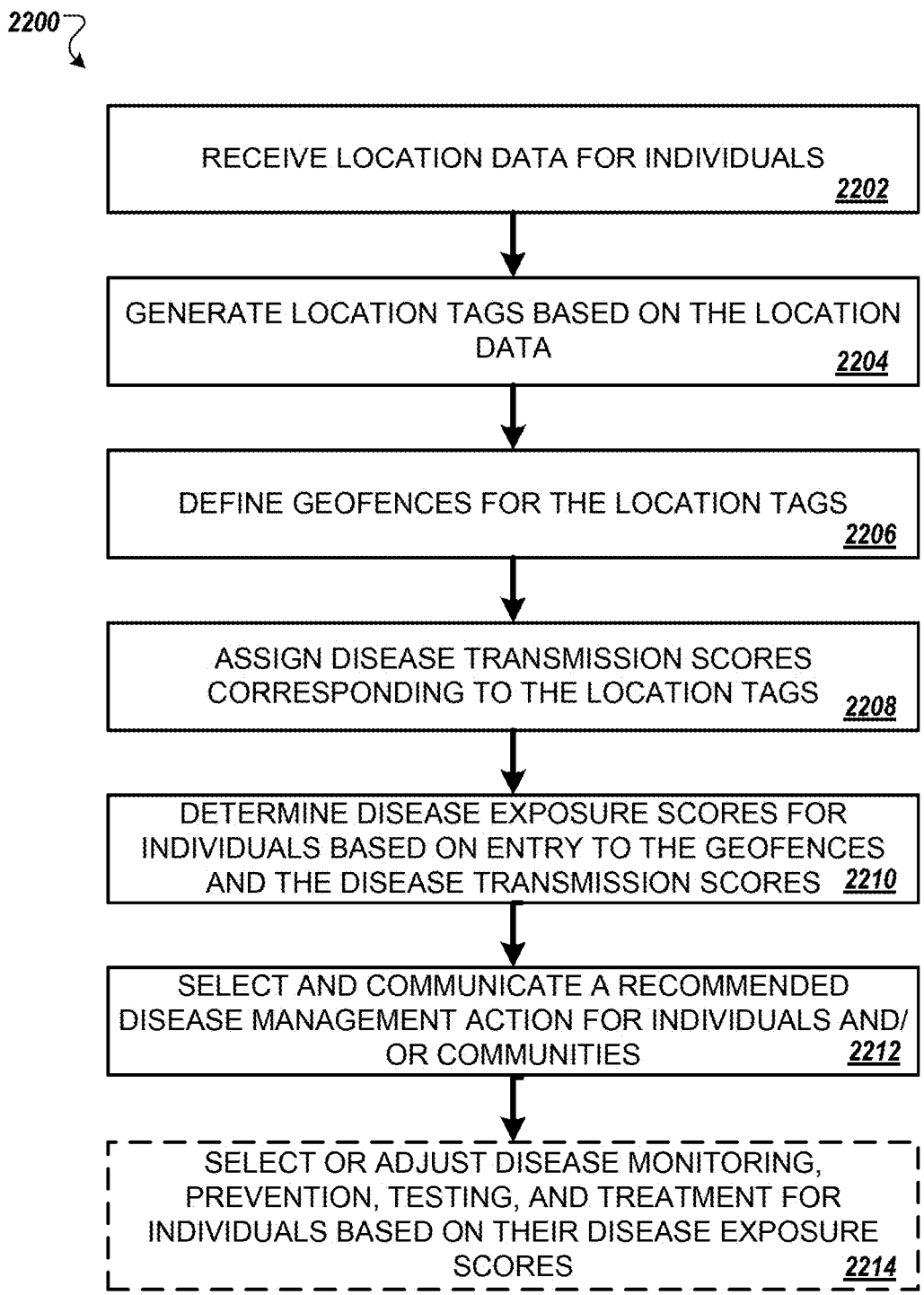
FIG. 22 is a flow diagram showing an example of a process for determining disease exposure using location tags and geofence information.

FIG. 22 is a flow diagram showing an example of a process 2200 of determining disease exposure using location tags and geofence information. The process 2200 can be performed by one or more computers, such as the computer system 110. In general, the operations of the process 2200 can be performed by one or more servers, one or more client devices, or a combination of them. In addition to the operations illustrated, the process 2200 can optionally include other operations discussed with respect to FIGS. 14-18. In the example, the disease mentioned can be COVID-19, or it can be another infectious disease.

In some implementations, rather than relying only on device-to-device information passing or human contact tracing staff, devices can check in with their locations to a server system. The locations that infected or likely to be infected people visit are tagged in the map data of the server. A series of geofence limits then track which other users enter the geofenced, tagged areas. The amount of time spent in the areas, as well as the length of time since the infected person visited are used to weight the exposure risk for each geofence entry event. The exposure estimates then drive targeted interactions with the user recommendations, sending testing kits, etc. The data is also aggregated across different users to generate an estimate of community-level exposure risks.

As discussed above, the computer system 110 can be used to improve location tracking and contact tracing for disease exposure estimation. Some technology-based contact tracing approaches rely on user devices to transmit and receive wireless messages to each other, so that reception of a message with a device's identifier indicates co-location with that device. When a user's phone detects a message from a phone of someone determined to have a case of COVID-19 (e.g., both devices are at the same location at the same time), the user can be notified of the exposure. However, COVID-19 transmission does not require being in the same place at the same time, because airborne infectious particles can remain viable for hours (e.g., sometimes 4 hours, 8 hours, 12 hours, etc. depending on the environment), and infectious particles can also remain on and be transmitted on surfaces for significant periods of time. In addition, a person may be contagious days before receiving a test and confirmation of a case of COVID-19, and exposures that occurred before the test need to be tracked and accounted for.

The present technology can account for these factors by, among other features, detecting exposure that occurs within a window of time that includes an infected person's presence at a location and a subsequent period of time afterward (e.g., 4 hours in a well-ventilated area or 12 hours in a poorly ventilated area, or with other times to account for periods of surface-contact transmission). In addition, the system 110 can account for exposures that occur before a positive test of an individual. The system 110 can track and store information about users' movements, such as through location tags representing visits at specific times and locations. For users who have tested positive for COVID-19, the location tags corresponding to their visits are marked or labeled to indicate this, for example, with a label indicating the health status of the visitor (e.g., positive case of COVID-19), an indication that actual exposure occurred, and/or with a disease transmission score indicating a high level of transmission risk to show actual exposure occurred.

Even if a user has not yet tested positive for COVID-19, the location tags can be used to represent the exposure risk. One way is by marking or associating location tags with the predicted infection likelihood generated using predictive models 230 (see FIG. 3). This allows the computer system 110 to use data about physiological attributes and behavior of a user (e.g., captured through user responses to questions, automatic capture of sensor data, etc.) to predict when a user is likely infected before a test result is available, and so provide earlier warnings and notifications to other users who visit the same places at the same or similar times.

In addition, once a positive test result is obtained for a user, the computer system 110 can update the data for location tags of the user to reflect this new information. For example, if a user tests positive, location tags for subsequent visits will be marked to show that they cause COVID-19 exposure. In addition, the location tags representing previous visits for some period of time (e.g., 5-10 days, which may vary depending on the stage of disease when tested) can all have their information updated to reflect the fact that those visits are now likely to have caused COVID-19 exposure. The disease transmission scores for the previous, pre-testing visits can be similarly updated to show a higher risk of transmission. Consequently, based on the updates to the disease transmission scores, the disease exposure scores for individuals that entered the geofences of those location tags can also be updated to reflect the new information that actual exposure occurred. This allows the computer system 110 to track and use exposure events that occur before diagnosis or testing of a user, which is often not possible to do accurately and efficiently with traditional contact tracing techniques.

The process 2200 can be performed to create a personalized disease exposure risk score for an individual, based on the locations that the individual visits over a period of time. The computer system 110 can track locations that individuals visit, using location monitoring data from a GPS receiver or through other means. The computer system 110 can additionally or alternatively track location using user-reported data, for example, provided in response to prompts or surveys. The locations that user visit are tracked, and when a user is confirmed to have COVID-19 or is classified as likely to have COVID-19 (e.g., such as for having an infection prediction likelihood above a threshold), the locations that user has visited are assigned a disease transmission score indicating the potential for that visit to transmit COVID-19. The visit by an infected or likely infected person is considered to present a level of exposure risk (quantified by the disease transmission score) to others that subsequently visit the location within some maximum period of time (e.g., the next 12 hours after the infected person leaves the location).

Having marked locations that present exposure risk, the computer system 110 can aggregate information about a user's visits over a period of time (e.g., a day, a week, etc.) to estimate the level of exposure to the disease or risk of contracting the disease based on past visits. More visits to areas with risk tags, and longer visits at those locations, result in greater levels of individual risk being estimated. One of the advantages of the system is that it can capture the potential for disease spread even when individuals are not in the same location at the same time. Even if a second user arrives after the first user has left, the system can still assess the risk of that visit. When determining the exposure score for a user, the transmission scores for locations can be weighted or decreased according to the amount of time that has passed since the infected or likely infected person left. If an first user, who has an active case of COVID-19, visited a store at 1:00 µm, and a second person arrived at 2:00 pm, there is still a risk that infectious COV-SARS-2 particles from the first person are still present in the air or on surfaces when the second person arrives. Nevertheless, the risk diminishes over time, and the risk to the second user would be much less at 8:00 pm. Thus, the aggregation of data about locations that the second user visits can be adjusted to account for factors such as time elapsed, nature of the activities being performed at the location, a degree of overlap between paths of the two users along the location, duration that the two users respectively spent at the location, and so on.

After an exposure score for a user is calculated, the computer system 110 may update the exposure score based on later-received information. For example, the computer system 110 may determine a low exposure score for a particular user for her activities on Monday. On Wednesday, however, new COVID-19 test results may be received, showing that one or more other users who on Monday visited a same location as the particular user have tested positive for COVID-19 and thus were likely infected during the Monday visits. As a result, the computer system 110 updates the location tags for those visits on Monday with increased disease transmission scores. The computer system 110 also updates the disease exposure score for the particular user for Monday to show that exposure to COVID-19 was higher than previously calculated now that the visits of the other users have been re-classified as visits causing exposure or having high likelihood of exposure.

The process 2200 includes receiving location data for individuals (step 2202). This can include automatic location sensing of the location of a user device of a user, e.g., a smart phone, wearable device, etc. For example, location data can be tracked using GPS data, and/or through reception of messages from wireless beacons, cellular towers, Wi-Fi access points, or other transmitters having known locations and identifiers. In addition or as an alternative, the system 100 can prompt a user for input to indicate locations the user has visited, and user responses can indicate locations of users at different times.

The process 2200 includes generating location tags based on the location data (step 2204). The location tags can be records or data entries that specify visits of the user devices to different locations indicated by the location tracking data. Location tags can be generated or recorded in response to determining that location tracking data meets certain criteria or has a predetermined set of characteristics. For example, at least a minimum duration of time at a location may be required to define a location tag, e.g., 1 minute, 5 minutes, etc. As another example, movement data can be assessed to determine whether the user's behavior represents the kind that may cause exposure. For example, a user traveling in a car would have a motion pattern that can be excluded, so that stopping at a stoplight does not create a location tag or exposure event for the corner store where the car stopped temporarily. In some implementations, visits that meet the criteria for timing and location or movement patterns are defined for all users. In other implementations, location tags are selectively generated for visits only in response to determining that there is a significant likelihood that the visiting user could transmit the disease (e.g., the user tested positive for the disease, whether before or after the visit; the infection likelihood score for the user at the time of the visit exceeds a threshold; etc.)

Each of the location tags can have corresponding data indicating a location of a visit, a time of the visit, and a user device or user corresponding to the visit. More specific information can be included, such as the time of entry, the time of exit, the nature of the visit, a path of movement during the visit (e.g., through store aisles or around a park), and so on.

As discussed above, location tags can be associated with various other types of information, such as characteristics of the location, location type, current conditions at the location, disease prevention measures in place at the location, compliance with disease prevention measures (e.g., by asking one or more users at the location through an EMA or other prompt), and so on. In addition, information about the user whose visit is represented by a location tag (e.g., the user whose presence represents a potential COVID-19 exposure to others at the location) can also be stored in or associated with the location tag, e.g., a user identifier (e.g., an anonymized identifier), a health status with respect to the disease (e.g., active case; recovered case; vaccinated; probable case based on symptoms or machine learning predictions; neither vaccinated, recovered, probable, nor confirmed case; etc.), whether the user used disease prevention measures and which ones, and so on.

The system 110 or a user's mobile device can initiate interactions with a user to collect information about the visit. This can include asking about the environment or conditions present, the number of other people present, the user's activity or task being performed, etc. The system 110 can ask whether the user is using (or previously used) a mask or other preventative measure during a visit.

Public transportation vehicles or routes can be considered to be locations and can be tagged based on use by individuals. For example, if a user gets on a bus, the specific bus may be tagged based on the user's presence. Similarly, if the user gets on a subway, the subway car or train may be tagged. In this case, the location tag specifies not a fixed location but an identifier for the vehicle and potentially the route the vehicle travels. In cases where it is not possible to tag the specific vehicle, the route of the vehicle may be tagged.

The process 2200 includes assigning geofences for the location tags (step 2206). The geofence represents a boundary or defined region to which the location tag applies. Each geofence encompasses or defines a geofenced area corresponding to the location tag. The geofenced area represents an area affected by the visit of the user whose presence led to the creation of the location tag. For example, the geofenced area can be an area in which the disease may be transmitted based on the visit of an infected person, e.g., an area in which the likelihood of infection for a concurrently-visiting or later-visiting user is increased if the user enters the geofenced area during a period of time (e.g., a window comprising the duration of the visit of an infected or likely infected individual plus an additional period of virus viability, such as 12 hours).

In some implementations, a separate geofence can be assigned for different location tags. For example, the size and shape of a geofence can be based on the range and path of movement of a user at the location. Thus, if a person visited a large store and only entered one section of the store, the geofence may be restricted to covering the section actually traversed during the visit. Nevertheless, in other implementations, the geofenced area can be a standard area for the location, e.g., a single geofenced area representing the entire store when the user visits any part of the store. In some implementations, the geofence may be specified by an address, and separate map data can be used to look up the boundaries that correspond to the address. As another example, a geofence may be specified by GPS coordinates and a radius or an address and a radius. As another example, a geofence may be specified using polygons or other shapes to specify the boundaries of the geofenced area.

The process 2200 includes assigning disease transmission scores corresponding to location tags (step 2208). Each location tag for a visit can be assigned one or more disease transmission scores indicative of the level or risk that the visit represents in terms of potentially exposing others who concurrently or subsequently visited the location. In other words, a disease transmission score can indicate a potential for disease transmission that occurred as a result of a user's visit to a location. The disease transmission scores can be based on data indicating a disease status of the user whose visit is represented by the location tag. The score can be based on actual confirmed diagnosis (such as a positive test based on a nasal swab testing kit), a probable infection such as due to likely exposure and symptoms indicating high infection likelihood, or a prediction of infection from a machine learning model.

In some implementations, the disease transmission score can be as simple as an indication (e.g., yes or no) whether the user had (or has subsequently received) a diagnosis or positive test indicating a confirmed case of COVID-19. In other implementations, the disease transmission score can be more nuanced, for example, having different values along a scale to indicate different levels of potential for disease transmission, e.g., a score of 10 for a confirmed case, a score of 7 for a probable case, a score of 3 for a relatively low infection prediction score, etc. The disease transmission score can vary according to collected data for a user, e.g., the current and recent signs and symptoms of the disease detected or reported for the user; based on different levels of infection likelihood prediction (e.g., score of 7 for a 70% likelihood prediction, a score of 2 for a 20% likelihood prediction, etc.); and so on.

The disease transmission scores can be generated or adjusted based on various factors other than the disease status of the user, to reflect how conditions present during the visit may have affected the ability of infectious particles to spread, persist, and infect others. For example, a value determined from the disease status of the user may be increased or reduced by additional terms that represent at least one of the activity of the user, characteristics of the user, whether the user used disease prevention measures, the characteristics of the location, the duration of the visit, and so on. The disease transmission scores can be generated or adjusted based on the conditions at the location and the behavior of the user and others. For example, if face masks are worn and people are following social distancing rules, the disease transmission score can be reduced, to reflect the lower likelihood or risk of infection under those conditions. Similarly, whether the infected user making the visit wore a face mask or not can affect the likelihood of transmission and thus the disease transmission score. As another example, the disease transmission score can vary according to the length of a user's visit (e.g., and the amount of time the user had to spread infectious particles), the movement of the user or activity or task of the user at the location, the type of location, the characteristics of the location, and so on.

For example, an infected person that visited a store can have a base disease transmission score of 10 to represent the exposure from an infected user. This base score can be modified based on one or more factors to more accurately reflect the risk the visit presents. For example, the base score may be: decreased because the user reported wearing a mask during the visit (e.g., an adjustment of –2); decreased based on social distancing being required by the store or city (e.g., an adjustment of –2); increased because of a large area covered by the user during the visit (e.g., +1); increased based on the duration of the visit being 45 minutes (e.g., +3, one point for each 15 minute period in the visit); increased based on the enclosed nature of the store and limited ventilation (e.g., +2); etc. As a result, the disease transmission score can be a combination of these factors, resulting in a score of 12 for the location tag.

Other techniques for generating disease transmission scores can be used. For example, a predictive model (e.g., a machine learning model, a statistical model, a rule-based model, etc.) can be trained based on training data showing disease transmission outcomes under different conditions (e.g., different combinations of location types, location characteristics, visit durations, disease prevention measures used, etc.). Based on the relationships demonstrated by the training data, the model can be generated or trained to determine the significance of different factors (e.g., the level of impact of different characteristics or inputs on disease spread), and can learn to provide outputs that quantify the potential for disease transmission. To determine the disease transmission score for a location tag, input data describing the collected data describing the visit (e.g., duration, location characteristics, preventative measures used, etc.) can be provided to the model, and the model can output a disease transmission score reflecting the overall risk of transmission for the visit. Disease transmission scores can be determined in other ways, such as with a function, equation, look-up table, etc. configured to assign appropriate risk levels as determined from training data.

The process 2200 includes determining disease exposure scores for individuals based on their entry to the geofenced areas (step 2020). The disease exposure score can be a measure of how likely and/or how intensely a person was exposed to COVID-19 or another disease. Using the location tracking data, the computer system 110 can determine, for each user participating, which geofenced areas the user entered during a particular time period (e.g., the last hour, the previous day, the previous week, etc.). The computer system 110 can then combine or aggregate the exposure risks for the different geofenced areas entered (e.g., transmission risk information for the applicable location tags) to determine a disease exposure score for the user for the particular time period. In this manner, the computer system 110 can regularly generate a disease exposure measure (e.g., every hour, every day, etc.) for each user. Disease exposure measures can also be generated in real time, responsive to new risks detected, such as in response to a new visit to a location by a user. In some implementations, a user can be considered to enter a geofenced area in a manner that receives exposure only when predetermined criteria about the visit to the area are satisfied, such as remaining in the area for at least a minimum amount of time (e.g., 1 minute, 5 minutes, etc.), the movement pattern is consistent with activity that would cause exposure (e.g., walking or being present in person, not merely driving through in a vehicle), etc.

The computer system 110 can compare the disease exposure measure for a user to reference data to determine notifications, recommendations, and other interventions to provide. For example, the computer system 110 can compare the disease exposure score to thresholds to determine a risk classification for the user's exposure level, and whether disease testing, disease treatment, a medical appointment, additional preventative measures, or other interventions should be provided. As another example, the computer system 110 can compare the disease exposure score to prior scores for the user to determine whether the exposure is increasing or decreasing, and inform the user accordingly.

In essence, the computer system 110 evaluates the overall, cumulative effect of all of the tracked visits for the user during a time period. The process can take into account how many times, and for what durations, the user's tracked visits overlapped in space with the geofenced area representing current or previous visits by any infected person. The process can also take into account the temporal closeness of a user's visits to prior visits of infected or likely infected individuals, such as by weighting or scaling the disease transmission scores according to how much time had elapsed between the user's visit and the prior visits of infected or likely infected individual.

One way to generate the disease exposure score is for the computer system 110 to aggregate the disease transmission scores for the location tags for which the user entered the corresponding geofenced area in the particular time period corresponding to the disease exposure score. For example, based on the location tracking data for a user, a user is determined to have entered at least one of the geofenced areas corresponding to the location tags representing potential disease-transmitting visits by other users. A disease exposure score is determined by aggregating disease transmission scores for different location tags for which the user device is determined to have entered the corresponding geofenced area. The aggregation can be done using any of various techniques, such as a summation, a weighted average, taking the maximum value of the disease transmission scores, providing data characterizing the visits and disease transmission scores to machine learning model for classification or regression, and so on.

When determining the disease exposure score for a user, the disease transmission score for a location can be adjusted or modified to reflect the situation and characteristics of the user's visit to the geofenced area. The disease transmission score associated with a location tag reflects only one side of the person-to-person transmission, the transmission potential by the transmitting user and environmental factors that affect the likelihood and extent of infectious particles spreading. This can be further modified or customized for the user potentially receiving exposure to the disease, since the receiving user's actions may cause the user to be exposed to a different degree (e.g., depending on factors such as whether preventive measures like masks are used, the duration of the visit to the exposed area, etc.)

Thus, in the aggregation to determine an exposure level received by a user, the level of exposure or exposure risk for each entered geofenced area can be based on various factors regarding the user, the visit, the location, and so on. A significant factor in the adjustment is the amount of time elapsed between (i) the departure of the user whose visit caused the location tag to be created and (ii) the arrival of the user whose exposure score is being determined. This difference is referred to as a "visit time difference" below. The visit time difference can be used to provide a gradual or incremental decrease in transmission potential in the period after an infected person leaves. For example, the effective exposure score for a visit can be calculated by retrieving the disease transmission score for the location tag and then scaling that value downward by an amount determined based on the visit time difference and decreasing function (e.g., decreasing linearly, quadratically, exponentially, according to a statistically determined or machine-learning determined pattern, etc.). For example, the adjustment can be a scaling factor determined based on the visit time difference, where an actual overlap in time of visits (e.g., a visit time difference of zero) can have a scaling factor of 1.0 (e.g., causing no adjustment to the full disease transmission score), a visit time difference of between one and two hours results in a scaling factor of 0.8, a visit time difference of between 6 and 8 hours results in a scaling factor of 0.4, and so on, until a maximum visit time difference (e.g., 12 hours or more) for which the scaling factor is zero to indicate that the visit would not contribute to disease exposure. Similarly, an amount of time two visits actually overlapped can be an additional adjustment factor, e.g., to increase the level of exposure a user received. Other factors that can adjust the transmission scores for the aggregation include the duration of time the user spent in the geofenced area, disease prevention measures of the user (e.g., whether the user wore a mask), the environment at and characteristics of the location, behavior or activity of the user at the location, etc.

As discussed above, the computer system 110 customizes the disease transmission score to obtain an exposure score for each visit, according to the nature of the visit and the user's corresponding potential to receive exposure. The computer system 110 then aggregates these exposure scores (e.g., adjusted disease transmission scores) for different visits to determine the overall disease exposure score for a time period. As noted above, the exposure scores for different visits can be summed or otherwise combined to show a measure of cumulative exposure. As an additional or alternative measure, the maximum value (e.g., highest exposure level) of these exposure measure can be used, quantifying a severity of the highest-exposure event for the time period. As another example, a machine learning model, trained based on examples of different exposure events and corresponding infection outcomes, can process information about the visits and/or exposure scores and can provide an aggregate measure of exposure to be used as the disease exposure measure.

Another approach to determining the disease exposure score is to scale each disease transmission score (e.g., with or without adjustments) by the amount of time the user spent at the location where exposure occurred. Thus, the disease exposure score can be represent an amount of time accumulated at different exposure levels. For example, a user may have in a day three visits to areas having transmission scores of 10, 15, and 20, respectively. The visits may have durations of 15 minutes, 30 minutes, and 15 minutes, respectively. With a scaling factor of 1.0 for one hour spent at a location, the cumulative exposure level can be: 0.25*10+0.5*15+0.25*20=15.

As discussed above for FIGS. 14-16D, additional location tags can be defined for other risks, such as the population levels or traffic levels at different areas and the types of locations (e.g., reflecting the way locations of that type are used). The computer system 110 can additionally or alternatively generate disease exposure scores for a user based on these tags. For example, the disease exposure score can aggregate exposure risk from any or all of visit-based location tags representing the presence of specific individuals at locations, population-based location tags indicating the volume and characteristics of people at a location (e.g., percentage of people vaccinated), and location-based tags representing the types of locations present. Disease transmission scores for the population-based tags and the location-type-based tags can be scaled based on visit duration, preventative measures used, and other factors as discussed above, and can be aggregated together for different visits as discussed above for the visit-based tags.

The exposure scores for a user can be modified based on information about the user, such as the disease status of the user. For example, in some implementations, the exposure score for a user may be modified if the user has previously been vaccinated or recovered from COVID-19, and so has a lower risk of contracting the disease.

The process 2200 includes selecting and communicating, by the one or more computers, a recommended disease management action for individuals and/or communities (step 2212). The computer system 110 can store mapping data that associates different conditions with corresponding disease management actions. For example, different combinations of user characteristics and different disease exposure score levels may have different corresponding actions. The condition of a user over 60 years old who has an exposure score of at least 10 may correspond to a recommendation to receive a vaccine as soon as possible. The condition of any user having an exposure score over 20 may be encouraged to take a test for COVID-19. The condition of a user having an exposure score over 5 for multiple consecutive days can correspond to a recommendation to wear a mask. The condition of a user that has an exposure score of over 30, who has one or more disease symptoms, and does not have a contraindication for a particular drug used to treat early-stage COVID-19 infection can correspond to recommending use of the drug, either to the user's doctor or directly to the user. Many other types of conditions and corresponding recommended disease management actions can be used.

The conditions and the corresponding actions can be determined based on statistical analysis of the effectiveness of disease management actions for the different exposure levels. In some implementations, the recommendations can be determined based on output of a machine learning model. The model can be trained based on examples of exposure scores, disease management actions applied, and corresponding disease outcomes. The training can teach the model to predict the effectiveness of or need for different disease management actions, given the exposure scores and other data describing a user's situation (e.g., user characteristics, collected data, community disease measures, etc.). Thus, the output provided by the model upon processing the exposure scores for a user can be scores indicating the respective applicability (e.g., level of need or level of predicted effectiveness) for the level of exposure that has occurred. In some cases, a model can be configured to receive and process feature values indicating detailed information about exposure events (e.g., duration of exposure, location type, preventative measures used, etc.) in addition to or instead of the disease exposure scores.

The computer system 110 can provide various outputs based on the exposure level analysis (e.g., exposure risk analysis). Individuals can be provided their disease exposure scores, exposure risk levels, classifications of the magnitude or types of exposure, or other information to characterize the exposure that has occurred. In addition, the computer system 110 can notify individuals of specific events that represent high exposure levels or high exposure risks, either as they are detected (e.g., in the context while the exposure is occurring) or retrospectively. As discussed above, the disease exposure scores can also trigger further data collection for individuals through sensor data collection, prompts or surveys, and so on.

The computer system 110 can also provide information about exposure at the community level, as well as recommendations for the community. The recommendations may be provided to community leaders, community businesses, and public health agencies, or in some implementations directly to community members. As with recommendations for individuals, mapping data can specify different predetermined conditions and corresponding disease management actions to recommend. For example, if the average exposure score for users in the community exceeds 5, then social distancing can be recommended. As another example, if at least a minimum number of exposure scores exceed 10, then a general alert can be recommended for the community. If exposure levels at a specific location or location type exceed a threshold, then disease prevention measures can be recommended (e.g., mask usage, social distancing, closing the location, etc.).

Community-level recommendations can include changing policies for disease prevention, such as enacting or removing specific disease prevention measures. Depending on the exposure levels and community characteristics, these may be provided for the community as a whole, for specific location types, for specific locations, etc.

The exposure levels throughout the community can be used to determine when disease prevention measures can be relaxed or removed. For example, based on a pattern of decreasing exposure levels or exposure levels below a threshold for at least a minimum length of time, the computer system 110 can recommend that preventative measures are no longer needed. For example, the computer system 110 can indicate periodically (e.g., daily) which preventative measures are appropriate for the current and recent pattern of exposure in the community, and as the exposure scores decrease, the set recommended can be changed to show that previously recommended measures (e.g., limit to 25% occupancy) may be lifted (e.g., limit to 50% occupancy or no need to limit occupancy). The recommended lifting of preventative measures can be done in a way that gradually or incrementally removes these measures.

The location tag information can be aggregated to determine the areas in a community that represent hotspots of disease transmission. Beyond aggregating the number of tags, the disease transmission scores for tags or the actual exposure scores for different exposure events can be used to show where the greatest level of exposure is occurring. Recommendations to modify use of hotspot locations, e.g., to limit occupancy, to enforce social distancing, to close the location, etc. can then be provided, along with data identifying the locations for which the measures are recommended.

Some community-level recommendations may include recommendations of vaccination programs, such as for certain sets of individuals or certain areas in the community, e.g. sets of individuals the computer system 110 identifies as having the highest exposure or risk levels; individuals that reside in, work at, or visit areas of highest disease transmission; areas determined to have at least a certain number of or percentage of individuals with high susceptibility to the disease (e.g., from user susceptibility scores, individual medical records, etc.); and so on. The computer system 110 can identify the locations, sets of individuals, or classes of individuals (e.g., user profiles or behavior profiles for individuals) that most need vaccinations. Other recommendations for a community include recommendations of testing, including identification of highest-exposure groups or locations to provide testing kits.

The computer system 110, through the geofencing and location tracking analysis, can identify specific exposure events (e.g., represented by visit-based location tags), the people potentially affected (e.g., those who concurrently or later visit the tagged, geofenced areas), as well as the degree affected (e.g., exposure scores for the visits to the tagged, geofenced areas. The computer system 110 can provide this information to community health organizations and governments, to assist in contact tracing and in characterizing the patterns of exposure that are present in the community. Thus, the system 110 can provide contact tracing style data indicating exposure events that meet certain thresholds or criteria. In addition, or as an alternative, data indicating aggregate measures of exposure for the community, including patterns, trends, and statistical measures of exposure, can be provided.

The process 2200 can optionally include selecting or adjusting disease monitoring, prevention, testing and treatment for individuals based on their disease exposure scores (step 2214). Not only can the computer system 110 select a disease monitoring action and communicate it as a recommendation, the computer system 110 can often carry out actions to implement needed actions to initiate treatment for COVID-19, change monitoring or testing, and so on. Thus the computer system 110 may implement recommended actions for individuals by providing digital therapeutics, scheduling vaccine appointments, initiating delivery of testing kits, and so on.

For example, based on a user's disease exposure score satisfying a threshold, the computer system 110 can adjust monitoring for COVID-19 for a user, such as by providing new EMAs or surveys, changing the collection of sensor data, and so on. Based on the disease exposure score the system can provide treatment for COVID-19, such as through digital therapeutics classified as addressing COVID-19 symptoms or risk, through medications, and so on. For example, the disease exposure score for a user can be an input that affects the generation of the user scores 240 such as infection likelihood prediction, as well as the selection of a vaccine, digital therapeutic, data monitoring process for a user, and more (see FIG. 5).

In a similar manner, the computer system 110 can carry out recommended actions at the community level, such as providing testing kits to recommended areas or individuals, initiating communication to instruct changes in disease prevention measures for members of the community (e.g., for the community as a whole or selectively for areas or groups of individuals with the highest disease transmission scores or disease exposure scores), and so on.

In general, in addition to or instead of selecting and performing actions based on an exposure score representing an aggregate or cumulative level of exposure, the computer system 110 can select and perform actions in response to detection of specific risks or interactions. For example, the computer system 110 can send data causing a user's mobile device to provide an intervention based on entry to a single location tag, or to a single location where the location tag(s) combine to present at least a minimum level of risk. For example, upon detecting that a user has entered a geofence area for a visit-based location tag, the computer system can initiate an exposure notification, an exposure risk notification, a disease management or treatment instruction or recommendation, etc.

Although the discussion of the process 2200 is focused on determining exposure levels and exposure risks for actions that have occurred, similar techniques can be used detect and notify of current or predicted exposure events. The system 110 detect entry to a geofenced area for a location tag and warn of the current presence of someone with a case of COVID-19, or of the presence of a person with a case of COVID-19 having been present within a threshold period of time (e.g., the previous 12 hours). As noted above, location tags can be associated with (e.g., can include or be marked, labeled, linked to metadata, etc.) information indicating whether the person whose visit the location tag represents has tested positive for COVID-19. Location tags can also be associated with infection likelihood predictions, or have disease transmission scores based on the infection likelihood predictions, allowing the system to warn others of likely exposure (e.g., probable cases) even before actual test results are available.

As another example, when a user enters a location or region where a corresponding disease transmission score exceeds a threshold, then the user can be warned of the exposure (e.g., exposure that has occurred or may occur) with a notification on the user's phone or other device. The disease transmission score can be for an individual location tag for which the user has entered the corresponding geofence, or for an aggregation of multiple location tags applicable to the location (e.g., a combination of multiple visit-based location tags, or a combination of visit-based, population-based, and location-type-based tags). As discussed further with respect to FIG. 23, the computer system 110 may also anticipate a user's plan or path leading to entry to a region with a high disease transmission score, and may warn the user or in advance of the user's arrival, to prevent exposure and not merely notify the user of exposure that has occurred.

Figure 23:
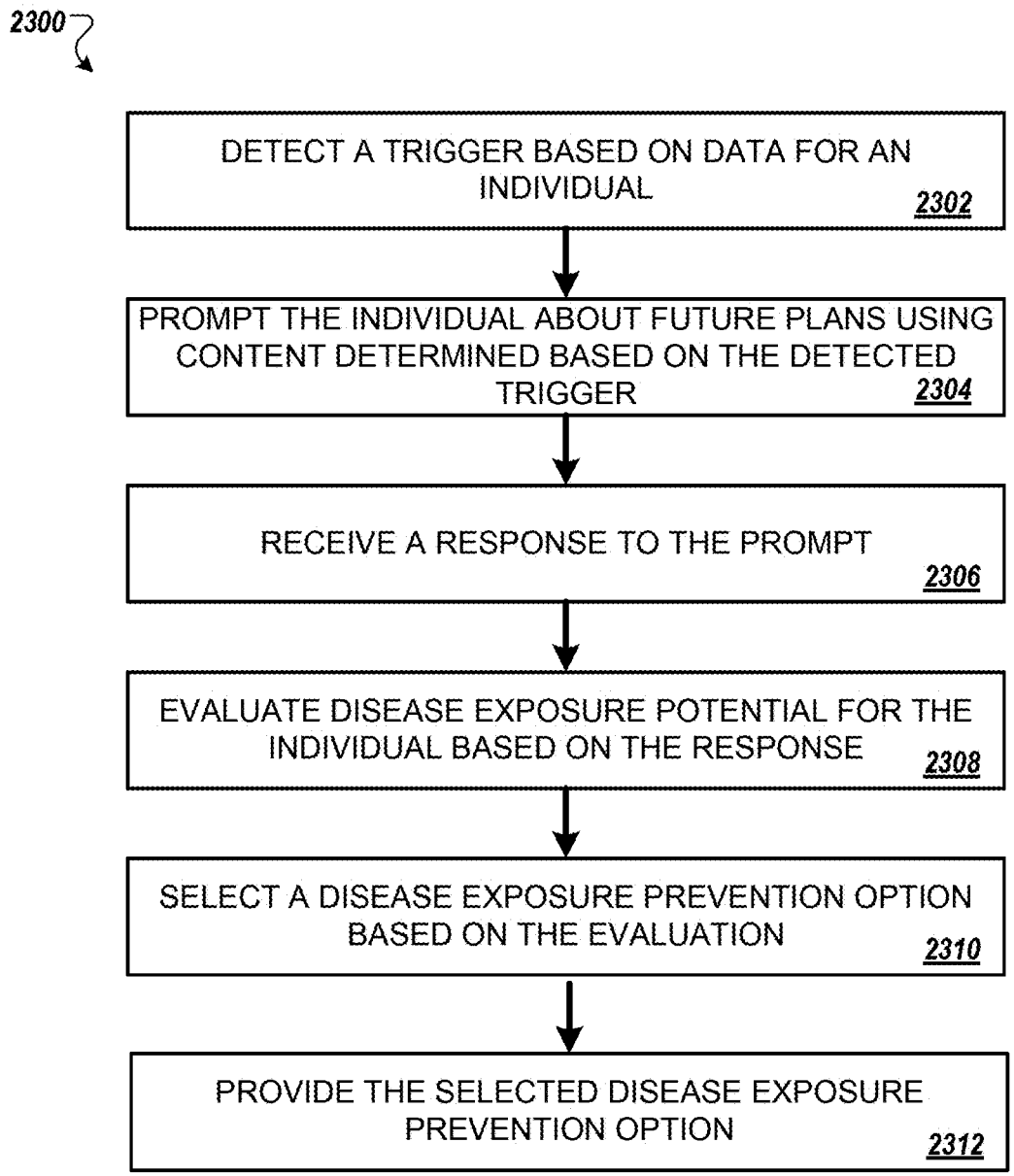
FIG. 23 is a flow diagram showing an example of a process for predicting future user actions and taking advance steps to limit or avoid disease exposure.

FIG. 23 is a flow diagram showing an example of a process 2300 for predicting future user actions and taking steps to limit or avoid disease exposure due to those actions. The process 2300 can be performed by one or more computers, such as the computer system 110. In general, the operations of the process 2300 can be performed by one or more servers, one or more client devices, or a combination of them. In addition to the operations illustrated, the process 2300 can optionally include other operations discussed with respect to FIG. 11. In the example, the disease mentioned can be COVID-19, or it can be another infectious disease.

The process 2300 can be used to predict user actions that pose a health risk, to initiate interactions to confirm or characterize the potential user actions and the associated health risk, and to provide interventions to lessen the health risk for the individual. As discussed above, the computer system 110 can collect a rich set of monitoring data for individuals and communities. The computer system 110 can use this collected data to predict future actions of users, for example, to detect that a specific user is likely to perform a specific action or type of action in the future. The computer system 110 can use this prediction capability to anticipate when a user is likely to act a manner that presents a health risk, such as a disease exposure risk for COVID-19. The computer system 110 can then respond with communications or other interventions to limit or avoid the disease exposure. For example, the computer system 110 can warn the user of a disease exposure risk, suggest a modification to reduce the risk (e.g., wearing a mask, limiting the duration of a visit, etc.), recommend an alternative action with lower risk (e.g., visiting at a different time, visiting a location with lower disease exposure risk, etc.), or take other actions.

The computer system 110 can detect conditions indicative of likely future action by a user, send a personalized EMA or survey asking about the user's plans, and based on the user's response initiate an interaction to reduce a disease exposure risk for the user. For example, if the user is approaching a store or other populated area, the system 110 can predict the user's destination and activity (e.g., shopping, exercising at a gym, etc.). The computer system 110 can ask about the predicted destination and the nature of the visit (e.g., planned duration, activity, etc.). Based on the user's response, the computer system 110 can provide interventions to reduce or avoid disease exposure, such as to instruct disease prevention measures or discourage the planned action.

These techniques can be used to predictively provide interventions with different timing with respect to a user's planned action. The computer system 110 can provide just-in-time interventions, such as those triggered by the user's context or provided shortly before a risky action by the user is expected. In other words, in some cases the interventions can be provided when the user action is imminent or is expected within a brief period of time (e.g., an hour, 30 minutes, 15 minutes, 5 minutes, 1 minute, etc.). The computer system 110 can provide interventions father in advance, such as hours or days in advance, based on data such as behavior patterns of the user, calendar data indicating scheduled appointments for the user, and so on.

The ability to predict and address future user actions before the user begins them provides significant advantages for supporting health and wellbeing. The computer system 110 is able to provide interventions during or in response to a user activity. However, once a user has begun an activity the user is usually much less likely to change plans and stop the activity to avoid a health risk. For example, once a user has traveled to a location and/or entered a location where there is a disease exposure risk, the user is much less likely to change plans and leave to avoid potential disease exposure. In addition, even if the user is willing to alter his behavior, it may be too late to make appropriate preparations or precautions once a user has arrived at a location or has begun an activity. For example, an intervention, provided upon a user entering a location, that instructs the user to wear a mask may be ineffective if the user did not remember to bring a mask. By contrast, by predicting user actions, confirming the user's plans, and providing an intervention well in advance, such as at the beginning of the day or as the user is leaving her house, the computer system 110 can enable much more likely adoption of recommendations and change in behavior. As a result, the system 110 can be configured to anticipate future user actions and provide instructions, before they arrive at a location involving a health risk and before they begin an activity that carries a health risk.

The recommendations and interactions that the system provides to avoid disease exposure may vary significantly based on type of activity predicted. For example, rather than simply stating a generic recommendation (e.g., "remember to wear a mask") every time the user leaves the house, the system can predict a location and/or activity for a future user action (e.g., grocery shopping at a certain store) and provide customized interactions for that predicted action's risk profile (e.g., "Store X is safer than Store Y for grocery shopping," or "remember to clean the handle of your shopping cart when you arrive.")

In addition, initiating interactions to confirming the user's planned action and the associated circumstances is also important to provide high-quality, useful interactions. For example, a reminder to a user to wear a mask, sent every time a user leaves the house, is likely to become annoying or be ignored or blocked by the user. By contrast, recommendations and interactions that are tailored for the user's specific needs and specific activities can be much more likely to be effective. Confirming the nature of the planned activity, e.g., purpose, duration, location, etc. can allow for much more customized recommendations. Interactions to request information from the user regarding potential future activities can serve multiple purposes, for example, to confirm user intent (e.g., is the user actually planning on performing the predicted activity), and characterize the activity and refine the risk potential for the activity. For example, the user may indicate that masks or other preventative measures are being used, which may lower the overall risk of the activity to an acceptable level.

The computer system 110 can predict a user's future activities based on various inputs, such as historical behavior patterns for the user, context data for the user, behavior of other users in the community, calendar data for the user, and so on. Context data indicating a current context of the user, for example, location tracking data indicating a location of the user's device, a speed and trajectory of the user's device, a path traveled by the device, etc. The speed, direction, and path that a person is traveling can indicate a likely destination for a user, especially when historical location tracking data shows the user has travelled the same path to the same location before.

The computer system 110 can also predict a potential future action by the user using historical information about the user, such as prior tracked actions showing prior visits to a particular location or other information indicating a behavior pattern for the user. For example, a user's location history may show that the user has visited a shopping mall several times in the last month. The computer system 110 can obtain current location tracking data for the user that indicates that the user is currently on route to the shopping mall, for example, due to the user's phone travelling in a direction toward the shopping mall, the user's phone being located within a certain level of proximity of the shopping mall (e.g., within half a mile), the user's phone being tracked along a route or path previously used to visit the shopping mall, the shopping mall being set as a destination for a navigation application, etc.

The computer system 110 can also predict a potential future action by the user based on behavior patterns of others, such as individuals in the user's community or other individuals having similar characteristics as the user. When the user's movement pattern (e.g., route, location, etc.) matches or is similar to the pattern that other users took to reach the location, the system can determine The computer system 110 can also predict a potential future action by the user based on calendar data, for example, appointments scheduled for later in the day. The computer system 110 may initiate communication and disease prevention interactions based on the calendar data alone, or based on using the calendar data along with other information (e.g., tracked context information) to verify that the user is proceeding toward the scheduled appointment.

In some implementations, the process 2300 can be used to provide just-in-time interventions responsive to the context of the user. For example, the computer system 110 can monitor the user's context in real time or near real time, and detect when an when an action by the user is imminent. Different triggers for various types of actions can be learned through the analysis of historical data for the user, e.g., to identify what movement patterns, data inputs, device usage patterns, etc. typically precede different types of action by the user. Similarly, the triggers can be determined based on analysis of the actions of other users. Changes in the context of the user, such as change in location or path of movement of the user's device, can signal that a certain action by a user is likely. Similarly, movement toward a location (e.g., gym, movie theater, etc.) can increase the likelihood of activities performed at the location. The computer system 110 can gather various signals of a user's potential future activity (e.g., prior behavior pattern, increasing proximity to a relevant location, etc.) and determine a confidence score indicating a likelihood of the future action. When the confidence score indicates a likelihood of that activity being performed in the future reaches a threshold, and/or that other conditions are met, such as a disease transmission metric and/or a user susceptibility metric indicate a risk above a threshold, the system can initiate communication (e.g., an EMA-type message regarding prospective actions of the user) and recommendations to avoid the disease transmission risk presented.

The process 2300 includes detecting a trigger based on data for an individual (step 2302). The computer system 110 evaluates collected data about a user, for example, and determines whether any of one or more triggering conditions are present. The detection of the trigger may be based on receiving user data indicating a potential action of a user of a mobile device. This user data can be context data for the user (e.g., movement data, location tracking data, etc.), self-reported data, calendar data, etc. In some cases, a trigger is detected based on determining that the user's device is entering or is near a high-risk area (e.g., based on location type, tagged exposure events, population, etc.).

For example, the computer system 110 can store records of prior behavior patterns of the individual of other individuals, and determined when the current context or a pattern of recent action matches the contexts or patterns that preceded the different types of user actions. When the computer system 110 determines that the similarity reaches a threshold level, the computer system 110 can trigger the remaining actions of the process 2300.

In general, the computer system 110 can determine a prediction of a particular type of activity that the individual is likely to perform, e.g., grocery shopping, exercising at a gym, attending a movie at a theater, etc. The trigger can be determining that the pattern of behavior, context, or other information collected for the user indicates with a particular confidence level that the user will perform that type of activity.

The prediction can additionally or alternatively be associated with a specific location, such as to go shopping at a particular store. When the prediction is associated with a location, the computer system 110 can use information about the location, including predictions of machine learning models (see FIGS. 11 and 19), based on location tags (see FIG. 22), community disease measures, and so on.

In some implementations, the computer system 110 may assess both (i) the likelihood of an activity of a user and/or the user's destination and (ii) the potential disease exposure risk for that activity and/or location in determining whether a trigger for further interaction and intervention is reached. For example, a sliding scale may quantify a tradeoff between likelihood and exposure risk. For example, a predicted activity with a high level of risk of contact with other (e.g., grocery shopping) may trigger further interactions and interventions even if the probability determined is relatively low (e.g., 30-40%). A predicted activity with a low risk (e.g., jogging outdoors) may not trigger interactions even if the likelihood of occurring is high (e.g., 70-80%). On the other hand, even a low risk activity may trigger interactions if the predicted location presents a high risk (e.g., a populated area, an area with high disease prevalence, an area with location-based tags indicating disease exposure, etc.).

As an example, the computer system 110 can determine a risk score for a predicted activity type, a risk score for a predicted location for the activity (e.g., disease transmission score for the location), and a predicted likelihood for the activity and/or location. The computer system 110 can then combine (e.g., add them together, determine a weighted average, etc.) the risk scores and likelihood scores to obtain a combined score. The combined score can be compared to a threshold or other criteria to determine. In other implementations, scores for activity risk, location risk, and likelihoods are compared to separate thresholds, to determine whether interaction with the user and/or disease prevention actions are needed. This analysis can be done for each of various potential activities and locations that are relevant to the user, based on the current context of the user and the historical actions of the user.

The process 2300 includes prompting the individual about future plans using content determined based on the detected trigger (step 2304). For example, the computer system 110 can send a transmission causing the user's mobile device to provide a question, EMA, survey, interactive UI, or other element that prompts the user to provide user about his future plans, and often about a specific prospective action and/or location that the computer system 110 predicted. The prompt can be for information describing or confirming the user's intentions or future plans. As a result, the interaction can be similar to an EMA, but rather than request information about the user's current context and experience, it can have a forward-looking focus to ask about a future event that is planned or likely. The prompt can request a prediction or estimate from the user (e.g., an amount of time the user is expected to perform an activity or stay in a location, an expected destination, etc.).

In general, the prompt can be for information that characterizes or describes a prospective action or activity a user intends to perform, whether or not the specific activity is predicted by the computer system 110. For example, certain changes in context or data patterns may indicate that action by the user is likely (e.g., some activity is likely to occur within a predetermined time frame), but may not specify the specific type or nature of action by the user. The prompts can thus request the information about a user's future plans, triggered by a data pattern, event, context, or other trigger criteria that may not indicate a specific predicted action or activity. Thus, while the triggers may correspond to specific actions or activities, the triggers may alternatively represent patterns or contexts which are correlated with or are predictive of future exposure risks of the user even if the specific actions are not defined or predicted. The triggers and/or predictions can be based on likelihood of activity or action within some defined period of time, such as a day, within 12 hours, within 4 hours, within 1 hour, within 15 minutes, within 5 minutes, etc.

Prompting the individual can include the computer system 110 providing content configured to cause the mobile device associated with the user to present a prompt for user input. The content can prompt for entry of the desired type of data with a question, a request for input, interactive controls, and so on. The prompt can be for user input to characterize a prospective action of the user. For example, the prompt may ask the user to confirm if an action is going to be performed, to indicate a duration of the action, the reasons for the activity, an indication of conditions at the proposed destination, preventative measures of the user, etc. Examples include "Do you plan to shop at Store A today?," "How long do you plan to spend at store B?," "Do you wear a mask when you go shopping?," "What is the purpose for your trip today?," "Is Store C your destination on this trip?," and so on. The prompts can include text entry fields, buttons to select predetermined options, and other means of receiving user input.

The content of the prompt can be determined based on the trigger that was detected or a predicted action or activity. The computer system 110 then prompts for information about the predicted activity. For example, if the computer system 110 detects that the user is approaching a store, and so is likely to shop at that store, the computer system 110 can tailor the prompt to ask for information relevant to the activity (e.g., shopping) and/or location (e.g., the particular store being approached).

The process 2300 includes receiving a response to the prompt (step 2306). This can include, for example, receiving user input to a touch screen, receiving voice input, etc. For example, a user may type an answer to a question, select a button indicating whether the action is planned to be performed or not, move a slider control to indicate a planned duration, etc. As discussed above, the response can indicate any of various aspects about the user's plans, such as: to confirm or deny that the prospective action will be performed; to indicate a different action or activity is planned; to indicate characteristics of the prospective action, including a location, duration, group of people involved, activity to be performed, etc.; to indicate conditions at the location; and so on.

The process 2300 includes evaluating disease exposure potential for the individual based on the response (step 2308). The level of disease exposure can be for the prospective action or activity predicted, if the user response(s) are consistent with or confirm the prediction. In other cases, the user response may indicate an action or activity that is a variation of or is completely different from the predicted activity. For example, the computer system 110 may detect, based on location data or a calendar entry that a user is planning on going to a mall, and may predict the user will be shopping, but the user response to a prompt may indicate that the user instead intends to visit a gym at the mall instead. In this example, the system was correct in predicting that travel and a visit to the general area would occur, but did not accurately predict the specific location or activity. When the response indicates a new action or activity intended by the user (e.g., an action or activity with changed parameters compared to the prediction, or a different action or activity altogether), the computer system 110 evaluates the disease exposure potential for the new action or activity. In some cases, if the user indicates that the prediction is incorrect (e.g., the user is actually going home rather than shopping, or isn't actually leaving the current location), the computer system 110 may determine that no intervention or further processing to limit risk is needed.

The system may determine a level of risk when evaluating potential triggers, the received information from the user may provide additional information that adjusts the calculation. For example, the user may confirm that the action is planned, indicating a likelihood of essentially 100%. The user may respond and indicate a planned duration of an activity, and so the risk for a 15 minute visit will be calculated to be much less than for a 3 hour visit. Similarly, the user response may indicate aspects such as: a destination different from the predicted one; an activity different from the predicted one; conditions at the destination; whether preventative measures like masks are used; and so on. Based on any or all of these factors, the computer system 110 updates its risk scoring for the planned activity to reflect the current information, and especially the user-confirmed information.

The evaluation of disease exposure potential can take into account factors such as the location tags for population, location type, and actual exposure. For example, a disease transmission score for a location, based on one or more types of location tags, can be determined. As another example, different location types can have different risk scores, e.g., a risk score of 9 for a hospital, a risk score of 6 for a post office, and so on. The evaluation of disease exposure potential can take into account the type of action or activity that the user intends to perform. For example, stored data may indicate risk scores for different activities that may contribute different levels of risk, e.g., a risk score of 5 for shopping, a risk score of 8 for exercising at a gym, etc. Similarly, the evaluation of disease exposure potential can take into account the user's personal susceptibility to the disease (e.g., based on a score from a machine learning model, or based on medical history for the user). In general, different locations or location types and different types of actions or activities can have different levels of risk associated with them, and the computer system 110 can store mapping data that indicates the levels of risk. Those levels can be updated or enhanced based on the particular circumstances (e.g., the location tags for exposures at locations) and based on a user's personal level of susceptibility to the disease. A combined score for various factors can be determined, for example, with a summation, selecting the maximum value among multiple component scores, applying an equation or function, etc.

In some implementations, a machine learning model is trained to predict disease exposure potential, based on an activity type and/or location type. This model can be trained based on the activities and corresponding locations for different users over time, and the corresponding instances of disease infection that occurred, to predict the relative risk or likelihood of disease transmission for different activities and location types. The model may further be trained to take into account other contextual factors related to activities and locations, such as whether disease prevention measures are used, levels of population at the locations, characteristics of the locations, and so on. The input to the model can be based on the responses to the prompt, as well as any other collected data for the user, including context data or other data evaluated to determine if a trigger for the process 2300 is detected.

The process 2300 includes selecting a disease exposure prevention option based on the evaluation (2310). The determination to select and provide an intervention to reduce disease risk can be conditioned on the exposure level or exposure risk being above a minimum level. In other words, if the evaluation indicates very low risk, no disease exposure prevention option need be selected and provided. On the other hand, when the disease exposure risk is above a threshold, the computer system 110 selects an option to reduce the risk.

Selecting the disease exposure prevention option can include selecting for the user that is predicted to reduce or avoid exposure of the user to the disease, wherein the disease exposure prevention option is selected or customized for the user based on at least one of the user data or the response data. The computer system 110 can store data indicating different options, such as to avoid the planned activity, to wear a mask, to perform the activity at an alternative location, to delay the planned activity, etc. Based on the disease exposure potential or risk level of the planned activity and the expected measure of decrease in risk for the different options, the computer system 110 select and recommends one or more of the options. For example, when the evaluation indicates high risk, the computer system may recommend to cancel the planned activity or may recommend a lower-risk alternative. If the evaluation indicates a moderate risk, or one that can be lowered to an acceptable level using a mask or other measure, the computer system 110 recommends the predicted measure(s) that can lower the risk level sufficiently.

In some implementations, the disease prevention option is selected based on output of a machine learning model. The output can be generated in response to the model receiving data indicating at least one of the prospective action or activity of the user, a location or location type for the prospective action, and collected data for the user (e.g., user disease status (e.g., vaccinated, recovered, etc.), behavior patterns, physiological measurements, user profile, etc.). The machine learning model can be one trained based on training data showing examples of actions performed with and without disease prevention measures, and the corresponding disease outcomes (whether at an individual or community level), so that the model learns the levels of transmission risk reduction provided by different disease prevention measures in different situations (e.g., for different locations, activities, types of users, etc.)

In some implementations, the disease prevention option is selected based on mapping data indicating predetermined disease prevention options that correspond to different contexts, activities, locations, and/or exposure risk levels. For example, stored mapping data can specify a preventative measure corresponding to the activity type of the prospective action, a location type for a location of the prospective action, a disease transmission level for the location and/or prospective action, a user disease susceptibility measure for the user, and/or user characteristics of the user. In other words, the mapping data associates different disease prevention options with different values of one or more of activity types, location types, disease transmission levels, user disease susceptibility measures, and/or user characteristics. Then, based on the various collected data for the user, including responses to prompts, the computer system 110 can look up the most applicable disease prevention option. In a simple example, there may be a set of disease prevention options associated with a particular activity, such as shopping, and the specific disease prevention option can be selected can be based on the exposure risk level (e.g., exposure risk level less than 10-stay 6 feet from others; exposure risk level between 10 and 20-wear a mask; exposure risk level greater than 20-stay home or go to a store that provides a lower risk level).

Many different disease prevention options are available to be recommended by the system. A few examples include: wearing personal protective equipment, including at least one of a mask or gloves; maintaining a distance between the user and others; limiting a duration of the prospective action of the user; changing a location of the prospective action of the user; replacing the prospective action of the user with a lower-risk activity; or avoiding the prospective action.

The process 2300 includes providing output data indicating the selected disease exposure prevention option (step 2312). For example, the system can provide content configured to cause the mobile device associated with the user to present the selected disease exposure prevention option. For example, the computer system 110 may indicate, "Instead of going to the gym where COVID-19 risk is high, try running outdoors today." As another example, the computer system 110 may inform a user, "The mall is busy today and people diagnosed with COVID-19 were there this morning. Can you postpone your trip?." Other examples include "Please limit your visit to less than 30 minutes," "Make sure to wear your mask while you are out," and "Shop at Store A instead of Store B. There was a confirmed COVID-19 exposure at Store B."

In general, the process 2300 can be used to detect potential future actions or activities that present health risks more generally, not only for risks of disease exposure. Similarly, the options selected and communicated to the user can be options determined to reduce or avoid the type of health risk detected. For example, if a user is recovering from foot surgery, certain activities or exercises can present a risk of injury. The system may detect locations, movements, calendar appointments, and other that indicate an activity that presents a high risk of re-injury given the user's condition, and then use the process to ask the user about his plans and provide interventions to reduce or avoid the risk. As another example, a user that is recovering from alcohol addiction may have a risk of substance abuse. The computer system 110 can evaluate the movement patterns, context, calendar appointments, and so on to determine when there is a risk that the user will consume or purchase alcohol and may use the process to select and provide interventions to reduce or avoid the risk. For example, if a user has a party scheduled on a calendar or is in proximity to a liquor store the system can weigh the risk level and likelihood of purchasing or consuming alcohol, send one or more interactions to find out more about the user's intent and context, and then if appropriate initiate an intervention (e.g., to discourage the user, to recommend an alternative, to encourage support of a family member or friend, etc.).

The data collected by the computer system 110 and used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected and used by the computer system 110 (e.g., to generate feature values for input to predictive models, to train predictive models, to validate and select actions and recommendations, to evaluate to determine whether to initiate interactions with users, to assign or determine disease transmission and exposure scores, etc.) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNA-comics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g., data from spirometers, pulse oximeters);

Neurological-related biodata (e.g., data from EEG monitors);

Behavior data (e.g., movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanisms);

Positioning and location data (e.g., GPS data, gyroscope data, altimeter data, accelerometer data, linear acceleration data, received signal strength indicator from nearby emitters such as Wi-Fi access points, Bluetooth sensors, sensor networks, and cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., Isopropyl$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2$ $CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method performed by one or more computers, the method comprising:

collecting, by the one or more computers, user data provided over a communication network from user devices of individuals from different communities, the user devices each having a software application configured to manage monitoring performed by the user devices, the user data indicating at least one of (i) measurement results for measurements made by the user devices of the individuals or (ii) responses provided by the individuals to prompts provided by the user devices of the individuals;

accessing, by the one or more computers, trigger data that defines multiple different data collection triggers associated with monitoring of a disease, the data collection triggers each specifying a predetermined correspondence between (i) one or more criteria for detecting occurrence of the data collection trigger, and (ii) one or more types of data to be collected when the one or more criteria of the data collection trigger are satisfied;

detecting, by the one or more computers and based on the accessed trigger data, different data collection triggers for different communities based on determining that the one or more criteria for the different data collection triggers are satisfied for different communities; and in response to determining that the one or more criteria for the different data collection triggers are satisfied for different communities, automatically varying, by the one or more computers, data collection performed by the user devices for the individuals in different communities such that the user devices perform different data collection operations for individuals in different communities, including performing, for each of at least some of the different communities, operations comprising:

in response to detecting a particular data collection trigger for the community, selecting, by the one or more computers, instructions configured to cause the software application on the user devices to initiate collection of user data of the one or more types of data specified by the particular data collection trigger detected for the community;

selecting, by the one or more computers, a set of multiple individuals associated with the community that have user devices with the software application configured to manage monitoring performed by the user devices; and transmitting, by the one or more computers, the instructions over the communication network to user devices associated with the individuals in the selected set of multiple individuals such that the instructions cause the software application on the user devices of the individuals in the selected set to alter a set of monitoring operations performed by the user devices to obtain, through one or more sensor measurements or one or more interactive modules, the one or more types of data specified by the particular data collection trigger detected for the community.

2. The method of claim 1, wherein the disease is coronavirus disease 2019 (COVID-19).

3. The method of claim 2, further comprising:
receiving, by the one or more computers, response data indicating responses to the prompts;
generating, for a particular individual in the selected set of individuals, an infection likelihood score indicating a likelihood that the individual has contracted COVID-19; and
providing, to the particular individual or a healthcare provider for the particular individual, data indicating a diagnosis whether the user has contracted COVID-19, wherein the diagnosis is based on the infection likelihood score.

4. The method of claim 2, further comprising:
receiving, by the one or more computers, response data indicating responses to the prompts;
using, by the one or more computers, the response data to assess suitability for one or more individuals of one or more digital therapeutics interventions classified as treating one or more aspects of COVID-19; and
in response to determining from the suitability assessment that the one or more digital therapeutic interventions are suitable for a particular individual, initiating, by the one or more computers, delivery of the one or more digital therapeutics interventions to the particular individual through a user device of the particular individual.

5. The method of claim 1,
wherein the method includes detecting, for at least one of the different communities, a data collection trigger by:
generating an output produced by a trained machine learning model in response to receiving a set of input data derived from at least the collected user data;
comparing the output of the trained machine learning model with a threshold; and
determining that the output of the trained machine learning model satisfies the threshold, wherein detection of the data collection trigger is based on the determination that the output of the trained machine learning model satisfies the threshold.

6. The method of claim 5, wherein the trained machine learning model is an artificial neural network.

7. The method of claim 1, wherein the user data comprises responses to prompts presented to the individuals by the user devices; and
wherein the user data indicates at least one of:
a location visited by an individual;
a sign or symptom of a disease reported by an individual;
a physiological attribute reported by an individual; or
a result of a laboratory test or a test for a disease.

8. The method of claim 1, wherein a data collection trigger is detected for at least one of the different communities based on at least one of:
a community disease measure for a community;
an electronic health record or one of the individuals in the community;
a physiological measurement for individuals in the community; or
sensor data captured by the user device of one or more individuals in the community.

9. The method of claim 1, wherein the data collection triggers are data collection triggers to trigger collection of data indicative of spreading of a disease, wherein at least one of the data collection triggers specifies criteria that includes detection of at least one of:
a physiological attribute or physiological change for one or more individuals in the community;
a sign or symptom of the disease for one or more individuals in the community;
a behavioral change for one or more individuals in the community;
a disease diagnosis for one or more individuals in the community;
a positive disease test result for one or more individuals in the community; or
a community disease measure for the community that satisfies a threshold.

10. The method of claim 1, wherein at least one of the data collection triggers specifies a type of data to be collected that includes at least one of:
a physiological measurement;
an indication a sign or symptom of the disease for one or more individuals in the community;
a behavioral change for one or more individuals in the community;
a disease diagnosis for one or more individuals in the community; or
a positive disease test result for one or more individuals in the community.

11. The method of claim 1, wherein collecting user data provided by one or more individuals in the community comprises collecting user input data regarding physiological attributes, behavior, and/or mental health through surveys that each include one or more prompts for user input regarding physiological attributes, behavior, and/or mental health.

12. The method of claim 11, wherein the surveys comprise ecological momentary assessments (EMAs) configured to assess an individual's current experience, behavior, and/or mood at a time the EMA is provided and in a current environment and context of the individual.

13. The method of claim 1, wherein collecting user data provided by one or more individuals in the community comprises collecting user data provided in response to a first survey provided to a first subset of members of the community;
wherein selecting the set of individuals comprises selecting a second subset of individuals in the community to receive a second survey, wherein the second subset is larger than the first subset, and wherein the second survey requests a different type of data than the first survey; and
wherein transmitting the instructions comprises sending instructions to the user devices of the second subset of individuals to cause the software application on the user devices of the second subset of individuals to present the second survey.

14. The method of claim 1, wherein the trigger data specifies, for a particular data collection trigger, a particular content item to provide to prompt collection of the type of data associated with the detected data collection trigger;
wherein, for at least one of the different communities, selecting the content configured to prompt user input of the type of data associated with the detected data collection trigger comprises selecting the particular content item specified by the trigger data; and
wherein the particular content item comprises a user interface element, text, a question, a survey, an ecological momentary assessment (EMA), a user interface, a media item, or an interactive element.

15. The method of claim 1, wherein the one or more criteria for the data collection triggers represent indicators of at least one of presence of the disease, spread of the disease, or risk factors for the disease; and the types of data respectively specified for the data collection triggers comprise types of data used by the one or more computers to assess spread of the disease in the community or impact of the disease in the community, the types of data comprising at least one of:

physiological data, comprising at least one of heart rate, blood pressure, respiration rate, oxygen saturation, lung capacity, or blood glucose level;

behavioral data, comprising a measure for at least one of travel, exercise, sleep, work, recreation, diet, or device usage; or mental health data, comprising an indicator for at least one of mood, responsiveness, anxiety level, or depression level.

16. The method of claim 1, comprising, for at least a particular community of the different communities:

selecting two or more different content items that are each configured to prompt user input of a same type of data associated with a data collection trigger detected for the particular community; and causing user devices associated with a set of individuals in the particular community to each present one of the two or more different content items, wherein the content item caused to be presented at each of the user devices is determined based on information about a recipient corresponding to the user device, the information comprising at least one of characteristics for the recipient, a user profile for the recipient, a prior interaction of the recipient, a medical history of the recipient, a disease status of the recipient with respect to the disease, a vaccination status of the recipient with respect to the disease, a sign or symptom of the disease indicated by the recipient, a physiological measure for the recipient, a behavior of the recipient, or a mental health attribute for the recipient.

17. A system comprising:

one or more computers;

one or more computer-readable media storing instructions that, when executed by the one or more computers, cause the one or more computers to perform operations comprising:

collecting, by the one or more computers, user data provided over a communication network from user devices of individuals from different communities, the user devices each having a software application configured to manage monitoring performed by the user devices, the user data indicating at least one of (i) measurement results for measurements made by the user devices of the individuals or (ii) responses provided by the individuals to prompts provided by the user devices of the individuals;

accessing, by the one or more computers, trigger data that defines multiple different data collection triggers associated with monitoring of a disease, the data collection triggers each specifying a predetermined correspondence between (i) one or more criteria for detecting occurrence of the data collection trigger, and (ii) one or more types of data to be collected when the one or more criteria of the data collection trigger are satisfied;

detecting, by the one or more computers and based on the accessed trigger data, different data collection triggers for different communities based on determining that the one or more criteria for the different data collection triggers are satisfied for different communities; and in response to determining that the one or more criteria for the different data collection triggers are satisfied for different communities, automatically varying, by the one or more computers, data collection performed by the user devices for the individuals in different communities such that the user devices perform different data collection operations for individuals in different communities, including performing, for each of at least some of the different communities, operations comprising:

in response to detecting a particular data collection trigger for the community, selecting, by the one or more computers, instructions configured to cause the software application on the user devices to initiate collection of user data of the one or more types of data specified by the particular data collection trigger detected for the community;

selecting, by the one or more computers, a set of multiple individuals associated with the community that have user devices with the software application configured to manage monitoring performed by the user devices; and transmitting, by the one or more computers, the instructions over the communication network to user devices associated with the individuals in the selected set of multiple individuals such that the instructions cause the software application on the user devices of the individuals in the selected set to alter a set of monitoring operations performed by the user devices to obtain, through one or more sensor measurements or one or more interactive modules, the one or more types of data specified by the particular data collection trigger detected for the community.

18. One or more non-transitory computer-readable media storing instructions that, when executed by one or more computers, cause the one or more computers to perform operations comprising:

collecting, by the one or more computers, user data provided over a communication network from user devices of individuals from different communities, the user devices each having a software application configured to manage monitoring performed by the user devices, the user data indicating at least one of (i) measurement results for measurements made by the user devices of the individuals or (ii) responses provided by the individuals to prompts provided by the user devices of the individuals;

accessing, by the one or more computers, trigger data that defines multiple different data collection triggers associated with monitoring of a disease, the data collection triggers each specifying a predetermined correspondence between (i) one or more criteria for detecting occurrence of the data collection trigger, and (ii) one or more types of data to be collected when the one or more criteria of the data collection trigger are satisfied;

detecting, by the one or more computers and based on the accessed trigger data, different data collection triggers for different communities based on determining that the one or more criteria for the different data collection triggers are satisfied for different communities; and in response to determining that the one or more criteria for the different data collection triggers are satisfied for different communities, automatically varying, by the one or more computers, data collection performed by the user devices for the individuals in different communities such that the user devices perform different data collection operations for individuals in different communities, including performing, for each of at least some of the different communities, operations comprising:

in response to detecting a particular data collection trigger for the community, selecting, by the one or more computers, instructions configured to cause the software application on the user devices to initiate collection of user data of the one or more types of data specified by the particular data collection trigger detected for the community;

selecting, by the one or more computers, a set of multiple individuals associated with the community that have user devices with the software application configured to manage monitoring performed by the user devices; and transmitting, by the one or more computers, the instructions over the communication network to user devices associated with the individuals in the selected set of multiple individuals such that the instructions cause the software application on the user devices of the individuals in the selected set to alter a set of monitoring operations performed by the user devices to obtain, through one or more sensor measurements or one or more interactive modules, the one or more types of data specified by the particular data collection trigger detected for the community.

19. The method of claim 1, wherein the data collection triggers respectively specify different criteria and different types of data to collect when the triggers are detected, wherein at least some of the data collection triggers each designate specific interactive content to provide in response to detection of the data collection trigger; and wherein communicating with user devices associated with the individuals in the set comprises providing a particular survey specified by the detected data collection trigger.

20. The method of claim 1, wherein transmitting the instructions to the user devices associated with the individuals in the selected set comprises providing software or configuration data over the communication network to the user devices associated with the individuals in the selected set.

21. The method of claim 1, wherein detecting the different data collection triggers comprises detecting a particular trigger for a community based on a pattern or trend indicted by the user data indicated by multiple different individuals in the community.

22. The method of claim 1, comprising varying the data collection performed for a particular community over time, including varying the set individuals in a community that are monitored and the types of data collected for the individuals, based on detection of different data collection triggers for the particular community over time.

23. The method of claim 1, wherein, for each of at least some of the data collection triggers, the trigger data specifies a correspondence among (i) the one or more criteria for the data collection trigger, (ii) the one or more types of data to be collected for the data collection trigger, and (iii) one or more selection criteria for selecting individuals from which to collect the one or more types of data corresponding to the data collection trigger;

wherein the method includes automatically varying, by the one or more computers, the sets of user devices that perform the data collection in different communities based on the selection criteria for data collection triggers detected for the different communities; and wherein the selection of the set of multiple individuals for a community is performed to identify members of the community that satisfy the selection criteria that the trigger data specifies for the data collection trigger detected for the community.

24. The method of claim 23, wherein, for at least one of the data collection triggers, the one or more selection criteria specify characteristics of individuals from which to collect the one or more types of data specified by the data collection trigger.

25. The method of claim 1, wherein, for at least one community, the particular data collection trigger detected for the community specifies a sensor measurement to perform to obtain data of the one or more types of data specified by the data collection trigger; and wherein, for the at least one community, the selected instructions cause the user devices that receive the instructions to perform the sensor measurement using one or more sensors of the user devices to obtain data of the one or more types of data specified by the particular data collection trigger detected for the at least one community.

26. The method of claim 1, wherein the trigger data specifies, for each of at least some of the data collection triggers, an interactive module or sensor measurement for obtaining the one or more types of data specified for the data collection trigger; and wherein transmitting the instructions comprises transmitting the instructions to cause the user devices of the individuals in the selected set to obtain the one or more types of data that the trigger data specifies for the data collection trigger using an interactive module or sensor measurement that the trigger data specifies for the data collection trigger.

* * * * *